(12) United States Patent
Garcia-Guzman et al.

(10) Patent No.: US 12,704,501 B2
(45) Date of Patent: Aug. 11, 2026

(54) METHODS FOR PHOTOIMMUNOTHERAPY AND RELATED BIOMARKERS

(71) Applicant: Rakuten Medical, Inc., San Mateo, CA (US)

(72) Inventors: Miguel Garcia-Guzman, San Diego, CA (US); Roger Heim, Del Mar, CA (US); Eileen Sun Chin, San Diego, CA (US); Jerry Fong, San Diego, CA (US); Deepak Yadav, San Diego, CA (US); Nikolai Suslov, San Diego, CA (US); C. Daniel De Magalhaes Filho, La Jolla, CA (US); Chung-Wein Lee, San Diego, CA (US)

(73) Assignee: Rakuten Medical, Inc., San Diego, CA (US)

( * ) Notice: Subject to any disclaimer, the term of this patent is extended or adjusted under 35 U.S.C. 154(b) by 1321 days.

(21) Appl. No.: 17/442,487

(22) PCT Filed: Mar. 27, 2020

(86) PCT No.: PCT/US2020/025465
§ 371 (c)(1),
(2) Date: Sep. 23, 2021

(87) PCT Pub. No.: WO2020/205623
PCT Pub. Date: Oct. 8, 2020

(65) Prior Publication Data

US 2022/0160871 A1 May 26, 2022

Related U.S. Application Data

(60) Provisional application No. 62/903,265, filed on Sep. 20, 2019, provisional application No. 62/826,932, filed on Mar. 29, 2019.

(51) Int. Cl.
*G01N 33/50* (2006.01)
*A61K 39/00* (2006.01)
(Continued)

(52) U.S. Cl.
CPC ...... *G01N 33/5011* (2013.01); *A61K 39/3955* (2013.01); *A61K 41/008* (2013.01);
(Continued)

(58) Field of Classification Search
CPC .............. A61K 39/3955; A61K 41/008; A61K 47/6803; A61K 47/6849; G01N 33/5011
See application file for complete search history.

(56) References Cited

U.S. PATENT DOCUMENTS 2,915,392 A 12/1959 Pedersen
5,196,005 A 3/1993 Doiron et al.
(Continued)

FOREIGN PATENT DOCUMENTS

CA 2994849 2/2017
CN 101023084 8/2007
(Continued)

OTHER PUBLICATIONS

Tadanobu et. al. (Near infrared photoimmunotherapy with avelumab, an anti-programmed death-ligand 1 (PD-L1) antibody. 2017. Oncotarget. vol. 8(5), pp. 8807-8817 (Year: 2017).*
(Continued)

*Primary Examiner* — Sue X Liu
(74) *Attorney, Agent, or Firm* — Morrison & Foerester LLP

(57) ABSTRACT

Provided are methods involving the use of biomarkers, in relation to photoimmunotherapy, such as photoimmunotherapy induced by activation of a phthalocyanine dye conjugated to a targeting molecule that binds a protein on tumor cell, for example, an IR700-antibody conjugate, and
(Continued)

combination therapies, for example, that include photoimmunotherapy and an additional therapeutic agent, such as an immune modulating agent. In some aspects, the provided embodiments can be used to identify or select subjects for photoimmunotherapy and/or the combination therapy, or to assess the likelihood of response to photoimmunotherapy and/or to the additional therapeutic agents. Features of the methods and uses provide various advantages, such as improved efficacy. In some aspects, the provided embodiments can be used to provide personalized medicine and tailored therapy regimens for subjects. Also provided are therapeutic methods involving the use of biomarkers in the treatment of diseases and conditions, including tumors or cancers.

17 Claims, 18 Drawing Sheets

(51) Int. Cl.
*A61K 39/395* (2006.01)
*A61K 41/00* (2020.01)
*A61K 47/68* (2017.01)
*A61P 35/00* (2006.01)

(52) U.S. Cl.
CPC ...... *A61K 47/6803* (2017.08); *A61K 47/6849* (2017.08); *A61P 35/00* (2018.01); *A61K 2039/505* (2013.01)

(56) References Cited

U.S. PATENT DOCUMENTS 5,494,793 A 2/1996 Schindele et al.
7,005,518 B2 2/2006 Peng et al.
7,219,016 B2 5/2007 Rimm et al.
7,498,029 B2 3/2009 Hasan et al.
8,524,239 B2 9/2013 Kobayashi
8,623,354 B2 1/2014 Brown et al.
9,358,306 B2 6/2016 Kobayashi
10,064,943 B2 9/2018 Dilley et al.
10,295,719 B2 5/2019 Rose et al.
10,416,366 B2 9/2019 Rose et al.
10,527,771 B2 1/2020 Rose et al.
10,537,641 B2 1/2020 Kobayashi
10,538,590 B2 1/2020 Kobayashi
10,588,972 B2 3/2020 Kovar
11,013,803 B2 5/2021 Kobayashi
11,141,483 B2 10/2021 Makings et al.
11,147,875 B2 10/2021 Biel et al.
11,154,620 B2 10/2021 Garcia-Guzman et al.
11,364,297 B2 6/2022 Kobayashi et al.
11,364,298 B2 6/2022 Kobayashi et al.
11,781,955 B2 10/2023 Kobayashi et al.
12,296,013 B2 5/2025 Kobayashi et al.
12,491,249 B2 12/2025 Markings et al.
2001/0044124 A1 11/2001 Bacus
2004/0120958 A1 6/2004 Bander et al.
2004/0171827 A1 9/2004 Peng et al.
2005/0147612 A1 7/2005 Yayon et al.
2006/0188509 A1 8/2006 Derynck et al.
2007/0042398 A1 2/2007 Peng et al.
2008/0073566 A1 3/2008 Frangioni
2008/0095699 A1 4/2008 Zheng et al.
2008/0095950 A1 4/2008 Hall-Goulle et al.
2008/0253960 A1 10/2008 Zheng et al.
2010/0136549 A1 6/2010 Christiansen et al.
2010/0215575 A1 8/2010 O'Neill et al.
2010/0255057 A1 10/2010 Hyde et al.
2011/0082412 A1 4/2011 Hyde et al.
2011/0111435 A1 5/2011 Dobson et al.
2011/0288234 A1 11/2011 Pandey et al.
2012/0010558 A1 1/2012 Kobayashi
2012/0070853 A1 3/2012 Johansen et al.
2012/0122094 A1 5/2012 May et al.
2012/0171290 A1 7/2012 Pierre
2013/0039861 A1 2/2013 Regino et al.
2013/0287688 A1 10/2013 Jain et al.
2013/0336995 A1 12/2013 Kobayashi et al.
2014/0120119 A1 5/2014 Kobayashi
2014/0309578 A1 10/2014 Anvari
2014/0314778 A1 10/2014 Alavattam
2015/0343060 A1 12/2015 Kovar
2015/0343084 A1 12/2015 Dilley
2015/0374819 A1 12/2015 Kovar
2016/0256564 A2 9/2016 Kobayashi et al.
2016/0345834 A1 12/2016 Hasan et al.
2017/0021017 A1 1/2017 Chen-Hsing
2017/0122853 A1 5/2017 Kobayashi et al.
2018/0113246 A1 4/2018 Rose et al.
2018/0113247 A1 4/2018 Rose et al.
2018/0236076 A1 8/2018 Kobayashi et al.
2018/0239074 A1 8/2018 Rose et al.
2018/0250405 A1 9/2018 Biel et al.
2018/0339048 A1 11/2018 Dilley et al.
2019/0015510 A1 1/2019 Makings et al.
2019/0070296 A1 3/2019 Wang et al.
2019/0282696 A1 9/2019 Biel et al.
2019/0365897 A1 12/2019 Garcia-Guzman et al.
2020/0085950 A1 3/2020 Kobayashi et al.
2020/0095331 A1 3/2020 Kobayashi et al.
2020/0166690 A1 5/2020 Rose et al.
2020/0179514 A1 6/2020 Kovar
2021/0010914 A1 1/2021 Kobayashi et al.
2021/0079112 A1 3/2021 Kobayashi et al.
2021/0205455 A1 7/2021 Manibusan
2021/0401985 A1 12/2021 Biel et al.
2021/0401986 A1 12/2021 Makings et al.
2022/0105184 A1 4/2022 Biel et al.
2022/0288208 A1 9/2022 Manibusan et al.
2022/0288210 A1 9/2022 Kobayashi et al.
2022/0296712 A1 9/2022 Garcia-Guzman et al.
2022/0313822 A1 10/2022 Garcia-Guzman et al.
2023/0028062 A1 1/2023 Garcia-Guzman et al.
2023/0050584 A1 2/2023 Kobayashi et al.
2024/0307541 A1 9/2024 Suslov et al.
2025/0145716 A1 5/2025 Steinger et al.
2025/0325669 A1 10/2025 Manibusan et al.

FOREIGN PATENT DOCUMENTS

CN 102585003 7/2012
CN 102686612 9/2012
CN 102725002 10/2012
CN 103781495 5/2014
CN 104203286 12/2014
DE 19717904 10/1998
EP 1512963 3/2005
JP 2003284757 10/2003
JP 2003344284 12/2003
JP 2006515892 6/2006
JP 2006517230 7/2006
JP 2007155722 6/2007
JP 2013503951 2/2013
JP 2014523907 9/2014
JP 2014533960 12/2014
JP 2017524002 8/2017
WO WO 2001057495 8/2001
WO WO 2003011106 2/2003
WO WO 2003083811 10/2003
WO WO 2004038378 5/2004
WO WO 2004067038 8/2004
WO WO 2004071571 8/2004
WO WO 2005099689 10/2005
WO WO 2006092598 9/2006
WO WO 2007092772 8/2007
WO WO 2007147001 12/2007
WO WO 2008120134 10/2008
WO WO 2008152424 12/2008
WO WO 2009092062 7/2009
WO WO 2010047611 4/2010
WO WO 2010085651 7/2010

(56) References Cited

FOREIGN PATENT DOCUMENTS

| | | |
|---|---|---|
| WO | WO 2010121163 | 10/2010 |
| WO | WO 2011025950 | 3/2011 |
| WO | WO 2011038006 | 3/2011 |
| WO | WO 2011039510 | 4/2011 |
| WO | WO 2011039511 | 4/2011 |
| WO | WO 2011056983 | 5/2011 |
| WO | WO 2011/097248 | 8/2011 |
| WO | WO 2012076631 | 6/2012 |
| WO | WO 2012082118 | 6/2012 |
| WO | WO 2013009475 | 1/2013 |
| WO | WO 2013044156 | 3/2013 |
| WO | WO 2013080187 | 6/2013 |
| WO | WO 2013139391 | 9/2013 |
| WO | WO 2014/012479 | 1/2014 |
| WO | 2014089247 | 6/2014 |
| WO | WO 2014084394 | 6/2014 |
| WO | WO 2014120974 | 8/2014 |
| WO | WO 2014127365 | 8/2014 |
| WO | 2014160497 | 10/2014 |
| WO | 2014168950 | 10/2014 |
| WO | 2014176284 | 10/2014 |
| WO | 2015042325 | 3/2015 |
| WO | 2015057692 | 4/2015 |
| WO | 2015061247 | 4/2015 |
| WO | 2015120198 | 8/2015 |
| WO | 2015187651 | 12/2015 |
| WO | 2015187677 | 12/2015 |
| WO | 2016022896 | 2/2016 |
| WO | 2017027247 | 2/2017 |
| WO | 2017031363 | 2/2017 |
| WO | 2017031367 | 2/2017 |
| WO | WO 2017040384 | 3/2017 |
| WO | 2018080952 | 5/2018 |
| WO | 2018156815 | 8/2018 |
| WO | WO 2018/175403 | 9/2018 |
| WO | 2019009941 | 1/2019 |
| WO | 2019036249 | 2/2019 |
| WO | 2019199751 | 10/2019 |
| WO | 2019232478 | 12/2019 |
| WO | 2020205623 | 10/2020 |
| WO | WO 2021000965 | 1/2021 |
| WO | 2021021882 | 2/2021 |
| WO | 2021026393 | 2/2021 |
| WO | 2021046100 | 3/2021 |
| WO | 2021113734 | 6/2021 |
| WO | 2021231795 | 11/2021 |
| WO | WO 2022/182483 | 9/2022 |
| WO | WO 2023/159182 | 8/2023 |
| WO | WO 2024/102941 | 5/2024 |

OTHER PUBLICATIONS

Kulangara et al. (Clinical utility of the CPS for PD-L1 expression and the approval of pembrolizumab for treatment of gastric cancer. Arch Pathol Lab Med. 2019. 143:330-337, Epub Jul. 2018) (Year: 2019).*

Kulangara et. al. (Clinical Utility of the Combined Positive Score for Programmed Death Ligand-1 Expression and the Approval of Pembrolizumab for Treatment of Gastric Cancer. Archives of Pathology and Laboratory Medicine. vol. 143(3), pp. 330-337) (Year: 2018).*

Ming et. al. (Biomarkers for predicting efficacy of PD-1/PD-L1 inhibitors. Molecular Cancer. vol. 17, article No. 129) (Year: 2018).*

Wang et al., Journal of Cancer. 13(2):481-495; 2022 (Year: 2022).*

Takahashi et al., International Journal of Molecular Sciences. 20(2578): 1-10; 2019 (Year: 2019).*

U.S. Appl. No. 17/632,756, filed Aug. 6, 2020, by Manibusan et al. (Copy not provided). (Copy not submitted herewith pursuant to the waiver of 37 C.F. R. § 1.98(a)(2)(iii) issued by the Office on Sep. 21, 2004).

U.S. Appl. No. 17/630,854, filed Jul. 29, 2020, by Garcia-Guzman et al. (Copy not provided). (Copy not submitted herewith pursuant to the waiver of 37 C.F. R. § 1.98(a)(2)(iii) issued by the Office on Sep. 21, 2004).

U.S. Appl. No. 17/638,147, filed Sep. 2, 2020, by Garcia-Guzman et al. (Copy not provided). (Copy not submitted herewith pursuant to the waiver of 37 C.F. R. § 1.98(a)(2)(iii) issued by the Office on Sep. 21, 2004).

Agostinis et al., "Photodynamic Therapy of Cancer: An Update," CA Cancer J Clin. (2011) 61(4): 250-281.

Alegria-Schaffer, "General Protein-Protein Cross-Linking," Methods Enzymol (2014) 539:81-87.

Ali et al., "Dynamic fluorescent imaging with indocyanine green for monitoring the therapeutic effects of photoimmunotherapy," Contrast Media Mol Imaging. Jul.-Aug. 2014;9(4):276-82.

Amoury et al., "Photoimmunotheranostic agents for triple-negative breast cancer diagnosis and therapy that can be activated on demand," Oncotarget. (2016) 7(34):54925-54936.

Anonymous, "Near Infrared Light for the Treatment of Painful Peripheral Neuropathy," U.S. National Institutes of Health, Aug. 2, 2012, XP002686617, retrieved from the internet: URL:http://clinicaltrials.gov/ct2/show/NCT00125268, retrieved on Nov. 7, 2011.

Ballou et al., "Tumor labeling in vivo using cyanine-conjugated monoclonal antibodies." Cancer Immunol Immunother. Oct. 1995;41(4):257-63.

Barrett et al., "In vivo diagnosis of epidermal growth factor receptor expression using molecular imaging with a cocktail of optically labeled monoclonal antibodies," Clin Cancer Res. Nov. 15, 2007;13(22 Pt 1):6639-48.

Bartl et al., "Emissivity of aluminium and its importance for radiometric measurement," Measurement of Physical Quantities (2004) 31-36.

Berger et al., "Phase I safety and pharmacokinetic study of CT-011, a humanized antibody interacting with PD-1, in patients with advanced hematologic malignancies," Clin Cancer Res (2008) 14:3044-3051.

BIO Clinica, 2004, vol. 19, p. 398-403 (In Japanese, with concise description in English).

Blank et al., "Contribution of the PD-L1/PD-1 pathway to T-cell exhaustion: an update on implications for chronic infections and tumor evasion," Cancer Immunol Immunother (2007) 56(5):739-745.

Blaudszun et al., "A photosensitizer delivered by bispecific antibody redirected T lymphocytes enhances cytotoxicity against EpCAM-expressing carcinoma cells upon light irradiation," J Control Release (2015) 197:58-68.

Blom et al., "Systems pathology by multiplexed immunohistochemistry and whole-slide digital image analysis," Sci Rep. (2017) 7(1): 15580.

Brahmer et al., "Safety and Activity of Anti-PD-L1 Antibody in Patients with Advanced Cancer," N Engl J Med (2012) 366:2455-2465.

Bui et al., "Intratumoral and peripheral exploratory biomarker analysis in patients with locoregional, recurrent head and neck squamous cell carcinoma (rHNSCC) treated with RM-1929 photoimmunotherapy," Abstract, Annals of Oncology (2019) 30 (suppl_5): v470.

Bui et al., "Intratumoral and peripheral exploratory biomarker analysis in patients with locoregional, recurrent head and neck squamous cell carcinoma (rHNSCC) treated with RM-1929 photoimmunotherapy," Poster 3725, ESMO 2019 Congress, Barcelona, Spain, Sep. 30, 2019.

Busch et al., "Increasing Damage to Tumor Blood Vessels during Motexafin Lutetium-PDT through Use of Low Fluence Rate," Radiat Res.(2010) 174(3): 331-340.

Butcher et al., "Visible Light," Tour of the Electromagnetic Spectrum, National Aeronautics and Space Administration, 2016, available at https://smd-prod.s3.amazonaws.com/science-pink/s3fs-public/atoms/files/Tour-of-the-EMS-TAGGED-v7_0.pdf.

Carcenac et al., "Internalisation enhances photo-induced cytotoxicity of monoclonal antibody-phthalocyanine conjugates." British Journal of Cancer, Nov. 30, 2001, vol. 85, No. 11, pp. 1787-1793.

(56) References Cited

OTHER PUBLICATIONS

Carter et al., "Identification and Validation of Cell Surface Antigens for Antibody Targeting in Oncology," Endocr Relat Cancer 11:659-687, 2004.
Chauhan et al., "Angiotensin inhibition enhances drug delivery and potentiates chemotherapy by decompressing tumour blood vessels," Nat Commun. (2013) 4: 2516.
Chen et al., "Tumor vascular permeabilization by vascular-targeting photosensitization: effects, mechanism, and therapeutic implications," Clin Cancer Res. 12:917-923, 2006.
Cheng et al., "Near infrared light-triggered drug generation and release from gold nanoparticle carriers for photodynamic therapy," Small (2014) 10(9):1799-1804.
Chiarello, K., "In between the light and the dark: developments in Photosensitive Pharmaceuticals," (2005) December 48-54.
Chopra, "IRDye 700DX-Labeled annexin V," Molecular Imaging and Contrast Agent Database (MICAD) [Internet]. Bethesda (MD): National Center for Biotechnology Information (US); 2004-2013. Oct. 27, 2009 [updated Dec. 17, 2009].
Chothia et al., "Canonical Structures for the Hypervariable Regions of Immunoglobulins," J Mol Biol. Aug. 20, 1987;196(4):901-17.
Clinical Trial Identifier NCT02422979, first posted on Apr. 22, 2015. Last updated on Sep. 20, 2019.
Clinical Trial Identifier NCT03769506, first posted on Dec. 7, 2018. Last updated on Apr. 1, 2021. "Photoimmunotherapy (PIT) Study in Recurrent Head/Neck Cancer for Patients Who Have Failed at Least Two Lines of Therapy," https://clinicaltrials.gov/ct2/show/NCT03769506. Retrieved Apr. 28, 2022.
Cognetti et al. "Results of a phase 2a, multicenter, open-label, study of RM-1929 photoimmunotherapy (PIT) in patients with locoregional, recurrent head and neck squamous cell carcinoma (rHNSCC)," J. Clin. Onc. 37(15) ASCO 2019. Abstract 6014.
COZAAR (losartan potassium) FDA datasheet. Revised Mar. 2013.
Dancey et al., "Phase I Trial of 131I-Labelled Anti-CD25 Antibody Basiliximab in the Treatment of Patients with Relapsed or Refractory Lymphoma," Blood (2007) 110(11):648.
De Boer et al., "A standardized light-emitting diode device for photoimmunotherapy," J Nucl Med. Nov. 2014;55(11):1893-8.
De Boer et al., "Biodistribution Study of Intravenously Injected Cetuximab-IRDye700DX in Cynomolgus Macaques," Mol Imaging Biol. Apr. 2016;18(2):232-42.
Del Governatore et al., "Experimental Photoimmunotherapy of Hepatic Metastases of Colorectal Cancer with a 17.1A Chlorine6 Immunoconjugate," Cancer Res. 60:4200-4205, 2000.
Denis et al., "Synthesis, bioanalysis and biodistribution of photosensitizer conjugates for photodynamic therapy," Bioanalysis (2013) 5:1099-1114.
Diop-Frimpong et al., "Losartan inhibits collagen I synthesis and improves the distribution and efficacy of nanotherapeutics in tumors," Proc Natl Acad Sci U S A.(2011) 108(7):2909-2914.
Doane et al., "Observation and Photophysical Characterization of Silicon Phthalocyanine J-Aggregate Dimers in Aqueous Solutions," Chem Eur J. 20:8030-8039, 2014.
Dolmans et al., "Targeting Tumor Vasculature and Cancer Cells in Orthotopic Breast Tumor by Fractionated Photosensitizer Dosing Photodynamic Therapy," (2002) Cancer Res. 62(15):4289-94.
Dougherty et al., "Photodynamic Therapy," J Natl Cancer Inst. 90:889-905, 1998.
Duska et al., "Combination Photoimmunotherapy and Cisplatin: Effects on Human Ovarian Cancer Ex Vivo," J Nat Cancer Inst. 91:1557-1563, 1999.
EC—PDT probe "Machinery and equipment 31 Medical ablation device," Apr. 2017 revision (No. 6 edition). English translation included.
Eisenhauer et al., "New response evaluation criteria in solid tumours: revised RECIST guideline (version 1.1)," Eur J Cancer (2009) 45(2):228-247.
Finger et al., "The human PD-1 gene: complete cDNA, genomic organization, and developmentally regulated expression in B cell progenitors," Gene (1997) 197(1-2):177-187.
Fracasso et al., "A Phase 1 Escalating Single-Dose andWeekly Fixed-Dose Study of Cetuximab: Pharmacokinetic and Pharmacodynamic Rationale for Dosing," Clin Cancer Res (2007) 13(3):986-996.
Gajewski et al., "The P815 Mastocytoma Tumor Model," Current Protocols in Immunology (2001) 43:20.4.1-20.4.18 by John Wiley & Sons, Inc., 2001.
Gao et al., "Enhanced Anti-Tumor Efficacy through a Combination of Integrin $\alpha v\beta 6$-Targeted Photodynamic Therapy and Immune Checkpoint Inhibition," Theranostics (2016) 6(5):627-637.
Gao et al., "In vivo cancer targeting and imaging with semiconductor quantum dots," Nat Biotechnol. Aug. 2004;22(8):969-76.
Gildener-Leapman et al., "Promising systemic immunotherapies in head and neck squamous cell carcinoma," Oral Oncol (2013) 49(12):1089-1096.
Gleysteen et al., "Fluorescently Labeled Cetuximab to Evaluate Head and Neck Cancer Response to Treatment," Cancer Biology & Therapy. 2007 6(8):e1-e5.
Gleysteen et al., "Update on Aspyrian Trial: Study of RM-1929 and Photoimmunotherapy in Patients with Recurrent Head and Neck Cancer," Abstract, submitted for 2017 Combined Otolaryngology Spring Meetings, American Head and Neck Cancer Society, Apr. 26, 2017, San Diego, CA, available online at: https://www.researchposters.com/display_posters.aspx?page=eposter&code=COSM2017.
Gleysteen et al., "Update on Aspyrian Trial: Study of RM-1929 and Photoimmunotherapy in Patients with Recurrent Head and Neck Cancer," Poster, Presented at 2017 Combined Otolaryngology Spring Meetings, American Head and Neck Cancer Society, Apr. 26, 2017, San Diego, CA, available online at https://www.researchposters.com/Posters/COSM/COSM2017/B043.pdf.
Green et al., "Mitochondria and Apoptosis," Science (1998) 281(5381):1309-1312.
Greish, K., "Enhanced permeability and retention of macromolecular drugs in solid tumors: a royal gate for targeted anticancer nanomedicines," J Drug Target. 15:457-464, 2007.
Han, Weiwei, Radio Exploration of the Four Colors, Jilin Fine Arts Publishing House, Jan. 2014, p. 139.
Hanaoka et al., "Glypican-3 targeted human heavy chain antibody as a drug carrier for hepatocellular carcinoma therapy," Mol Pharm. Jun. 1, 2015;12(6):2151-7.
Hanaoka et al., "Photoimmunotherapy of hepatocellular carcinoma-targeting Glypican-3 combined with nanosized albumin-bound paclitaxel," Nanomedicine (Lond). (2015);10(7):1139-47.
Heukers et al., "Nanobody-photosensitizer conjugates for targeted photodynamic therapy," Nanomedicine (2014) 10(7):1441-51.
Hiroshima et al., "Photoimmunotherapy Inhibits Tumor Recurrence After Surgical Resection on a Pancreatic Cancer Patient-Derived Orthotopic Xenograft (PDOX) Nude Mouse Model," Ann Surg Oncol. Dec. 2015;22 Suppl 3:S1469-74.
Hsu et al., "Cancer cell-targeted photoimmunotherapy (PIT) elicits immunogenic cell death and activates the immune system in the tumor microenvironment," AACR 2019 Poster, Abs 3734.
Hsu et al., "Cancer cell-targeted photoimmunotherapy elicits immunogenic cell death and activates the innate and adaptive immune response in the tumor microenvironment," Cancer Res (2019) 79 (13_Supplement): Abs. 3734.
Hsu et al., "Intratumoral depletion of regulatory T cells using CD25 targeted photoimmunotherapy (PIT) elicits anti-cancer immune activity and synergizes with PD1 checkpoint blockade in immunocompetent mouse models," SITC 2019; Nov. 15, 2019; Poster; P774.
Hsu et al., "P774-Intratumoral depletion of regulatory T cells using CD25 targeted photoimmunotherapy elicits anti-cancer immune activity and synergizes with PD1 checkpoint blockade in immunocompetent mouse models," 34th Annual Meeting & Pre-Conference PrJ Immunother Cancer. 2019; 7(Suppl 1): 283. Abstract. p. 327. Published online Nov. 6, 2019. doi: 10.1186/s40425-019-0764-0.
Ishida et al., "Trastuzumab-Based Photoimmunotherapy Integrated with Viral HER2 Transduction Inhibits Peritoneally Disseminated HER2-Negative Cancer," Mol Cancer Ther. Mar. 2016;15(3):402-11.

(56) References Cited

OTHER PUBLICATIONS

Ishii et al., "Defucosylated Humanized Anti-CCR4 Monoclonal Antibody KW-0761 as a Novel Immunotherapeutic Agent for Adult T-cell Leukemia/Lymphoma," Clin Cancer Res. 16:1520-1531, 2010.
Ito et al., "Combination photoimmunotherapy with monoclonal antibodies recognizing different epitopes of human epidermal growth factor receptor 2: an assessment of phototherapeutic effect based on fluorescence molecular imaging," Oncotarget. Mar. 22, 2016;7(12):14143-52.
Ito et al., "Molecular targeted photoimmunotherapy for HER2-positive human gastric cancer in combination with chemotherapy results in improved treatment outcomes through different cytotoxic mechanisms," BMC Cancer. Jan. 25, 2016;16:37.
Jeong et al., "Indium gallium nitride-based ultraviolet, blue, and green lightemitting diodes functionalized with shallow periodic hole patterns," (2017) Scientific Reports 7:45726.
Jia et al., "Cannabinoid CB2 receptor as a new phototherapy target for the inhibition of tumor growth," Mol Pharm. Jun. 2, 2014;11(6):1919-29.
Jing et al., "Imaging and Selective Elimination of Glioblastoma Stem Cells with Theranostic Near-Infrared-Labeled CD133-Specific Antibodies," Theranostics. Apr. 12, 2016;6(6):862-74.
Kabolizadeh et al., "The role of cetuximab in the management of head and neck cancers," Exp Opin Biol Ther (2012) 12(4):517-528.
Kijanka et al., "Optical imaging of pre-invasive breast cancer with a combination of VHHs targeting CAIX and HER2 increases contrast and facilitates tumour characterization," EJNMMI Res. (2016) 6(1):14.
Kines et al., "HPV Based Photodynamic Therapy: A New Approach for Anti-Cancer Therapy," J. Immunol. 192(1): Supplement 206.8, 2014.
Kirveliene et al., "Schedule-Dependent Interaction Between Doxorubicin and mTHPC-Mediated Photodynamic Therapy in Murine Hepatoma In Vitro and In Vivo," Cancer Chemother. Pharmacol. 57:65-72, 2005.
Kishimoto et al., "Evaluation of oxygen dependence on in vitro and in vivo cytotoxicity of photoimmunotherapy using IR-700-antibody conjugates," Free Radic Biol Med. Aug. 2015;85:24-32.
Kobayashi et al., "Near-infrared photoimmunotherapy of cancer: A new approach that kills cancer cells and enhances anti-cancer host immunity," Int Immunol. Published online Jun. 4, 2020 DOI:10.1093/intimm/dxaa037, Retrieved from the internet: https://watermark.silverchair.com/dxaa 037.pdf.
Kobayashi et al., "Near-Infrared Photoimmunotherapy: Photoactivatable Antibody-Drug Conjugates (ADCs)," Bioconjugate Chem. (2020) 31(1):28-36.
Kobayashi, "Activatable Fluorescent Imaging Probes for Cancer Detection and Diagnosis," Abstract presented at the American Chemical Society meeting in San Francisco, 2014.
Kobayashi, "Near infrared photoimmunotherapy for cancer," 2019 Conference on Lasers and Electro-Optics (CLEO), OSA, May 5, 2019, pp. 1-2 DOI:10.23919/CLEO.2019.8750194 [retrieved on Jun. 27, 2019].
Kobayashi, "Near infrared photoimmunotherapy for cancer: enhanced anti-tumor immunity when combined with immuno-activation therapies," Conference Presentation, Mar. 4, 2019 https://www.spiedigitallibrary.org/con ference-proceedings-of-spie/10893/1089302/ Near-infrared-photoirrmunotherapy-for-cancer--enhanced-anti-tumor-irrmunity/10.1117/12.2506637.full?SSO=I [retrieved on Dec. 3, 2020].
Kobayashi, "Near infrared photoimmunotherapy for cancer: enhanced anti-tumor immunity when combined with immuno-activation therapies-abstract," Mar. 4, 2019 https://www.spiedigitallibrary.org/con ference-proceedings-of-spie/10893/1089302/ Near-infrared-photoirrmunotherapy-for-cance r--enhanced-anti-tumor-irrmunity/10.1117/12.2506637.full?SSO=I [retrieved on Jun. 8, 2020].
Kobayashi, "Near infrared photoimmunotherapy: A new cancer therapy kills cancer cells with exposure of harmless near infrared light," Poster Presentation, at NEST Conference, Tokyo, Japan, Apr. 2018.
Kobayashi, "Near infrared photoimmunotherapy: A new type of immune theranostic technology for cancer," Proceedings of SPIE; [Proceedings of SPIE ISSN 0277-786X], SPIE, 1000 20th St. Bellingham, WA 98225-6705 USA, vol. 11362, Apr. 1, 2020, pp. 113620S-113620S, ISSN: 0277-786X, DOI: 10.1117/12.2554486, ISBN: 978-1-5106-3927-0.
Kobayashi, "Near-infrared photoimmunotherapy of cancer," Accounts of Chemical Research, Jul. 2019; vol. 52, No. 8, pp. 2332-2339.
Kochuparambil et al., "A Phase 1, Multicenter, Open-label, Dose-escalation, Combination Study of RM-1929 and Photoimmunotherapy in Patients with Recurrent Head and Neck Cancer," Abstract, Annals of Oncology, vol. 28, Issue suppl_5, Sep. 1, 2017, mdx374.008, Published: Sep. 18, 2017, available online at: https://doi.org/10.1093/annonc/mdx374.008.
Kochuparambil et al., "A Phase 1, Multicenter, Open-label, Dose-escalation, Combination Study of RM-1929 and Photoimmunotherapy in Patients with Recurrent Head and Neck Cancer," Poster, Presented at 2017 European Society for Medical Oncology, Sep. 8-12, 2017, Madrid, Spain.
Kovar et al., "A Systematic Approach to the Development of Fluorescent Contrast Agents for Optical Imagining of Mouse Cancer Models," Anal. Biochem. 367(1): 1-12, 2007.
Kroemer et al., "Immunogenic Cell Death in Cancer Therapy," Annual Review of Immunology (2013) 31:51-72.
Kuhn et al., "The Role of Interleukin-2 Receptor Alpha in Cancer," Frontiers in Bioscience (2005) 10:1462-1474.
Li et al., "A Novel Tumor Targeting Drug Carrier for Optical Imaging and Therapy," Theranostics (2014) 4(6):642-659.
Licor, "High Photostability of IRDye® 700DX," Retrieved on Aug. 23, 2018. Retrieve on https://www.licor.com/bio/products/reagents/irdye/700dx/photostability.html.
Li-Cor, "IRDye® Infrared Dyes: Advancing Discovery with Infrared Imaging," 2010.
Lin et al., "Comparison of Cherenkov excited fluorescence and phosphorescence molecular sensing from tissue with external beam irradiation," Phys Med Biol. May 21, 2016;61(10):3955-68.
Lipson et al., "Durable cancer regression off-treatment and effective reinduction therapy with an anti-PD-1 antibody," Clin Cancer Res (2013) 19(2):462-468.
Maawy et al., "Near infra-red photoimmunotherapy with anti-CEA-IR700 results in extensive tumor lysis and a significant decrease in tumor burden in orthotopic mouse models of pancreatic cancer," PLoS One. Mar. 23, 2015;10(3):e0121989.
Maawy et al., "Photoimmunotherapy lowers recurrence after pancreatic cancer surgery in orthotopic nude mouse models," J Surg Res. Jul. 2015;197(1):5-11.
Marabelle et al., "Depleting tumor-specific Tregs at a single site eradicates disseminated tumors." J Clin Invest. 2013;123(6):2447-2463.
Maron et al., "Targeted Therapies for Targeted Populations: Anti-EGFR Treatment for EGFR-Amplified Gastroesophageal Adenocarcinoma," Cancer Discovery (2018) 8(6):696-713.
Maruoka et al., "Combined CD44- and CD25-targeted Near-Infrared Photoimmunotherapy to Selectively Kill Cancer and Regulatory T cells in Syngeneic Mouse Cancer Models," Cancer Immunol Res. 8:345-355, 2020.
Maya et al., "Synthesis, Aggregation Behavior and Nonlinear Absorption Properties of Lead Phthalocyanines Substituted with Siloxane Chains," J Materials Chem. 13: 1603-1613, 2003.
McHugh et al., "The role of suppressor T cells in regulation of immune responses." J Allergy Clin Immunol. Nov. 2002;110(5):693-702.
Meading et al., "Boosting tumor-specific immunity using PDT," Cancer (2016) 8:91.
Medical Sci Digest., 2004, vol. 30, p. 545-548 (In Japanese, with concise description in English).
Menzies et al., "New combinations and immunotherapies for melanoma: latest evidence and clinical utility," Ther Adv Med Oncol (2013) 5:278-285.
Mitchell et al., "Comparison of Two Infrared Devices in Their Effectiveness in Reducing Symptoms Associated with RLS," Physiother. Theory Pract. 27:352-359, 2011.

(56) References Cited

OTHER PUBLICATIONS

Mitsunaga et al., "Abstract 3618: Target-Specific Photo-Activatable Immunotherapy (PIT) for Cancer Based on a Monoclonal Antibody-Photosensitizer Conjugate," in Proceedings of the 102nd Annual Meeting of the American Association for Cancer Research; Apr. 2-6, 2011; Orlando, FL. Philadelphia (PA): AACR; Cancer Res. 71:3618, 2011.
Mitsunaga et al., "Cancer cell-selective in vivo near infrared photoimmunotherapy targeting specific membrane molecules," Nat Med. Nov. 6, 2011;17(12):1685-91.
Mitsunaga et al., "Immediate in vivo target-specific cancer cell death after near infrared photoimmunotherapy," BMC Cancer. (2012) Aug. 8, 2012;12:345.
Mitsunaga et al., "Near-infrared theranostic photoimmunotherapy (PIT): repeated exposure of light enhances the effect of immunoconjugate," Bioconjug Chem. Mar. 21, 2012;23(3):604-9.
Moore et al., "Photoimmunotherapy of residual disease after incomplete surgical resection in head and neck cancer models," Cancer Med. Jul. 2016;5(7):1526-34.
Moreira et al., "Targeted Therapy in Head and Neck Cancer: An Update on Current Clinical Developments in Epidermal Growth Factor Receptor-Targeted Therapy and Immunotherapies," Drugs (2017) 77:843-857.
Nagaya et al., "Host Immunity Following Near-Infrared Photoimmunotherapy is Enhanced with PD-1 Checkpoint Blockade to Eradicate Established Antigenic Tumors," Cancer Immunol Res. 7(3):401-413, 2019.
Nagaya et al., "Improved micro-distribution of antibody-photon absorber conjugates after initial near infrared photoimmunotherapy (NIR-PIT)," J Control Release. Jun. 28, 2016;232:1-8.
Nagaya et al., "Near infrared photoimmunotherapy of B-cell lymphoma," Mol Oncol. Jul. 29, 2016. 10(9):1404-1414.
Nagaya et al., "Near infrared photoimmunotherapy targeting bladder cancer with a canine anti-epidermal growth factor receptor (EGFR) antibody," Oncotarget 9:19026-19038, 2018.
Nagaya et al., "Near Infrared Photoimmunotherapy Targeting EGFR Positive Triple Negative Breast Cancer: Optimizing the Conjugate-Light Regimen," PLoS One. Aug. 27, 2015;10(8):e0136829.
Nagaya et al., "Near infrared photoimmunotherapy with avelumab, an anti-programmed death-ligand 1 (PD-L1) antibody," Oncotarget 8:8807-8817, 2017.
Nagaya et al., "Syngeneic Mouse Models of Oral Cancer are Effectively Targeted by Anti-CD44-Based NIR-PIT," Mol Cancer Res. 15:1667-1677, 2017.
Nakajima et al., "Improving the efficacy of Photoimmunotherapy (PIT) using a cocktail of antibody conjugates in a multiple antigen tumor model," Theranostics. Apr. 23, 2013;3(6):357-365.
Nakajima et al., "Real-time monitoring of in vivo acute necrotic cancer cell death induced by near infrared photoimmunotherapy using fluorescence lifetime imaging," Cancer Res. Sep. 15, 2012;72(18):4622-8.
Nakajima et al., "The effects of conjugate and light dose on photo-immunotherapy induced cytotoxicity," BMC Cancer. May 30, 2014;14:389.
Nakamura et al., "MR imaging biomarkers for evaluating therapeutic effects shortly after near infrared photoimmunotherapy," Oncotarget. Mar. 29, 2016;7(13):17254-64.
National Optical Astronomy Observatory, "Recommended Light Levels," retrieved from https://www.noao.edu/education/QLTkit/ACTIVITY_Documents/Safety/LightLevels_outdoor+indoor.pdf.
New Pharmacology (New Yakurigaku), Nankodo Co., Ltd., 2012, the third impression of the revised sixth edition, p. 558-559. (In Japanese, with translation).
North et al., "A new clustering of antibody CDR loop conformations," J Mol Biol. Feb. 18, 2011; 406(2): 228-256.
Nowis et al., "The influence of photodynamic therapy on the immune response," Photodiagnosis Photodyn Ther. Dec. 2005;2(4):283-98.
Ogawa et al., "In vivo molecular imaging of cancer with a quenching near-infrared fluorescent probe using conjugates of monoclonal antibodies and indocyanine green," Cancer Res. Feb. 15, 2009;69(4):1268-72.
Okamura et al., "Combination treatment of cancer cell-targeted photoimmunotherapy plus anti-PD1 leads tosynergistic anticancer activity in an immunocompetentmouse model," Cancer Res. (2019) 79(13_Supplement): Abstract 2255.
Olejko et al., "An ion-controlled four-color fluorescent telomeric switch on DNA origami structures," Nanoscale. May 21, 2016;8(19):10339-47.
Onizuka et al., "Tumor Rejection by in Vivo Administration of Anti-CD25 (Interleukin-2 Receptor a) Monoclonal Antibody," Cancer Res. 1999; 59:3128-3133.
Ott et al., "CTLA-4 and PD-1/PD-L1 Blockade: New Immunotherapeutic Modalities with Durable Clinical Benefit in Melanoma Patients," Clin Cancer Res (2013) 19:5300-5309.
Package Insert of Cetuximab, "Anti-malignant tumor agent Anti-human EGFR Monochrome antibody," Revised Mar. 2021 (2nd edition) English translation included.
Pardoll, "The blockade of immune checkpoints in cancer immunotherapy," Nature Reviews Cancer (2012) 12:252-264.
Parra et al., "Validation of multiplex immunofluorescence panels using multispectral microscopy for immune-profiling of formalin-fixed and paraffin-embedded human tumor tissues," Sci Rep. (2017) 7(1):13380.
Peng et al., "Phthalocyanine dye as an extremely photostable and highly fluorescent near-infrared labeling reagent," Proc SPIE Int Soc Opt Eng. vol. 6097, 60970E (2006).
Pharmaceutical and Food Safety Bureau, Evaluation Division, Report on the deliberation results [Trade Name] ERBITUX Injection 100 mg, Jun. 2, 2008, pp. 1-52 (Dosage and Administration in English).
Porter, W., "Shining Some Light on Photostability Testing | IVT" , Dec. 16, 2014, available online at: http://www.ivtnetwork.com/article/shiningsomelightphotostabilitytesting.
Radvanyi et al., "Antagonist Antibodies to PD-1 and B7-H1 (PD-L1) in the Treatment of Advanced Human Cancer-Letter," Clin Cancer Research (2013) 19:5541.
Rakuten Medical, "An open-label study using ASP-1929 photoimmunotherapy in combination with anti-PD1 therapy in EGFR expressing advanced solid tumors," Mar. 12, 2020, https://clinicaltrials.gov/ct2/show/record/NCT04305795?term=rakuten&draw=2&rank=1 [retrieved on Dec. 2, 2020].
Robert et al., "What is the role of cytotoxic T lymphocyte-associated antigen 4 blockade in patients with metastatic melanoma?" Oncologist (2009) 14(8):848-861.
Rosas-Arellano et al., "A simple solution for antibody signal enhancement in immunofluorescence and triple immunogold assays," Histochem Cell Biol (2016) 146:421-430.
Rosenthal et al., "In Vivo Detection of Head and Neck Cancer Orthotopic Xenografts by Immunofluorescence," Laryngoscope (2006) 116: 1636-1641.
Samkoe et al., "High vascular delivery of EGF, but low receptor binding rate is observed in AsPC-1 tumors as compared to normal pancreas," Mol Imaging Biol. (2012) Aug. 2012;14(4):472-9.
Sanchez-Barcelo et al., "Recent Patents on Light Based Therapies: Photodynamic Therapy, Photothermal Therapy and Photoimmunotherapy," Recent Patents on Endocrine, Metabolic & Immune Drug Discovery 2014, 8, 1-8.
Sano et al., "Acute cytotoxic effects of photoimmunotherapy assessed by 18F-FDG PET," J Nucl Med. May 2013;54(5):770-5.
Sano et al., "The effect of photoimmunotherapy followed by liposomal daunorubicin in a mixed tumor model: a demonstration of the super-enhanced permeability and retention effect after photoimmunotherapy," Mol Cancer Ther. Feb. 2014;13(2):426-32.
Sano et al., "Markedly Enhanced Permeability and Retention Effects Induced by Photo-Immunotherapy of Tumors," ACS Nano. Jan. 22, 2013; 7:717-724.
Sasikumar et al., "Small-molecule Immune Checkpoint Inhibitors Targeting PD-1/PD-L1 and Other Emerging Checkpoint Pathways," BioDrugs (2018) 32:481-497.

(56) References Cited

OTHER PUBLICATIONS

Sato et al., "Comparative effectiveness of light emitting diodes (LEDs) and Lasers in near infrared photoimmunotherapy," Oncotarget. Mar. 22, 2016;7(12):14324-35.

Sato et al., "Near infrared photoimmunotherapy for lung metastases," Cancer Lett. Aug. 28, 2015;365(1):112-21.

Sato et al., "Near infrared photoimmunotherapy in the treatment of disseminated peritoneal ovarian cancer," Mol Cancer Ther. Jan. 2015;14(1):141-50.

Sato et al., "Near infrared photoimmunotherapy in the treatment of pleural disseminated NSCLC: preclinical experience," Theranostics. Mar. 19, 2015;5(7):698-709.

Sato et al., "Photoimmunotherapy of gastric cancer peritoneal carcinomatosis in a mouse model," PLoS One. Nov. 17, 2014;9(11):e113276.

Sato et al., "Photoimmunotherapy: comparative effectiveness of two monoclonal antibodies targeting the epidermal growth factor receptor," Mol Oncol. May 2014;8(3):620-32.

Sato et al., "Photoinduced Ligand Release from a Silicon Phthalocyanine Dye Conjugated with Monoclonal Antibodies: A Mechanism of Cancer Cell Cytotoxicity after Near-Infrared Photoimmunotherapy," ACS Cent Sci. 4:1559-1569, 2018.

Sato et al., "Selective cell elimination in vitro and in vivo from tissues and tumors using antibodies conjugated with a near infrared phthalocyanine," RSC Adv. (2015) Mar. 3, 2015;5(32):25105-25114.

Sato et al., "Spatially selective depletion of tumor-associated regulatory T cells with near-infrared photoimmunotherapy." Sci Transl Med. Aug. 17, 2016;8(352):352ra110.

Savellano et al., "Multiepitope HER2 Targeting Enhances Photoimmunotherapy of HER2-Overexpressing Cancer Cells with Pyropheophorbide-a Immunoconjugates," Cancer Res. 65:6371-6379, 2005.

Scully et al., "Application of Fluorescence Lifetime Imaging Microscopy to the Investigation of Intracellular PDT Mechanisms," Bio imaging (1997) 5 :9-18.

Sekkat et al., "Like a bolt from the Blue: Phthalocyanines in Biomedical Optics," Molecules (2012) 17:98-144.

Serebrovskaia et al., "Genetically Encoded Photoimmunosensitizer," abstract (in English); Bioorg. Khim. 2011 37(1):137-44.

Serebrovskaya et al., "Targeting Cancer Cells by Using an Antireceptor Antibody-Photo sensitizer Fusion Protein," Proc Nat Acad Sci. 106:9221-9225, 2009.

Shimoyama et al., "Viral transduction of the HER2-extracellular domain expands trastuzumab-based photoimmunotherapy for HER2-negative breast cancer cells," Breast Cancer Res Treat. Feb. 2015;149(3):597-605.

Shinohara et al., "Structure and chromosomal localization of the human PD-1 gene (PDCD1)," Genomics (1994) 23(3):704-706.

Shirasu et al., "Potent and specific antitumor effect of CEA-targeted photoimmunotherapy," Int J Cancer. Dec. 1, 2014;135(11):2697-710.

Snyder et al., "Photodynamic therapy: a means to enhanced drug delivery to tumors," Cancer Res. 63:8126-8131, 2003.

Soukos et al., "Epidermal Growth Factor Receptor-Targeted Immunophotodiagnosis and Photoimmunotherapy of Oral Precancer in Vivo," Cancer Res. 61 :4490-4496, 2001.

Specenier et al., "Cetuximab: its unique place in head and neck cancer treatment," Biologics (2013) 7:77-90.

Steele et al., "Suppressor deletion therapy: selective elimination of T suppressor cells in vivo using a hematoporphyrin conjugated monoclonal antibody permits animals to reject syngeneic tumor cells." Cancer Immunol Immunother. 1988;26(2):125-31.

Steiner et al., "Efficient Selection of DARPins with Sub-nanomolar Affinities using SRP Phage Display," J Mol Biol (2008) 382(5):1211-1227.

Sugiyama et al., "Anti-CCR4 mAb selectively depletes effector-type FoxP3+CD4+ regulatory T cells, evoking antitumor immune responses in humans." Proc Natl Acad Sci U S A. Oct. 29, 2013;110(44):17945-50.

Supplementary materials from Gao et al., "In vivo cancer targeting and imaging with semiconductor quantum dots," Nat Biotechnol. Aug. 2004;22(8):969-76.

Supplementary materials from Mitsunaga et al., "Cancer Cell-Selective in Vivo Near Infrared Photomimmunotherapy Targeting Specific Membrance Molecules," Nat. Med. 17:1685-1691, 2011.

Supplementary materials from Sugiyama et al., "Anti-CCR4 mAb selectively depletes effector-type FoxP3+CD4+ regulatory T cells, evoking antitumor immune responses in humans." Proc Natl Acad Sci U S A. Oct. 29, 2013;110(44):17945-50.

Supplementary materials from Zhang et al., "Target-selective phototherapy using a ligand-based photosensitizer for type 2 cannabinoid receptor," Chem Biol. Mar. 20, 2014;21(3):338-44.

Supplementary materials from Zhang et al., "Tumor mitochondria-targeted photodynamic therapy with a translocator protein (TSPO)-specific photosensitizer," Acta Biomater. Dec. 28, 2015:160-70.

Tamaskovic et al., "Designed ankyrin repeat proteins (DARPins) from research to therapy," Methods Enzymol (2012) 503:101-134.

Templeton et al., "Implications of Photostability on the Manufacturing, Packaging, Storage, and Testing of Formulated Pharmaceutical Products," Pharmaceutical Technology Mar. 2005 68-86.

Therasse et al., "New guidelines to evaluate the response to treatment in solid tumors. European Organization for Research and Treatment of Cancer, National Cancer Institute of the United States, National Cancer Institute of Canada," J Natl Cancer Inst (2000)92(3):205-216.

Topalian et al., "Safety, Activity, and Immune Correlates of Anti-PD-1 Antibody in Cancer," N Engl J Med (2012) 366:2443-2454.

Tsujikawa et al., "Quantitative Multiplex Immunohistochemistry Reveals Myeloid-Inflamed Tumor-Immune Complexity Associated with Poor Prognosis," Cell Rep. (2017) 19(1):203-217.

Turner et al., Administration of substances to laboratory animals: routes of administration and factors to consider. J Am Assoc Lab Anim Sci. 2011;50(5):600-613.

U.S. Department of Veterans Affairs, "Lighting Design Manual," Dec. 2015, retrieved from https://www.cfm.va.gov/til/dManual/dmLighting.pdf.

U.S. Environmental Protection Agency, "Laboratories for the 21st Century: Best Practice Guide," Aug. 2006, U.S. Environmental Protection Agency, retrieved from http://labs21.lbl.gov/docs/Lighting_reduced_R11.pdf.

Van Cutsem et al., "Cetuximab and chemotherapy as initial treatment for metastatic colorectal cancer," The New England Journal of Medicine (2009) 360:1408-1417.

Van Cutsem et al., "Intrapatient cetuximab dose escalation in metastatic colorectal cancer according to the grade of early skin reactions: the randomized EVEREST study," J Clin Oncol. Aug. 10, 2012;30(23):2861-8.

Van Dongen et al., "Photosensitizer-Antibody Conjugates for Detection and Therapy of Cancer," Adv Drug Deliv Rev. 56:31-52, 2004.

Van Driel et al., "EGFR targeted nanobody-photosensitizer conjugates for photodynamic therapy in a pre-clinical model of head and neck cancer," J Control Release. May 10, 2016;229:93-105.

Von Felbert et al., "A specific photoimmunotheranostics agent to detect and eliminate skin cancer cells expressing EGFR," J Cancer Res Clin Oncol. May 2016;142(5):1003-11.

Vrouenraets et al., "Targeting of aluminum (III) phthalocyanine tetrasulfonate by use of internalizing monoclonal antibodies: improved efficacy in photodynamic therapy." Cancer Research, Mar. 1, 2001, vol. 61, No. 5, pp. 1970-1975.

Wada et al., "Sequencing CTLA-4 blockade with cell-based immunotherapy for prostate cancer," J Transl Med (2013) 11:89.

Wagner-Rousset et al., "Antibody-drug conjugate model fast characterization by LC-MS following IdeS proteolytic digestion," mAbs (2014) 6(1):173-184.

Waite and Roth, "Nanoscale drug delivery systems for enhanced drug penetration into solid tumors: current progress and opportunities," Crit Rev Biomed Eng. 40:21-41, 2012.

Wang et al., "Theranostic Agents for Photodynamic Therapy of Prostate Cancer by Targeting Prostate-Specific Membrane Antigen," Mol Cancer Ther. Aug. 2016;15(8):1834-44.

(56) References Cited

OTHER PUBLICATIONS

Wang, Changhui et al., New Progress in the Diagnosis and Treatment of Respiratory Interventional Therapy, Shanghai Science and Technology Press, Jun. 2015, p. 152.
Watanabe et al., "Photoimmunotherapy targeting prostate-specific membrane antigen: are antibody fragments as effective as antibodies?," J Nucl Med. Jan. 2015;56(1):140-4.
Weber, "Review: anti-CTLA-4 antibody ipilimumab: case studies of clinical response and immune-related adverse events," Oncologist (2007) 12(7):864-872.
Wessels et al., "Advances in cellular, subcellular, and nanoscale imaging in vitro and in vivo," Cytometry A:77:667-676, 2010.
Whiteside, "The tumor microenvironment and its role in promoting tumor growth," Oncogene (2008) 27(45):5904-5912.
Wollina, "Cetuximab in non-melanoma skin cancer," Exp Opin Biol Ther (2012) 12(7):949-956.
Wooldridge et al., "Immunostimulatory Oligodeoxynucleotides Containing CpG Motifs Enhance the Efficacy of Monoclonal Antibody Therapy of Lymphoma," Blood 89:2994-2998, 1997.
Xu et al., "Antibody Conjugated Magnetic Iron Oxide Nanoparticles for Cancer Cell Separation in Fresh Whole Blood," Biomaterials 32:9758-9765, 2011.
Xu, Deyu et al., Tumor Photodynamic Therapy Principles, Drugs, and Clinical Introduction, China Medical Science and Technology Press, May 1996, pp. 172-174.
Yoon et al., "Advance in Photosensitizers and Light Delivery for Photodynamic Therapy," Clin Endosc. 2013;46(1):7-23.
Zhang et al., "Inhibition of tumor growth and metastasis by photoimmunotherapy targeting tumor-associated macrophage in a sorafenib-resistant tumor model," Biomaterials Jan. 2016; vol. 84:1-12.
Zhang et al., "Target-selective phototherapy using a ligand-based photosensitizer for type 2 cannabinoid receptor," Chem Biol. Mar. 20, 2014;21(3):338-44.
Zhang et al., "Tumor mitochondria-targeted photodynamic therapy with a translocator protein (TSPO)-specific photosensitizer," Acta Biomater. Dec. 28, 2015:160-70.
Zhen et al. Tumor vasculature targeted photodynamic therapy for enhanced delivery of nanoparticles. (2014) ACS Nano. 8(6):6004-6013.
Zhen et al., "Protein nanocage mediated FAP-targeted photoimmunotherapy to enhance cytotoxic T cell infiltration and tumor control," Nano Lett. (2016); 27 pages. Downloaded from http://pubs.acs.org on Dec. 29, 2016.
Zhu et al., "Visualization of P53264-2n/HLA-A *0201 Complexes Naturally Presented on Tumor Cell Surface by a Multimeric Soluble Single-Chain T Cell Receptor," J Immunol. 176:3223-3232, 2006.
Zinn et al., "IND-Directed Safety and Biodistribution Study of Intravenously Injected Cetuximab-IRDye800 in Cynomolgus Macaques." Molecular Imaging Biology, Feb. 5, 2015, vol. 17, No. 1, pp. 49-57.
Zuluaga et al., "Combination of Photodynamic Therapy With Anti-Cancer Agents," Curr Med Chem. 15:1655-1673, 2008.
Azoury, "The Evolving Role of Immune Checkpoint Inhibitors in Immune Checkpoint Inhibitors for Cancer Therapy: Clinical Efficacy and Safety", Current Cancer Drug Targets, (2015) 15/6. pp. 452-462.
Carcenac et al., 'Preparation, Phototoxicity and Biodistribution Studies of Anti-Carcinoembryonic Antigen Monoclonal Antibody-Phthalocyanine Conjugates', Photochemistry and Photobiology 70(6): 930-936 [1999].
Chung et al. (Mar. 13, 2008), "Cetuximab-Induced Anaphylaxis and IgE Specific for Galactose-$\alpha$-1,3-Galactose," N Engl J Med., 2008, 358(11), 9 pages.
Forde et al., "Enhancement of electroporation facilitated immunogene therapy via T-reg depletion," Cancer Gene Therapy (Jul. 18, 2014), vol. 21, p. 349-354.
Fujimura et al., 'Conjugation Ratio, Light Dose, and pH Affect the Stability of Panitumumab IR700 for Near-Infrared Photoimmunotherapy', ACS Med. Chem. Lett. 2020, 11, 1598-1604.
Kobayashi et al. (Jan. 2019), "Near infrared photoimmunotherapy for cancer," Cancer and Chemotherapy, 46(1), in 6 pages.
Maczynska et al., "Immunomodulatory activity of IR700-labelled affibody targeting HER2," Cell Death and Disease (2020) 11:886.
Mitsunaga et al., "Cancer cell-selective in vivo near infrared photoimmunotherapy targeting specific membrane molecules," Nat Med. Nov. 6, 2011;17(12): Supplemental Information.
Mittendorf et al. (Apr. 2014), "PD-L1 expression in triple-negative breast cancer," *Cancel Immunol Res*, 2014, 2(4), 17 pages.
Spring et al., "Selective treatment and monitoring of disseminated cancer micrometastases in vivo using dual-function, activatable immunoconjugates," Proceedings of the National Academy of Sciences (Mar. 11, 2014), vol. 111, Issue 10, p. E933-E942.
Vrouenraets et al., 'Comparison of Aluminium (Iii) Phthalocyanine Tetrasulfonate and Meta-Tetra Hydroxyphenylchlorin-Monoclonal Antibody Conjugates for Their Efficacy in Photodynamic Therapy In Vitro', Int. J. Cancer: 98, 793-798 [2002].
Wang et al. (2016), "Acid-Activatable Versatile Micelleplexes for PD-L1 Blockade-Enhanced Cancer Photodynamic Immunotherapy," Nano Letters, 16(9), in 11 pages.
Whiteley et al. (Jul. 2021), "Leukaemia: a model metastatic disease," *Nat Rev Cancer.*, 21(7), in 39 pages.
Mizeret et al. (1996), "Cylindrical fiberoptic light diffuser for medical applications," Laser in Surgery and Medicine, 19, 159-167.
Norde et al. (2013), "4 P.D.," Novel Immunotherapeutic Strategies After Stem Cell Transplantation, 71:87.
Rudikoff et al. (Mar. 1982), "Single amino acid substitution altering antigen-binding specificity," PNAS, 79(), 1979-1983.
Shah et al. (Jul. 15, 2009), "Imaging Biomarkers Predict Response to Anti-HER2 (ErbB2) Therapy in Preclinical Models of Breast Cancer," Clincial Cancer Research, 15(14), 4712-4721.
Vargas et al. (Apr. 18, 2017), "FC-Optimized Anti-CD25 Depletes Tumor-Infiltrating Regulatory T Cells and Synergizes with PD-1 Blockade to Eradicate Established Tumors," Immunity Report, 46, 577-586.
U.S. Appl. No. 19/379,647, filed Nov. 4, 2025, by Markings et al. (Copy not provided). (Copy not submitted herewith pursuant to the waiver of 37 C.F. R. § 1.98(a)(2)(iii) issued by the Office on Sep. 21, 2004).
Cuzick, J. (2017) Preventive therapy for cancer Lancet Oneal 18; e472-e482 (Year: 2017).
De Censi et al., "Barriers to preventative therapy for breast and other major cancers and strategies to improve uptake ecancer," (2015) 9(595); 1-12.
Kobayashi et al., "Near-infrared photoimmunotherapy of cancer: a new approach that kills cancer cells and enhances anti-cancer host immunity," Int Immunol (2021) 33(1)7-15.
Lewandowska, AM., et al (2017) Environmental risk factors for cancer—review paper Ann. Agric. Environ. Med. 26(1); 1-7 (Year: 2017).
Rosenthal et al. (Apr. 1, 2007), "Use of fluorescent labeled anti-epidermal growth factor receptor antibody to image head and neck squamous cell carcinoma xenografts," Molecular Cancer Therapeutics, 6(4), 1230-1238.
Tang et al., "Tumor cells versus host immune cells: whose PD-L 1 contributes to PD-1/PD-L 1 blockade mediated cancer immunotherapy?" Cell Biosci (2018) 8(34); 1-8.
Wojtczak, A (2002) Glossary of Medical Education Terms Medical Teacher 24(4): 357; 1-25 (Year: 2002).

* cited by examiner

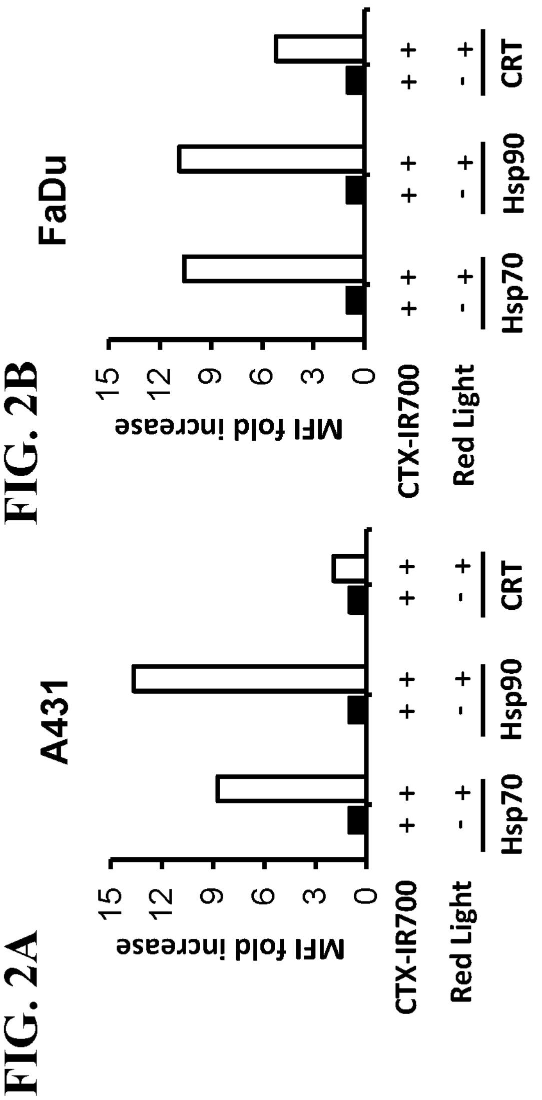
FIG. 2A
FIG. 2B
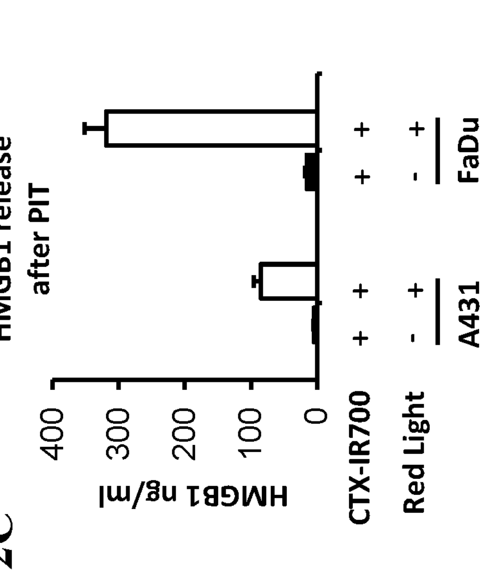
FIG. 2C

DC activation after PIT
MFI Fold Change
CTX-IR700
Red Light
CD86
MHCII

CT26-EphA2 expression
Isotype control
Anti-EphA2
Relative counts
EphA2

Anti-EphA2-IR700 fluorescence in the tumor
Fluorescence intensity (photons/sec)
8×10^8
6×10^8
4×10^8
2×10^8
0
0 10 20 30 40 50
Hours post dose CT26-EphA2 tumor growth
Anti-EphA2-IR700 no red light
Anti-EphA2-IR700 + red light
Anti-EphA2-IR700
Light
Average tumor volume (±SEM)
2500 2000 1500 1000 500 0
3 6 9 12 15 18 21
Days post implant MHCII^high
% of CD11c+
CD80
% of CD11c+
CD69
% of CD3- DX5+
CD107a
% of CD3- DX5+
Anti-EphA2-IR700
Red light PD-L1+ cells
% of CD11c+
CD3+ CD8+ cells
% of CD45+
PD1+ cells
% of CD8+
CTLA4+ cells
% of CD8+
Anti-EphA2-IR700
Red light
Ab-IR700

Part I: 3+3 dose escalation

Part II: Repeated Cycles

PD-L1 Expression (Part I)
Pre
Post
CPS score (per biopsy)
100
80
60
40
20
0
1
2
3
4
Patient ID PD-L1 Expression (Part IIa)
Pre
Post
CPS score (per biopsy)
80
60
40
20
0
1
2
3
4
5
6
7
8
Patient ID IL-2
Concentration (pg/mL)
60
50
40
30
20
10
0
*
responder
non responder
IL-7
Concentration (pg/mL)
4.0
3.5
3.0
2.5
2.0
1.5
1.0
0.5
0.0
*
responder
non responder
IL-22
Concentration (pg/mL)
500
450
400
350
300
250
200
150
100
50
0
*
responder
non responder
IL-27
Concentration (pg/mL)
1,600
1,400
1,200
1,000
800
600
400
200
0
**
responder
non responder
CXCL1 (GroA)
Concentration (pg/mL)
60
50
40
30
20
10
0
**
responder
non responder

| | | CR.1 | CR.2 | CR.3 | CR.4 | CR.5 | PR.1 | PR.2 | PR.3 | PR.4 | PR.5 |
|---|---|---|---|---|---|---|---|---|---|---|---|
| Innate Immunity | DCs | 0/6 | 0/4 | 0/5 | 0/4 | 0/3 | 0/3 | 0/3 | 0/4 | 0/1 | 0/2 |
| | NK | 0/12 | 2/8 | 3/10 | 0/8 | 2/6 | 1/6 | 1/6 | 0/8 | 0/2 | 0/4 |
| | Cytokine secretion by monocytes | 0/12 | 4/8 | 6/8 | 3/8 | 0/6 | 1/6 | 2/6 | 4/8 | 0/2 | 1/4 |
| Adaptive Immunity | Lymph | 0/12 | 0/8 | 1/10 | 0/8 | 0/6 | 1/6 | 0/6 | 0/8 | 0/2 | 0/4 |
| | CD4 | 0/6 | 0/4 | 2/5 | 0/4 | 0/3 | 0/3 | 0/3 | 2/4 | 0/1 | 0/2 |
| | CD8 | 0/6 | 0/4 | 0/5 | 1/4 | 1/3 | 0/3 | 0/3 | 0/4 | 0/1 | 0/2 |

| | | SD.1 | SD.2 | SD.3 | SD.4 | SD.5 | SD.6 | PD.1 | PD.2 |
|---|---|---|---|---|---|---|---|---|---|
| Innate Immunity | DCs | 0/3 | 0/3 | 0/4 | 0/3 | 0/7 | 0/3 | 0/2 | 0/3 |
| | NK | 0/4 | 1/6 | 2/8 | 1/6 | 4/14 | 0/6 | 0/4 | 0/6 |
| | Cytokine secretion by monocytes | 0/6 | 2/6 | 4/8 | 1/6 | 3/14 | 0/4 | 0/6 | 4/6 |
| Adaptive Immunity | Lymph | 0/6 | 0/6 | 3/8 | 0/4 | 0/14 | 0/6 | 1/4 | 0/6 |
| | CD4 | 0/3 | 0/3 | 0/4 | 0/4 | 0/7 | 0/3 | 1/2 | 0/3 |
| | CD8 | 1/3 | 0/3 | 0/4 | 0/3 | 0/7 | 0/3 | 0/2 | 1/3 |

Tumor Cells Expressing PD-L1 in Whole Tissue
P=0.015
PD-L1+ tumor cell density of whole tissue/mm²
3500
3000
2500
2000
1500
1000
500
0
Responder
NonResponder PD-L1 Cell Density in Whole Tissue
P=0.02
PD-L1+ cell density of whole tissue/mm²
5000
4000
3000
2000
1000
0
Responder
NonResponder TPS of Whole Tissue
* P=0.009
TPS of PD-L1
100
80
60
40
20
0
-20
Responder
Nonresponder CPS of Whole Tissue
* P=0.012
CPS of PD-L1
100
50
0
Responder
Nonresponder Tumor Cells Expressing PD-L1 in Tumor Region
PD-L1+ tumor cell density of tumor region/mm²
6000
4000
2000
0
* P=0.037
Responder
Nonresponder Cells Expressing PD-L1 in Tumor Region
PD-L1+ cell density of tumor region/mm²
6000
4000
2000
0
* P=0.032
Responder
Nonresponder TPS in Tumor Region
TPS of PD-L1
100
50
0
* P=0.034
Responder
Nonresponder CPS in Tumor Region
CPS of PD-L1
100
50
0
* P=0.036
Responder
Nonresponder

METHODS FOR PHOTOIMMUNOTHERAPY AND RELATED BIOMARKERS

RELATED APPLICATIONS

This application is a national stage application under 35 U.S.C. § 371 of International Application No. PCT/US2020/025465, filed internationally on Mar. 27, 2020, which claims priority from U.S. provisional application No. 62/826,932, filed Mar. 29, 2019, entitled "METHODS FOR PHOTOIMMUNOTHERAPY AND RELATED BIOMARKERS", and from U.S. Provisional Application No. 62/903,265, filed Sep. 20, 2019, entitled "METHODS FOR PHOTOIMMUNOTHERAPY AND RELATED BIOMARKERS", the contents of which are incorporated by reference in their entirety.

FIELD

The present disclosure relates to methods involving the use of biomarkers, in relation to photoimmunotherapy, such as photoimmunotherapy induced by activation of a phthalocyanine dye conjugated to a targeting molecule that binds a protein on tumor cell, for example, an IR700-antibody conjugate, and combination therapies, for example, that include photoimmunotherapy and an additional therapeutic agent, such as an immune modulating agent. In some aspects, the provided embodiments can be used to identify or select subjects for photoimmunotherapy and/or the combination therapy, or to assess the likelihood of response to photoimmunotherapy and/or to the additional therapeutic agents. Features of the methods and uses provide various advantages, such as improved efficacy. In some aspects, the provided embodiments can be used to provide personalized medicine and tailored therapy regimens for subjects. Also provided are therapeutic methods involving the use of biomarkers in the treatment of diseases and conditions, including tumors or cancers.

BACKGROUND

Various therapies are available for treating disease, such as cancer. For example, photoimmunotherapy (PIT) is a method that uses a photosensitizer conjugated to an antibody or other targeting molecule to target a cell surface protein in order to permit the targeted killing of specific cells. In some cases, PIT can selectively target disease cells, such as tumor cells, and thereby selectively kill such cells without damaging healthy cells. Improved strategies are needed to improve photoimmunotherapy methods, for example, to increase the effectiveness of treatment and provide tailored therapies for patient subpopulations. Provided are methods, uses and compositions that meet such needs.

SUMMARY

Provided herein are methods and uses involving one or more biomarkers related to photoimmunotherapy (PIT), for the treatment of a lesion associated with a disease or condition, such as a tumor. In some of any of the provided embodiments, the biomarker includes an immune checkpoint biomarker. In some of any of the provided embodiments, the methods and uses involve measuring the level of one or more biomarkers, such as an immune checkpoint biomarker, in a sample from a subject having a disease or condition, such as a tumor. In some of any of the provided embodiments, the methods and uses involve comparing the level of the one or more biomarker to a threshold level. In some of any of the provided embodiments, the methods also involve identifying or selecting a subject in which the measured level of the one or more biomarker is higher than, or lower than a threshold value. In some of any of the provided embodiments, the methods and uses involve selecting or identifying a subject for treatment, such as PIT treatment, and/or treatment with an additional therapeutic agent, such as an immunomodulatory agent, such as an immune checkpoint inhibitor. In some of any of the provided embodiments, the methods and uses involve administering a treatment, such as PIT treatment, and/or treatment with an additional therapeutic agent, such as an immunomodulatory agent, such as an immune checkpoint inhibitor, to the subject, such as a subject that is identified or selected in accordance with any of the embodiments provided herein.

Provided herein are methods of treating a tumor in a subject, involving: a) administering to a subject having a tumor a conjugate comprising a phthalocyanine dye linked to a targeting molecule that binds to a protein on the surface of a cell present in the microenvironment of the tumor; b) measuring in a sample from the subject the level of expression of at least one biomarker(s); c) irradiating an area proximal to a tumor at a wavelength of 500 nm to 900 nm at a dose of at least 1 J $cm^{-2}$ or 1 J/cm of fiber length; d) measuring the level of expression of the at least one biomarker(s) after the irradiation and determining whether the level of the at least biomarker is increased in the subject relative to the level measured prior to the irradiation; and e) if the level is increased, administering an immune modulating agent to the subject, thereby treating the tumor.

Provided herein are methods of improving the efficacy of a tumor treatment, involving: a) measuring in sample from a subject having a tumor the level of expression of at least one biomarker(s) and determining whether the level of expression of the at least one biomarker(s) is at or above a threshold; b) administering to the subject a conjugate comprising a phthalocyanine dye linked to a targeting molecule that binds to a protein on the surface of a cell present in the microenvironment of the tumor; c) irradiating an area proximal to a tumor at a wavelength of 500 nm to 900 nm at a dose of at least 1 J $cm^{-2}$ or 1 J/cm of fiber length; and d) if the level of expression of the at least one biomarker(s) is at or above the threshold, further administering an immune modulating agent to the subject; thereby improving the efficacy of the tumor treatment.

Provided herein are methods of improving the efficacy of a tumor treatment, involving: a) measuring in sample from a subject having a tumor the level of expression of at least one biomarker(s) and determining whether the level of expression of the at least one biomarker(s) is at or below a threshold; b) administering to the subject a conjugate comprising a phthalocyanine dye linked to a targeting molecule that binds to a protein on the surface of a cell present in the microenvironment of the tumor; c) irradiating an area proximal to a tumor at a wavelength of 500 nm to 900 nm at a dose of at least 1 J $cm^{-2}$ or 1 J/cm of fiber length; and d) if the level of expression of the at least one biomarker(s) is at or below the threshold, further administering an immune modulating agent to the subject; thereby improving the efficacy of the tumor treatment.

Provided herein are methods of improving the efficacy of a tumor treatment, involving: a) measuring in sample from a subject having a tumor the level of expression of at least one checkpoint pathway marker(s) and determining whether the level of expression of the at least one checkpoint pathway marker(s) is at or above a threshold; b) administering to the subject a conjugate comprising a phthalocyanine dye linked to a targeting molecule that binds to a protein on the surface of a cell present in the microenvironment of the tumor; c) irradiating an area proximal to a tumor at a wavelength of 500 nm to 900 nm at a dose of at least 1 J $cm^{-2}$ or 1 J/cm of fiber length; and d) if the level of expression of the at least one checkpoint pathway marker(s) is at or above the threshold, further administering checkpoint inhibitor to the subject; thereby improving the efficacy of the tumor treatment.

Provided herein are methods of treating subjects having a high likelihood of response within a population of subjects having a tumor comprising: a) measuring in a sample from each of the subjects in the population the level of expression of at least one biomarker(s); b) identifying the subject as having a high likelihood of response if the expression of the at least one biomarker(s) is at or above a threshold; c) administering to the subjects identified as having a high likelihood of response a conjugate comprising a phthalocyanine dye linked to a targeting molecule that binds to a protein on the surface of a cell present in the microenvironment of the tumor; and d) irradiating an area proximal to a tumor at a wavelength of 500 nm to 900 nm at a dose of at least 1 J $cm^{-2}$ or 1 J/cm of fiber length, thereby treating the tumor in the subjects identified as having a high likelihood of response. In some of any such embodiments, the method also involves: e) measuring in a sample from the subject the level of expression of the at least one biomarker(s) after the irradiation and determining whether the level of the at least one at least one biomarker(s) is increased in the subject compared to the level measured prior to the irradiation; and f) if the level is increased, administering an immune modulating agent to the subject.

Provided herein are methods of treating a tumor in a subject, involving: a) measuring in a sample from each of the subjects in the population the level of expression of at least one biomarker(s); b) selecting the subject for treatment if the expression of the at least one biomarker(s) is at or above a threshold; c) administering to the selected subject a conjugate comprising a phthalocyanine dye linked to a targeting molecule that binds to a protein on the surface of a cell present in the microenvironment of the tumor; and d) irradiating an area proximal to a tumor at a wavelength of 500 nm to 900 nm at a dose of at least 1 J $cm^{-2}$ or 1 J/cm of fiber length, thereby treating the tumor. In some of any such embodiments, the method also involves: e) measuring in a sample from the subject the level of expression of the at least one biomarker(s) after the irradiation and determining whether the level of the at least one at least one biomarker(s) is increased in the subject compared to the level measured prior to the irradiation; and f) if the level is increased, administering an immune modulating agent to the subject. In some of any such embodiments, the method also involves: e) measuring in a sample from the subject the level of expression of the at least one biomarker(s) after the irradiation and determining whether the level of the at least one at least one biomarker(s) is increased in the subject compared to the level measured prior to the irradiation; and f) if the level is decreased, administering an immune modulating agent to the subject.

Provided herein are methods of increasing expression of at least one biomarker(s) in a subject having a tumor, involving: a) administering to a subject having a tumor, a conjugate comprising a phthalocyanine dye linked to a targeting molecule that binds to a protein on the surface of a cell present in the microenvironment of the tumor; and b) after administering the conjugate, irradiating an area proximal to a tumor at a wavelength of 500 nm to 900 nm at a dose of at least 1 J $cm^{-2}$ or 1 J/cm of fiber length; thereby increasing the expression of the at least one biomarker(s) compared to the expression of the at least one biomarker(s) without the irradiation.

Provided herein are methods of selecting subjects for treatment with an immune modulating agent, involving: a) administering to a subject a conjugate comprising a phthalocyanine dye linked to a targeting molecule capable of binding to a molecule on the surface of a cell present in the microenvironment of the tumor; b) irradiating an area proximal to a tumor at a wavelength of 500 nm to 900 nm at a dose of at least 1 J $cm^{-2}$ or 1 J/cm of fiber length; c) measuring the level of expression of at least one biomarker(s) in a sample from a subject; and d) if the level of expression of the at least one biomarker(s) is at or above a threshold level, selecting the subject for treatment with an immune modulating agent. In some of any such embodiments, the method also involves administering to the selected subject a therapeutically effective amount of the immune modulating agent.

Provided herein are methods of selecting subjects for treatment with a conjugate comprising a phthalocyanine dye linked to a targeting molecule, involving: a) measuring the level of expression of at least one biomarker(s) in a sample from a subject; and b) if the level of expression of the at least one biomarker(s) is at or above a threshold level, selecting the subject for treatment with a conjugate comprising a phthalocyanine dye linked to a targeting molecule capable of binding to a molecule on the surface of a cell present in the microenvironment of the tumor.

Provided herein are methods of assessing the likelihood of response to treatment with a conjugate comprising a phthalocyanine dye linked to a targeting molecule, involving: a) measuring the level of expression of at least one biomarker(s) in a sample from a subject; and b) identifying the subject as having a high likelihood of response to treatment with a conjugate comprising a phthalocyanine dye linked to a targeting molecule capable of binding to a molecule on the surface of a cell present in the microenvironment of the tumor if the level of expression of the at least one biomarker(s) is at or above a threshold level.

Provided herein are methods of selecting subjects for treatment with a conjugate comprising a phthalocyanine dye linked to a targeting molecule, involving: a) measuring the level of expression of at least one biomarker(s) in a sample from a subject; and b) selecting the subject for treatment with a conjugate comprising a phthalocyanine dye linked to a targeting molecule capable of binding to a molecule on the surface of a cell present in the microenvironment of the tumor and an immune modulating agent if the level of expression of the at least one biomarker(s) is at or below a threshold level.

Provided herein are methods of assessing the likelihood of response to treatment with a conjugate comprising a phthalocyanine dye linked to a targeting molecule, involving: a) measuring the level of expression of at least one biomarker(s) in a sample from a subject; and b) identifying the subject as having a low likelihood of response to treatment with a conjugate comprising a phthalocyanine dye linked to a targeting molecule capable of binding to a molecule on the surface of a cell present in the microenvironment of the tumor if the level of expression of the at least one biomarker(s) is at or below a threshold level. In some of any such embodiments, the method also involves administering to the selected subject a therapeutically effective amount of the conjugate. In some of any such embodiments, the method also involves irradiating an area proximal to a tumor at a wavelength of 500 nm to 900 nm at a dose of at least 1 J $cm^{-2}$ or 1 J/cm of fiber length. In some embodiments, if the subject is identified as having a low likelihood of response, the method also involves administering to the subject a therapeutically effective amount of an immune modulating agent.

Provided herein are methods of monitoring a response to treatment with a conjugate comprising a phthalocyanine dye linked to a targeting molecule, involving: a) administering to a subject a conjugate comprising a phthalocyanine dye linked to a targeting molecule capable of binding to a molecule on the surface of a cell present in the microenvironment of the tumor; b) irradiating an area proximal to a tumor at a wavelength of 500 nm to 900 nm at a dose of at least 1 J $cm^{-2}$ or 1 J/cm of fiber length; and c) measuring the level of expression of at least one biomarker(s) in a sample from a subject; wherein the subject is identified as having a high likelihood of response if the level of expression of the at least one biomarker(s) is at or above a threshold level.

Provided herein are methods of monitoring a response to treatment with a conjugate comprising a phthalocyanine dye linked to a targeting molecule, involving: a) administering to a subject a conjugate comprising a phthalocyanine dye linked to a targeting molecule capable of binding to a molecule on the surface of a cell present in the microenvironment of the tumor; b) irradiating an area proximal to a tumor at a wavelength of 500 nm to 900 nm at a dose of at least 1 J $cm^{-2}$ or 1 J/cm of fiber length; and c) measuring the level of expression of at least one biomarker(s) in a sample from a subject; wherein the subject is identified as having a high likelihood of response if the level of expression of the at least one biomarker(s) is at or below a threshold level.

Provided herein are methods of treating a tumor in a subject, involving: a) administering to a subject a conjugate comprising a phthalocyanine dye linked to a targeting molecule capable of binding to a molecule on the surface of a cell present in the microenvironment of the tumor; b) irradiating an area proximal to a tumor at a wavelength of 500 nm to 900 nm at a dose of at least 1 J $cm^{-2}$ or 1 J/cm of fiber length, wherein the treatment of the tumor with the conjugate followed by light irradiation primes activation of immune cells; c) measuring the level of expression of at least one biomarker(s) in a sample from a subject; d) if the level of expression of the at least one biomarker is at or above a threshold level, administering to the subject a therapeutically effective amount of an immune modulating agent; thereby treating the tumor.

Provided herein are methods of treating a tumor in a subject, involving: a) administering to a subject a conjugate comprising a phthalocyanine dye linked to a targeting molecule capable of binding to a molecule on the surface of a cell present in the microenvironment of the tumor; b) irradiating an area proximal to a tumor at a wavelength of 500 nm to 900 nm at a dose of at least 1 J $cm^{-2}$ or 1 J/cm of fiber length, wherein the treatment of the tumor with the conjugate followed by light irradiation primes activation of immune cells; c) measuring the level of expression of at least one biomarker(s) in a sample from a subject; d) if the level of expression of the at least one biomarker is below a threshold level, administering to the subject one or more additional doses of the conjugate and irradiating the area proximal to the tumor; thereby treating the tumor.

Provided herein are methods and uses of treating a tumor in a subject, involving: measuring in a sample from the subject having a tumor a first level of an immune checkpoint biomarker; comparing the first level from the subject to a first threshold level; and if the first level from the subject is lower than the first threshold level, administering a photoimmunotherapy (PIT) treatment to the subject, thereby treating the tumor.

Provided herein are methods and uses of selecting a subject for treatment, involving: measuring in a sample from the subject having a tumor a first level of an immune checkpoint biomarker; comparing the first level from the subject to a first threshold level; and if the first level from the subject is lower than the first threshold level, selecting the subject for a PIT treatment.

Provided herein are methods and uses of assessing the likelihood for response to a treatment in a subject, involving: measuring in a sample from the subject having a tumor a first level of an immune checkpoint biomarker; comparing the first level from the subject to a first threshold level; and if the first level from the subject is lower than the first threshold level, identifying the subject as having a high likelihood for response to a PIT treatment.

Provided herein are methods and uses of selecting a subject for treatment, involving: measuring in a sample from the subject having a tumor a first level of an immune checkpoint biomarker; comparing the first level from the subject to a first threshold level; and if the first level from the subject is higher than the first threshold level, selecting the subject for treatment with an immune checkpoint inhibitor prior to a PIT treatment. In some of any of the provided embodiments, the immune checkpoint biomarker is selected from the group consisting of PD-L1, PD-1 and PD-L1:PD-1 ratio.

Provided herein are methods and uses of selecting a subject for treatment, involving: measuring in a sample from the subject having a tumor a first level of a first biomarker; comparing the first level from the subject to a first threshold level of the first biomarker; and if the first level of the first biomarker from the subject is lower than a first threshold level of the first biomarker, selecting the subject for a PIT treatment.

Provided herein are methods and uses of assessing the likelihood for response to a treatment in a subject, involving: measuring in a sample from the subject having a tumor a first level of a first biomarker; comparing the first level from the subject to a first threshold level of the first biomarker; and if the first level of the first biomarker from the subject is lower than a first threshold level of the first biomarker, identifying the subject as having a high likelihood for response to a PIT treatment.

Provided herein are methods and uses of selecting a subject for treatment, involving: measuring in a sample from the subject having a tumor a first level of a first biomarker; comparing the first level from the subject to a first threshold level of the first biomarker; and if the first level of the first biomarker from the subject is higher than a first threshold level of the first biomarker, selecting the subject for a PIT treatment.

Provided herein are methods and uses of assessing the likelihood for response to a treatment in a subject, involving: measuring in a sample from the subject having a tumor a first level of a first biomarker; comparing the first level from the subject to a first threshold level of the first biomarker; and if the first level of the first biomarker from the subject is higher than a first threshold level of the first biomarker, identifying the subject as having a high likelihood for response to a PIT treatment.

In some of any of the provided embodiments, the methods, uses or treatments also involve administering a PIT treatment to the selected or the identified subject, thereby treating the tumor. In some of any of the provided embodiments, the PIT treatment comprises administering a conjugate comprising a silicon phthalocyanine dye and a targeting molecule. In some of any of the provided embodiments, the targeting molecule comprises an EGFR binding molecule. In some of any of the provided embodiments, the PIT treatment comprises irradiating an area proximal to the tumor at a wavelength of at or about 500 nm to at or about 900 nm. In some of any of the provided embodiments, the irradiation is at a wavelength of at or about 660 nm to at or about 740 nm. In some of any of the provided embodiments, the PIT treatment comprises irradiating an area proximal to the tumor at a dose of at least at or about 1 J $cm^{-2}$ or at or about 1 J/cm of fiber length. In some of any of the provided embodiments, the irradiation is at a dose of at or about 25 J $cm^{-2}$ to at or about 400 J $cm^{-2}$ or at or about 25 J/cm of fiber length to at or about 500 J/cm of fiber length.

Provided herein are methods and uses of treating a tumor in a subject, involving: measuring in a sample from the subject having a head and neck cancer, a first level of PD-L1; comparing the first level of PD-L1 from the subject to a first threshold level; and if the first level from the subject is lower than the first threshold level, administering a PIT treatment comprising administering a conjugate comprising a silicon phthalocyanine dye and an EGFR binding molecule to the subject and irradiating an area proximal to the tumor at a wavelength of at or about 660 nm to at or about 740 nm at a dose of at or about 25 J $cm^{-2}$ to at or about 400 J $cm^{-2}$ or at or about 25 J/cm of fiber length to at or about 500 J/cm of fiber length, thereby treating the tumor.

Provided herein are methods and uses of selecting a subject for treatment, involving: measuring in a sample from the subject having a head and neck cancer, a first level of PD-L1; comparing the first level of PD-L1 from the subject to a first threshold level; and if the first level from the subject is lower than the first threshold level, selecting the subject for a PIT treatment comprising administering a conjugate comprising a silicon phthalocyanine dye and an EGFR binding molecule to the subject and irradiating an area proximal to the tumor at a wavelength of at or about 660 nm to at or about 740 nm at a dose of at or about 25 J $cm^{-2}$ to at or about 400 J $cm^{-2}$ or at or about 25 J/cm of fiber length to at or about 500 J/cm of fiber length.

Provided herein are methods and uses of assessing the likelihood for response to a treatment in a subject, involving: measuring in a sample from the subject having a head and neck cancer, a first level of PD-L1; comparing the first level of PD-L1 from the subject to a first threshold level; and if the first level from the subject is lower than the first threshold level, identifying the subject as having a high likelihood for response to a PIT treatment comprising administering a conjugate comprising a silicon phthalocyanine dye and an EGFR binding molecule to the subject and irradiating an area proximal to the tumor at a wavelength of at or about 660 nm to at or about 740 nm at a dose of at or about 25 J $cm^{-2}$ to at or about 400 J $cm^{-2}$ or at or about 25 J/cm of fiber length to at or about 500 J/cm of fiber length.

Provided herein are methods and uses of selecting a subject for treatment, involving: measuring in a sample from the subject having a head and neck cancer, a first level of PD-L1; comparing the first level of PD-L1 from the subject to a first threshold level; and if the first level from the subject is higher than the first threshold level, selecting the subject for treatment with an immune checkpoint inhibitor prior to a PIT treatment comprising administering a conjugate comprising a silicon phthalocyanine dye and an EGFR binding molecule to the subject and irradiating an area proximal to the tumor at a wavelength of at or about 660 nm to at or about 740 nm at a dose of at or about 25 J $cm^{-2}$ to at or about 400 J $cm^{-2}$ or at or about 25 J/cm of fiber length to at or about 500 J/cm of fiber length.

In some of any of the provided embodiments, the EGFR binding molecule is an anti-EGFR antibody, antibody fragment or antibody-like molecule. In some of any of the provided embodiments, the EGFR binding molecule is cetuximab or a fragment thereof. In some of any of the provided embodiments, the irradiation is at a wavelength of at or about 690±20 nm. In some of any of the provided embodiments, the irradiation is at a dose of at or about 50 J $cm^{-2}$ or 100 J/cm of fiber length.

In some of any of the provided embodiments, the first biomarker is a protein, a cell, or an mRNA. In some of any of the provided embodiments, the first biomarker is an immune cell, CD11c, CD14, CD68, CD163, or PD-L1. In some of any of the provided embodiments, the cell expresses CD3, CD4, and PD-1.

In some of any of the provided embodiments, the first biomarker is an mRNA selected from among an mRNA of APOE, BATF3, BCL6B, CASP9, CCND1, COL11A2, CSF2, CSF3, CTNNB1, DLL4, EGF, EIF2B4, ESR1, GLS, HDAC5, HSD11B1, IL11RA, IL32, MAP3K12, NLRP3, NOTCH2, P4HA1, PF4, PGPEP1, PLOD2, RIPK2, RPTOR, SF3A1, SNAIL SPP1, SRP54, STC1, TMEM140, TNFSF12, and VEGFA.

In some of any of the provided embodiments, the first biomarker is an mRNA selected from among an mRNA of ANGPT1, CPA3, CXCL14, IL18, KIT, MAP3K5, OAZ1, RB1, STAT3, SYK, TICAM1, and TPSAB1/B2.

In some of any of the provided embodiments, the sample is a tumor sample. In some of any of the provided embodiments, the sample is a tumor biopsy sample. In some of any of the provided embodiments, the immune checkpoint biomarker, the first biomarker or PD-L1 is measured in the whole tissue of the sample or a tumor region of the sample.

In some of any of the provided embodiments, he level of the immune checkpoint biomarker, the first biomarker or PD-L1 is measured using a multiplexed bioassay; and/or wherein the agent for measuring the level of the immune checkpoint biomarker, the first biomarker or PD-L1 is comprised in a multiplexed bioassay. In some of any of the provided embodiments, the multiplexed bioassay comprises one or more assays selected from immunofluorescence, fluorescence in-situ hybridization, immunohistochemistry and/or high-throughput nucleic acid sequencing.

In some of any of the provided embodiments, the first level and/or the threshold level(s) is/are measured as a Combined Positive Score (CPS) equal to the number of cells staining positive for the immune checkpoint biomarker, the first biomarker or PD-L1 divided by the total number of tumor cells, multiplied by 100.

In some of any of the provided embodiments, the first level and/or the threshold level(s) is/are measured as a Tumor Proportion Score (TPS) equal to the number of tumor cells staining positive for the immune checkpoint biomarker, the first biomarker or PD-L1 divided by the total number of tumor cells, multiplied by 100.

In some of any of the provided embodiments, the tumor comprises EGFR expressing cells in the tumor or tumor microenvironment. In some of any of the provided embodiments, the tumor is a head and neck cancer.

In some of any of the provided embodiments, the silicon phthalocyanine dye is IR700 dye.

In some of any of the provided embodiments, if the first level of the immune checkpoint biomarker, the first biomarker or PD-L1 from the subject is equal to or higher than the first threshold level, the methods, uses or treatments also involve administering an immune checkpoint inhibitor to the subject. In some of any of the provided embodiments, the methods, uses or treatments also involve administering a PIT treatment to the subject subsequent to the administration of the immune checkpoint inhibitor.

In some of any of the provided embodiments, the methods, uses or treatments also involve administering an immune checkpoint inhibitor to the subject subsequent to the administration of the PIT treatment.

In some of any of the provided embodiments, the methods, uses or treatments also involve: measuring a second level of the immune checkpoint biomarker, the first biomarker or PD-L1 in a second sample from the subject after PIT treatment; determining whether the second level of the immune checkpoint biomarker, the first biomarker or PD-L1 is increased in the subject relative to the first level measured prior to the PIT treatment; and if the second level is increased relative to the first level, administering an immune checkpoint inhibitor to the subject.

In some of any of the provided embodiments, the methods, uses or treatments also involve measuring a third level of immune cells positive for CD3, CD4, and PD-1 from a non-tumor region sample from the subject prior to the PIT treatment, comparing the third level to a third threshold and wherein if the third level is higher than the third threshold, selecting the subject for treatment with PIT.

Provided herein are methods and uses of assessing the response of a subject to PIT treatment comprising: measuring a first level of expression of a biomarker in a first sample from the subject prior to a PIT treatment; administering the PIT treatment to the subject; and measuring a second level of expression of the biomarker in a second sample from the subject subsequent to the PIT treatment; wherein if the first level is lower than the second level, identifying the subject as responding to the PIT treatment.

Provided herein are methods and uses of assessing the response of a subject to PIT treatment comprising: measuring a first level of expression of a biomarker in a first sample from the subject prior to a PIT treatment; administering the PIT treatment to the subject; and measuring a second level of expression of the biomarker in a second sample from the subject subsequent to the PIT treatment; wherein if the first level is higher than the second level, identifying the subject as responding to the PIT treatment.

In some of any of the provided embodiments, the biomarker is selected from the group consisting of FoxP3, CD11c, CD14, or CD68 and CD163.

In some of any of the provided embodiments, the biomarker expression in first and second samples are measured in whole tissue or a tumor region of the samples.

In some of any of the provided embodiments, if the first level is lower than the second level after a first administration of the PIT treatment to the subject, the methods, uses or treatments also involve administering a second PIT treatment and/or an immune checkpoint inhibitor to the subject.

In some of any of the provided embodiments, the immune checkpoint inhibitor is an inhibitor of PD-L1, PD-1, or CTLA4. In some of any of the provided embodiments, the immune checkpoint inhibitor comprises an antibody, antibody fragment or antibody-like molecule. In some of any of the provided embodiments, the immune checkpoint inhibitor is an antibody selected from BMS-935559, MEDI4736, MPDL3280A, MSB0010718C, nivolumab, pembrolizumab, pidilizumab, lambrolizumab or AMP-224, or an antigen-binding fragment thereof.

In some of any of the provided embodiments, the method provides a synergistic treatment effect compared to treatment by the conjugate alone or the immune modulating agent alone. In some of any of the provided embodiments, the method provides a synergistic treatment effect compared to treatment by the conjugate alone or the checkpoint inhibitor alone.

In some of any of the provided embodiments, the administration of the conjugate followed by irradiation primes activation of immune cells.

In some of any of the provided embodiments, the at least one biomarker(s) comprises a cell surface marker.

In some of any of the provided embodiments, the cell surface marker is an immune cell surface marker. In some of any of the provided embodiments, the cell surface marker is an antigen presenting cell marker. In some of any of the provided embodiments, the cell surface marker is a dendritic cell marker. In some of any of the provided embodiments, the cell surface marker is selected from among one or more of CD86, CD80 or MHCII. In some of any of the provided embodiments, the cell surface marker is a macrophage marker. In some of any of the provided embodiments, the cell surface marker is a natural killer cell marker. In some of any of the provided embodiments, the cell surface marker is selected from among one or more of CD69 or CD107a.

In some of any of the provided embodiments, the cell surface marker is a checkpoint pathway marker. In some of any of the provided embodiments, the cell surface marker is selected from among one or more of PD-1, PD-L1 or CTLA-4.

In some of any of the provided embodiments, the cell surface marker is an immunogenic cell death marker. In some of any of the provided embodiments, the cell surface marker is selected from among one or more of heat shock protein 70 (Hsp70), Hsp90 and calreticulin (CRT).

In some of any of the provided embodiments, the at least one biomarker(s) comprises a soluble marker or a serum marker.

In some of any of the provided embodiments, the soluble marker is a cytokine or a chemokine. In some of any of the provided embodiments, the cytokine or the chemokine is selected from among one or more of tumor necrosis factor alpha (TNF-α), IFN-γ-Inducible Protein 10 (IP-10)/CXCL10, MIP-1α (Macrophage Inflammatory Protein-1 alpha)/CCL3, MIP-1β (Macrophage Inflammatory Protein-1 beta)/CCL4, interleukin-1 beta (IL-1(3), interleukin-8 (IL-8)/CXCL8, 6CKine, BCA-1, CTACK, EGF, ENA-78, Eotaxin/CCL11, Eotaxin-2, Eotaxin-3, FGF-2, Flt-3 ligand, Fractalkine, G-CSF, GM-CSF, GRO, GRO alpha/CXCL1, 1-309, ICAM-1/CD54, IFN alpha (IFN-α), IFN gamma (IFN-γ), IFN-α2, IFN-γ, IL-1 alpha (IL-1α), IL-10, IL-12 p40, IL-12p70, IL-13, IL-15, IL-16, IL-17A, IL-17A/CTLA-8, IL-18, IL-2, IL-20, IL-21, IL-22, IL-23, IL-27, IL-28A, IL-3, IL-31, IL-33, IL-4, IL-5, IL-6, IL-7, IL-9, interleukin-1 receptor antagonist (IL-1ra), IP-10, LIF, MCP-1, MCP-1/CCL2, MCP-2, MCP-3, MCP-4, MDC (CCL22), MIP-1d, PDGF-AA, PDGF-AB/BB, RANTES/CCL5, sCD40L, SCF, SDF-1α/CXCL12, SDF-1a+B, sE-Selectin, sP-Selectin, TARC, TGFα, tumor necrosis factor beta (TNF-β)/LTA, TPO, TRAIL, TSLP or VEGF. In some of any of the provided embodiments, the cytokine or the chemokine is selected from among one or more of tumor necrosis factor alpha (TNF-α), IFN-γ-Inducible Protein 10 (IP-10)/CXCL10, MIP-1α (Macrophage Inflammatory Protein-1 alpha)/CCL3, MIP-1β (Macrophage Inflammatory Protein-1 beta)/CCL4, interleukin-1 beta (IL-1β), interleukin-8 (IL-8)/CXCL8, Eotaxin/CCL11, GRO alpha/CXCL1, GM-CSF, IFN alpha (IFN-α), IFN gamma (IFN-γ), IL-1 alpha (IL-1α), interleukin-1 receptor antagonist (IL-1ra), IL-2, IL-4, IL-5, IL-6, IL-7, IL-9, IL-10, IL-12p70, IL-13, IL-15, IL-17A/CTLA-8, IL-18, IL-21, IL-22, IL-23, IL-27, IL-31, MCP-1/CCL2, RANTES/CCL5, SDF-1α/CXCL12, and tumor necrosis factor beta (TNF-β)/LTA. In some of any of the provided embodiments, the cytokine or the chemokine is selected from among one or more of tumor necrosis factor alpha (TNF-α), IFN-γ-Inducible Protein 10 (IP-10), MIP-1α (Macrophage Inflammatory Protein-1 alpha), MIP-1β (Macrophage Inflammatory Protein-1 beta), interleukin-1 beta (IL-1β) and interleukin-8 (IL-8)/CXCL8.

In some of any of the provided embodiments, the soluble marker is a danger associated molecular patterns (DAMPs) marker. In some of any of the provided embodiments, the DAMPs marker is high-mobility group-box protein (HMGB1).

In some of any of the provided embodiments, the at least biomarker(s) is 2, 3, 4, 5, 6, 7 or more biomarkers. In some of any of the provided embodiments, the at least biomarker(s) is 2 biomarkers. In some of any of the provided embodiments, the at least biomarker(s) is 3 biomarkers. In some of any of the provided embodiments, the at least biomarker(s) is 4 biomarkers. In some of any of the provided embodiments, the at least biomarker(s) is 5 biomarkers.

In some of any of the provided embodiments, the sample is a tumor sample and/or the sample comprises or is likely to comprise tumor cells. In some of any of the provided embodiments, the sample comprises a tumor biopsy. In some of any of the provided embodiments, the sample is or comprises a blood sample, a plasma sample, a serum sample, a lymph node sample, a bone marrow sample, a buccal swab, a fecal sample or a urine sample.

In some of any of the provided embodiments, the irradiation is at a wavelength of 600 nm to 850 nm at a dose of from at or about 25 J $cm^{-2}$ to at or about 400 J $cm^{-2}$ or from at or about 25 J/cm of fiber length to at or about 500 J/cm of fiber length. In some of any of the provided embodiments, the irradiation is at a wavelength of at or about 660 nm to at or about 740 nm. In some of any of the provided embodiments, the irradiation is at a wavelength of at or about 690±50 nm or at a wavelength of at or about 690±20 nm. In some of any of the provided embodiments, the irradiation is at a dose of at or about 2 J $cm^{-2}$ to at or about 400 J $cm^{-2}$ or from at or about 2 J/cm fiber length to at or about 500 J/cm fiber length. In some of any of the provided embodiments, the irradiation is at a dose of at least at or about 2 J $cm^{-2}$, 5 J $cm^{-2}$, 10 J $cm^{-2}$, 25 J $cm^{-2}$, 50 J $cm^{-2}$, 75 J $cm^{-2}$, 100 J $cm^{-2}$, 150 J $cm^{-2}$, 200 J $cm^{-2}$, 300 J $cm^{-2}$, 400 J $cm^{-2}$, or 500 J $cm^{-2}$; or the irradiation is at a dose of at least at or about 2 J/cm fiber length, 5 J/cm fiber length, 10 J/cm fiber length, 25 J/cm fiber length, 50 J/cm fiber length, 75 J/cm fiber length, 100 J/cm fiber length, 150 J/cm fiber length, 200 J/cm fiber length, 250 J/cm fiber length, 300 J/cm fiber length, 400 J/cm fiber length or 500 J/cm fiber length.

In some of any of the provided embodiments, the phthalocyanine dye has a maximum absorption wavelength from at or about 600 nm to at or about 850 nm.

In some of any of the provided embodiments, the phthalocyanine dye is linked directly or indirectly to the targeting molecule.

In some of any of the provided embodiments, the phthalocyanine dye comprises the formula:

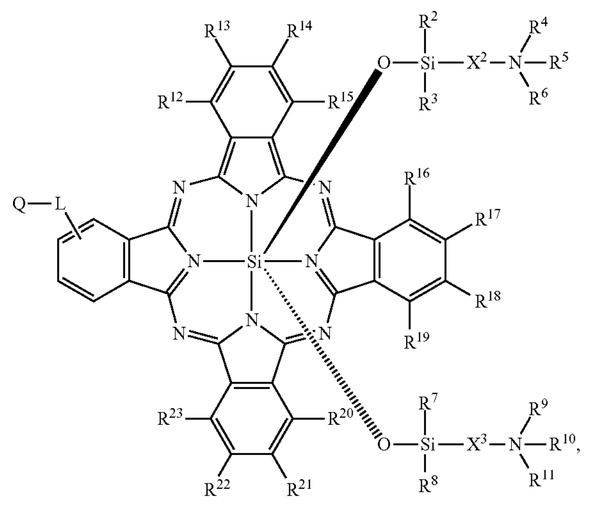

wherein:

L is a linker;

Q is a reactive group for attachment of the dye to the targeting molecule;

$R^2$, $R^3$, $R^7$, and $R^8$ are each independently selected from optionally substituted alkyl and optionally substituted aryl;

$R^4$, $R^5$, $R^6$, $R^9$, $R^{10}$, and $R^{11}$ are each independently selected from hydrogen, optionally substituted alkyl, optionally substituted alkanoyl, optionally substituted alkoxycarbonyl, optionally substituted alkylcarbamoyl, and a chelating ligand, wherein at least one of $R^4$, $R^5$, $R^6$, $R^9$, $R^{10}$, and $R^{11}$ comprises a water soluble group;

$R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ are each independently selected from hydrogen, halogen, optionally substituted alkylthio, optionally substituted alkylamino and optionally substituted alkoxy; and $X^2$ and $X^3$ are each independently $C_1$-$C_{10}$ alkylene, optionally interrupted by a heteroatom.

In some of any of the provided embodiments, the phthalocyanine dye comprises the formula:

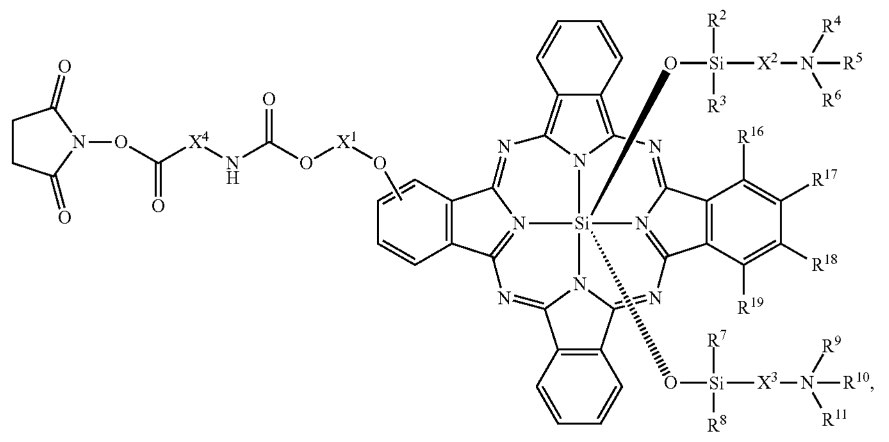

wherein:

$X^1$ and $X^4$ are each independently a $C_1$-$C_{10}$ alkylene optionally interrupted by a heteroatom;

$R^2$, $R^3$, $R^7$, and $R^8$ are each independently selected from optionally substituted alkyl and optionally substituted aryl;

$R^4$, $R^5$, $R^6$, $R^9$, $R^{10}$, and $R^{11}$ are each independently selected from hydrogen, optionally substituted alkyl, optionally substituted alkanoyl, optionally substituted alkoxycarbonyl, optionally substituted alkylcarbamoyl, and a chelating ligand, wherein at least one of $R^4$, $R^5$, $R^6$, $R^9$, $R^{10}$, and $R^{11}$ comprises a water soluble group; and $R^{16}$, $R^{17}$, $R^{18}$ and $R^{19}$ are each independently selected from hydrogen, halogen, optionally substituted alkylthio, optionally substituted alkylamino and optionally substituted alkoxy.

In some of any of the provided embodiments, the phthalocyanine dye comprises IRDye 700DX (IR700).

In some of any of the provided embodiments, the targeting molecule is an antibody or an antigen-binding antibody fragment.

In some of any of the provided embodiments, the antibody is an antigen-binding antibody fragment that is a Fab, single $V_H$ domain, a single chain variable fragment (scFv), a multivalent scFv, a bispecific scFv or an scFv-$C_H3$ dimer.

In some of any of the provided embodiments, the targeting molecule binds to a protein selected from among HER1/EGFR, HER2/ERBB2, CD20, CD25 (IL-2Ra receptor), CD33, CD52, CD133, CD206, CEA, CEACAM1, CEACAM3, CEACAM5, CEACAM6, cancer antigen 125 (CA125), alpha-fetoprotein (AFP), Lewis Y, TAG72, Caprin-1, mesothelin, PDGF receptor, PD-1, PD-L1, CTLA-4, IL-2 receptor, vascular endothelial growth factor (VEGF), CD30, EpCAM, EphA2, Glypican-3, gpA33, mucins, CAIX, PSMA, folate-binding protein, gangliosides (such as GD2, GD3, GM1 and GM2), VEGF receptor (VEGFR), integrin αVβ3, integrin α5β1, ERBB3, MET, IGF1R, EPHA3, TRAILR1, TRAILR2, RANKL, FAP, tenascin, AFP, BCR complex, CD3, CD18, CD44, CTLA-4, gp72, HLA-DR 10β, HLA-DR antigen, IgE, MUC-1, nuC242, PEM antigen, metalloproteinases, Ephrin receptor, Ephrin ligands, HGF receptor, CXCR4, CXCR4, Bombesin receptor, and SK-1 antigen.

In some of any of the provided embodiments, the targeting molecule binds to a protein selected from among CD25, PD-1 (CD279), PD-L1 (CD274, B7-H1), PD-L2 (CD273, B7-DC), CTLA-4, LAG3 (CD223), TIM3 (HAVCR2), 4-1BB (CD137, TNFRSF9), CXCR2, CXCR4 (CD184), CD27, CEACAM1, Galectin 9, BTLA, CD160, VISTA (PD1 homologue), B7-H4 (VCTN1), CD80 (B7-1), CD86 (B7-2), CD28, HHLA2 (B7-H7), CD28H, CD155, CD226, TIGIT, CD96, Galectin 3, CD40, CD40L, CD70, LIGHT (TNFSF14), HVEM (TNFRSF14), B7-H3 (CD276), Ox40L (TNFSF4), CD137L (TNFSF9, GITRL), B7RP1, ICOS (CD278), ICOSL, KIR, GALS, NKG2A (CD94), GARP, TL1A, TNFRSF25, TMIGD2, BTNL2, Butyrophilin family, CD48, CD244, Siglec family, CD30, CSF1R, MICA (MHC class I polypeptide-related sequence A), MICB (MHC class I polypeptide-related sequence B), NKG2D, KIR family (Killer-cell immunoglobulin-like receptor, LILR family (Leukocyte immunoglobulin-like receptors, CD85, ILTs, LIRs), SIRPA (Signal regulatory protein alpha), CD47 (IAP), Neuropilin 1 (NRP-1), a VEGFR, and VEGF.

In some of any of the provided embodiments, the antibody or an antigen-binding antibody fragment is selected from among cetuximab, panitumumab, zalutumumab, nimotuzumab, Tositumomab (Bexxar®), Rituximab (Rituxan, MabThera), Ibritumomab tiuxetan (Zevalin), Daclizumab (Zenapax), Gemtuzumab (Mylotarg), Alemtuzumab, CEA-scan Fab fragment, OC125 monoclonal antibody, ab75705, B72.3, Bevacizumab (Avastin®), Basiliximab, nivolumab, pembrolizumab, pidilizumab, MK-3475, BMS-936559, MPDL3280A, ipilimumab, tremelimumab, IMP321, BMS-986016, LAG525, urelumab, PF-05082566, TRX518, MK-4166, dacetuzumab, lucatumumab, SEA-CD40, CP-870, CP-893, MED16469, MEDI6383, MEDI4736, MOXR0916, AMP-224, PDR001, MSB0010718C, rHIgM12B7, Ulocuplumab, BKT140, Varlilumab (CDX-1127), ARGX-110, MGA271, lirilumab (BMS-986015, IPH2101), IPH2201, AGX-115, Emactuzumab, CC-90002 and MNRP1685A or is an antigen-binding antibody fragment thereof. In some of any of the provided embodiments, the conjugate is selected from among cetuximab-IR700, panitumumab-IR700, zalutumumab-IR700, nimotuzumab-IR700, Tositumomab-IR700, Rituximab-IR700, Ibritumomab tiuxetan-IR700, Daclizumab-IR700, Gemtuzumab-IR700, Alemtuzumab-IR700, CEA-scan Fab fragment-IR700, OC125-IR700, ab75705-IR700, B72.3-IR700, Bevacizumab-IR700, Basiliximab-IR700, nivolumab-IR700, pembrolizumab-IR700, pidilizumab-IR700, MK-3475-IR700, BMS-936559-IR700, MPDL3280A-IR700, ipilimumab-IR700, tremelimumab-IR700, IMP321-IR700, BMS-986016-IR700, LAG525-IR700, urelumab-IR700, PF-05082566-IR700, TRX518-IR700, MK-4166-IR700, dacetuzumab-IR700, lucatumumab-IR700, SEA-CD40-IR700, CP-870-IR700, CP-893-IR700, MED16469-IR700, MED16383-IR700, MEDI4736-IR700, MOXR0916-IR700, AMP-224-IR700, PDR001-IR700, MSB0010718C-IR700, rHIgM12B7-IR700, Ulocuplumab-IR700, BKT140-IR700, Varlilumab-IR700, ARGX-110-IR700, MGA271-IR700, lirilumab-IR700, IPH2201-IR700, AGX-115-IR700, Emactuzumab-IR700, CC-90002-IR700 and MNRP1685A-IR700.

In some of any of the provided embodiments, the targeting molecule is an antibody that is cetuximab or is an antigen-binding antibody fragment thereof or the conjugate is cetuximab-IR700.

In some of any of the provided embodiments, the conjugate is administered systemically. In some of any of the provided embodiments, the conjugate is administered intravenously.

In some of any of the provided embodiments, the irradiation is carried out 24 hours±3 hours after administering the conjugate.

In some of any of the provided embodiments, the tumor is a superficial tumor. In some of any of the provided embodiments, the tumor is less than 10 mm thick. In some of any of the provided embodiments, the irradiation is carried out using a microlens-tipped fiber for surface illumination. In some of any of the provided embodiments, the irradiation dose is from or from about 5 J/cm$^2$ to about 200 J/cm$^2$.

In some of any of the provided embodiments, the lesion is a tumor that is an interstitial tumor. In some of any of the provided embodiments, the tumor is greater than 10 mm deep or is a subcutaneous tumor. In some of any of the provided embodiments, the irradiation is carried out using cylindrical diffusing fibers comprising a diffuser length of 0.5 cm to 10 cm and spaced 1.8±0.2 cm apart. In some of any of the provided embodiments, the light irradiation dose is from or from about 20 J/cm fiber length to about 500 J/cm fiber length.

In some of any of the provided embodiments, the immune modulating agent is capable of increasing the activity of the immune cell. In some of any of the provided embodiments, the immune modulating agent is selected from among GM-CSF, CpG-ODN (CpG oligodeoxynucleotides), lipopolysaccharide (LPS), monophosphoryl lipid A (MPL), alum, recombinant Leishmania polyprotein, imiquimod, MF59, poly I:C, poly A:U, type 1 IFN, Pam3Cys, Pam2Cys, complete freund's adjuvant (CFA), alpha-galactosylceramide, RC-529, MDF2β, Loxoribine, anti-CD40 agonist, SIRPa antagonist, AS04, AS03, Flagellin, Resiquimod, DAP (diaminopimelic acid), MDP (muramyl dipeptide) CAF01 (cationic adjuvant formulation-01), anthracyclines (e.g., doxorubicin, mitoxantrone), BK channel agonists, bortezomib, bortezomib plus mitomycin C plus hTERT-Ad, Cardiac glycosides plus non-Immunogenic cell death inducers, cyclophosphamide, GADD34/PP1 inhibitors plus mitomycin, LV-tSMAC, and oxaliplatin.

In some of any of the provided embodiments, the immune modulating agent is a Toll-like receptor (TLR) agonist, an adjuvant or a cytokine or a chemokine.

In some of any of the provided embodiments, the immune modulating agent is a TLR agonist and the TLR agonist is TLR agonist is a TLR4 agonist, a TLR7 agonist, a TLR8 agonist, or a TLR9 agonist. In some of any of the provided embodiments, the TLR agonist is selected from among triacylated lipoprotein, diacylated lipopeptide, lipoteichoic acid, peptidoglycan, zymosan, Pam3CSK4, dsRNA, poly(I:C), Poly G10, Poly G3, CpG, 3M003, flagellin, lipopolysaccharide (LPS) Leishmania homolog of eukaryotic ribosomal elongation and initiation factor 4a (LeIF), MEDI9197, SD-101, and imidazoquinoline TLR agonists.

In some of any of the provided embodiments, the immune modulating agent is a cytokine and the cytokine is IL-4, TNF-α, GM-CSF or IL-2.

In some of any of the provided embodiments, the immune modulating agent is an immune checkpoint inhibitor. In some of any of the provided embodiments, the immune modulating agent comprises an antibody or antigen binding fragment thereof that specifically binds a molecule selected from among CD25, PD-1, PD-L1, PD-L2, CTLA-4, LAG-3, TIM-3, 4-1BB, GITR, CD40, CD40L, OX40, OX40L, CXCR2, B7-H3, B7-H4, BTLA, HVEM, CD28 and VISTA. In some of any of the provided embodiments, the immune modulating agent is selected from among nivolumab, pembrolizumab, pidilizumab, MK-3475, BMS-936559, MPDL3280A, ipilimumab, tremelimumab, IMP31, BMS-986016, urelumab, TRX518, dacetuzumab, lucatumumab, SEQ-CD40, CP-870, CP-893, MED16469, MED14736, MOXR0916, AMP-224, and MSB001078C, or is an antigen-binding fragment thereof of any of the foregoing.

In some of any of the provided embodiments, the immune modulating agent is an antibody or antibody fragment that binds to PD-L1. In some of any of the provided embodiments, the immune modulating agent is an antibody selected from BMS-935559, MEDI4736, MPDL3280A and MSB0010718C, or an antigen-binding fragment thereof.

In some of any of the provided embodiments, the immune modulating agent is an antibody or antibody fragment that binds to PD-1. In some of any of the provided embodiments, the immune modulating agent is an antibody selected from nivolumab, pembrolizumab, pidilizumab, lambrolizumab or AMP-224, or an antigen-binding fragment thereof.

In some of any of the provided embodiments, the immune modulating agent further comprises a second phthalocyanine dye. In some of any of the provided embodiments, the second phthalocyanine dye comprises IRDye 700DX (IR700).

In some of any of the provided embodiments, the immune modulating agent is administered greater than or greater than about 30 minutes, 1 hour, 2 hours, 6 hours, 12 hours, 24 hours, 48 hours, 96 hours, one week, two weeks, three weeks or one month prior to irradiating the area proximal to the tumor.

In some of any of the provided embodiments, the method comprises continued administration of the immune modulating agent subsequent to the irradiation three times a week, two times a week, once every week, once every two weeks, once every three weeks or once a month.

In some of any of the provided embodiments, the irradiation is carried out either i) after administration of the immune modulating agent and after administration of the conjugate or ii) only after administration of the conjugate.

In some of any of the provided embodiments, the conjugate is administered prior to, simultaneously or subsequently to administration of the immune modulating agent.

In some of any of the provided embodiments, the immune modulating agent is administered after the irradiation. In some of any of the provided embodiments, the conjugate is administered from or from about 12 hours to 48 hours prior to the irradiation and the immune modulating agent is administered from or from about 12 hours to about 1 month after irradiating the tumor.

In some of any of the provided embodiments, the conjugate is administered after administering the immune modulating agent but prior to the irradiation. In some of any of the provided embodiments, the conjugate is administered from or from about 12 hours to 48 hours prior to the irradiation and the immune modulating agent is administered from or from about 12 hours to about 1 month prior to irradiating the tumor.

In some of any of the provided embodiments, the tumor is a cancer. In some of any of the provided embodiments, the cancer is a cancer located at the head and neck, breast, liver, colon, ovary, prostate, pancreas, brain, cervix, bone, skin, eye, bladder, stomach, esophagus, peritoneum, or lung. In some of any of the provided embodiments, the tumor is a sarcoma or carcinoma. In some of any of the provided embodiments, the tumor is a carcinoma that is a squamous cell carcinoma, basal cell carcinoma or adenocarcinoma. In some of any of the provided embodiments, the tumor is a carcinoma that is a carcinoma of the bladder, pancreas, colon, ovary, lung, breast, stomach, prostate, cervix, esophagus or head and neck.

In some of any of the provided embodiments, the method reduces the size or volume of the tumor by at least 30%, at least 40%, at least 50%, at least 60%, at least 70%, at least 80% at least 90% or more within one month of the irradiation compared to the size or volume of the tumor prior to the administration and irradiation.

In some of any of the provided embodiments, in a population of treated subjects, effects an improvement of a tumor-related parameter compared to a similarly situated population of subjects that have not been treated with the method, wherein the parameter is selected from one or more of: a) objective response rate (ORR); b) progression free survival (PFS); c) overall survival (OS); d) reduction in toxicity; e) tumor response; f) quality of life; g) symptom endpoint; h) disease-free survival; h) complete response (CR); or i) time to progression. In some of any of the provided embodiments, the parameter is improved by at least 10%, at least 20%, at least 30%, at least 40%, at least 50%, at least 60%, at least 70%, at least 80%, at least 90%, at least 100% or more. In some of any of the provided embodiments, in a population of treated subjects, effects an objective response rate (ORR) of at least 15%, at least 25%, at least 50%, at least 55%, at least 60%, at least 65%, at least 70%, at least 75%, at least 80%, at least 85%, at least 90%, at least 95% or more.

BRIEF DESCRIPTION OF THE DRAWINGS

FIGS. 2A-2B show the fold increase in mean fluorescence intensity (MFI) of cell surface expression of immunogenic cell death markers heat shock protein 70 (Hsp70), Hsp90 and calreticulin (CRT) assessed by flow cytometry, in EGFR-expressing A431 (FIG. 2A) and FaDu (FIG. 2B) human cancer cells after photoimmunotherapy (PIT) by incubation with CTX-IR700 and with (+) illumination with red light at 690 nm, or without (−) illumination as control. FIG. 2C depicts the amount of danger associated molecular patterns (DAMPs) marker high-mobility group-box protein (HMGB1) released into the culture supernatant of A431 and FaDu cells after incubation after incubation with CTX-IR700 and with (+) or without (−) light treatment, as assessed by enzyme-linked immunosorbent assay (ELISA).

FIG. 6A shows the treatment schema and dosing cohorts for part I of the study, including dose escalation, and FIG. 6B shows part II of the study, including treatment with repeated cycles of the treatment.

DETAILED DESCRIPTION

Figures 1A, 1B:
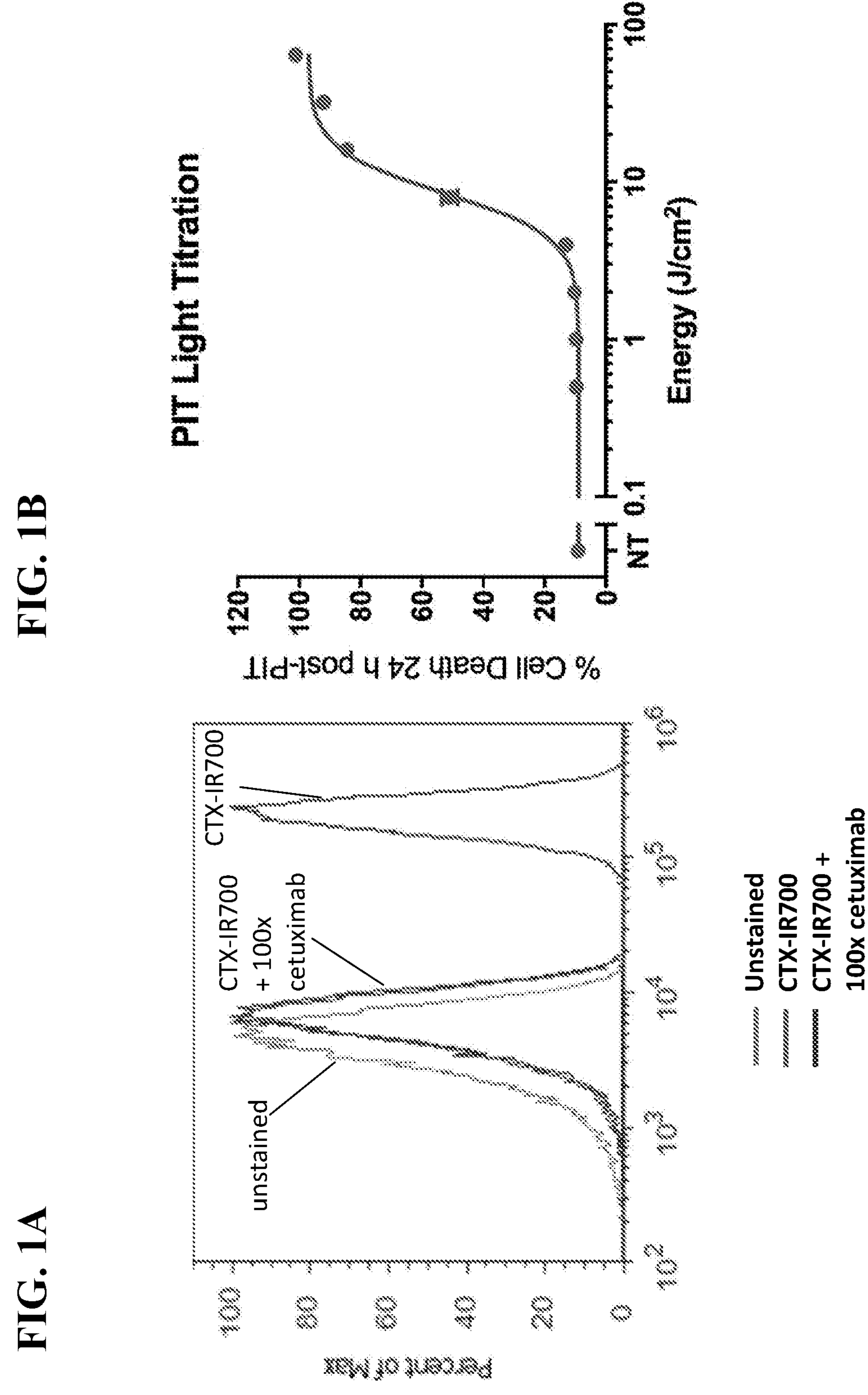
FIG. 1A shows cell binding of cetuximab-IRDye 700DX (CTX-IR700) to the surface of epidermal growth factor receptor (EGFR)-expressing BxPC3 tumor cells, as detected by flow cytometry of the intrinsic fluorescence of IRDye 700DX, compared to cells alone (unstained) or cells with CTX-IR700, competed with 100-fold excess of unlabeled cetuximab.
FIG. 1B shows the percent cell death at 24 hours after light treatment, plotted against varying light fluence ($J/cm^{-2}$).

Provided herein are methods related to and involving photoimmunotherapy (PIT), as a monotherapy and/or combination therapy. In some aspects, the provided methods involve the assessment of one or more biomarkers, such as biomarkers that are associated with particular result from PIT and/or particular therapeutic outcome. In some aspects, the provided methods involving the assessment of biomarkers can be used in therapeutic applications, in improving efficacy of a therapy or treatment, in identification and selection of subjects for particular therapy or treatment, in assessing the likelihood of an outcome (e.g., response) following treatment and in monitoring an outcome (e.g., response) following treatment. In some aspects, the provided embodiments can be employed in tailoring or customizing aspects of therapeutic regimen, such as for personalized medicine.

Provided herein are methods and uses involving one or more biomarkers related to photoimmunotherapy, for the treatment of a lesion associated with a disease or condition, such as a tumor. In some of any of the provided embodiments, the biomarker includes an immune checkpoint biomarker. In some of any of the provided embodiments, the methods involve measuring the level of one or more biomarkers, such as an immune checkpoint biomarker, in a sample from a subject having a disease or condition, such as a tumor. In some of any of the provided embodiments, the methods involve comparing the level of the one or more biomarker to a threshold level. In some of any of the provided embodiments, the methods also involve identifying or selecting a subject in which the measured level of the one or more biomarker is higher than, or lower than a threshold value. In some of any of the provided embodiments, the methods involve selecting or identifying a subject for treatment, such as PIT treatment, and/or treatment with an additional therapeutic agent, such as an immunomodulatory agent, such as an immune checkpoint inhibitor. In some of any of the provided embodiments, the methods involve administering a treatment, such as PIT treatment, and/or treatment with an additional therapeutic agent, such as an immunomodulatory agent, such as an immune checkpoint inhibitor, to the subject, such as a subject that is identified or selected in accordance with any of the embodiments provided herein.

Provided are methods and uses for treatment, methods and uses for selecting a subject for treatment, methods and uses for assessing the likelihood for response and/or methods f and uses or assessing the response to treatment, of a disease or condition and/or a lesion associated with a disease or condition, such as a tumor. In some of any of the embodiments, provided are diagnostic and/or therapeutic methods and uses, such as methods for treatment or uses of a composition for treatment or in the manufacture of a medicament for treatment of a disease or disorder, such as a tumor; or methods for diagnosis or uses of a composition for the diagnosis of a disease or a disorder, such as a tumor; or a method of monitoring the status of a disease or disorder, including before and after a treatment, such as a PIT treatment. Any of the features described herein, can be employed in any of the embodiments provided herein, such as any of the methods, uses or compositions or kits provided herein.

In some aspects, PIT is a molecular targeted therapy that utilizes a target-specific photosensitizer based on phthalocyanine dye, such as a near infrared (NIR) phthalocyanine dye (e.g., IR700), conjugated to a targeting molecule targeting a protein, such as a cell surface protein on a cell in a disease or condition, such as a tumor. For example, in some cases a phthalocyanine dye-conjugate used in PIT can include conjugation to an antibody or antigen-binding fragment that specifically targets or binds a cell surface protein receptor or receptor expressed on a cell in the environment of a disease lesion, such as a tumor microenvironment, which can include tumor cells and other infiltrating cells such as immune cells. PIT provides a highly selective and localized therapeutic method for treating a disease or condition, such as a tumor. Because the therapy is targeted specifically to disease cells, such as cells in a tumor, its effects are highly selective to disease tissue compared to healthy tissue or cells.

In some aspects, improved methods to monitor outcomes of treatment, evaluate the likelihood of a particular outcome (e.g., response to treatment) and identify subjects for treatment with PIT as a monotherapy and/or combination therapy, such as subjects with a high likelihood of response, is desired. For example, such methods would be useful to increase the effectiveness of the treatment and prevent ineffective treatment to subjects who may not respond to the treatment. In some aspects, such methods are also are desired to increase the effectiveness of the treatment, such as by administration of additional therapeutic agents that can enhance or augment the therapeutic outcome of the PIT. In some embodiments, the provided methods involve assessing one or more biomarkers. In some aspects, such assessment, such as measurement of the level, amount or concentration of one or more biomarkers, can be used to guide the therapeutic regimen for a particular subject, such as determining the dosing, timing, or the suitability of additional doses and/or additional therapeutic agents.

In some embodiments, the provided methods are based on observations that certain biomarkers, such as certain markers associated with immune cell activation or immune checkpoint pathways, are associated with PIT-mediated killing of target cells. In some aspects, PIT-mediated killing of target cells can result in immunogenic cell death, for example, by inducing a strong immunogenic response due to the killing of the immunosuppressive tumor cells and activation of immune cells, such as cells in the innate or adaptive immune system. In some aspects, certain biomarkers, such as certain markers associated with immune cell activation or immune checkpoint pathways, may be associated with therapeutic outcomes, such as response to the PIT. In some aspects, the assessment of biomarkers can be used as a guide for identifying and/or selecting subjects that are likely to respond to the treatment. In some aspects, the assessment of biomarkers can be used as a guide for improving the effectiveness of the response, for example, by administration of additional doses and/or additional therapeutic agents, such as an immune modulating agent or an anti-cancer agent. The provided embodiments offer an advantage of improving the effectiveness of the therapy.

All publications, including patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The section headings used herein are for organizational purposes only and are not to be construed as limiting the subject matter described.

I. METHODS FOR PHOTOIMMUNOTHERAPY AND RELATED BIOMARKERS

Provided herein are methods related to one or more biomarkers in the context of photoimmunotherapy (PIT), as a monotherapy and/or in a combination therapy. Provided are methods of treatment that involve one or more aspects of PIT, and uses of one or more biomarkers, to guide the treatment and/or to identify and select subjects. In some aspects, certain biomarkers that are associated with particular result from PIT and/or particular therapeutic outcome. In some aspects, the provided methods involve assessing the level, amount or concentration of one or more of such biomarkers in a sample from a subject who is a candidate for treatment with PIT, as a monotherapy and/or in a combination therapy, to identify or select a subject for a particular treatment or to assess the likelihood of an outcome of the therapy, such as the likelihood of responding to the therapy. In some aspects, the provided methods involve assessing the level, amount or concentration of one or more of such biomarkers in a sample from a subject who has received one or more steps of PIT and/or combination therapy that includes PIT, for monitoring the response to the therapy, to identify subjects for administration of an additional therapeutic agent (in a combination therapy) or additional doses of the PIT and/or to improve the efficacy or effectiveness of treatment. In some aspects, the provided methods involve assessing the level, amount or concentration of one or more of such biomarkers in a sample from a subject before and after performing one or more steps of the PIT as a monotherapy and/or in a combination therapy, and determining the change in the level, amount or concentration of the one or more biomarkers, in guiding treatment, such as for monitoring the response to the therapy, to identify subjects for administration of an additional therapeutic agent (in a combination therapy) or additional doses of the PIT and/or to improve the efficacy or effectiveness of treatment.

In some aspects, provided are methods of treating a lesion of a disease or condition in a subject, such as a tumor, involving PIT and assessment of one or more biomarkers as descried herein. In some embodiments, the methods involve one or more steps of PIT. In some aspects, PIT is a molecular targeted therapy that utilizes a target-specific photosensitizer based on phthalocyanine dye, such as a near infrared (NIR) phthalocyanine dye (e.g., IR700), conjugated to a targeting molecule (such as an antibody or antigen-binding fragment thereof) that specifically binds, recognizes or targets a protein, such as a cell surface protein on a cell in the environment of a disease lesion, such as a tumor microenvironment, which can include tumor cells and other infiltrating cells such as immune cells. In some aspects, PIT also involves irradiating the areas surrounding, proximal to or near the lesion, to activate the conjugate. In some embodiments, activation of the conjugate by irradiation with absorbing light, such as NIR light, excites the photosensitizer and results in cell killing, thereby reducing or eliminating the lesion (e.g., tumor) and treating the disease or condition. In some aspects, the PIT can be used as a monotherapy, e.g., in a method involving administration of the conjugate and irradiation. In other aspects, the PIT can be used as a part of a combination therapy, e.g., in a method involving further administration of an additional therapeutic agent, such as an immune modulating agent, an anti-cancer agent, or an additional dose or administration of the PIT. In some embodiments, the additional therapeutic agent is a second conjugate comprising a phthalocyanine dye and a targeting molecule. In some aspects, the second conjugate contains the same or different phthalocyanine dye and/or targeting molecule as the conjugate.

In some embodiments, one or more of the biomarkers described herein, can be assessed before, during and/or after one or more steps of the therapy involving PIT (both as a monotherapy and/or a combination therapy), to monitor, evaluate and/or guide the therapy and the treatment regime. In some aspects, the one or more of the biomarkers described herein can be employed in monitoring of the therapy and/or diagnostic, prognostic purposes and/or to increase or improve the efficacy or effectiveness of the treatment.

In some aspects, the one or more biomarker(s) measured can be employed to select subjects for particular treatment, or modification of a particular treatment or for treatment with an additional therapeutic agent (e.g., a combination therapy), such as for tailoring or customizing aspects of therapeutic regimen, e.g., for personalized medicine.

In some of any of the provided embodiments, the level, concentration and/or amount of at least one biomarker(s) present in a sample from a subject, e.g., a subject who is a candidate for and/or has received PIT, can be assessed using any of the exemplary methods for assessing biomarkers described herein, e.g., in Section II. In some of any of the provided embodiments, the therapeutic regimen of PIT as a monotherapy and/or combination therapy can be selected based on the assessment of one or more of the biomarkers. In some embodiments, exemplary steps for implementing the PIT as a monotherapy and/or as a part of a combination therapy and reagents, include those described herein, e.g., in Section III. In some aspects, exemplary phthalocyanine-targeting molecule conjugates used as part of the PIT in any of the embodiments provided herein, include those described herein, e.g., in Section IV.

In some aspects, provided herein are methods of treating a tumor in a subject that involves the steps of: a) administering to a subject having a tumor a conjugate comprising a phthalocyanine dye linked to a targeting molecule that binds to a protein on the surface of a cell present in the microenvironment of the tumor; b) measuring in a sample from the subject the level of expression of at least one biomarker(s), such as an immune cell surface marker (e.g., indicative of immune cell activation), a checkpoint pathway marker, a cytokine and/or a chemokine; c) irradiating an area proximal to a tumor, for example, with absorbing light, such as NIR light, for example, at a wavelength of 500 nm to 900 nm at a dose of at least 1 J $cm^{-2}$ or 1 J/cm of fiber length; and d) measuring the level of expression of the at least one biomarker(s) after the irradiation and determining whether the level of the at least biomarker is increased in the subject relative to the level measured prior to the irradiation. In some embodiments, if the level is increased, the subject is administered an additional therapeutic agent, e.g., administering immune modulating agent or an anti-cancer agent, thereby treating the tumor. In some aspects, the increase of the level of the one or more biomarkers, such as checkpoint pathway markers, is a result of cell death mediated by PIT. In some aspects, administering an additional therapeutic agent can increase the efficacy of the treatment.

In some aspects, the provided methods involve measuring or assessing the biomarker after performing one or more steps of the PIT, e.g., administering the conjugate and/or irradiation with light. In some aspects, the provided methods of treating a tumor in a subject include: a) administering to a subject a conjugate comprising a phthalocyanine dye linked to a targeting molecule capable of binding to a molecule on the surface of a cell present in the microenvironment of the tumor; b) irradiating an area proximal to a tumor with absorbing light, such as NIR light, for example, at a wavelength of 500 nm to 900 nm at a dose of at least 1 J $cm^{-2}$ or 1 J/cm of fiber length, wherein the treatment of the tumor with the conjugate followed by light irradiation primes activation of immune cells; and c) measuring the level of expression of at least one biomarker(s), such as a checkpoint pathway marker, in a sample from a subject. In some embodiments, if the level of expression of the at least one biomarker is at or above a threshold level, the methods include administering to the subject a therapeutically effective amount of an additional therapeutic agent, e.g., an immune modulating agent or an anti-cancer agent; thereby treating the tumor.

In some aspects, the provided methods of treating a tumor in a subject include: a) administering to a subject a conjugate comprising a phthalocyanine dye linked to a targeting molecule capable of binding to a molecule on the surface of a cell present in the microenvironment of the tumor; b) irradiating an area proximal to a tumor at a wavelength of 500 nm to 900 nm at a dose of at least 1 J $cm^{-2}$ or 1 J/cm of fiber length, wherein the treatment of the tumor with the conjugate followed by light irradiation primes activation of immune cells; and c) measuring the level of expression of at least one biomarker(s), such as an immune cell surface marker (e.g., indicative of immune cell activation, a cytokine and/or a chemokine, in a sample from a subject. In some embodiments, if the level of expression of the at least one biomarker is below a threshold level, administering to the subject one or more additional doses of the conjugate and irradiating the tumor; thereby treating the tumor. In some aspects, administering an additional therapeutic agent can increase the efficacy of the treatment.

In some aspects, the provided methods of treating a tumor in a subject, in which the subject is selected for treatment based on the level of expression of at least one biomarker(s) measured prior to and/or after performing one or more steps of PIT. In some embodiments, the provided methods of treating a tumor in a subject involve a) measuring in a sample from each of the subjects in the population the level of expression of at least one biomarker(s); b) selecting the subject for treatment if the expression of the at least one biomarker(s) is at or above a threshold; c) administering to the selected subject a conjugate comprising a phthalocyanine dye linked to a targeting molecule that binds to a protein on the surface of a cell present in the microenvironment of the tumor; and d) irradiating an area proximal to a tumor at a wavelength of 500 nm to 900 nm at a dose of at least 1 J $cm^{-2}$ or 1 J/cm of fiber length, thereby treating the tumor.

In some aspects, the methods also include e) measuring in a sample from the subject the level of expression of the at least one biomarker(s), such as a checkpoint pathway marker, after the irradiation and determining whether the level of the at least one at least one biomarker(s) is increased in the subject compared to the level measured prior to the irradiation; and f) if the level is increased, administering an additional therapeutic agent, e.g., an immune modulating agent, such as a checkpoint inhibitor, or an anti-cancer agent, to the subject.

In some aspects, the methods also include e) measuring in a sample from the subject the level of expression of the at least one biomarker(s), such as an immune cell surface marker that is indicative of immune cell activation, a cytokine and/or a chemokine, after the irradiation and determining whether the level of the at least one at least one biomarker(s) is increased in the subject compared to the level measured prior to the irradiation; and f) if the level is decreased, administering an additional therapeutic agent, e.g., an immune modulating agent or an anti-cancer agent, to the subject. In some aspects, administering an additional therapeutic agent can increase the efficacy of the treatment.

In some aspects, provided herein are methods of improving the efficacy of treatment of disease or a condition, such as a tumor treatment. In some embodiments, the methods involve: a) measuring in sample from a subject having a tumor the level of expression of at least one biomarker(s), such as an immune cell surface marker that is indicative of immune cell activation, a checkpoint pathway marker, a cytokine and/or a chemokine, and determining whether the level of expression of the at least one biomarker(s) is at or above a threshold; b) administering to the subject a conjugate comprising a phthalocyanine dye linked to a targeting molecule that binds to a protein on the surface of a cell present in the microenvironment of the tumor; and c) irradiating an area proximal to a tumor at a wavelength of 500 nm to 900 nm at a dose of at least 1 J $cm^{-2}$ or 1 J/cm of fiber length. In some embodiments, if the level of expression of the at least one biomarker(s), such as a checkpoint pathway marker, is at or above the threshold, the methods include administering an additional therapeutic agent, e.g., an immune modulating agent, such as a checkpoint inhibitor, or an anti-cancer agent, to the subject; thereby improving the efficacy of the tumor treatment.

In some aspects, the provided methods of improving the efficacy of a tumor treatment includes: a) measuring in sample from a subject having a tumor the level of expression of at least one checkpoint pathway marker(s) and determining whether the level of expression of the at least one checkpoint pathway marker(s) is at or above a threshold; b) administering to the subject a conjugate comprising a phthalocyanine dye linked to a targeting molecule that binds to a protein on the surface of a cell present in the microenvironment of the tumor; and c) irradiating an area proximal to a tumor at a wavelength of 500 nm to 900 nm at a dose of at least 1 J $cm^{-2}$ or 1 J/cm of fiber length. In some embodiments, if the level of expression of the at least one checkpoint pathway marker(s) is at or above the threshold, further administering checkpoint inhibitor to the subject; thereby improving the efficacy of the tumor treatment. In some aspects, high levels of certain biomarkers, such as a checkpoint pathway marker, in a sample obtained prior to PIT, may be associated with certain outcomes of treatment, such as having a reduced likelihood of response to PIT.

In some aspects, the provide method of improving the efficacy of a tumor treatment involve the steps of: a) measuring in sample from a subject having a tumor the level of expression of at least one biomarker(s) and determining whether the level of expression of the at least one biomarker(s), such as an immune cell surface marker, a cytokine and/or a chemokine, is at or below a threshold; b) administering to the subject a conjugate comprising a phthalocyanine dye linked to a targeting molecule that binds to a protein on the surface of a cell present in the microenvironment of the tumor; and c) irradiating an area proximal to a tumor at a wavelength of 500 nm to 900 nm at a dose of at least 1 J $cm^{-2}$ or 1 J/cm of fiber length. In some embodiments, if the level of expression of the at least one biomarker(s) is at or below the threshold, the methods include administering an additional therapeutic agent, e.g., an immune modulating agent or an anti-cancer agent, to the subject; thereby improving the efficacy of the tumor treatment. In some aspects, high levels of certain biomarkers, such as cytokines, in a sample obtained prior to PIT, may be associated with certain outcomes of treatment, such as having an objective response to PIT, as a monotherapy and/or for a combination therapy.

In some aspects, the methods involving measurement and assessment of one or more biomarker(s), can be employed to monitor the outcome of treatment, e.g., response, of a subject to a treatment, e.g., PIT as a monotherapy and/or in a combination therapy. In some aspects, the one or more biomarkers can be assessed in a sample obtained after performing one or more steps of the PIT and/or the combination therapy. In some aspects, the level of biomarkers can be indicative of or is associated with the progression of treatment, and/or associated with the likelihood of achieving a particular outcome, e.g., response. For example, in some aspects, certain biomarkers, e.g., markers indicative of immune cell activation, cytokine or chemokine production, and immunogenic cell death markers, are indicative of tumor cell death by PIT. In some aspects, the markers can be also indicative of generation of an immunosuppressive tumor microenvironment (TME). In some aspects, the methods can also be used to monitor the outcome of treatment and to identify, tailor or modify the therapeutic regimen, such as doses, timing, treatment regime and/or administration of an additional therapeutic agent, for a particular subject.

In some aspects, the provided methods of monitoring a response to treatment with PIT, e.g., involving administering a conjugate comprising a phthalocyanine dye linked to a targeting molecule and light treatment, include: a) administering to a subject a conjugate comprising a phthalocyanine dye linked to a targeting molecule capable of binding to a molecule on the surface of a cell present in the microenvironment of the tumor; b) irradiating an area proximal to a tumor at a wavelength of 500 nm to 900 nm at a dose of at least 1 J $cm^{-2}$ or 1 J/cm of fiber length; and c) measuring the level of expression of at least one biomarker(s) in a sample from a subject; wherein the subject is identified as having a high likelihood of response if the level of expression of the at least one biomarker(s) is at or above a threshold level.

In some aspects, the provided methods of monitoring a response to treatment with PIT involves a) administering to a subject a conjugate comprising a phthalocyanine dye linked to a targeting molecule capable of binding to a molecule on the surface of a cell present in the microenvironment of the tumor; b) irradiating an area proximal to a tumor at a wavelength of 500 nm to 900 nm at a dose of at least 1 J $cm^{-2}$ or 1 J/cm of fiber length; and c) measuring the level of expression of at least one biomarker(s) in a sample from a subject; wherein the subject is identified as having a high likelihood of response if the level of expression of the at least one biomarker(s) is at or below a threshold level.

In some aspects, the methods involving measurement and assessment of one or more biomarker(s), can be employed to assess the likelihood of response of a subject to a treatment, e.g., PIT as a monotherapy and/or in a combination therapy. In some aspects, the methods can also be used to identify and/or select subjects for therapy that exhibit a high likelihood of responding to the therapy. In some embodiments, such assessment or evaluation can be used in identifying, tailoring or modifying therapeutic regimen, such as doses, timing, treatment regime and/or administration of an additional therapeutic agent, for a particular subject.

In some aspects, provided are methods of assessing the likelihood of response to treatment with PIT, e.g., involving administering a conjugate comprising a phthalocyanine dye linked to a targeting molecule accompanied by or followed by light treatment. In some aspects, provided are methods of assessing the likelihood of response to treatment with PIT as a monotherapy and/or a combination therapy. In some embodiments, the methods involve a) measuring the level of expression of at least one biomarker(s) in a sample from a subject; and b) identifying the subject as having a high likelihood of response to treatment with a conjugate comprising a phthalocyanine dye linked to a targeting molecule capable of binding to a molecule on the surface of a cell present in the microenvironment of the tumor if the level of expression of the at least one biomarker(s) is at or above a threshold level. In some aspects, high levels of certain biomarkers, such as cytokines, in a sample obtained prior to PIT, may be associated with certain outcomes of treatment, such as having an objective response to PIT, as a monotherapy and/or for a combination therapy.

In some aspects, the provided methods of assessing the likelihood of response to treatment with a conjugate comprising a phthalocyanine dye linked to a targeting molecule involve a) measuring the level of expression of at least one biomarker(s) in a sample from a subject; and b) identifying the subject as having a low likelihood of response to treatment with a conjugate comprising a phthalocyanine dye linked to a targeting molecule capable of binding to a molecule on the surface of a cell present in the microenvironment of the tumor if the level of expression of the at least one biomarker(s) is at or below a threshold level. In some aspects, high levels of certain biomarkers, such as a checkpoint pathway marker, in a sample obtained prior to PIT, may be associated with certain outcomes of treatment, such as having a reduced likelihood of response to PIT.

In some of any such embodiments, the methods can also involve administering to the selected subject a therapeutically effective amount of the conjugate. In some of any such embodiments, the methods can also involve irradiating an area proximal to a tumor with absorbing light, such as NIR light, for example, at a wavelength of 500 nm to 900 nm at a dose of at least 1 J $cm^{-2}$ or 1 J/cm of fiber length.

In some of any of the embodiments provided herein, if the subject is identified as having a low likelihood of response, the methods also include administering to the subject a therapeutically effective amount of an additional therapeutic agent, e.g., an immune modulating agent or an anti-cancer agent., and/or an additional administration of the PIT, e.g., administering a conjugate comprising a phthalocyanine dye linked to a targeting molecule accompanied by or followed by light treatment.

In some aspects, provided herein are methods of treating subjects having a high likelihood of response within a population of subjects having a tumor. In some aspects, the methods involve identifying subjects that have a high likelihood of response, based on assessment or measurement of the level, amount or concentration of one or more biomarkers, such as any described herein. In some aspects, the methods involve: a) measuring in a sample from each of the subjects in the population the level of expression of at least one biomarker(s); b) identifying the subject as having a high likelihood of response if the expression of the at least one biomarker(s) is at or above a threshold; c) administering to the subjects identified as having a high likelihood of response a conjugate comprising a phthalocyanine dye linked to a targeting molecule that binds to a protein on the surface of a cell present in the microenvironment of the tumor; and d) irradiating an area proximal to a tumor at a wavelength of 500 nm to 900 nm at a dose of at least 1 J $cm^{-2}$) or 1 J/cm of fiber length, thereby treating the tumor in the subjects identified as having a high likelihood of response.

In some aspects, the methods involve identifying and treating subjects that have a high likelihood of response, based on assessment or measurement of the level, amount or concentration of one or more biomarkers, such as any described herein. In some aspects, the methods involve: a) measuring in a sample from each of the subjects in the population the level of expression of at least one biomarker(s), for example, immune cell surface markers and/or checkpoint pathway markers; b) identifying the subject as having a high likelihood of response if the expression of the at least one biomarker(s) is at or above a threshold; c) administering to the subjects identified as having a high likelihood of response a conjugate comprising a phthalocyanine dye linked to a targeting molecule that binds to a protein on the surface of a cell present in the microenvironment of the tumor; and d) irradiating an area proximal to a tumor at a wavelength of 500 nm to 900 nm at a dose of at least 1 J $cm^{-2}$ or 1 J/cm of fiber length, thereby treating the tumor in the subjects identified as having a high likelihood of response. In some embodiments, the methods also include e) measuring in a sample from the subject the level of expression of the at least one biomarker(s) after the irradiation and determining whether the level of the at least one at least one biomarker(s) is increased in the subject compared to the level measured prior to the irradiation; and f) if the level is increased, administering an additional therapeutic agent, e.g., an immune modulating agent, for example, a checkpoint inhibitor, or an anti-cancer agent, to the subject.

In some aspects, the methods involve: a) measuring in a sample from each of the subjects in the population the level of expression of at least one biomarker(s); b) identifying the subject as having a high likelihood of response if the expression of the at least one biomarker(s) is at or below a threshold; c) administering to the subjects identified as having a high likelihood of response a conjugate comprising a phthalocyanine dye linked to a targeting molecule that binds to a protein on the surface of a cell present in the microenvironment of the tumor; and d) irradiating an area proximal to a tumor at a wavelength of 500 nm to 900 nm at a dose of at least 1 J $cm^{-2}$ or 1 J/cm of fiber length, thereby treating the tumor in the subjects identified as having a high likelihood of response. In some embodiments, the methods also include e) measuring in a sample from the subject the level of expression of the at least one biomarker(s) after the irradiation and determining whether the level of the at least one at least one biomarker(s) is increased in the subject compared to the level measured prior to the irradiation; and f) if the level is decreased, administering an additional therapeutic agent, e.g., an immune modulating agent or an anti-cancer agent, to the subject.

Also provided are methods of selecting subjects for treatment with PIT, e.g., as a monotherapy and/or a combination therapy, based on the assessment of one or more biomarkers. In some aspects, subjects who are likely to respond to the treatment with PIT, as a monotherapy and/or in a combination therapy, are selected for PIT and/or a combination therapy involving PIT.

In some aspects, provided are methods of selecting subjects for treatment with an additional therapeutic agent, e.g., an immune modulating agent, such as an immune checkpoint inhibitor, or an anti-cancer agent, in addition to the PIT, for example, as a combination therapy. In some embodiments, the methods involve: a) administering to a subject a conjugate comprising a phthalocyanine dye linked to a targeting molecule capable of binding to a molecule on the surface of a cell present in the microenvironment of the tumor; b) irradiating an area proximal to a tumor at a wavelength of 500 nm to 900 nm at a dose of at least 1 J $cm^{-)}$ or 1 J/cm of fiber length; and c) measuring the level of expression of at least one biomarker(s) in a sample from a subject. In some embodiments, if the level of expression of the at least one biomarker(s) is at or above a threshold level, the subject is selected for treatment with an additional therapeutic agent, e.g., an immune modulating agent or an anti-cancer agent. In some of any such embodiments, the methods also involve administering to the selected subject a therapeutically effective amount of the additional therapeutic agent, e.g., immune modulating agent or anti-cancer agent.

In some embodiments, the provided methods of selecting subjects for treatment with a conjugate comprising a phthalocyanine dye linked to a targeting molecule involve: a) measuring the level of expression of at least one biomarker(s) in a sample from a subject; b) if the level of expression of the at least one biomarker(s) is at or above a threshold level, selecting the subject for treatment with a conjugate comprising a phthalocyanine dye linked to a targeting molecule capable of binding to a molecule on the surface of a cell present in the microenvironment of the tumor.

In some embodiments, the provided methods of selecting subjects for treatment with a conjugate comprising a phthalocyanine dye linked to a targeting molecule, the method comprising: a) measuring the level of expression of at least one biomarker(s) in a sample from a subject; and b) selecting the subject for treatment with a conjugate comprising a phthalocyanine dye linked to a targeting molecule capable of binding to a molecule on the surface of a cell present in the microenvironment of the tumor and an additional therapeutic agent, e.g., an immune modulating agent or an anti-cancer agent, if the level of expression of the at least one biomarker(s) is at or below a threshold level.

Also provided are methods of increasing expression of at least one biomarker(s) in a subject having a tumor. In some aspects, by virtue of tumor cell killing by the PIT, the level, concentration and expression of certain biomarkers can be altered, e.g., increased, in a sample from the subject. In some aspects, PIT can result in immunogenic cell death of the target cells, a specific type of cell death exhibited by necrotic cells, which is characterized by increased presentation and release of immune stimulatory markers. In some of any of the embodiments provided herein, the administration of the conjugate followed by irradiation primes activation of immune cells. In some aspects, the provided methods can result in increased expression of one or more biomarkers. In some aspects, the methods involve a) administering to a subject having a tumor, a conjugate comprising a phthalocyanine dye linked to a targeting molecule that binds to a protein on the surface of a cell present in the microenvironment of the tumor; and b) after administering the conjugate, irradiating an area proximal to a tumor at a wavelength of 500 nm to 900 nm at a dose of at least 1 J $cm^{-2}$ or 1 J/cm of fiber length; thereby increasing the expression of the at least one biomarker(s) compared to the expression of the at least one biomarker(s) without the irradiation.

In some of any of the embodiments provided herein, the methods, such as methods of treatment using PIT as a monotherapy and/or in a combination therapy, informed by assessment based on the one or more biomarkers, provides a synergistic and/or additive treatment effect compared to treatment by the conjugate alone or the additional therapeutic agent, e.g., an immune modulating agent such as a checkpoint inhibitor, a cytokine and/or a chemokine, or an anti-cancer agent, alone. In some aspects, the method provides a synergistic and/or additive treatment effect compared to treatment by the conjugate alone or the immune modulating agent alone. In some embodiments, the method provides a synergistic and/or additive treatment effect compared to treatment by the conjugate alone or the checkpoint inhibitor alone. In some embodiments, the method provides a synergistic treatment effect compared to treatment by the conjugate alone or the immune modulating agent alone. In some embodiments, the method provides a synergistic treatment effect compared to treatment by the conjugate alone or the checkpoint inhibitor alone.

In some of any of the provided embodiments, the measured level, concentration or amount of expression of the one or more biomarkers can be compared to a threshold level or value of that particular biomarker. In some embodiment, the threshold level or value for the particular biomarker can be determined as described herein, for example, by evaluating the level, concentration or amount of expression of the particular biomarker in a group of subjects who ultimately exhibit a particular outcome of treatment, such as objective response (OR), partial response (PR) or complete response (CR), for example, a group of responders. In some aspects, the threshold for the particular one or more biomarker can be determined as described herein, for example, by evaluating the level, concentration or amount of expression of the particular biomarker in a group of subjects who ultimately exhibit other a particular outcome of treatment, such as stable disease (SD) and/or progressive disease (PD), for example, non-responders.

In some aspects, the provided embodiments, including methods of treatment and methods of assessing likelihood of a response to a photoimmunotherapy (PIT) as a monotherapy and/or combination therapy involve assessing a sample for the level, amount or concentration of expression of at least one biomarker(s), and comparing the level, amount or concentration to a threshold level. In some aspects, the provided embodiments, including methods of treatment and methods of assessing likelihood of a response to a PIT monotherapy and/or combination therapy involve assessing a sample for the level, amount or concentration of expression of at least one biomarker(s), and comparing the level, amount or concentration to the level, amount or concentration of the biomarker from a different sample or at a different time point. In some embodiments, the threshold is determined by a subject's or population of subjects' the level, amount or concentration of at least one biomarker(s) under a first condition. The first condition may be a baseline (untreated level) level, amount or concentration from the same cells or tissues or a different set of cells or tissue. The first condition may be a level, amount or concentration measured at a first time point.

In some embodiments, the subject is likely to achieve a response when treated with the PIT if the level of at least one biomarker(s) is at or above the threshold value; or the subject is not likely to achieve a response when treated with the PIT if the level of at least one biomarker(s) is below the threshold value. In some embodiments, the subject is likely to achieve a response when treated with the PIT if the level of at least one biomarker(s) is below the threshold value; or the subject is not likely to achieve a response when treated with the PIT if the level of at least one biomarker(s) is at or above the threshold value. In some embodiments, the threshold value is within 25%, within 20%, within 15%, within 10% or within 5% and/or is within a standard deviation above the median or mean level of at least one biomarker(s) in samples obtained from a group of subjects, wherein each of the subjects of the group went on to exhibit stable disease (SD) and/or progressive disease (PD) and/or did not respond to the therapy. In some embodiments, the threshold level is within 25%, within 20%, within 15%, within 10% or within 5% and/or is within one or two standard deviation(s) below the median or mean level of at least one biomarker(s) in samples obtained from a group of subjects, wherein each of the subjects of the group went on to achieve a response after administration of the PIT. In some embodiments, the threshold value of at least one biomarker(s) is determined based on a median level of at least one biomarker(s) observed from a group of subjects that achieved a response after administration of the PIT. In some embodiments, the response achieved by the group of subjects is a complete response (CR) and/or a partial response (PR). In some embodiments, the response is durable at 3 months. In some embodiments, the threshold value of at least one biomarker(s) is within 25%, within 20%, within 15%, within 10% or within 5% and/or is within one or two standard deviation(s) below the median or mean level of at least one biomarker(s) in samples obtained from a group of subjects after the initiation of administration of the PIT that achieved a complete response (CR). In some embodiments, the threshold value of at least one biomarker(s) is within 25%, within 20%, within 15%, within 10% or within 5% and/or is within a standard deviation below the median or mean level of at least one biomarker(s) in samples obtained from a group of subjects that achieved a partial response (PR).

In some embodiments, the response achieved by a subject can be based on any appropriate criteria known for the particular indication, e.g., particular type of cancer. In some embodiments, the response is a complete response (CR) and/or a partial response (PR). In some embodiments, the response is durable. In some embodiments, the response is durable for greater than 3 months, 4 months, 5 months, or 6 months. In some aspects, the response includes a durable response, e.g., a response that is durable for at least 3, 4, 5, 6, 7, 8, 9, 10, 11, 12 or 18 months or longer, such as 2 years, 3 years, 4 years or longer, when treated with the PIT and/or combination therapy. In some embodiments, the at least one biomarker(s) is associated with a particular response, efficacy or survival outcome, such as partial response (PR) or partial remission, complete response (CR) or complete remission, progression-free survival (PFS), objective response rate (ORR), overall survival (OS), event-free survival (EFS), symptom endpoints (patient reported outcomes), disease-free survival (DFS), time to progression, increased duration of response (DOR) or increased survival rate. In some aspects, upon administration of a therapeutic composition or a unit dose, a plurality of subjects among the group is likely to exhibit or is associated with increased progression-free survival (PFS). In some aspects, the provided methods employing at least one biomarker(s) can be used to determine the likelihood of a subject to achieve a particular response, efficacy or survival outcome. In some embodiments, a threshold value for a particular biomarker can be obtained based on measurements or values obtained from a group of subjects who ultimately achieved the particular response, efficacy or survival outcome.

In some embodiments, the methods involve assessing a parameter associated with the at least one biomarker(s), such as a change in the level, expression or level of a biomarker between one or more time points, e.g., prior to initiation of PIT as a monotherapy and/or combination therapy and after initiation of PIT as a monotherapy and/or combination therapy. In some embodiments, the degree or magnitude of the change, e.g., increase or decrease, is assessed to determine the likelihood of response and/or to select subjects for treatment.

In some embodiments, the methods of assessing likelihood of a response to a PIT as a monotherapy and/or combination therapy involves assessing the change in the level, amount or concentration of the at least one biomarker(s) in one or more sample(s) from a subject. In some embodiments, the change is determined between a first sample obtained prior to administration of therapy and a second sample obtained after the initiation of administration of the PIT as a monotherapy and/or combination therapy. In some embodiments, pre- and post-treatment samples are obtained from the same subject. In some embodiments, the pre- and post-treatment samples are compared. In some embodiments, paired samples from a subject can be taken pre-treatment as a baseline for assessing likelihood of response and post-treatment, after the PIT or after a combination therapy to assess or monitor response.

In some embodiments, the subject has a disease or condition, and has previously received administration of a PIT and/or combination therapy comprising administration of a conjugate comprising a phthalocyanine dye linked to a targeting molecule, for treating the disease or condition. In some embodiments, the methods involve comparing the increase in the level, amount or concentration of the at least one biomarker(s) in the second sample compared to the first sample or to a threshold value, thereby determining a likelihood that a subject will achieve a response when treated with the PIT as a monotherapy and/or combination therapy. In some embodiments, the subject is likely to achieve a response when treated with the PIT as a monotherapy and/or as a combination therapy if the increase in the level, amount or concentration of the at least one biomarker(s) in the second sample compared to the first sample is at or above a threshold level; or the subject is not likely to achieve a response when treated with the PIT as a monotherapy and/or combination therapy if the increase in the level, amount or concentration of the at least one biomarker(s) in the second sample compared to the first sample that is below the threshold value. In some embodiments, if the subject is determined not likely to achieve a response at a desired level with a first administration of PIT, the subject can be selected for administration of with an additional therapeutic agent, such as an immune modulating agent, e.g., a checkpoint inhibitor, or one or more additional doses of the PIT.

In some embodiments, provided are methods of selecting a subject for treatment with an agent that involves assessing the level, amount or concentration of the at least one biomarker(s) in one or more sample(s) from a subject having a tumor, said subject being a candidate for administration of a PIT as a monotherapy and/or combination therapy comprising administration of a conjugate comprising a phthalocyanine dye linked to a targeting molecule, wherein a first sample is obtained from the subject prior to administration of the PIT and/or combination therapy and a second sample is obtained after the initiation of administration of the PIT and/or combination therapy, wherein the subject is selected for administration of a subsequent therapeutic agent if an increase in the level, amount or concentration of the at least one biomarker(s) in the second sample compared to the first sample is below a threshold level.

In some embodiments, the methods of assessing likelihood of a response to a PIT as a monotherapy and/or combination therapy involves assessing the change in the level, amount or concentration of the at least one biomarker(s) in one or more sample(s) from a subject. In some embodiments, the change is determined between a first sample obtained prior to administration of the PIT as a monotherapy and a second sample obtained after the initiation of administration of the PIT.

In some embodiments, the assessment can be performed using a second sample from the subject that is obtained after the initiation of administration of the PIT as a monotherapy and/or combination therapy. In some embodiments, the second sample from the subject is obtained within or within about 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 days after the initiation of administration of the PIT and/or the combination therapy. In some embodiments, the second sample from the subject is obtained after or after about 10, 20, 30, 40, 50, 60, 70, 80, 90 days or more, or about 1, 2, 3, 4, 5, 6, 7, 8, 9, 10, 11, 12 month or more after the initiation of administration of the therapy or one or more steps of the therapy, e.g., PIT and/or combination therapy. In some embodiments, the assessment can be performed more than once, e.g., at more than one different time points after the initiation of administration of the PIT and/or combination therapy, e.g., for monitoring and/or periodic assessment of the treated subjects.

In some of any such embodiments, an exemplary threshold level can be determined based on the increase in the level, amount or concentration of the at least one biomarker(s) in the second sample compared to the first sample observed in a subject group that ultimately did not show objective response, e.g., from a subject group wherein each of the subjects went on to exhibit stable disease (SD) and/or progressive disease (PD). In some embodiments, the threshold level is within 25%, within 20%, within 15%, within 10% or within 5% and/or is within a standard deviation above the median or mean increase in the level, amount or concentration of the at least one biomarker(s) in the second sample compared to the first sample obtained from a group of subjects after the initiation of administration of the PIT and/or combination therapy, wherein each of the subjects of the group went on to exhibit stable disease (SD) and/or progressive disease (PD).

In some of any such embodiments, an exemplary threshold level can be determined based on the increase in the level, amount or concentration of the at least one biomarker(s) in the second sample compared to the first sample observed in a subject group that ultimately achieved objective response, e.g., from a subject group wherein each of the subjects went on to achieve complete response (CR) and/or a partial response (PR). In some embodiments, the threshold level is within 25%, within 20%, within 15%, within 10% or within 5% and/or is within a standard deviation above the median or mean increase in the level, amount or concentration of the at least one biomarker(s) in the second sample compared to the first sample obtained from a group of subjects after the initiation of administration of the PIT and/or combination therapy, wherein each of the subjects of the group went on to achieve a complete response (CR) and/or a partial response (PR).

II. ASSESSMENT OF BIOMARKERS

Provided herein are methods to methods of treating a tumor in a subject, methods of selecting subjects for treatment, and methods to assess, predict, infer, monitor, and/or estimate likelihood of a response to a treatment or a therapy, such as a photoimmunotherapy (PIT) as a monotherapy and/or a combination therapy, based on measurement of the level, amount or concentration of a specified biomarker. Provided are methods of assessing the likelihood of a response and/or method of predicting a response to a treatment, e.g., PIT. Also provided are methods to identify and/or select subjects for PIT and/or a combination therapy, based on measurement of the level, amount or concentration of a specified biomarker. Methods also are provided for monitoring a subject for response, such as for the likelihood of developing or achieving a response to the therapy.

In certain embodiments, the biomarker, e.g., immune cell biomarker or a tumor cell biomarker, is assessed in a sample obtained from a subject that has a disease or condition and/or is suspected of having a disease or condition, such as a tumor or a cancer. In some embodiments, the subject has received, will receive, or is a candidate to receive a therapy for the disease or condition, such as a tumor or a cancer. In some embodiments, the therapy is a PIT. In some embodiments, the therapy is a combination therapy, such as a combination therapy with a PIT and an additional therapeutic agent, e.g., an immune modulating agent, such as an immune checkpoint inhibitor, or an anti-cancer agent. In certain embodiments, the PIT and/or combination therapy treats and/or is capable of treating the disease or condition, such as a tumor or a cancer.

In some embodiments, the methods involve assessing particular parameters associated with the biomarker in a sample from a subject. In particular embodiments, the sample is taken, collected, and/or obtained from a subject who has been, who will be, or is a candidate to be administered a therapy. In some embodiments the level of a biomarker in the sample is compared to a threshold level and then administered a PIT therapy to treat a disease or condition, such as a tumor, or is selected for PIT treatment, if the biomarker is higher or lower than a threshold, depending on the biomarker. In particular embodiments, subjects are administered a PIT therapy to treat a disease or condition, such as a tumor, if the measured level of a biomarker, such as an immune checkpoint biomarker, is lower than a threshold level for the biomarker. In such embodiments, the PIT therapy can be administered to a subject who has been, who will be, or is a candidate for a therapy, such as a surgery, chemotherapy, or immunotherapy. In some embodiments, the subject is treated with another therapy, such as a surgery, chemotherapy, or immunotherapy before and/or after administration of a PIT therapy.

In some embodiments, the method of selecting subjects for PIT treatment includes one or more steps including comparing the measured level of a biomarker to a threshold level for the biomarker. In some embodiments, the method for assessing the likelihood of a subject responding to a PIT includes one or more steps including comparing the assessed presence or level of a biomarker to a threshold value for the biomarker. In some embodiments, the method for assessing likelihood of a subject responding to a therapy includes assessing a change, e.g., an increase or decrease of a one or more biomarkers or the frequency or number of cells expressing such biomarkers, or an increase or decrease of one or more parameters associated with one or more biomarkers.

In some embodiments, the biomarker is assessed in a sample obtained from the subject. In particular embodiments of the provided methods, the sample is a biological sample, such as a tumor sample or a blood or serum sample, that is taken, collected, and/or obtained from a subject. In particular embodiments, the sample is taken, collected, and/or obtained from a subject who has been, who will be, or is a candidate to be administered a therapy. In particular embodiments, the sample is taken, collected, and/or obtained prior to the initiation of treatment with or administration of the therapy, e.g., the PIT. In some embodiments, the sample is taken, collected, and/or obtained after administration of the treatment with the therapy, e.g., the PIT. In some embodiments, the sample is a tumor biopsy sample or a serum or whole blood sample.

In some embodiments, one or more, such as at least one, biomarkers can be assessed and employed together. In some embodiments, 2, 3, 4, 5 or more biomarkers, such as 2, 3, 4, 5 or more of any of the biomarkers described herein, can be assessed together or using independent assays. In some embodiments, the at least biomarker(s) is 2 biomarkers. In some embodiments, the at least biomarker(s) is 3 biomarkers. In some embodiments, the at least biomarker(s) is 4 biomarkers. In some embodiments, the at least biomarker(s) is 5 biomarkers. In some embodiments of any of the methods and uses provided herein, at least one, such as 1, 2, 3, 4, 5 or more biomarkers, such as from any of the biomarkers described herein, are assessed and employed in the methods, e.g., to assess likelihood of response, identify and/or select subjects for treatment, and/or select treatment regimen and/or dosing of the therapy, e.g., the PIT and/or combination therapy. In some embodiments, two or more biomarkers are assessed in a sample. For example, the two or more biomarkers are part of a panel of biomarkers is assessed in a sample. In some further embodiments, one or more panels of biomarkers, each containing more than one biomarker, is assessed in a sample.

In particular embodiments, the biomarker, e.g., immune cell biomarker, is assessed in a subject who has been, who will be, or is a candidate to be administered a therapy.

In some embodiments, the assessing of the sample includes determining a frequency of cells expressing a particular biomarker. In some embodiments, frequency or number of cells can be assessed by flow cytometry or genomic analysis of the cells in a sample from a subject, such as a tumor sample. In some aspects, the biomarker is a soluble biomarker, and the level or concentration of a particular biomarker can be assessed, such as in a sample of serum or whole blood. Such assessment can be performed using any known methods or any described herein.

In some embodiments, the biomarker, e.g., immune cell biomarker, is assessed in a sample obtained from a subject that has or is suspected of having a condition or disease. In some embodiments, the subject has or is suspected of having a tumor, a cancer or proliferative disease. In particular embodiments, the subject has a disease or condition, or is suspected of having a disease or condition, that is associated with an antigen and/or is associated with diseased cells that express the antigen.

In some embodiments, the subject is administered, will be administered, or is a candidate to be administered a therapy, e.g., a PIT as a monotherapy and/or as a combination therapy. Further provided herein are methods of administering a PIT, such as methods of selecting a subject and administering a dose of PIT, wherein the subject is selected based on the likelihood of a response in the subject to a therapy. Also provided herein are methods of administering a PIT, such as methods of monitoring response in a subject after administration of the PIT. In some embodiments, provided are methods for selecting a subject for treatment: treatment with a PIT as a monotherapy and/or as a combination therapy with additional agent(s) or doses based on the likelihood of a response in the subject to one or more of the therapeutic agents.

In certain embodiments, the methods include steps to assess, determine, measure, and/or quantify the likelihood that a subject will respond to a PIT. In some embodiments, the subject's likelihood of response is assessed, determined, measured and/or quantified by a method of assessing a biomarker, such as described herein. In particular embodiments, if the subject is determined to be likely to, or highly likely to, respond to the therapy, the subject is administered a dose, such as an initial dose, of a PIT. In certain embodiments, the subject is determined to not be likely to have a response or to have a lesser response to the administered PIT, the subject is administered a modified dose of a PIT, for example a dose that is greater than the initial dose or an additional dose of the PIT. In particular embodiments, the subject is determined to not be likely to have a response or to have a lesser response to the administered PIT, the subject is also administered an additional agent or treatment capable of stimulating, amplifying, potentiating, and/or enhancing an anti-tumor immune response, such as any as an immune modulating agent.

In accord with methods, uses, compositions and articles of manufacture described herein, the biomarker, e.g., immune cell biomarker, is associated with and/or correlate to likelihood of response to the therapy.

A. Exemplary Biomarkers

In some embodiments, exemplary biomarkers assessed in the provided methods, e.g., involving photoimmunotherapy (PIT) as a monotherapy and/or a combination therapy, include markers associated with immune cell subtypes, subpopulations, phenotypes, activity and/or states; markers associated with disease state or disease burden, such as tumor-associated biomarkers; markers associated with a specific activity, function and/or a specific microenvironment, such as markers associated with activity or function, such as activation of immune cells, including cells of the innate or adaptive immune system. In some embodiments, the biomarker is any biomarker that can be measured by an assay, such as a bioassay. In some embodiments, the biomarker is a protein, nucleic acid (such as a messenger RNA (mRNA), DNA, mRNA mutation or DNA mutation), a lipid, or any combination thereof. In some embodiments, the biomarker is multiple molecules. In some embodiments, the biomarker is a cell type or a cell having a particular phenotype, such as a particular cell surface phenotype. In some embodiments, the biomarker is the density of a molecule or molecules, the density of a cell type or various cell types, the distance between molecules, the proximity of molecules, the distance between cells of the same type or different cell types, the proximity of a cells of the same type or different cell types. In some embodiments the biomarker is a ratio of molecules or cell types, wherein the ratio is of levels, densities, distances, proximities, of a molecule or molecules, cells of the same type or different cell types. In some embodiments, the biomarker is tumor mutational load or tumor mutational burden (TMB).

In some aspects, the biomarker is associated with an immunosuppressive state, such as factors involved in the checkpoint pathway. In some aspects, the exemplary biomarkers are associated with cells in the tumor microenvironment, such as immune cells present among the tumor cells and/or the tumor cells. In some aspects, the exemplary biomarkers are associated with immune function and/or immunogenic cell death. In some aspects, such biomarkers can be assessed in a sample from a subject, such as a sample from a subject who is a candidate for or has been administered a PIT, before the initiation of administration of PIT and/or after the initiation of administration of PIT. In some embodiments, the presence, number, frequency and/or density of cells expressing the at least one biomarker in a sample from the subject can be assessed using any of the methods or assays described herein.

In some embodiments, the assessed biomarker is a biomarker associated with a subtype and/or phenotype of immune cells. In some embodiments, the assessed biomarker is a biomarker indicative of and/or associated with a particular activity, function, phenotype or subtype of immune cells. In some embodiments, the biomarker is the presence or absence of one or more specific molecules, including surface molecules, transcription factors, and/or molecules that may accumulate or be produced by the cells or a subpopulation of immune cells. In some embodiments, the phenotype, as indicated by the presence, absence and/or expression of a biomarker, directly or inversely, indicates or is indicative of a biological activity of the cells or of a population of cells.

In some embodiments, the assessed biomarker is a marker expressed on immune cells, such as particular types of immune cells. In particular embodiments, the biomarker is present on, absent on and/or expressed on a type of immune cells, such as antigen-presenting cells (APCs), including dendritic cells (DCs), macrophages (MDs); natural killer cells (NK cells); and/or lymphocytes, such as T cells and/or B cells. In some embodiments, the biomarker is present on, absent on and/or expressed on immune cells from the body of the subject. In some embodiments, the assessed biomarker is an APC biomarker, e.g., a marker expressed on APCs. In some embodiments, the assessed biomarker is a DC biomarker, e.g., a marker expressed on DCs. In some embodiments, the assessed biomarker is a MO biomarker, e.g., a marker expressed on MOs. In some embodiments, the assessed biomarker is a NK cell biomarker, e.g., a marker expressed on NK cells. In some embodiments, the assessed biomarker is a T cell biomarker, e.g., a marker expressed on T cells. In some embodiments, the assessed biomarker is a biomarker indicative of or associated with a subtype, a subpopulation and/or phenotype of a T cell.

In some embodiments, the biomarker is a marker associated with a specific activity, function and/or a specific microenvironment, such as markers associated with immune system activity or function. In some embodiments, the biomarker is associated with activation of immune cells, such as cells in the innate immune system or adaptive immune system. In some embodiments, two or more, such as 2, 3 or 4 or more markers associated with immune cell activity and/or function, such as activity and/or function of APCs, DCs, MDs and/or NK cells, can be employed as biomarkers in any of the provided methods and uses. Exemplary biomarkers include, but are not limited to, one or more biomarkers selected from CCR4, CCR6, CD11c, CD123, CD127, CD14, CD141, CD16, CD163, CD1C, CD25, CD3, CD33, CD4, CD44, CD45RA, CD45RO, CD56, CD62L, CD68, CD69, CD8, CD86, CXCR3, HLA-DR, IL-10, IL-12p40, IL-6 PD1, PD-L1, and/or TNF.

In some aspects, the biomarker is a marker associated with activity and/or function of antigen-presenting cells (APCs). In some aspects, the biomarker is a marker that is expressed by or on the cell surface upon activation or is associated with differentiation and/or maturation of a particular immune cell, such as an APC, e.g., a DC or a MED. In some aspects, DCs can be identified by certain phenotypic markers, such as cells expressing or that is positive for cluster of differentiation 11c (CD11c), such as $CD11c^+$ cells. Exemplary biomarkers associated with activation and/or maturation of DCs include, but are not limited to, cluster of differentiation 80 (CD80), CD86, CD40 and major histocompatibility complex II (MHCII). In some aspects, some of such biomarkers are costimulatory molecules, for example, CD80, CD86 and CD40. In some embodiments, the biomarker is or includes or includes a high level of expression of MHCII ($MHCII^{high}$). In some embodiments, the at least one biomarker is selected from among one or more of CD80, CD86, CD40 and $MHCII^{high}$. In some embodiments, the biomarker is or includes CD80. In some embodiments, the biomarker is or includes CD86. In some embodiments, the biomarker is or includes CD40. In some embodiments, the at least one biomarker is CD86 and $MHCII^{high}$. In some embodiments, the at least one biomarker is CD86 and CD80. In some embodiments, the at least one biomarker is CD80 and $MHCII^{high}$. In some embodiments, the at least one biomarker is CD80, CD86 and $MHCII^{high}$.

In some aspects, the biomarkers are associated with activation and/or maturation of DCs and/or are expressed by DCs. In some aspects, exemplary biomarkers associated with activation and/or maturation of DCs include, but are not limited to, production of cytokines, such as pro-inflammatory cytokines. In some aspects, exemplary biomarkers associated with activation of DCs include, but are not limited to, one or more markers selected from tumor necrosis factor (TNF), IFN-γ-Inducible Protein 10 (IP-10), MIP-1α (Macrophage Inflammatory Protein-1 alpha), MIP-1β (Macrophage Inflammatory Protein-1 beta), interleukin-1 beta (IL-1β) and/or interleukin-8 (IL-8). In some aspects, other exemplary biomarkers associated with DCs include, but are not limited to, one or more markers selected from CD123, CD141, 7-AAD, CD14, HLA-DR and/or CD1C.

In some aspects, biomarkers are those associated with or expressed by monocytes. In some embodiments, exemplary biomarkers that are associated with or expressed by monocytes include, but are not limited to, one or more markers selected from CD16, CD86, 7-AAD, CD14, HLA-DR or CD163. In some aspects, other exemplary markers expressed by monocytes include CD4. In some aspects, the biomarkers include a cytokine or a chemokine expressed by or produced by monocytes. In some aspects, exemplary of such cytokines or chemokines expressed by or produced by monocytes include, but are not limited to, one or more of TNF, IL-10, IL-6 or IL-12p40.

In some aspects, the biomarker is or includes a marker associated with activity and/or function of natural killer cells (NK cells) or is expressed by NK cells. In some aspects, NK cells can be identified by certain phenotypic markers, such as cells expressing or that is positive for a marker, such as Integrin alpha-2 (also known as cluster of differentiation 49b (CD49b); in some aspects recognized by a monoclonal antibody designated DX5). In some aspects, NK cells can be identified by the lack of expression of certain phenotypic markers, such as cells that do not express or cells that are negative for a marker, such as cluster of differentiation 3 (CD3). In some aspects, NK cells can include CD3-CD49b+ cells (also referred to as CD3-DX5+ cells). In some embodiments, the biomarker is or includes associated with activation, maturation and/or cytolytic activity of NK cells. Exemplary biomarkers associated with activation, maturation and/or cytolytic activity of NK cells include, but are not limited to, CD69 and CD107a. In some embodiments, the biomarker is or includes CD69. In some embodiments, the biomarker is or includes CD107a. In some embodiments, the at least one biomarker is CD69 and CD107a. In some aspects, exemplary biomarker associated with NK cells include, but are not limited to, one or more of CD16, CD69, 7-AAD, CD33, CD56 and CD3.

In some embodiments, the biomarker is or includes biomarkers that are associated with and/or expressed by helper T cells, such as CD4+ helper T cells. In some embodiments, the biomarker is or includes biomarkers that are associated with activation and/or function of helper T cells. In some embodiments, exemplary biomarkers that are associated with helper T cells include, but are not limited to, one or more of CXCR3, CCR4, 7-AAD, CCR6, CD4 or CD3.

In some embodiments, the biomarker is or includes biomarkers that are associated with and/or expressed by effector or memory T cells, such as effector or memory CD8+ T cells. In some embodiments, the biomarker is or includes biomarkers that are associated with activation and/or function of effector or memory T cells. In some embodiments, exemplary biomarkers that are associated with effector or memory T cells include, but are not limited to, one or more of CXCR3, CD45RA, CD44, 7-AAD, CD8, CD45RO or CD62L.

In some embodiments, the biomarker is or includes a marker associated with immunosuppressive function, activity and/or immunosuppressive conditions, e.g., immunosuppressive conditions in the TME. In some embodiments, the biomarker is or includes markers associated with immunosuppression mediated by tumor cells in the TME. In some embodiments, the biomarker is expressed by various cells in the TME, for example, tumor cells. In some aspects, biomarkers can be expressed on immune cells such as DCs, Th1, Th2, CD8+ regulatory T cells (Tregs), B cells, CD4+ regulator T cells (Tregs), neutrophils, NK cells, γδ, and memory CD8+ (αβ) T cells. In some embodiments, the at least one biomarkers is or includes one or more of PD-1 (CD279), PD-L1 (CD274, B7-H1), PD-L2, CTLA-4, LAG-3 (CD223), TIM-3, 4-1BB (CD137), 4-1BBL (CD137L), GITR (TNFRSF18, AITR), CD40, OX40 (CD134, TNFRSF4), CXCR2, tumor associated antigens (TAA), B7-H3, B7-H4, BTLA, HVEM, GAL9, B7H3, B7H4, VISTA, KIR, 2B4 (belongs to the CD2 family of molecules and is expressed on all NK, γδ, and memory CD8+ (αβ) T cells), CD160 (also referred to as BY55) and/or CGEN-15049.

In some embodiments, two or more, such as 2, 3, 4, 5 or more checkpoint pathway markers, e.g., an immune checkpoint biomarker, can be employed as biomarkers in any of the provided methods and uses. For example, in some embodiments, the biomarker is or includes one or more of PD-1, PD-L1 and/or CTLA-4. In some embodiments, the biomarker, such as a an immune checkpoint biomarker, is or includes PD-1. In some embodiments, the biomarker, such as a an immune checkpoint biomarker, is or includes PD-L1. In some embodiments, the biomarker, such as a an immune checkpoint biomarker, is or includes CTLA-4. In some embodiments, the at least one biomarker is PD-1 and PD-L1. In some embodiments, the biomarker is a ratio of PD-L1 to PD-1 (PD-L1:PD-1 ratio). In some embodiments, the at least one biomarker is PD-1 and CTLA-4. In some embodiments, the at least one biomarker is PD-L1 and CTLA-4.

In some embodiments, the biomarker is associated with, expressed by, and/or is indicative of activation or function of regulatory T cells. In some aspects, exemplary biomarkers include, but are not limited to, one or more of CD4, CD127, 7-AAD, CD8, CD25 or CD3. In some embodiments the biomarkers include CD3, CD4 and PD1.

In some embodiments, the biomarker is or includes a marker associated with immunogenic cell death (ICD). In some aspects, immunogenic cell death is a specific type of cell death exhibited by necrotic cells and is characterized by increased presentation and release of immune stimulatory markers. Cells exhibiting ICD display membrane changes such as elevated surface expression of heat shock protein 90 (Hsp90), heat shock protein 70 (Hsp70), and secretion of soluble, intracellular markers known as danger associated molecular patterns (DAMPs), such as ATP and high-mobility group-box protein (HMGB1) (Kromer et al. (2013) Annual Review of Immunology, 31:51-72). In some aspects, at least one biomarker(s) is or includes one or more of Hsp90, Hsp70 and HMGB1. In some aspects, the biomarker is or includes HMGB1. In some aspects, the biomarker is or includes Hsp90. In some aspects, the biomarker is or includes Hsp70.

In some embodiments, the assessed biomarker is a biomarker associated with disease state or disease burden. In some embodiments, the assessed biomarker is a biomarker that is present and/or expressed in a disease or condition, e.g., a disease or condition to be treated with the PIT, e.g., as described herein. In some embodiments, the assessed biomarker is a molecule, an antigen or a marker associated with a cancer, a proliferative disease or a tumor. In some embodiments, the assessed biomarker is a biomarker that is expressed on cancer or tumor cells. In some embodiments, the biomarker is an antigen associated with a tumor or a cancer. Exemplary antigens associated with a tumor or cancer include, but are not limited to, epidermal growth factor receptor (EGFR) or Ephrin type-A receptor 2 (EphA2). In some embodiments, the biomarker is a biomarker expressed on one or more other cells in the tumor microenvironment (TME), such as tumor cells, endothelial cells, fibroblasts, adipocytes and/or pericytes. In some embodiments, the biomarker is or comprises a circulating tumor cell. In some embodiments, the biomarker is expressed in a circulating tumor cell. In some embodiments, the biomarker is expressed on tumor cells. In some embodiments, the biomarker is an antigen, e.g. a tumor antigen. In some embodiments, the biomarker is an antigen specifically targeted by the PIT, e.g., an antigen that is recognized by the targeting molecule contained in the conjugate for PIT. In some embodiments, the biomarker is indicative of tumor burden in a subject. In some embodiments, the biomarker is indicative of immunosuppressive pathway or activity in the subject.

In some embodiments, the at least one biomarker is a cell surface marker, and/or a soluble marker, such as a marker that can be produced by and/or secreted into the environment, and/or is present in the systemic circulation. In some embodiments, the at least one biomarker is or includes a cell surface marker. In some embodiments, the at least one biomarker is or includes a soluble marker, such as a secreted factor. In some embodiments, the at least one biomarker is a circulating tumor cell or is a marker expressed on a circulating tumor cell.

In particular embodiments, the biomarker is or includes the production or secretion of a soluble factor in response to one or more stimulations. In some embodiments, the biomarker is or includes a lack or production or secretion of a soluble factor in response to one or more stimulations. In certain embodiments, the soluble factor is a cytokine or a chemokine.

In some embodiments, the biomarker or the at least one biomarker is or include(s) one or more cytokines or chemokines. In some aspects, the concentration or relative concentration of production of the cytokine or chemokine is assessed. In some aspects, the biomarker is or includes one or more cytokines or chemokines selected from among one or more of tumor necrosis factor alpha (TNF-α), IFN-γ-Inducible Protein 10 (IP-10)/CXCL10, MIP-1α (Macrophage Inflammatory Protein-1 alpha)/CCL3, MIP-1β (Macrophage Inflammatory Protein-1 beta)/CCL4, interleukin-1 beta (IL-1β), interleukin-8 (IL-8)/CXCL8, 6CKine, BCA-1, CTACK, EGF, ENA-78, Eotaxin/CCL11, Eotaxin-2, Eotaxin-3, FGF-2, Flt-3 ligand, Fractalkine, G-CSF, GM-CSF, GRO, GRO alpha/CXCL1, I-309, ICAM-1/CD54, IFN alpha (IFN-α), IFN gamma (IFN-γ), IFN-α2, IFN-γ, IL-1 alpha (IL-1α), IL-10, IL-12 p40, IL-12p70, IL-13, IL-15, IL-16, IL-17A, IL-17A/CTLA-8, IL-18, IL-2, IL-20, IL-21, IL-22, IL-23, IL-27, IL-28A, IL-3, IL-31, IL-33, IL-4, IL-5, IL-6, IL-7, IL-9, interleukin-1 receptor antagonist (IL-1ra), IP-10, LIF, MCP-1, MCP-1/CCL2, MCP-2, MCP-3, MCP-4, MDC (CCL22), MIP-1d, PDGF-AA, PDGF-AB/BB, RANTES/CCL5, sCD40L, SCF, SDF-1α/CXCL12, SDF-1α+B, sE-Selectin, sP-Selectin, TARC, TGFα, tumor necrosis factor beta (TNF-β)/LTA, TPO, TRAIL, TSLP or VEGF.

In some aspects, the biomarker is or includes one or more cytokines or chemokines selected from among one or more of tumor necrosis factor alpha (TNF-α), IFN-γ-Inducible Protein 10 (IP-10)/CXCL10, MIP-1α (Macrophage Inflammatory Protein-1 alpha)/CCL3, MIP-1β (Macrophage Inflammatory Protein-1 beta)/CCL4, interleukin-1 beta (IL-1β), interleukin-8 (IL-8)/CXCL8, Eotaxin/CCL11, GRO alpha/CXCL1, GM-CSF, IFN alpha (IFN-α), IFN gamma (IFN-γ), IL-1 alpha (IL-1α), interleukin-1 receptor antagonist (IL-1ra), IL-2, IL-4, IL-5, IL-6, IL-7, IL-9, IL-10, IL-12p70, IL-13, IL-15, IL-17A/CTLA-8, IL-18, IL-21, IL-22, IL-23, IL-27, IL-31, MCP-1/CCL2, RANTES/CCL5, SDF-1α/CXCL12, and tumor necrosis factor beta (TNF-β)/LTA. In particular embodiments, the biomarker is or includes one or more cytokines or chemokines selected from among one or more of tumor necrosis factor alpha (TNF-α), IFN-γ-Inducible Protein 10 (IP-10), MIP-1α (Macrophage Inflammatory Protein-1 alpha), MIP-1β (Macrophage Inflammatory Protein-1 beta), interleukin-1 beta (IL-1β) and interleukin-8 (IL-8)/CXCL8.

In some of any of the provided embodiments, two or more, such as 2, 3, 4, 5 or more cytokines can be employed as biomarkers in any of the provided methods and uses.

In some embodiments, the assessed biomarker is a nucleic acid. In some embodiments, the biomarker is a DNA or an RNA, such as an mRNA. In some aspects, the concentration or relative concentration of one or more mRNA transcripts is assessed. In some embodiments, the biomarker is one or more mRNA transcripts selected from among APOE, BATF3, BBC3, BCL6B, CASP9, CCNB1, CCND1, CD40, CDC25C, CNTFR, COL11A2, CSF1, CSF2, CSF3, CTNNB1, DKK1, DLL4, EGF, EIF2B4, ERCC3, ESR1, FADD, FCGRT, FGF18, FUT4, FYN, GLS, GPC4, GZMK, HDAC5, HSD11B1, ICAM5, IFI35, IL11, IL11RA, IL2, IL2RA, IL32, ITGAV, KIR2DL3, LIF, LOXL2, MAP3K12, MFGE8, NCAM1, NFATC2, NFIL3, NLRP3, NOTCH2, P4HA1, PF4, PGPEP1, PIK3R2, PLOD2, POLD1, POS_D (2), POS_F(0.125), PRKACB, PSMBS, RAD51C, RIPK2, ROR2, RPTOR, RRM2, SERPINAL SF3A1, SNAIL SPP1, SRP54, STC1, TBX21, TIEL TMEM140, TNFRSF8, TNFSF12, TNFSF13, TWIST1, VEGFA, WNT11, and WNTSB.

In some aspects, the biomarker is or includes one or more mRNA transcripts of APOE, BATF3, BCL6B, CASP9, CCND1, COL11A2, CSF2, CSF3, CTNNB1, DLL4, EGF, EIF2B4, ESR1, GLS, HDAC5, HSD11B1, IL11RA, IL32, MAP3K12, NLRP3, NOTCH2, P4HA1, PF4, PGPEP1, PLOD2, RIPK2, RPTOR, SF3A1, SNAIL SPP1, SRP54, STC1, TMEM140, TNFSF12, and/or VEGFA.

In some aspects, the biomarker is or includes one or more mRNA transcript(s) of BATF3, CASP9, CSF3, CTNNB1, DLL4, EGF, ESR1, GLS, PGPEP1, RIPK2, RPTOR, SF3A1, SNAIL SPP1, STC1, TNFSF12, and VEGFA.

In some aspects, the biomarker is or includes one or more mRNA transcripts of ANGPT1, CPA3, CXCL14, IL18, KIT, MAP3K5, OAZ1, RB1, STAT3, SYK, TICAM1, and/or TPSAB1/B2. In some aspects, the biomarker is or includes one or more mRNA transcripts of CPA3, CXCL14, IL18, MAP3K5, and STAT3.

B. Samples and Detection Methods for Assessing Biomarkers

In certain embodiments, the sample that is assessed, for example to determine the level, amount, concentration and/or expression of one or more biomarkers, is a biological sample. In certain embodiments, the sample is a tissue sample. In particular embodiments, the sample is or includes a tissue affected, or suspected of being affected, by a disease or condition, such as a tumor, cancer or a proliferative disease. In some embodiments, the sample is a tumor sample and/or the sample comprises or is likely to comprise tumor cells.

In certain embodiments, the sample is collected from a tissue having or suspected of having a tumor. In particular embodiments, the sample is or includes a tumor and/or a tumor microenvironment. In particular embodiments, the tumor is precancerous or cancerous, or is suspected of being cancerous or precancerous. In certain embodiments, the tumor is a primary tumor, i.e., the tumor is found at the anatomical site where the lesion initially developed or appeared. In some embodiments, the tumor is a secondary tumor, e.g., a cancerous tumor that originated from a cell within a primary tumor located within a different site in the body. In some embodiments, the sample contains one or more cells that are cancer cells and/or tumor cells. In some embodiments, the sample is a tumor biopsy.

In some embodiments, the sample contains tumor cells, such as a solid tumor cell, such as a sarcoma or carcinoma, fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, pancreatic cancer, breast cancer, ovarian cancer, prostate cancer, hepatocellular carcinoma, lung cancer, colorectal cancer, squamous cell carcinoma, basal cell carcinoma, adenocarcinoma, for example adenocarcinoma of the pancreas, colon, ovary, lung, breast, stomach, prostate, cervix, or esophagus, sweat gland carcinoma, sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, bladder carcinoma, CNS tumors, such as a glioma, astrocytoma, medulloblastoma, craniopharyngioma, ependymoma, pinealoma, hemangioblastoma, acoustic neuroma, oligodendroglioma, meningioma, melanoma, neuroblastoma and retinoblastoma. In some embodiments, the tumor to be treated is a head and neck cancer. In some embodiments, the cancer is a squamous cell carcinoma of the head and neck. In some embodiments, the tumor to be treated is an esophageal cancer.

Exemplary tumors, such as cancers include solid tumors, such as breast carcinomas, such as lobular and duct carcinomas, sarcomas, carcinomas of the lung, such as non-small cell carcinoma, large cell carcinoma, squamous carcinoma, and adenocarcinoma, mesothelioma of the lung, colorectal adenocarcinoma, stomach carcinoma, prostatic adenocarcinoma, ovarian carcinoma, such as serous cystadenocarcinoma and mucinous cystadenocarcinoma, ovarian germ cell tumors, testicular carcinomas and germ cell tumors, pancreatic adenocarcinoma, biliary adenocarcinoma, hepatocellular carcinoma, bladder carcinoma, including, for instance, transitional cell carcinoma, adenocarcinoma, and squamous carcinoma, renal cell adenocarcinoma, endometrial carcinomas, including, for instance, adenocarcinomas and mixed Mullerian tumors (carcinosarcomas), carcinomas of the endocervix, ectocervix, and vagina, such as adenocarcinoma and squamous carcinoma of each of same, tumors of the skin, such as squamous cell carcinoma, basal cell carcinoma, malignant melanoma, skin appendage tumors, Kaposi sarcoma, cutaneous lymphoma, skin adnexal tumors and various types of sarcomas and Merkel cell carcinoma, esophageal carcinoma, carcinomas of the nasopharynx and oropharynx, including squamous carcinoma and adenocarcinomas of same, salivary gland carcinomas, brain and central nervous system tumors, including, for example, tumors of glial, neuronal, and meningeal origin, tumors of peripheral nerve, soft tissue sarcomas and sarcomas of bone and cartilage, and lymphatic tumors, including B-cell and T-cell malignant lymphoma. In some embodiments, the tumor is an adenocarcinoma.

In some embodiments, the sample is a tissue sample, e.g., a tissue biopsy. In particular embodiments, the sample is obtained, collected, or taken from connective tissue, muscle tissue, nervous tissue, or epithelial tissue. In certain embodiments, the lesion is present on the heart, vasculature, salivary glands, esophagus, stomach, liver, gallbladder, pancreas, intestines, colon, rectum, hypothalamus, pituitary gland, pineal gland, thyroid, parathyroid, adrenal gland, kidney, ureter, bladder, urethra, lymphatic system, lymph nodes, skin, muscle, brain, spinal cord, nerves, ovaries, uterus, testes, prostate, pharynx, larynx, trachea, bronchi, lungs, diaphragm, bone, cartilage, ligaments, or tendons. In particular embodiments, the sample is obtained, collected, or taken from the lymph node or the bone marrow.

In particular embodiments, the sample contains immune cells, such as immune cells present in the tumor microenvironment (TME), such as antigen-presenting cells (APCs), including dendritic cells (DCs), macrophages (MΦs); natural killer cells (NK cells); neutrophils, and/or lymphocytes, such as T cells and/or B cells.

In certain embodiments, the sample is obtained, collected, or taken from the subject at one or more time points prior to or after treatment with the therapy, e.g., a PIT as a monotherapy and/or as a combination therapy. In particular embodiments, the sample is obtained, collected, and/or taken from the subject prior to one or more steps of a therapy, e.g., a PIT, such as administration of one or more doses a conjugate containing a targeting molecule and a phthalocyanine dye, and/or irradiation or illumination with light (i.e., light treatment) and/or administration of one or more doses of an additional agent, e.g., an immune modulating agent. In particular embodiments, the sample is obtained, collected, and/or taken from the subject after one or more steps of a therapy, e.g., a PIT, such as administration of one or more doses of a conjugate containing a targeting molecule and a phthalocyanine dye, and/or irradiation or illumination with light (i.e., light treatment) and/or administration of one or more doses of an additional agent, e.g., an immune modulating agent. In some embodiments, the sample is sample is obtained, collected, or taken from the subject at one or more time points between any of the steps, phases or doses of the therapy, e.g., a PIT, such as administration of one or more doses a conjugate containing a targeting molecule and a phthalocyanine dye, and/or irradiation or illumination with light (i.e., light treatment) and/or administration of one or more doses of an additional agent, e.g., an immune modulating agent.

In some embodiments, the sample is or comprises a blood sample, a plasma sample, a serum sample, a tissue sample, a tumor biopsy sample, a lymph node sample, a bone marrow sample, a buccal swab, a fecal sample or a urine sample. In particular embodiments, the sample is or contains lymph node tissue. In some embodiments, the lymph node sample contains, or is suspected of containing, at least one diseased cell or cancer cell. In particular embodiments, the sample is or contains tumor cells, such as from a tumor biopsy. In some embodiments, the sample contains tumor cells and cells from the tumor microenvironment. In particular embodiments, the sample is or contains tissue near or surrounding a tumor. In particular embodiments, the sample is or contains bone marrow. In some embodiments, the sample is or contains bone marrow aspirates. In some embodiments, the bone marrow sample contains, or is suspected of containing, at least one diseased cell or cancer cell. In some embodiments, the sample is a blood sample. In certain embodiments, the sample is a serum sample. In some embodiments, the sample is a peripheral blood sample. In some embodiments, the blood sample contains, or is suspected of containing, at least one biomarker, such as a secreted marker, e.g., a cytokine or a chemokine, or danger associated molecular patterns (DAMPs).

In some embodiments, the sample contains immune cells. In some embodiments, the sample containing immune cells includes immune cells from the tumor microenvironment, such as immune cells present in or that have infiltrated the tumor microenvironment. In particular embodiments, the sample contains immune cells expressing a biomarker provided herein. In some embodiments, the T cells express markers of immunosuppressive pathways. In some instances, the sample contains myeloid cells, monocytes, macrophages, and/or dendritic cells, lymphocytes, Th1 cells, Th2 cells, CD4+ or CD8+ T cells.

In some embodiments, one or more sample(s) are obtained from a subject who has been, who will be, or is a candidate to be administered a therapy, e.g., a PIT. In some embodiments, a sample is obtained from the subject prior to initiation of administration of the PIT. In some embodiments, a sample is obtained from the subject after initiation of administration of the PIT. In some embodiments, a sample is obtained from the subject prior to and after the initiation of administration of the PIT. In some embodiments, a sample is obtained from the subject after initiation of administration of the PIT and prior to the initiation of administration of a subsequent therapeutic agent.

In particular embodiments, the biomarker is assessed prior to the initiation of treatment with or administration of the therapy or one or more steps of the therapy, e.g., the PIT and/or combination therapy, such as anti-EGFR-IR700 PIT. In some embodiments, the biomarker is assessed within or within about 0, 1, 2, 3, 4, 5, 6, 9, 12, 18 or 24 hours, or 2, 3, 4, 5, 6, 7, 8, 9, 10, 11, 12, 14, 21 or 28 days or 6, 8, or 12 weeks, or 1, 2, 3, 4, 5, 6 months prior to the initiation of administration of the therapy, e.g., PIT and/or combination therapy, such as anti-EGFR-IR700 PIT. In particular embodiments, the biomarker is assessed within or within about 0, 1, 2, 3, 4, 5, 6, 9, 12, 18 or 24 hours, or 2, 3, 4, 5, 6, 7, 8, 9, 10, 11, 12, 14, 21 or 28 days or 1, 2, or 3 months prior to the initiation of administration of the therapy, e.g., PIT and/or combination therapy, such as anti-EGFR-IR700 PIT. In particular embodiments, the biomarker is assessed after the initiation of treatment, or with administration of the therapy, or one or more steps of the therapy, e.g., the PIT and/or combination therapy, such as anti-EGFR-IR700 PIT. In some embodiments, the biomarker is assessed within or within about 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 days after the initiation of administration of the therapy, e.g., PIT and/or combination therapy. In some embodiments, the biomarker is assessed after or after about 10, 20, 30, 40, 50, 60, 70, 80, 90 days or more, or about 1, 2, 3, 4, 5, 6, 7, 8, 9, 10, 11, 12 month or more after the initiation of administration of the therapy or one or more steps of the therapy, e.g., PIT and/or combination therapy, such as anti-EGFR-IR700 PIT.

In some embodiments, the same biomarker is assessed and/or compared in the one or more samples. In some embodiments, one or more different biomarkers and/or parameters associated with the one or more biomarkers is assessed and/or compared in the one or more samples. For example, the same biomarker can be measured in one or more samples obtained from a subject before and after one or more steps of the therapy, e.g., PIT and/or combination therapy, and compared to the measurement of the same biomarker in samples from a different time point. In some aspects, changes in the level or concentration, or relative differences, can be employed for assessment.

In some embodiments, the biomarker is indicative of a cell phenotype, e.g., an immune cell phenotype. In some embodiments, the biomarker is indicative of a lineage, differentiation state and/or activity of an immune cell. In some embodiments, the biomarker is associated with activity, phenotypes, proliferation and/or function of the cells used for therapy. In some embodiments, the biomarker is a marker expressed on the surface of an immune cell, e.g., a lymphoid cell and/or a myeloid cell. In some embodiments, the biomarker is an intracellular marker. In some embodiments, the biomarker is a secreted molecule. In some embodiments, the biomarker can be released from a cell upon a specific event.

In some embodiments, one or more parameters associated with one or more biomarkers can be used in assessment. In some embodiments, the parameter includes a change and/or an alteration, e.g., an increase, an elevation, a decrease or a reduction, in levels, values or measurements of a biomarker compared to the levels, values or measurements of the same biomarker in a different time point of assessment, a different condition, a reference point and/or a different subject is determined or assessed. For example, in some embodiments, an increase or decrease in particular biomarkers in a sample, compared to the same biomarker in a different condition, e.g., before or after one or more steps of the therapy, e.g., PIT and/or combination therapy, can be determined. In some embodiments, the change, e.g., an increase or decrease is greater than or greater than about 0.1%, 0.25%, 0.5%, 0.75%, 1%, 2%, 3%, 4%, 5%, 6%, 7%, 8%, 9%, 10%, 11%, 12%, 13%, 14%, 15% or 20%. In some embodiments, the change, e.g., an increase or decrease is greater than or greater than about 1.2-fold, 1.5-fold, 2-fold, 3-fold, 4-fold, 5-fold, 10-fold or more. In some embodiments, the levels, values or measurements of two or more biomarkers are determined, and relative levels and/or ratios are determined. In some embodiments, the determined levels, values or measurements of biomarkers are compared to the levels, values or measurements from a control sample or an untreated sample. In some embodiments, the determined levels, values or measurements of biomarkers are compared to the levels from a sample from the same subject but at a different time point. The values obtained in the quantification of individual biomarker can be combined for the purpose of disease assessment, e.g., by forming an arithmetical or logical operation on the levels, values or measurements of biomarkers by using multi-parametric analysis. In some embodiments, a ratio of two or more specific biomarkers can be calculated.

Also provided are articles of manufacture containing a reagent capable of detecting or that is specific for a biomarker. In some embodiments, instructions are provided for assessing a biological sample for the biomarker from a subject that is a candidate for treatment with a PIT as a monotherapy and/or as a combination therapy. Also provided are instructions for using the reagents to detect the biomarker and assess the one or more biomarker in a sample obtained from a subject that is a candidate for treatment with a PIT.

In some embodiments, methods or assays to detect or determine the level, presence, concentration, activity and/or effect of the biomarker includes any of the known methods for detecting levels of metabolites, proteins, nucleic acids or other biomolecules in a biological sample. For example, the methods for detection include immunohistochemistry, enzyme-linked immunosorbent assay (ELISA), enzyme immunoassay (EIA), immunofluorescence, polymerase chain reaction (PCR), reverse transcriptase PCR (RT-PCR), in situ PCR, quantitative PCR, flow cytometry, fluorescence-activated cell sorting (FACS), enzymatic activity assays, mass cytometry (CyTOF), gas chromatography/mass spectroscopy (GC/MS), high performance liquid chromatography (HPLC), liquid chromatography—dual mass spectrometry (LC-MS/MS), liquid chromatography—electrospray ionization—tandem mass spectrometry (LC-ESI-MS), nuclear magnetic resonance (NMR), in situ hybridization, Western blot, Northern blot, Southern blot, in vivo imaging, microarrays, whole-exome sequencing (WES), gene-targeted sequencing, transcriptome sequencing, and/or any high throughput methods. In some embodiments, the one or more biomarkers is assessed using an in vitro ELISA, a colorimetric test, an immunoassay, in situ hybridization, multiplexed cytokine assay, multiplexed ELISA, immunohistochemistry, multiplexed immunohistochemistry, immunofluorescence, multiplexed immunofluorescence or 5-plex fluorescent immunohistochemistry. In some embodiments, the one or more biomarkers is assessed using a multiplexed sandwich ELISA assay. In some embodiments, the one or more biomarkers is assessed flow cytometry. In some embodiments, the one or more biomarkers is assessed using an intracellular cytokine staining (ICS) assay. In some embodiments, the one or more biomarkers is assessed using immunohistochemistry.

In some embodiments, the tumor mutational burden (TMB) or mutational load is the biomarker. TMB is the total number of nonsynonymous mutations per coding area of a tumor genome. TMB can be assessed, for example, using whole exome sequencing or gene-targeted sequencing. In some embodiments, whole exome sequencing results of tumor tissue and matched non-tumor tissue are compared to measure the TMB of a sample. In some embodiments, gene panels are used for targeted gene sequencing of tumor tissue and matched non-tumor tissue, and the results are compared to determine the TMB of a sample.

In some embodiments, the biomarker is one or more defects in DNA repair pathways. In some embodiments, the biomarker is a deficiency in DNA mismatch repair (dMMR). For example, in some embodiments the biomarker is impaired expression or mutation(s) of one or more genes involved in the mismatch repair (MMR) pathway, such as MSH2, MSH6, MLH1, and/or PMS2. In some embodiments, the biomarker is a deficiency in homology-dependent recombination (HR). For example, in some embodiments, the biomarker is one or more mutation(s) in HR pathway proteins, such as BRCA1, BRCA2, and/or PALB2. In some embodiments, the biomarker is a defect in the base excision repair pathway. For example, in some embodiments, the biomarker is a mutation in MUTYH. In some embodiments, the biomarker is a defect in the nucleotide excision repair (NER) pathway. For example, in some embodiments, the biomarker is a mutation in one or more of the ERCC genes, such as a single nucleotide polymorphism in ERCC1. In some embodiments, the biomarker is a mutation in DNA polymerase. In some embodiments the biomarker is a mutation in one or more genes encoding DNA proofreading enzymes such as polymerase δ (POLD1) and polymerase ε (POLE). In some embodiments, the biomarker is enhanced endogenous mutator activity. For example, in some embodiments, the biomarker is enhanced activity of one or more APOBEC cytidine deaminases, such as APOBEC3.

The term "antibody" herein is used in the broadest sense and includes polyclonal and monoclonal antibodies, including intact antibodies and functional (antigen-binding) antibody fragments, including fragment antigen binding (Fab) fragments, $F(ab')_2$ fragments, Fab' fragments, Fv fragments, recombinant IgG (rIgG) fragments, single chain antibody fragments, including single chain variable fragments (scFv), and single domain antibodies (e.g., sdAb, sdFv, nanobody) fragments. The term encompasses genetically engineered and/or otherwise modified forms of immunoglobulins, such as intrabodies, peptibodies, chimeric antibodies, fully human antibodies, humanized antibodies, and heteroconjugate antibodies, multispecific, e.g., bispecific, antibodies, diabodies, triabodies, and tetrabodies, tandem di-scFv, tandem tri-scFv. Unless otherwise stated, the term "antibody" should be understood to encompass functional antibody fragments thereof. The term also encompasses intact or full-length antibodies, including antibodies of any class or sub-class, including IgG and sub-classes thereof, IgM, IgE, IgA, and IgD.

In some embodiments, the one or more biomarkers described herein, e.g., immune cell biomarkers can be detected using an immunoconjugate for detection, e.g., attached to a label, which can generate a detectable signal, indirectly or directly. These immunoconjugates can be used for research or diagnostic applications. In some cases, the label is capable of producing, either directly or indirectly, a detectable signal. For example, the label may be radio-opaque or a radioisotope, such as $^{3}H$, $^{14}C$, $^{32}P$, $^{35}S$, $^{124}I$, $^{125}I$, $^{131}I$; a fluorescent (fluorophore) or chemiluminescent (chromophore) compound, such as fluorescein isothiocyanate, rhodamine or luciferin; an enzyme, such as alkaline phosphatase, β-galactosidase or horseradish peroxidase; an imaging agent; or a metal ion. In some embodiments, the label is a radioactive atom for scintigraphic studies, for example $^{99}Tc$ or $^{123}I$, or a spin label for nuclear magnetic resonance (NMR) imaging (also known as magnetic resonance imaging, MRI), such as zirconium-89, iodine-123, iodine-131, indium-111, fluorine-19, carbon-13, nitrogen-15, oxygen-17, gadolinium, manganese or iron. Zirconium-89 may be complexed to various metal chelating agents and conjugated to antibodies, e.g., for PET imaging (WO 2011/056983). In some cases, the label is a phthalocyanine dye, such as any described herein.

In some embodiments, the immunoconjugates for detection is detectable indirectly. For example, a secondary antibody that is specific for the antibody against the marker expressed on a population of myeloid cells and contains a detectable label can be used to detect the primary antibody.

In some embodiments, the biomarker is determined by assessing the presence or absence of one or more specific molecules, including surface molecules and/or molecules that may accumulate or be produced by the immune cells. In some embodiments, biomarker may include cell activity, such as production of a factor (e.g., cytokine) in response to a stimulus. In certain embodiments, assessment of a cell composition is performed to identify, detect, or quantify a biomarker of the cell composition. In particular embodiments, a measurement of a cell composition is performed to identify, detect, or quantify the presence, absence, degree of expression or level of a specific molecule.

Examples of methods that can be used to detect a specific molecule and/or analyze a biomarker of the cells include, but are not limited to, biochemical analysis; immunochemical analysis; image analysis; cytomorphological analysis; molecule analysis such as PCR, sequencing, high-throughput sequencing, determination of DNA methylation; proteomics analysis such as determination of protein glycosylation and/or phosphorylation pattern; genomic analysis; epigenetic or epigenomic analysis (e.g., ChIP-seq); transcriptomic analysis (e.g., RNA-seq); and any combination thereof. In some embodiments, exemplary methods for detection can include, such as transcription analysis, transcriptome analysis, transcription factor occupancy assays, RNAseq, protein expression, proteomic analysis, protein modification analysis, functional activity assays, flow cytometry and/or intracellular cytokine staining (ICS).

In some aspects, determination of any of the biomarkers can be assessed in high-throughput, automated and/or by single-cell-based methods. In some aspects, large-scale or genome-wide methods, can be used to identify one or more molecular signatures. In some aspects, large-scale or genome-wide methods, can be used to identify molecular signatures that are associated with outcomes of therapy, e.g., efficacy and safety, or pharmacokinetic parameters. In some aspects, one or more molecular signatures, e.g., expression of specific RNA or proteins in the cell, can be determined. In some embodiments, molecular features of the biomarker analyzed by image analysis, PCR (including the standard and all variants of PCR), single molecule counting, such as multiplexed single molecule counting (e.g., nanoString nCounter® technology), microarray (including, but not limited to DNA microarray, MMchips for microRNA, protein microarray, cellular microarray, antibody microarray, and carbohydrate array), sequencing, biomarker detection, or methods for determining DNA methylation or protein glycosylation pattern. In particular embodiments, the specific molecule is a polypeptide, i.e. a protein. In some embodiments, the specific molecule is a polynucleotide. In some embodiments the polynucleotide is an mRNA.

In some embodiments, positive or negative expression of a specific molecule is determined by incubating cells with one or more antibodies or other binding agent that specifically bind to one or more surface markers expressed or expressed ($marker^{+}$) at a relatively higher level ($marker^{high}$) on the positively or negatively selected cells, respectively. In particular embodiments, the positive or negative expression is determined by flow cytometry, immunohistochemistry, or any other suitable method for detecting specific markers.

In some embodiments, the biomarker is indicated by the presence, absence, or level of expression in a cell of one or more specific molecules, such as certain surface markers indicative of the biomarker, e.g., surface proteins, intracellular markers indicative of the biomarker, or nucleic acids, such as mRNA, indicative of the biomarker or other molecules or factors indicative of the biomarker. In some embodiments, the biomarker is or comprises a positive or negative expression of the one or more of specific molecules. In some embodiments, the specific molecules include, but are not limited to, a surface marker, e.g., a membrane glycoprotein or a receptor; a marker associated with apoptosis or viability; or a specific molecule that indicates the status of an immune cells, e.g., a marker associated with activation, exhaustion, or a mature or naïve biomarker. In some embodiments, any known method for assessing or measuring, counting, and/or quantifying cells based on specific molecules can be used to determine the number of cells of the biomarker.

In some embodiments, a biomarker is or includes a positive or negative expression of one or more specific molecules in a cell. In some embodiments, the positive expression is indicated by a detectable amount of the specific molecule in the cell. In certain embodiments, the detectable amount is any detected amount of the specific molecule in the cell. In particular embodiments, the detectable amount is an amount greater than a background, e.g., background staining, signal, etc., in the cell. In certain embodiments, the positive expression is an amount of the specific molecule that is greater than a threshold, e.g., a predetermined threshold. Likewise, in particular embodiments, a cell with negative expression of a specific molecule may be any cell not determined to have positive expression or is a cell that lacks a detectable amount of the specific molecule or a detectable amount of the specific molecule above background. In some embodiments, the cell has negative expression of a specific molecule if the amount of the specific molecule is below a threshold. One of skill in the art will understand how to define a threshold to define positive and/or negative expression for a specific molecule as a matter of routine skill, and that the thresholds may be defined according to specific parameters of, for example, but not limited to, the assay or method of detection, the identity of the specific molecule, reagents used for detection, and instrumentation.

In some embodiments a threshold for one or more biomarkers is determined by the level of expression of the one or more biomarkers. In some embodiments, the threshold is determined based on the expression of the one or more biomarkers in the tumor of the subject to be treated or the non-tumor tissue of the subject to be treated. In some embodiments, the threshold is determined based on the expression of the one or more biomarkers in a healthy individual, not having a disease or condition such as a cancer or tumor. In some embodiments, the threshold is based on an average expression level of the one or more biomarkers in a population of subjects having a disease or condition to be treated such as a tumor. In some embodiments, the threshold for the same biomarker depends on the type or location of the tumor, such that the threshold for a given biomarker can be different in different types of tumors. In some embodiments, the threshold for a biomarker is determined in only tumor tissue, in the tissue surrounding the tumor and/or in tissue distal from the site of a tumor.

In some embodiments, the threshold is set based on a calculated Combined Positive Score (CPS) or Tumor Proportion Score (TPS). Such measurements are routine for the skilled artisan. Exemplary CPS values can be calculated using the formula 100*(Number of biomarker+ cells/total number of viable tumor cells), where the biomarker+ cells is the sum of biomarker-expressing tumor cells and biomarker-expressing non-tumor cells (e.g., immune cells and any other infiltrating cell). The CPS value to be used as a threshold is dependent on the biomarker to be evaluated and the tumor type and can be empirically determined by the skilled artisan. The CPS score can be calculated in the whole tissue or in the tumor region only of a sample.

In some embodiments, the threshold is measured in whole tissue and is a CPS value that is 90 or less, 80 or less, 70 or less, 60 or less, 50 or less, 40 or less, 30 or less, 20 or less, or 10 or less, such as 90, 85, 80, 75, 70, 65, 60, 55, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, or less. In some embodiments, the threshold is measured in the whole tissue and is a CPS value that is 70 or less, 50 or less, or 40 or less. In some embodiments, the biomarker is PD-L1 and the threshold is a CPS score in whole tissue that is 90 or less, 80 or less, 70 or less, 60 or less, 50 or less, 40 or less, 30 or less, 20 or less, or 10 or less, such as 90, 85, 80, 75, 70, 65, 60, 55, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, or less. In some embodiments, the biomarker is PD-L1 and the threshold is a CPS score in whole tissue is 80 or less, 70 or less, 60, or less, 50 or less, or 40 or less. In some embodiments, the biomarker is PD-L1 and the threshold is a CPS score in whole tissue that is 70 or less. In some embodiments, the biomarker is PD-L1 and the threshold is a CPS score in whole tissue that is 50 or less. In some embodiments, the biomarker is PD-L1 and the threshold is a CPS score in whole tissue that is 40 or less. In some embodiments, the biomarker is PD-L1 and the threshold is a CPS score in whole tissue is a range of 15 to 80, 20 to 70, or 40 to 70. In some embodiments, the threshold for PD-L1 is for head and neck cancer. The PD-L1 threshold can be adjusted based on tumor type.

In some embodiments, the threshold is measured in the tumor region of the sample and is a CPS value that is 80 or less, 75 or less, 70 or less, 60 or less, 50 or less, 40 or less, 30 or less, 20 or less, or 10 or less, such as 80, 75, 70, 75, 70, 65, 60, 55, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, or less. In some embodiments, the threshold is measured in the tumor region of a sample and the CPS value is 70 or less, 50 or less, or 40 or less. In some embodiments, the biomarker is PD-L1 and the threshold is a CPS calculated in the tumor region of the sample that is 80 or less, 75 or less, 70 or less, 65 or less, 60 or less, 55 or less, 50 or less, 55 or less, 40 or less, 35 or less, 30 or less, 25 or less, 20 or less, 15 or less, or 10 or less, such as 80, 75, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, or less. In some embodiments, the biomarker is PD-L1 and the threshold is a CPS score in the tumor region of the sample that is 70 or less, 50 or less, or 40 or less, 30 or less or 20 or less. In some embodiments, the biomarker is PD-L1 and the threshold is a CPS score in the tumor region of the sample that is 70 or less. In some embodiments, the biomarker is PD-L1 and the threshold is a CPS score the tumor region of the sample that is 50 or less. In some embodiments, the biomarker is PD-L1 and the threshold is a CPS score in the tumor region of the sample that is 40 or less. In some embodiments, the biomarker is PD-L1 and the threshold is a CPS score in the tumor region of the sample is a range of 15 to 80, 20 to 70, or 40 to 70. In some embodiments, the threshold for PD-L1 is for head and neck cancer. The PD-L1 threshold can be adjusted based on tumor type.

Exemplary TPS values can be calculated using the formula 100*(number of biomarker+ viable tumor cells/the number of viable tumor cells). The TPS value to be used as a threshold is dependent on the biomarker to be evaluated and the tumor type and can be empirically determined by the skilled artisan. In some embodiments, the TPS is 60 or less, 50 or less, 40 or less, 30 or less, 20 or less, or 10 or less, such as 60, 55, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, or less. In some embodiments, the TPS value to be used as a threshold is 50 or less, 30 or less, or 25 or less. In some embodiments, the threshold is a TPS value of 50 or less. In some embodiments, the threshold is a TPS value of 30 or less. In some embodiments, the threshold is a TPS value of 25 or less. In some embodiments, the biomarker is PD-L1 and the threshold is a CPS that is 60 or less, 50 or less, 40 or less, 30 or less, 20 or less, or 10 or less, such as 60, 55, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, or less. In some embodiments, the biomarker is PD-L1 and the threshold is a TPS score in the tumor region of the sample that is 50 or less, 40 or less, 30 or less or 20 or less. In some embodiments, the TPS value to be used as a threshold for a PD-L1 biomarker is 50 or less, 30 or less, or 25 or less. In some embodiments, the threshold for a PD-L1 biomarker is a TPS value of 50 or less. In some embodiments, the threshold is a TPS value of 30 or less. In some embodiments, the threshold is a TPS value of 25 or less. In some embodiments, the biomarker is PD-L1 and the threshold is a CPS score in the tumor region of the sample is a range of 10 to 60, 15 to 50, or 20 to 50 or 25 to 30. In some embodiments, the threshold for PD-L1 is for head and neck cancer. The PD-L1 threshold can be adjusted based on tumor type.

In some embodiments, the threshold is a determined biomarker+ (e.g., cells expressing the particular biomarker, biomarker-positive cells, or cells staining positive for the particular biomarker) cell density, such as the number of biomarker+ cells (including biomarker+ tumor and non-tumor cells) per unit area (e.g., number of biomarker+ cells/mm$^2$). In some embodiments, the threshold is set as a determined biomarker+ tumor cell density, such as the number of biomarker+ viable tumor cells per unit area (e.g., number of biomarker+ tumor cells/mm$^2$). The threshold value of biomarker+ cell density or biomarker+ tumor cell density depends on the biomarker and the tumor type and can be empirically determined by the skilled artisan. Such threshold values can be calculated in the whole tissue or only in the tumor region of a sample.

In some examples, the threshold is [the total number of biomarker+ cells/mm$^2$ whole tissue] that is less than 3000 biomarker+ cells/mm$^2$ such as less than 2500 biomarker+ cells/mm$^2$, 2250 biomarker+ cells/mm$^2$, 2,000 biomarker+ cells/mm$^2$, 1750 biomarker+ cells/mm$^2$, 1500 biomarker+ cells/mm$^2$, 1250 biomarker+ cells/mm$^2$, or 1000 biomarker+ cells/mm$^2$ whole tissue. In particular embodiments, the biomarker is PD-L1 and the threshold is the total number of PD-L1+ cells/mm$^2$ whole tissue. In some embodiments, the threshold is [the number of biomarker+ tumor cells/mm$^2$ whole tissue] that is less than 1750 biomarker+ tumor cells/mm$^2$, less than 1600 biomarker+ tumor cells/mm$^2$, less than 1500 biomarker+ tumor cells/mm$^2$, 1400 biomarker+ tumor cells/mm$^2$, 1300 biomarker+ tumor cells/mm$^2$, 1200 biomarker+ tumor cells/mm$^2$, 1100 biomarker+ tumor cells/mm$^2$, 1000 biomarker+ tumor cells/mm$^2$, 500 biomarker+ tumor cells/mm$^2$ whole tissue. In particular embodiments, the biomarker is PD-L1 and the threshold is the total number of PD-L1+ cells/mm$^2$ whole tissue. In some embodiments, tumor cells are PanCK-expressing tumor cells. In particular embodiments, the biomarker is PD-L1 and the threshold is the total number of PD-L1+ PanCK+ tumor cells/mm$^2$ whole tissue.

In some embodiments, the threshold is [the total number of biomarker+ cells/mm$^2$ tumor region] that is less than 3000 biomarker+ cells/mm$^2$ such as less than 2500 biomarker+ cells/mm$^2$, 2250 biomarker+ cells/mm$^2$, 2,000 biomarker+ cells/mm$^2$, 1750 biomarker+ cells/mm$^2$, 1500 biomarker+ cells/mm$^2$, 1250 biomarker+ cells/mm$^2$, or 1000 biomarker+ cells/mm$^2$ tumor region. In some embodiments, the threshold is [the number of biomarker+ tumor cells/mm$^2$ tumor tissue] that is less than 1750 biomarker+ tumor cells/mm$^2$, less than 1500 biomarker+ tumor cells/mm$^2$, 1400 biomarker+ tumor cells/mm$^2$, 1300 biomarker+ tumor cells/mm$^2$, 1200 biomarker+ tumor cells/mm$^2$, 1100 biomarker+ tumor cells/mm$^2$, 1000 biomarker+ tumor cells/mm$^2$, 500 biomarker+ tumor cells/mm$^2$ tumor region. In some embodiments, tumor cells are PanCK-expressing tumor cells. In particular embodiments, the biomarker is PD-L1 and the threshold is the total number of PD-L1+ PanCK+ tumor cells/mm$^2$ tumor region.

In some embodiments, antibodies capable of detecting or that is specific the inflammatory markers provided herein may be identified, screened for, or characterized for their physical/chemical properties and/or biological activities by various known assays. In one aspect, the antibody is tested for its antigen binding activity, e.g., by known methods such as an immunoassay, ELISA, Western blotting, and/or flow cytometric assays, including cell-based binding assays.

In some embodiments, the level, presence, amount or concentration, of the biomarker or biomarkers is assayed using histochemistry (HC), immunohistochemistry (IHC) or immunofluorescence (IF). In some aspects, HC, IHC or IF staining methods can be carried out to detect one or more biomarkers based on enzymatic reactions using a reagent or reagents that binds the biomarker, such as an antibody (e.g. monoclonal or polyclonal antibodies). In some cases, the IHC is multiplex IHC in which 2, 3, 4, 5, 6, 7, 8, 9, or 10 or more biomarkers are assessed. In some cases, the IF is multiplex IF in which 2, 3, 4, 5, 6, 7, 8, 9, or 10 or more biomarkers are assessed.

In particular embodiments, expression of a specific molecule is assessed with flow cytometry. Flow cytometry is a laser- or impedance-based, biophysical technology employed in cell counting, cell sorting, biomarker detection and protein engineering, by suspending cells in a stream of fluid and passing them by an electronic detection apparatus. It allows simultaneous multiparametric analysis of the physical and chemical characteristics of up to thousands of particles per second.

The data generated by flow-cytometers can be plotted in a single dimension, to produce a histogram, or in two-dimensional dot plots or even in three dimensions. The regions on these plots can be sequentially separated, based on fluorescence intensity, by creating a series of subset extractions, termed "gates." Specific gating protocols exist for diagnostic and clinical purposes especially in relation to immunology. Plots are often made on logarithmic scales. Because different fluorescent dyes' emission spectra overlap, signals at the detectors have to be compensated electronically as well as computationally. Data accumulated using the flow cytometer can be analyzed using software, e.g., JMP (statistical software), WinMDI, Flowing Software, and web-based Cytobank), Cellcion, FCS Express, FlowJo, FACSDiva, CytoPaint (aka Paint-A-Gate), VenturiOne, CellQuest Pro, Infinicyt or Cytospec.

Flow Cytometry is a standard technique in the art and one of skill would readily understand how to design or tailor protocols to detect one or more specific molecules and analyze the data to determine the expression of one or more specific molecules in a population of cells. Standard protocols and techniques for flow cytometry are found in Lloyd "Flow Cytometry in Microbiology"; Practical Flow Cytometry by Howard M. Shapiro; Flow Cytometry for Biotechnology by Larry A. Sklar, Handbook of Flow Cytometry Methods by J. Paul Robinson, et al., Current Protocols in Cytometry, Wiley-Liss Pub, Flow Cytometry in Clinical Diagnosis, v4, (Carey, McCoy, and Keren, eds), ASCP Press, 2007, Ormerod, M. G. (ed.) (2000) Flow Cytometry—A practical approach. 3rd edition. Oxford University Press, Oxford, UK, Ormerod, M. G. (1999) Flow Cytometry. 2nd edition. BIOS Scientific Publishers, Oxford., and Flow Cytometry—A basic introduction. Michael G. Ormerod, 2008.

In some embodiments, cells are sorted by biomarker for further analysis. In some embodiments, cells of different biomarkers within the same cell composition are sorted by Fluorescence-activated cell sorting (FACS). FACS is a specialized type of flow cytometry that allows for sorting a heterogeneous mixture of cells into two or more containers, one cell at a time, based upon the specific light scattering and fluorescent characteristics of each cell. It is a useful scientific instrument as it provides fast, objective and quantitative recording of fluorescent signals from individual cells as well as physical separation of cells of particular interest.

In some embodiments, the HC, IHC or IF assays for use in the methods herein include those that use a reagent that is a binding partner to detect various biomarkers of interest. The reagent can be labeled or unlabeled. Typically, the assaying includes a detection system that makes the presence of the markers visible, to either the human eye or a digital system, such as an automated scanning system, for qualitative or quantitative analyses. In a direct IHC or IF assay, binding is determined directly upon binding of the binding partner (e.g. first antibody) to the tissue or biomarker due to the use of a labeled reagent. In an indirect IHC or IF assay, a secondary antibody or second binding partner is necessary to detect the binding of the first binding partner, as it is not labeled. In such methods, generally a slide-mounted tissue sample (e.g. a formalin-fixed paraffin-embedded (FFPE) tissue section) is stained with a labeled reagent.

In some embodiments, the reagent is conjugated to small molecules, e.g., biotin, that are detected via a labeled binding partner or antibody. In some examples, the reagent is conjugated to or linked to a detectable moiety, e.g., a fluorescent (fluorophore) or chemiluminescent (chromophore) compound or a fluorescent, chemiluminescent or a bioluminescent protein or an enzyme. Exemplary detectable moieties can include fluorescein isothiocyanate (FITC), phycoerythrin, peridinin, chlorophyll protein or luciferin. In some embodiments, the reagent is conjugated to or linked to a fluorophore. Exemplary fluorophores hydroxycoumarin, Cascade Blue, DyLight 405, Pacific Orange, Alexa Fluor 430, Fluorescein, Oregon Green, Alexa Fluor 488, BODIPY 493, 2.7-Diochlorofluorescien, ATTO 488, Chromeo 488, DyLight 488, HiLyte 488, Alexa Fluor 555, ATTO 550, BODIPY TMR-X, CF 555, Chromeo 546, Cy3, Brilliant Violet dyes such as BV421, BV510, BV605, BV650, BV711, BV786, Brilliant ultra violet dyes such as BUV395, BUV496, BUV661, BUV737, BUV805, Brilliant Blue 515 (BB515), TMR, TRITC, Dy547, Dy548, Dy549, HiLyte 555, DyLight 550, BODIPY 564, Alexa Fluor 568, Alexa Fluor 594, Rhodamine, Rhodamine 6G, Texas Red, Red610, Alexa Fluor 610, Alexa Fluor 633, DyLight 633, Alexa Fluor 647, APC, ATTO 655, CF633, CF640R, Chromeo642, Cy5, DyLight 650, Alexa Fluor 680, Alexa Fluor 700, Cy 5.5, ICG, Alexa Fluor 750, DyLight 755, Cy7, Cy7.5, Alexa Fluor 790, DyLight 800, Qdot® 525, Qdot® 565, Qdot® 605, Qdot® 655, Qdot® 705, Qdot® 800, coumarin, DCC and FAM (carboxyfluorescein).

In other examples, the reagents are conjugated to detectable proteins which permit direct detection, such as, for example, conjugated to a fluorescent protein, bioluminescent protein or enzyme. Exemplary enzymatic staining methods for detecting a protein of interest include enzymatic interactions that can be visualized using different enzymes such as peroxidase, alkaline phosphatase, or different chromogens. Additional examples of enzyme labels include horseradish peroxidase, alkaline phosphatase, glucose oxidase, and β-galactosidase. Colorimetric substrates for horseradish peroxidase include ABTS (2,2'-azino-bis (3-ethylbenzothiazoline-6-sulphonic acid)), OPD (o-phenylenediamine dihydrochloride), TMB (tetramethylbenzidine), 4CN (4-chloro-1-napthol), DAB (3,3'-diaminobenzidine), and AEC (3-amino-9-ethylcarbazole). Colorimetric substrates for alkaline phosphatase include BCIP (5-bromo-4-chloro-3-indolyl-phosphate), and NBT (nitro-blue tetrazolium chloride)—often used together. Colorimetric substrates for glucose oxidase include NBT. Colorimetric substrates for β-galactosidase include X-Gal (5-bromo-4-chloro-3-indolyl-β-D-galactopyranoside) alone or in combination may be used. In other examples, the reagent is conjugated to peptides or proteins that can be detected via a labeled binding partner or antibody. In some particular embodiments, the methods include contacting the section with a biomarker specific reagent, contacting the section with a labeled antibody (conjugated to an enzyme label) and contacting the section with a colorimetric substrate of the enzyme label.

In some embodiments, the biomarker is detected using a reagent that can be detected by labeled secondary reagents, such as labeled antibodies that recognize the biomarker. In some aspects, the reagent is a binding reagent that specifically binds the biomarker, e.g., immune cell biomarker. In some cases, the binding reagent is an antibody or antigen-binding fragment thereof, an aptamer or a nucleic acid probe. The antibodies that bind the biomarker can be labeled for detection or can be detected with a secondary antibody that binds the first antibody.

In some embodiments, the HC, IHC or HF may be performed to be used to detect one or more biomarkers, e.g. multiplex IHC or multiplex IF. For example, the method comprises performing serial immunohistochemistry (IHC) or immunofluorescence (IF) on one sample (e.g., one section). See e.g., Parra et al., Sci Rep. (2017) 7(1):13380; Tsujikawa et al., Cell Rep. (2017) 19(1): 203-217; Blom et al., Sci Rep. (2017) 7(1): 15580. In some examples, the methods for assessing biomarkers is performed using commercially available regents or using reagents compatible with commercially available systems for multiplex IHC or multiplex IF. In some embodiments, the commercially available systems include reagents for assessing biomarkers. See e.g., Bio-Plex (Bio-Rad Laboratories, Inc.), Meso Scale Discovery multiplex assay kits, Multi-Analyte Profiling (MAP) (Myriad RBM), DISCOVERY 5-plex system (Ventana Medical Systems, Inc.) or Opal Multiplex Immunohistochemistry (PerkinElmer).

The image can be quantitatively or semi-quantitatively analyzed and scored based on staining intensity of the sample. Quantitative or semi-quantitative histochemistry, immunohistochemistry or immunofluorescence refers to method of scanning and scoring samples that have undergone histochemistry, immunohistochemistry or immunofluorescence, to identify and quantitate the presence, level, amount or concentration of a specified biomarker. Quantitative or semi-quantitative methods can employ imaging software to detect staining densities or amount of staining or methods of detecting staining by the human eye, where a trained operator ranks results numerically. For example, images can be quantitatively analyzed using a pixel count algorithms and other methods that measure or quantitate or semi-quantitate the degree of staining; see e.g. U.S. Pat. No. 7,219,016; published U.S. Pat. Appl. Nos. US20100136549 and 20110111435.

In some embodiments, the number of biomarker positive cells is assessed and quantified, for example, by flow cytometry or based on the total area or the total number of cells in the assessed area of an image is quantified. The various quantifications can be used to determine a percentage or ratio of cells that are positive for one or more biomarkers in sampled area or volume or a unit area or volume.

III. PHOTOIMMUNOTHERAPY AND COMBINATION THERAPY

In some embodiments, the provided methods involve assessing one or more biomarkers, in the context of photoimmunotherapy (PIT). In some aspects, PIT as employed in the provided methods involve administering a conjugate comprising a photosensitizer, such as a phthalocyanine dye, and a targeting molecule, such as an antibody or antigen-binding fragment thereof that specifically targets a molecule on the surface of the target cell, e.g., tumor cell. In some aspects, the provided methods include assessing one or more biomarkers in a therapeutic application employing PIT as a monotherapy and/or as part of a combination therapy. As described in Section I, the provided are methods of treatment that involve one or more aspects of PIT and uses of one or more biomarkers to guide the treatment and/or to identify and select subjects. In some aspects, provided are methods of treating a lesion of a disease or condition in a subject, such as a tumor, involving PIT and assessment of one or more biomarkers. In some embodiments, the methods involve one or more steps of PIT.

In some aspects, the provided methods involve measurement and assessment of one or more biomarker(s) in the context of a treatment for a tumor that involves PIT. In some aspects, the assessment of the one or more biomarker(s) can be performed before, during and/or after one or more steps of the PIT and/or a combination therapy. In some embodiments, such assessment can be used to monitor the outcome of treatment and to identify, tailor or modify the therapeutic regimen, such as doses, timing, treatment regime and/or administration of an additional therapeutic agent, for a particular subject, according to the methods described herein, e.g., in Sections I and II. In some aspects, the provided methods can be applied to select certain subjects for treatment. In some embodiments, the methods can be applied to select subjects by using one or more of the biomarkers described herein to identify or select a subject prior to photoimmunotherapy, after an initial administration of photoimmunotherapy, and prior to selecting an additional therapeutic agent, for example an immune modulating agent or other therapeutic agent, for use in combination with photoimmunotherapy. In some aspects, the subject for PIT and/or for administration of one or more therapeutic agents (e.g., a combination therapy), can be selected based on the level of expression of one or more biomarkers, according to any of the methods described herein. Exemplary specific steps for implementing the PIT as a monotherapy and/or as a part of a combination therapy and reagents are described herein, for example, in this section. In some embodiments, certain aspects of implementing the PIT, may be performed, modified or tailored based on the assessment of one or more biomarkers, according to the methods described herein, e.g., in Sections I and II.

In some aspects, the provided methods and uses involve PIT, for example, involving administration of a conjugate comprising a phthalocyanine dye linked to a targeting molecule that binds to a protein on the surface of a cell present in the microenvironment of the tumor and light irradiation, that are useful in a variety of therapeutic, diagnostic and prophylactic applications and indications. For example, the conjugate comprising a phthalocyanine dye linked to a targeting molecule are useful in treating a variety of diseases and disorders in a subject, such as a tumor. Such methods and uses include therapeutic methods and uses, for example, involving administration of the conjugate comprising a phthalocyanine dye linked to a targeting molecule, or compositions containing the same, to a subject having a disease, condition, or disorder, such as a tumor or cancer.

In some aspects, the methods also include assessment of one or more biomarkers in relation to the PIT, and performing, modifying and/or tailoring a therapeutic regimen based on the assessment. In some embodiments, the conjugate comprising a phthalocyanine dye linked to a targeting molecule is administered in an effective amount to effect treatment of the disease or disorder, such as a tumor, and is subject to light treatment, e.g., irradiation or illumination. In some aspects, the methods include a combination therapy, e.g., administering an additional therapeutic agent in addition to the PIT, based on the assessment of one or more biomarkers, in accordance with the methods provided herein, for example, as described in Section I. Uses include uses of the conjugate comprising a phthalocyanine dye linked to a targeting molecule in such methods and treatments, including in combination therapy, and in the preparation of a medicament in order to carry out such therapeutic methods, including combination therapy. In some embodiments, the methods are carried out by administering the conjugate comprising a phthalocyanine dye linked to a targeting molecule, or compositions comprising the same, to the subject having or suspected of having the disease or condition, such as a tumor. In some aspects, the methods or uses are implemented or modified based on the assessment of one or more biomarkers, in accordance with the methods provided herein. In some embodiments, the methods can be used for treating a tumor or a cancer, whereby an administered phthalocyanine-dye targeting molecule conjugate (IR700-targeting molecule conjugate, such as IR700-antibody conjugate) is targeted to a cell associated with a tumor, thereby resulting in photolysis of such cell and, in some cases, resulting in treatment of the tumor. In some embodiments, the methods thereby treat the disease or condition or disorder in the subject.

In some embodiments, with respect to the PIT, activation of the phthalocyanine dye-containing conjugate by irradiation with absorbing light, such as NIR light, excites the photosensitizer and results in cell killing, thereby reducing or eliminating the lesion (e.g., tumor) and treating the disease or condition. In some cases, the use of light in the NIR range leads to deeper tissue penetration resulting in successful eradication of tumors after only a single dose of external NIR light irradiation.

Generally, targeted phototoxicity appears to be primarily dependent on binding of the dye-conjugate to the cell membrane via the specific targeting molecule (e.g., a macromolecule, such as an antibody). For example, studies using an exemplary antibody-IR700 molecule indicate that the conjugate must be bound to the cellular membrane to be active, and that cell killing does not require intracellular localization to be effective (see, e.g., U.S. Pat. No. 8,524,239 and U.S. published application No. US20140120119). Photo-activation of the conjugate-bound cells results in rapid cell death and necrosis.

Typically, PIT results in cell death primarily of those cells to which the phthalocyanine-dye conjugate, such as IR700-antibody conjugate, binds after the cells are irradiated with NIR, while cells that do not express the cell surface protein recognized by the targeting molecule (e.g., antibody) are not killed in significant numbers. Thus, because the therapy is targeted specifically to disease cells, such as cells in a tumor, its effects are highly selective to disease tissue compared to healthy tissue or cells. For example, although a targeted photosensitizer can be distributed throughout the body, it is only active where intense light is applied, reducing the likelihood of off-target effects. This is in contrast to non-PIT-based methods in which the activity of similar therapeutic targeting molecules (e.g., therapeutic antibodies) that are not conjugated to a photosensitizer (e.g., IR700) cannot be localized, thereby resulting in significant risks of off-target side effects. In some embodiments, the phototoxic agent is a phthalocyanine dye-targeting molecule conjugate. In some embodiments, the phthalocyanine dye is IR700.

In some embodiments, the methods include administration of a phthalocyanine dye-targeting molecule conjugate (e.g., IR-700 antibody conjugate) to the subject under conditions in which, generally, a cell targeted for killing is contacted with the conjugate. In some embodiments, the methods result in the binding of the targeting molecule (e.g., antibody) portion of the conjugate to a cell surface protein associated with a tumor or cancer. After contacting or administering the conjugate, a local area of the subject containing the targeted cells, e.g., a cell or cells associated with a tumor, is exposed or irradiated with light absorbed by the dye, generally NIR light, thereby activating the conjugate to effect specific cell killing.

A. Tumors and Subjects to be Treated

In some embodiments, the lesion of the disease or disorder to be treated according to the methods and uses provided herein, is or is associated with a tumor. In some embodiments, the tumor is a cancer. In some embodiments, the cancer is a cancer of the head and neck, breast, liver, colon, ovary, prostate, pancreas, brain, cervix, bone, skin, lung, or blood. In some embodiments, cancer may include a malignant tumor characterized by abnormal or uncontrolled cell growth. Other features that may be associated with cancer include metastasis, interference with the normal functioning of neighboring cells, release of cytokines or other secretory products at abnormal levels and suppression or aggravation of inflammatory or immunological response, invasion of surrounding or distant tissues or organs, such as lymph nodes, etc. Metastatic disease may refer to cancer cells that have left the original tumor site and migrated to other parts of the body, for example via the bloodstream or lymph system. In some embodiments, a cell targeted by the disclosed methods is a cancer cell or an immune cell. In some embodiments, the cancer cell is a cancer stem cell. In some embodiments, a cell targeted by the disclosed methods is a cell that is a cancer cell, a tumor cell, an inflammatory cell, an immune cell, a neuron, a stem cell, a proliferating cell, or a cell in a hyperplasia.

The target cell can be a cell that is not desired or whose growth is not desired, such as a tumor or cancer cell. In some embodiments, the cells can be growing in culture, or present in a mammal to be treated, such as a subject with cancer. Any target cell can be treated with the claimed methods. In some embodiments, the target cell expresses a cell surface protein that is not substantially found on the surface of other normal cells. In some embodiments, an antibody can be selected that specifically binds to such protein, and a phthalocyanine dye-antibody conjugate may be generated for that protein. In some embodiments, the cell surface protein is a tumor-specific protein.

In some embodiments, the cell is a solid tumor cell, such as a sarcoma or carcinoma, fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, pancreatic cancer, breast cancer, ovarian cancer, prostate cancer, hepatocellular carcinoma, lung cancer, colorectal cancer, squamous cell carcinoma, basal cell carcinoma, adenocarcinoma, for example adenocarcinoma of the pancreas, colon, ovary, lung, breast, stomach, prostate, cervix, or esophagus, sweat gland carcinoma, sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, bladder carcinoma, CNS tumors, such as a glioma, astrocytoma, medulloblastoma, craniopharyngioma, ependymoma, pinealoma, hemangioblastoma, acoustic neuroma, oligodendroglioma, meningioma, melanoma, neuroblastoma and retinoblastoma. In some embodiments, the cancer is a squamous cell carcinoma of the head and neck.

Exemplary tumors, such as cancers, that can be treated with the claimed methods include solid tumors, such as breast carcinomas, such as lobular and duct carcinomas, sarcomas, carcinomas of the lung, such as non-small cell carcinoma, large cell carcinoma, squamous carcinoma, and adenocarcinoma, mesothelioma of the lung, colorectal adenocarcinoma, stomach carcinoma, prostatic adenocarcinoma, ovarian carcinoma, such as serous cystadenocarcinoma and mucinous cystadenocarcinoma, ovarian germ cell tumors, testicular carcinomas and germ cell tumors, pancreatic adenocarcinoma, biliary adenocarcinoma, hepatocellular carcinoma, bladder carcinoma, including, for instance, transitional cell carcinoma, adenocarcinoma, and squamous carcinoma, renal cell adenocarcinoma, endometrial carcinomas, including, for instance, adenocarcinomas and mixed Mullerian tumors (carcinosarcomas), carcinomas of the endocervix, ectocervix, and vagina, such as adenocarcinoma and squamous carcinoma of each of same, tumors of the skin, such as squamous cell carcinoma, basal cell carcinoma, malignant melanoma, skin appendage tumors, Kaposi sarcoma, cutaneous lymphoma, skin adnexal tumors and various types of sarcomas and Merkel cell carcinoma, esophageal carcinoma, carcinomas of the nasopharynx and oropharynx, including squamous carcinoma and adenocarcinomas of same, salivary gland carcinomas, brain and central nervous system tumors, including, for example, tumors of glial, neuronal, and meningeal origin, tumors of peripheral nerve, soft tissue sarcomas and sarcomas of bone and cartilage, and lymphatic tumors, including B-cell and T-cell malignant lymphoma. In some embodiments, the tumor is an adenocarcinoma.

In some embodiments, the conjugate is targeted to a protein expressed on the surface of a lesion or on the surface of a cell present in the microenvironment of the lesion. For example, in some embodiments, the conjugate is targeted to a protein expressed on the surface of a cell in the tumor or on the surface of a cell in the microenvironment of the tumor. Exemplary of such cell surface proteins are any as described herein, including those described above.

In some embodiments, the protein on the cell surface of the target cell to be targeted is not present in significant amounts on other cells. For example, the cell surface protein can be a receptor that is only found on the target cell type.

In some embodiments, the protein expressed in the tumor, e.g., tumor-specific protein, can be HER1/EGFR, HER2/ERBB2, CD20, CD25 (IL-2Ra receptor), CD33, CD52, CD133, CD206, CEA, cancer antigen 125 (CA125), alpha-fetoprotein (AFP), Lewis Y, TAG72, vascular endothelial growth factor (VEGF), CD30, EpCAM, EphA2, Glypican-3, gpA33, mucins, CAIX, PSMA, folate-binding protein, gangliosides (such as GD2, GD3, GM1 and GM2), VEGF receptor (VEGFR), integrin $\alpha V\beta 3$, integrin $\alpha 5\beta 1$, ERBB3, MET, IGF1R, EPHA3, TRAILR1, TRAILR2, RANKL, FAP, tenascin, AFP, BCR complex, CD3, CD18, CD44, CTLA-4, gp72, HLA-DR 10β, HLA-DR antigen, IgE, MUC-1, nuC242, PEM antigen, SK-1 antigen or PD-L1. In some embodiments, the tumor-specific protein is PD-L1, HER1/EGFR, HER2, CD20, CD25, CD33, CD52, prostate specific membrane antigen (PSMA), EpCAM, EphA2, CD206, CD44, CD133, Mesothelin, Glypican-3, or carcinoembryonic antigen (CEA). Other cell surface proteins include any as described above.

In some embodiments, the cell surface protein is associated with a tumor, such as is a tumor-specific protein or tumor-specific antigen, such as members of the EGF receptor family (e.g., HER1, 2, 3, and 4) and cytokine receptors (e.g., CD20, CD25, IL-13R, CD5, CD52, etc.). In some embodiments, tumor specific proteins are those proteins that are unique to cancer cells or are much more abundant on them, as compared to other cells, such as normal cells. For example, HER2 is generally found in breast cancers, while HER1 is typically found in adenocarcinomas, which can be found in many organs, such as the pancreas, breast, prostate and colon.

Exemplary proteins associated with a tumor that can be found on a target cell, and to which targeting molecule, e.g. antibody or antibody fragment, specific for that protein can be used to formulate a phthalocyanine dye-antibody conjugate, include but are not limited to: any of the various MAGEs (Melanoma-Associated Antigen E), including MAGE 1, MAGE 2, MAGE 3, and MAGE 4, any of the various tyrosinases, mutant ras, mutant p53, p97 melanoma antigen, human milk fat globule (HMFG) which may be associated with breast tumors, any of the various BAGEs (Human B melanoma-Associated Antigen E), including BAGE1 and BAGE2, any of the various GAGEs (G antigen), including GAGE1, GAGE2-6, various gangliosides, and CD25.

Other proteins associated with a tumor include the HPV 16/18 and E6/E7 antigens associated with cervical cancers, mucin (MUC 1)-KLH antigen which may be associated with breast carcinoma, CEA (carcinoembryonic antigen) which may be associated with colorectal cancer, gp100 which may be associated with for example melanoma, MARTI antigens which may be associated with melanoma, cancer antigen 125 (CA125, also known as mucin 16 or MUC16) which may be associated with ovarian and other cancers, alpha-fetoprotein (AFP) which may be associated with liver cancer, Lewis Y antigen which may be associated with colorectal, biliary, breast, small-cell lung, and other cancers, tumor-associated glycoprotein 72 (TAG72) which may be associated with adenocarcinomas, and the PSA antigen which may be associated with prostate cancer.

Other exemplary proteins associated with a tumor further include, but are not limited to, PMSA (prostate membrane specific antigen), which may be associated with solid tumor neovasculature, as well prostate cancer, HER-2 (human epidermal growth factor receptor 2) which may be associated with breast cancer, ovarian cancer, stomach cancer and uterine cancer, HER-1 which may be associated with lung cancer, anal cancer, and glioblastoma as well as adenocarcinomas, NY-ESO-1 which may be associated with melanoma, sarcomas, testicular carcinomas, and other cancers, hTERT (aka telomerase), proteinase 3, and Wilms tumor 1 (WT-1).

In some embodiments, the protein associated with a tumor is CD52 and may be associated with chronic lymphocytic leukemia, CD33 and may be associated with acute myelogenous leukemia, or CD20 and may be associated with Non-Hodgkin lymphoma.

Thus, the disclosed methods can be used to treat any cancer that expresses a tumor-specific protein. In some embodiments, the targeting molecule of the conjugate used in PIT is an antibody, an antigen binding fragment, a protein, a glycoprotein, a peptide, a polypeptide, a virus, a viral capsid, or a viral particle. In some embodiments, the targeting molecule is an antibody or an antigen binding fragment.

In some embodiments, the subject is a human or non-human mammal. In some embodiments, the subject is a human or veterinary subject, such as a mouse. In some embodiments, the subject is a mammal, such as a human, who has cancer, or is being treated for cancer. In some embodiments the disclosed methods are used to treat a subject who has a tumor, such as a tumor described herein. In some embodiments, the tumor has been previously treated, such as surgically or chemically removed, and the disclosed methods are used subsequently to kill any remaining undesired tumor cells that may remain in the subject.

The disclosed methods can be used to treat any mammalian subject, such as a human, who has a tumor, such as a cancer, or has had such previously removed or treated. Subjects in need of the disclosed therapies can include human subjects having cancer, wherein the cancer cells express a tumor-specific protein on their surface that can specifically bind to phthalocyanine dye-targeting molecule conjugate. For example, the disclosed methods can be used as initial treatment for cancer either alone, or in combination with radiation or other chemotherapy. The disclosed methods can also be used in patients who have failed previous radiation or chemotherapy. Thus, in some embodiments, the subject is one who has received other therapies, but those other therapies have not provided a desired therapeutic response. The disclosed methods can also be used in patients with localized and/or metastatic cancer.

In some embodiments, the method includes selecting a subject that will benefit from the disclosed therapies, such as selecting a subject having a tumor that expresses a cell surface protein, such as a tumor-specific protein, that can specifically bind to a phthalocyanine dye-targeting molecule conjugate. For example, if the subject is determined to have a breast cancer that expresses HER1, the subject may be selected to be treated with an anti-HER1-IR700 molecule, such as cetuximab-IR700. The methods herein can be applied to further refine such selection by using one or more of the biomarkers described herein to assess a subject prior to photoimmunotherapy, after an initial administration of photoimmunotherapy, and prior to selecting an additional therapeutic agent, for example an immune modulating agent or other therapeutic agent, for use in combination with photoimmunotherapy. In some aspects, the subject for PIT and/or for administration of one or more therapeutic agents (e.g., a combination therapy), can be selected based on the level of expression of one or more biomarkers, according to any of the methods described herein, for example, in Sections I and II.

B. Dosage and Administration

The compositions provided herein containing a phthalocyanine dye-targeting molecule conjugate (e.g., IR700-antibody conjugate) are administered in amounts that are sufficient to exert a therapeutically useful effect. Typically, the active agents are administered in an amount that does not result in undesirable side effects of the patient being treated, or that minimizes or reduces the observed side effects as compared to dosages and amounts required for single treatment with one of the above agents.

Methods of determining optimal dosages of a phthalocyanine dye-targeting molecule conjugate (e.g., IR700-antibody conjugate) to a patient in need thereof, either alone or in combination with one or more other agents, may be determined based on standard dose-response and toxicity studies that are well known. Additionally, the methods described herein can be applied to define and further refine appropriate dosage and timing, based on the assessment of one or more of the biomarkers described herein, for example in Sections I and II, to assess a subject's predicted likelihood of response and magnitude of response to PIT. In some aspects, treatment regimen, such as dosing, timing, can be adjusted as appropriate, as well as for dosing an immune modulating agent or other therapeutic agent for use in combination with photoimmunotherapy.

In some aspects, the biomarker assessment can be performed before the subject receiving a treatment of PIT. In some aspects, the dosage and timing of the PIT (including dosage, frequency, relative timing of the conjugate and/or light administration) can be based on the assessment of the one or more biomarkers described herein. In some aspects, the biomarker assessment may inform the dosing and timing, and/or the administration of one or more additional treatment using PIT, and/or an additional therapeutic agent, such as an immune modulating agent or an anti-cancer agent. The dosage and timing of the additional PIT treatment and/or additional therapeutic agent can be selected, e.g., according to the methods provided herein. In some embodiments, the additional therapeutic agent is a second conjugate comprising a phthalocyanine dye and a targeting molecule. In some aspects, the second conjugate contains the same or different phthalocyanine dye and/or targeting molecule as the conjugate used in the initial PIT.

In some aspects, for example in the context of a combination therapy involving a PIT, the biomarker assessment can be performed after the subject receiving an initial treatment of PIT. In some aspects, the initial treatment can be according to any of the dosage and timing described herein. In some aspects, after the biomarker assessment, the subject may receive one or more additional treatment using PIT, and/or an additional therapeutic agent. The dosage and timing of the additional PIT treatment (including dosage, frequency, relative timing of the conjugate and/or light administration) and/or additional therapeutic agent can be selected, e.g., according to the methods provided herein.

The amount of a therapeutic agent, such as the phthalocyanine dye-targeting molecule conjugate (e.g., IR700-antibody conjugate) that is administered to a human or veterinary subject will vary depending upon a number of factors associated with that subject, for example the overall health of the subject. In some embodiments, an effective amount of the agent can be determined by varying the dosage of the product and measuring the resulting therapeutic response, such as the regression of a tumor. In some embodiments, effective amounts can be determined through various in vitro, in vivo or in situ immunoassays. In some embodiments, the disclosed agents can be administered in a single dose, or in several doses, as needed to obtain the desired response. In some embodiments, the effective amount is dependent on the source applied, the subject being treated, the severity and type of the condition being treated, and the manner of administration.

In some embodiments, a therapeutically effective amount is an amount of a composition that alone, or together with an additional therapeutic agent, such as a chemotherapeutic agent, is sufficient to achieve a desired effect in a subject, or in a cell, being treated with the composition. The effective amount of the therapeutic agent, such as the phthalocyanine dye-targeting molecule conjugate (e.g., IR700-antibody conjugate) can be dependent on several factors, including, but not limited to the subject or cells being treated, the particular therapeutic agent, and the manner of administration of the therapeutic composition. In some embodiments, a therapeutically effective amount or concentration is one that is sufficient to prevent advancement, such as metastasis, delay progression, or to cause regression of a disease, or which is capable of reducing symptoms caused by the disease, such as cancer. In some embodiments, a therapeutically effective amount or concentration is one that is sufficient to increase the survival time of a patient with a tumor.

In some embodiments, a therapeutically effective dose of the conjugate is between or between about 10 $mg/m^2$ and 5000 $mg/m^2$, such as between or between about 10 $mg/m^2$ and 3000 $mg/m^2$, 10 $mg/m^2$ and 1500 $mg/m^2$, 10 $mg/m^2$ and 750 $mg/m^2$, 10 $mg/m^2$ and 500 $mg/m^2$, 10 $mg/m^2$ and 250 $mg/m^2$, 10 $mg/m^2$ and 200 $mg/m^2$, 10 $mg/m^2$ and 100 $mg/m^2$, 10 $mg/m^2$ and 75 $mg/m^2$, 10 $mg/m^2$ and 50 $mg/m^2$, 10 $mg/m^2$ and 25 $mg/m^2$, 25 $mg/m^2$ and 5000 $mg/m^2$, 25 $mg/m^2$ and 3000 $mg/m^2$, 25 $mg/m^2$ and 1500 $mg/m^2$, 25 $mg/m^2$ and 750 $mg/m^2$, 25 $mg/m^2$ and 500 $mg/m^2$, 25 $mg/m^2$ and 250 $mg/m^2$, 25 $mg/m^2$ and 200 $mg/m^2$, 25 $mg/m^2$ and 100 $mg/m^2$, 25 $mg/m^2$ and 75 $mg/m^2$, 25 $mg/m^2$ and 50 $mg/m^2$, 50 $mg/m^2$ and 5000 $mg/m^2$, 50 $mg/m^2$ and 3000 $mg/m^2$, 50 $mg/m^2$ and 1500 $mg/m^2$, 50 $mg/m^2$ and 750 $mg/m^2$, 50 $mg/m^2$ and 500 $mg/m^2$, 50 $mg/m^2$ and 250 $mg/m^2$, 50 $mg/m^2$ and 200 $mg/m^2$, 50 $mg/m^2$ and 100 $mg/m^2$, 50 $mg/m^2$ and 75 $mg/m^2$, 75 $mg/m^2$ and 5000 $mg/m^2$, 75 $mg/m^2$ and 3000 $mg/m^2$, 75 $mg/m^2$ and 1500 $mg/m^2$, 75 $mg/m^2$ and 1000 $mg/m^2$, 75 $mg/m^2$ and 750 $mg/m^2$, 75 $mg/m^2$ and 500 $mg/m^2$, 75 $mg/m^2$ and 250 $mg/m^2$, 75 $mg/m^2$ and 225 $mg/m^2$, 75 $mg/m^2$ and 200 $mg/m^2$, 75 $mg/m^2$ and 100 $mg/m^2$, 100 $mg/m^2$ and 5000 $mg/m^2$, 100 $mg/m^2$ and 3000 $mg/m^2$, 100 $mg/m^2$ and 1500 $mg/m^2$, 100 $mg/m^2$ and 750 $mg/m^2$, 100 $mg/m^2$ and 500 $mg/m^2$, 100 $mg/m^2$ and 250 $mg/m^2$, 100 $mg/m^2$ and 200 $mg/m^2$, 100 $mg/m^2$ and 150 $mg/m^2$, 150 $mg/m^2$ and 5000 $mg/m^2$, 150 $mg/m^2$ and 3000 $mg/m^2$, 150 $mg/m^2$ and 1500 $mg/m^2$, 150 $mg/m^2$ and 750 $mg/m^2$, 150 $mg/m^2$ and 500 $mg/m^2$, 150 $mg/m^2$ and 250 $mg/m^2$, 150 $mg/m^2$ and 200 $mg/m^2$, 200 $mg/m^2$ and 5000 $mg/m^2$, 200 $mg/m^2$ and 3000 $mg/m^2$, 200 $mg/m^2$ and 1500 $mg/m^2$, 200 $mg/m^2$ and 750 $mg/m^2$, 200 $mg/m^2$ and 500 $mg/m^2$, 200 $mg/m^2$ and 250 $mg/m^2$, 250 $mg/m^2$ and 5000 $mg/m^2$, 250 $mg/m^2$ and 3000 $mg/m^2$, 250 $mg/m^2$ and 1500 $mg/m^2$, 250 $mg/m^2$ and 750

$mg/m^2$, 250 $mg/m^2$ and 500 $mg/m^2$, 500 $mg/m^2$ and 5000 $mg/m^2$, 500 $mg/m^2$ and 3000 $mg/m^2$, 500 $mg/m^2$ and 1500 $mg/m^2$, 500 $mg/m^2$ and 750 $mg/m^2$, 750 $mg/m^2$ and 5000 $mg/m^2$, 750 $mg/m^2$ and 3000 $mg/m^2$, 750 $mg/m^2$ and 1500 $mg/m^2$, 1500 $mg/m^2$ and 5000 $mg/m^2$, 1500 $mg/m^2$ and 3000 $mg/m^2$, and 3000 $mg/m^2$ and 5000 $mg/m^2$. In some embodiments, the therapeutically effective dose of the conjugate is no more than 10 $mg/m^2$, 50 $mg/m^2$, 75 $mg/m^2$, 100 $mg/m^2$, 150 $mg/m^2$, 200 $mg/m^2$, 225 $mg/m^2$, 250 $mg/m^2$, 300 $mg/m^2$, 400 $mg/m^2$, 500 $mg/m^2$, 600 $mg/m^2$, 700 $mg/m^2$, 800 $mg/m^2$, 900 $mg/m^2$, 1000 $mg/m^2$, 1250 $mg/m^2$, 1500 $mg/m^2$, 2000 $mg/m^2$, 2500 $mg/m^2$, 3000 $mg/m^2$, 3500 $mg/m^2$, 4000 $mg/m^2$, 4500 $mg/m^2$, or 5000 $mg/m^2$. In some embodiments, the dose is from or from about 50 $mg/m^2$ to about 5000 $mg/m^2$, from about 250 $mg/m^2$ to about 2500 $mg/m^2$, from about 750 $mg/m^2$ to about 1250 $mg/m^2$ or from about 100 $mg/m^2$ to about 1000 $mg/m^2$. In some embodiments, the dose is or is about 160 $mg/m^2$, 320 $mg/m^2$, 640 $mg/m^2$ or 1280 $mg/m^2$.

In some embodiments, a therapeutically effective dose of the conjugate is between or between about 0.25 mg/kg and 150 mg/kg, 0.25 mg/kg and 100 mg/kg, 0.25 mg/kg and 75 mg/kg, 0.25 mg/kg and 60 mg/kg, 0.25 mg/kg and 50 mg/kg, 0.25 mg/kg and 25 mg/kg, 0.25 mg/kg and 10 mg/kg, 0.25 mg/kg and 7.5 mg/kg, 0.25 mg/kg and 5.0 mg/kg, 0.25 mg/kg and 2.5 mg/kg, 0.25 mg/kg and 1.0 mg/kg, 0.25 mg/kg and 0.5 mg/kg, 0.50 mg/kg and 150 mg/kg, 0.50 mg/kg and 100 mg/kg, 0.50 mg/kg and 75 mg/kg, 0.50 mg/kg and 60 mg/kg, 0.50 mg/kg and 50 mg/kg, 0.50 mg/kg and 25 mg/kg, 0.50 mg/kg and 10 mg/kg, 0.50 mg/kg and 7.5 mg/kg, 0.50 mg/kg and 5.0 mg/kg, 0.50 mg/kg and 2.5 mg/kg, 0.50 mg/kg and 1.0 mg/kg, 1.0 mg/kg and 150 mg/kg, 1.0 mg/kg and 100 mg/kg, 1.0 mg/kg and 75 mg/kg, 1.0 mg/kg and 60 mg/kg, 1.0 mg/kg and 50 mg/kg, 1.0 mg/kg and 25 mg/kg, 1.0 mg/kg and 10 mg/kg, 1.0 mg/kg and 7.5 mg/kg, 1.0 mg/kg and 5.0 mg/kg, 1.0 mg/kg and 2.5 mg/kg, 2.5 mg/kg and 150 mg/kg, 2.5 mg/kg and 100 mg/kg, 2.5 mg/kg and 75 mg/kg, 2.5 mg/kg and 60 mg/kg, 2.5 mg/kg and 50 mg/kg, 2.5 mg/kg and 25 mg/kg, 2.5 mg/kg and 10 mg/kg, 2.5 mg/kg and 7.5 mg/kg, 2.5 mg/kg and 5.0 mg/kg, 5.0 mg/kg and 150 mg/kg, 5.0 mg/kg and 100 mg/kg, 5.0 mg/kg and 75 mg/kg, 5.0 mg/kg and 60 mg/kg, 5.0 mg/kg and 50 mg/kg, 5.0 mg/kg and 25 mg/kg, 5.0 mg/kg and 10 mg/kg, 5.0 mg/kg and 7.5 mg/kg, 7.5 mg/kg and 150 mg/kg, 7.5 mg/kg and 100 mg/kg, 7.5 mg/kg and 75 mg/kg, 7.5 mg/kg and 60 mg/kg, 7.5 mg/kg and 50 mg/kg, 7.5 mg/kg and 25 mg/kg, 7.5 mg/kg and 10 mg/kg, 10 mg/kg and 150 mg/kg, 10 mg/kg and 100 mg/kg, 10 mg/kg and 75 mg/kg, 10 mg/kg and 60 mg/kg, 10 mg/kg and 50 mg/kg, 10 mg/kg and 25 mg/kg, 25 mg/kg and 150 mg/kg, 25 mg/kg and 100 mg/kg, 25 mg/kg and 75 mg/kg, 25 mg/kg and 60 mg/kg, 25 mg/kg and 50 mg/kg, 50 mg/kg and 150 mg/kg, 50 mg/kg and 100 mg/kg, 50 mg/kg and 75 mg/kg, 50 mg/kg and 60 mg/kg, 60 mg/kg and 150 mg/kg, 60 mg/kg and 100 mg/kg, 60 mg/kg and 75 mg/kg, 75 mg/kg and 150 mg/kg, 75 mg/kg and 100 mg/kg, and 100 mg/kg and 150 mg/kg. In some embodiments, the therapeutically effective dose of the conjugate is no more than 0.25 mg/kg, 0.5 mg/kg, 1.0 mg/kg, 2.0 mg/kg, 3.0 mg/kg, 4.0 mg/kg, 5.0 mg/kg, 6.0 mg/kg, 7.0 mg/kg, 8.0 mg/kg, 9.0 mg/kg, 10.0 mg/kg, 15 mg/kg, 20 mg/kg, 25 mg/kg, 30 mg/kg, 40 mg/kg, 50 mg/kg, 60 mg/kg, 70 mg/kg, 75 mg/kg, 80 mg/kg, 90 mg/kg, 100 mg/kg, 125 mg/kg or 150 mg/kg.

In some embodiments, the therapeutically effective amount is at least or at least about 0.01 mg, 0.1 mg, 0.5 mg, 1 mg, 5 mg, 10 mg, 50 mg, 100 mg, 200 mg, 500 mg, 600 mg, 700 mg, 800 mg, 900 mg, 1000 mg, 2000 mg, 3000 mg or more.

In some embodiments, the methods include administering to a subject having a disease or condition a therapeutically effective amount of a phthalocyanine dye-targeting molecule conjugate, e.g., IR700-antibody conjugate. In some embodiments, the phthalocyanine dye-targeting molecule conjugate is targeted to a cell present in the microenvironment of a tumor, lesion or hyperplasia. In some embodiments, a therapeutically effective dose of the conjugate is administered intravenously. In some embodiments, a therapeutically effective dose of the conjugate is administered intratumorally.

In some embodiments, the dose of the conjugate is at least 10 μg/kg, such as at least 100 μg/kg, at least 500 μg/kg, or at least 500 μg/kg, for example 10 μg/kg to 1000 μg/kg, such as a dose of about 100 μg/kg, about 250 μg/kg, about 500 μg/kg, about 750 μg/kg, or about 1000 μg/kg, for example when administered intratumorally or intraperitoneally (IP). In some embodiments, the dose is at least 1 μg/ml, such as at least 500 μg/ml, such as between 20 μg/ml to 100 μg/ml, such as about 10 μg/ml, about 20 μg/ml, about 30 μg/ml, about 40 μg/ml, about 50 μg/ml, about 60 μg/ml, about 70 μg/ml, about 80 μg/ml, about 90 μg/ml or about 100 μg/ml, for example administered in topical solution.

In some embodiments, the therapeutically effective dose is a dose administered to a human. In some embodiments, the weight of an average human is 60 to 85 kg, such as about or approximately 75 kg.

In some embodiments, a therapeutically effective dose is one in which an administered conjugate containing a phthalocyanine dye conjugated to a targeting molecule (e.g., antibody or antigen-binding antibody fragment) achieves a systemic exposure that is no more than the therapeutically effective systemic exposure of the targeting molecule (e.g., antibody or antigen-binding antibody fragment) that is not so conjugated, such as occurs upon administration of a clinically acceptable dose of the drug targeting molecule drug alone. In some embodiments, the therapeutically effective amount is between about 75 mg and 500 mg, 75 mg and 400 mg, 75 mg and 400 mg, 75 mg and 300 mg, 75 mg and 200 mg, 75 mg and 150 mg, 150 mg and 500 mg, 150 mg and 400 mg, 150 mg and 300 mg, 150 mg and 200 mg, 200 mg and 500 mg, 200 mg and 400 mg, 200 mg and 300 mg, 300 mg and 500 mg, 300 mg and 400 mg or 400 mg and 500 mg. In some embodiments, the conjugate is IR700-cetuximab. In some embodiments, the therapeutically effective amount of IR700-cetuximab conjugate is at least or about at least or is or is about 160 $mg/m^2$, 320 $mg/m^2$ or 640 $mg/m^2$. In some embodiments, the therapeutically effective amount of IR700-cetuximab conjugate is at least or about at least or is or is about 4.3 mg/kg, 8.6 mg/kg or 17 mg/kg.

In some aspects, the biomarker assessment can be performed before the subject receiving a treatment of PIT, for example, using the IR700-cetuximab conjugate. In some aspects, the dosage and timing of the IR700-cetuximab conjugate, and the light administration, can be based on the assessment of the one or more biomarkers described herein. In some aspects, the biomarker assessment may inform the dosing and timing, and/or the administration of one or more additional treatment of PIT using the IR700-cetuximab conjugate, and/or an additional therapeutic agent, such as an immune modulating agent or an anti-cancer agent or a PIT treatment using a second conjugate. The dosage and timing of the additional PIT treatment and/or additional therapeutic agent can be selected, e.g., according to the methods provided herein. In some embodiments, the dosage of IR700-cetuximab conjugate to be administered in the PIT treatment is at least or about at least or is or is about 160 $mg/m^2$, 320 $mg/m^2$ or 640 $mg/m^2$. In some embodiments, the dosage of IR700-cetuximab conjugate is at least or about at least or is or is about 4.3 mg/kg, 8.6 mg/kg or 17 mg/kg.

In some aspects, for example in the context of a combination therapy involving a PIT, for example, using the IR700-cetuximab conjugate, the biomarker assessment can be performed after the subject receiving an initial treatment of PIT using the IR700-cetuximab conjugate. In some aspects, the initial treatment can be according to any of the dosage and timing described herein. In some aspects, after the biomarker assessment, the subject may receive one or more additional treatment of PIT using the IR700-cetuximab conjugate, and/or an additional therapeutic agent, such as an immune modulating agent or an anti-cancer agent or a PIT treatment using a second conjugate. The dosage and timing of the additional PIT treatment and/or additional therapeutic agent can be selected, e.g., according to the methods provided herein. In some embodiments, the dosage of IR700-cetuximab conjugate to be administered in the initial or additional PIT treatment is at least or about at least or is or is about 160 $mg/m^2$, 320 $mg/m^2$ or 640 $mg/m^2$. In some embodiments, the dosage of IR700-cetuximab conjugate for the initial or additional PIT treatment is at least or about at least or is or is about 4.3 mg/kg, 8.6 mg/kg or 17 mg/kg.

In some embodiments, the therapeutically effective dose of the conjugate is for single dosage administration. In some embodiments, the therapeutically effective dose is administered as only a single injection or a single infusion in a dosage schedule or cycle, for example, is administered only one time in a dosage schedule or cycle. For example, in a dosing schedule or cycle, a subsequent dose of the conjugate is not administered. In some embodiments, the dosing schedule can be repeated. In some embodiments, the repeated dose, such as repeated single dose, is administered at a time in which the first dose has been cleared from the subject, which, in some cases, is a time at which there is no detectable systemic exposure of the conjugate. Thus, in some embodiments, the dosing of the conjugate is not administered to achieve a continuous systemic exposure of the conjugate, which is different than many existing therapies, including antibody therapies, in which repeating dosing in a dosing schedule or cycle is required to maintain continuous systemic exposure. In some embodiments, the dosing schedule or cycle is repeated once a week, every two weeks, once a month, twice a year, once a year or at a lesser frequency as needed. The methods herein can be applied to select appropriate timing and selection of an administration schedule.

In some embodiments, in any of the methods for treating provided herein, the dosing schedule is repeated, if residual lesion remains after a prior treatment with the conjugate. In some embodiments, the method additionally includes assessing the subject for the presence of a residual lesion and if residual lesion remains repeating the dosing schedule. In some embodiments, the dosing schedule is repeated if a residual lesion remains at a time that is more than or about or 1 week, 2 weeks, 3 weeks, 4 weeks, 2 months, 6 months or 1 year after initiation of the prior administration of the conjugate. In some embodiments, the dosing schedule is repeated if a residual lesion remains at or about 4 weeks after initiation of the prior administration of the conjugate. In some embodiments, one or more biomarkers is assessed and the level, amount or concentration of the biomarker at one or more time points indicates the presence or likely presence of a residual lesion and such subject is a candidate for a repeated dosing schedule for photoimmunotherapy and/or photoimmunotherapy as a combination therapy.

A skilled person will recognize that higher or lower dosages of the phthalocyanine dye-targeting molecule conjugate can also be used, for example depending on the particular agent. In some embodiments, dosages, such as daily dosages, are administered in one or more divided doses, such as 2, 3, or 4 doses, or in a single formulation. The phthalocyanine dye-targeting molecule conjugate can be administered alone, in the presence of a pharmaceutically acceptable carrier, or in the presence of other therapeutic agents, such as an immune-modulating agent, anti-cancer agent or other anti-neoplastic agents.

In some embodiments, the phthalocyanine dye-targeting molecule conjugate may be administered either systemically or locally to the organ or tissue to be treated. Exemplary routes of administration include, but are not limited to, topical, injection (such as subcutaneous, intramuscular, intradermal, intraperitoneal, intratumoral, and intravenous), oral, sublingual, rectal, transdermal, intranasal, vaginal and inhalation routes. In some embodiments, the phthalocyanine dye-targeting molecule conjugate is administered intravenously. In some embodiments, the phthalocyanine dye-targeting molecule conjugate is administered parenterally. In some embodiments, the phthalocyanine dye-targeting molecule conjugate is administered enterally. In some embodiments, the conjugate is administered by local injection. In some embodiments, the conjugate is administered as a topical application.

The compositions comprising the phthalocyanine dye-targeting molecule conjugate can be administered locally or systemically using any known method, for example to subjects having a tumor, such as a cancer, or who has had a tumor previously removed, for example via surgery. Although specific examples are provided, a skilled person will appreciate that alternative methods of administration of the disclosed agents can be used. Such methods may include for example, the use of catheters or implantable pumps to provide continuous infusion over a period of several hours to several days into the subject in need of treatment.

In some embodiments, the phthalocyanine dye-targeting molecule conjugate is administered by parenteral means, including direct injection or infusion into a tumor, such as intratumorally. In some embodiments, the phthalocyanine dye-targeting molecule conjugate is administered to the tumor by applying the agent to the tumor, for example by bathing the tumor in a solution containing the agent, such as the phthalocyanine dye-targeting molecule conjugate, or by pouring the agent onto the tumor.

In addition, or alternatively, the disclosed compositions can be administered systemically, for example intravenously, intramuscularly, subcutaneously, intradermally, intraperitoneally, subcutaneously, or orally, to a subject having a tumor, such as cancer.

The dosages of the phthalocyanine dye-targeting molecule conjugate to be administered to a subject are not subject to absolute limits, but will depend on the nature of the composition and its active ingredients and its unwanted side effects, such as immune response against the agent, the subject being treated, and the type of condition being treated and the manner of administration. Generally, the dose will be a therapeutically effective amount, such as an amount sufficient to achieve a desired biological effect, for example an amount that is effective to decrease the size, such as volume and/or weight, of the tumor, or attenuate further growth of the tumor, or decrease undesired symptoms of the tumor.

In some embodiments, the compositions used for administration of the agent, such as the phthalocyanine dye-targeting molecule conjugate contain an effective amount of the agent along with conventional pharmaceutical carriers and excipients appropriate for the type of administration contemplated. For example, in some embodiments, parenteral formulations may contain a sterile aqueous solution or suspension of the conjugate. In some embodiments, compositions for enteral administration may contain an effective amount of the phthalocyanine dye-targeting molecule conjugate in aqueous solution or suspension that may optionally include buffers, surfactants, thixotropic agents, and flavoring agents.

C. Dosage Regime and Photoimmunotherapy

In some embodiments of the methods and uses provided herein, the PIT includes administration of a composition containing the phthalocyanine dye-targeting molecule conjugate (e.g., IR700-antibody conjugate) followed by irradiation. In some embodiments, the method includes irradiating areas proximal to or surrounding the tumor and/or the tumor.

In some embodiments, after the cells are contacted with the phthalocyanine dye-targeting molecule conjugate, the areas proximal to or surrounding the tumor and/or the tumor are irradiated. Methods of irradiation are known. As only cells expressing the cell surface protein will typically be recognized by the targeting molecule, generally only those cells will have sufficient amounts of the conjugate bound to it. This may decrease the likelihood of undesired side effects, such as killing of normal cells, as the irradiation may only kill the cells to which the conjugate is bound, and generally not other cells.

In some embodiments, a cell is irradiated in vivo, for example irradiating a subject who has previously been administered the phthalocyanine dye-targeting molecule conjugate. In some embodiments, the subject is irradiated, for example a tumor in the subject can be irradiated.

In some embodiments, the irradiation is effected after administration of the phthalocyanine dye-targeting molecule conjugate. In some embodiments, the irradiation or illumination is carried out or effected between or between about 30 minutes and 96 hours after administering the phthalocyanine dye-targeting molecule conjugate (e.g., IR700-antibody conjugate), such as between 30 minutes and 48 hours, 30 minutes and 24 hours or 12 hours and 48 hours, such as generally at least 30 minutes, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours or more, such as 2, 3, 4, 5, 6, 7 days, 1, 2, 3 or 4 weeks or more after administering the conjugate. For example, the irradiation can be performed within about 24 hours after administering the conjugate. In some embodiments, greater than 6 hours prior to irradiating or illuminating the tumor, the subject has been administered the conjugate comprising the targeting molecule, wherein the conjugate associates with the tumor. In some embodiments, the conjugate has been previously administered to the subject greater than or greater than about 12 hours, 24 hours, 26 hours, 48 hours, 72 hours or 96 hours prior to irradiating or illuminating the tumor.

In some embodiments, irradiation is performed at a wavelength of 500 nm to 900 nm. In some embodiments, the irradiation is at a wavelength of at or about 660 nm to at or about 740 nm. In some embodiments, the irradiation is at a wavelength of at or about 690±50 nm or at a wavelength of at or about 690±20 nm. In some embodiments, the irradiation is at a wavelength of at or about 690 nm. In some embodiments, the irradiation is performed at a dose of at least 1 J $cm^{-2}$ or at least 1 J/cm of fiber length. In some embodiments, the irradiation is performed at a wavelength of 500 nm to 900 nm at a dose of at least 1 J $cm^{-2}$ or 1 J/cm of fiber length.

In some embodiments, the irradiation is at a dose of at or about 2 J $cm^{-2}$ to at or about 400 J $cm^{-2}$ or from at or about 2 J/cm fiber length to at or about 500 J/cm fiber length. In some embodiments, the irradiation is at a dose of at least at or about 2 J $cm^{-2}$, 5 J $cm^{-2}$, 10 J $cm^{-2}$, 25 J $cm^{-2}$, 50 J $cm^{-2}$, 75 J $cm^{-2}$, 100 J $cm^{-2}$, 150 J $cm^{-2}$, 200 J $cm^{-2}$, 300 J $cm^{-2}$, 400 J $cm^{-2}$, or 500 J $cm^{-2}$. In some embodiments, the irradiation is at a dose of at least at or about 2 J/cm fiber length, 5 J/cm fiber length, 10 J/cm fiber length, 25 J/cm fiber length, 50 J/cm fiber length, 75 J/cm fiber length, 100 J/cm fiber length, 150 J/cm fiber length, 200 J/cm fiber length, 250 J/cm fiber length, 300 J/cm fiber length, 400 J/cm fiber length or 500 J/cm fiber length. In some embodiments, irradiation is performed at a wavelength of 600 nm to 850 nm at a dose of at least 1 J $cm^{-2}$ or at least 1 J/cm of fiber length, such as at a dose of from at or about 25 J $cm^{-2}$ to at or about 400 J $cm^{-2}$ or from at or about 25 J/cm of fiber length to at or about 500 J/cm of fiber length. In some embodiments, the methods of administering a phthalocyanine dye-targeting molecule conjugate (e.g., IR700 antibody conjugate) include methods described in U.S. Pat. No. 8,524,239 or U.S. publication No. US 2014/0120119 and WO 2017/031367.

In some embodiments, an anti-EGFR-IR700 conjugate is administered, and irradiation is performed at a wavelength of 500 nm to 900 nm. In some of such embodiments, the irradiation is at a wavelength of at or about 660 nm to at or about 740 nm. In some of such embodiments, the irradiation is at a wavelength of at or about 690±50 nm or at a wavelength of at or about 690±20 nm. In some of such embodiments, the irradiation is at a wavelength of at or about 690 nm.

In some embodiments, the biomarker is an immune checkpoint biomarker and, an anti-EGFR-IR700 conjugate is administered, and irradiation is performed at a wavelength of 500 nm to 900 nm. In some of such embodiments, the irradiation is at a wavelength of at or about 660 nm to at or about 740 nm. In some of such embodiments, the irradiation is at a wavelength of at or about 690±50 nm or at a wavelength of at or about 690±20 nm. In some of such embodiments, the irradiation is at a wavelength of at or about 690 nm.

In some embodiments, the biomarker is a cell, such as an immune cell, a dendritic cell, or a cell that expresses CD3, CD4, and PD-1; a protein, such as one or more of CD11c, CD14, CD68, CD163, or PD-L1, an anti-EGFR-IR700 conjugate is administered, and irradiation is performed at a wavelength of 500 nm to 900 nm. In some of such embodiments, the irradiation is at a wavelength of at or about 660 nm to at or about 740 nm. In some of such embodiments, the irradiation is at a wavelength of at or about 690±50 nm or at a wavelength of at or about 690±20 nm. In some of such embodiments, the irradiation is at a wavelength of at or about 690 nm.

D. Combination Therapy

In some aspects, the provided methods involve measurement and assessment of one or more biomarker(s) in the context of a treatment for a tumor that involves PIT and administering or involving an additional therapeutic agent. In some aspects, a combination therapy of PIT and an additional therapeutic agent, is employed, based on the assessment of one or more biomarkers as described herein, e.g., in Sections I and II. In some embodiments, such assessment can be used to monitor the outcome of treatment and to identify, tailor or modify the therapeutic regimen, such as administration of an additional therapeutic agent, for a particular subject. In some aspects, the provided methods can be applied to select certain subjects for treatment, e.g., with an additional therapeutic agent in combination with the PIT. Exemplary specific steps for implementing the PIT as a part of a combination therapy and reagents are described herein, for example, in this section. In some embodiments, certain aspects of implementing the combination, may be performed, modified or tailored based on the assessment of one or more biomarkers, according to the methods described herein, e.g., in Sections I and II.

In some embodiments, an additional therapeutic agent, such as an immune modulating agent or anti-cancer agent is administered in conjunction with a photoimmunotherapy agent, such as a phthalocyanine dye conjugate, for example an IR700-antibody conjugate. In some embodiments, the combination therapy can include administration of a phthalocyanine dye conjugate, for example an IR700-antibody conjugate, in combination with an anti-cancer agent or immune modulating agent, such as an immune checkpoint inhibitor. In some embodiments, the additional therapeutic agent is a second conjugate comprising a phthalocyanine dye and a targeting molecule. In some aspects, the second conjugate contains the same or different phthalocyanine dye and/or targeting molecule as the first conjugate.

In some embodiments, at the time of or after the irradiation, the subject can receive one or more other therapies (e.g., immune-modulating agent or anti-cancer agent) as described herein. In some embodiments, after the irradiation step of the PIT treatment, the level, concentration or amount of the biomarkers can be assessed in a sample from the subject, e.g., according to the methods described herein. In some aspects, the subject can be selected to receive an additional therapeutic agent, such as an immune modulating agent. In some cases, the one or more other therapies are thus also administered after administration of the phthalocyanine dye-targeting molecule conjugate (e.g., IR700-antibody conjugate). In some embodiments, the additional therapy is administered within or within about 0 to 4 weeks, such as within at or about 0 hours to 24 hours of the irradiation, such as within or within about 5 minutes, 10 minutes, 30 minutes, 1 hour, 2 hours, 6 hours, 12 hours or 24 hours, 2, 3, 4, 5, 6, 7 days, 1, 2, 3 or 4 weeks of the irradiation.

In some embodiments, the additional therapeutic agent is administered between or between about 12 hours and 2 months after administration of the conjugate for PIT, such as between 12 hours and 1 month, 12 hours and 3 weeks, 12 hours and 2 weeks, 12 hours and 1 week, and 1 week and 1 month, such as generally at least 12 hours, 24 hours, 48 hours, 96 hours, one week, two weeks, three weeks, or one month after administering the conjugate for PIT.

The methods herein can be applied to the selection of subjects for additional therapeutic agents and the timing of administration of additional therapeutic agents and the type of therapeutic agents using one or more biomarkers assessed prior to or subsequent to photoimmunotherapy for guiding the use of additional therapeutic agents for combination therapies.

In some aspects, the additional therapeutic agent is administered based on the assessment of the one or more biomarkers. In some embodiments, the provided methods involve: a) administering to a subject having a tumor a conjugate comprising a phthalocyanine dye linked to a targeting molecule that binds to a protein on the surface of a cell present in the microenvironment of the tumor; b) measuring in a sample from the subject the level of expression of at least one biomarker(s); c) irradiating an area proximal to a tumor at a wavelength of 500 nm to 900 nm at a dose of at least 1 J $cm^{-2}$ or 1 J/cm of fiber length; and d) measuring the level of expression of the at least one biomarker(s) after the irradiation and determining whether the level of the at least biomarker is increased in the subject relative to the level measured prior to the irradiation; and e) if the level is increased, administering an additional therapeutic agent, e.g., an immune modulating agent or an anti-cancer agent, to the subject, thereby treating the tumor. In some embodiments, the provided methods include: a) measuring in sample from a subject having a tumor the level of expression of at least one biomarker(s) and determining whether the level of expression of the at least one biomarker(s) is at or above a threshold; b) administering to the subject a conjugate comprising a phthalocyanine dye linked to a targeting molecule that binds to a protein on the surface of a cell present in the microenvironment of the tumor; and c) irradiating an area proximal to a tumor at a wavelength of 500 nm to 900 nm at a dose of at least 1 J $cm^{-2}$ or 1 J/cm of fiber length; and d) if the level of expression of the at least one biomarker(s) is at or above the threshold, further administering an additional therapeutic agent, e.g., an immune modulating agent or an anti-cancer agent, to the subject; thereby improving the efficacy of the tumor treatment.

In some embodiments, the methods involving administration of an additional therapeutic agent, e.g., an immune modulating agent, is used to improve the efficacy of tumor treatment, for example, in a method that involves: a) measuring in sample from a subject having a tumor the level of expression of at least one biomarker(s) and determining whether the level of expression of the at least one biomarker(s) is at or below a threshold; b) administering to the subject a conjugate comprising a phthalocyanine dye linked to a targeting molecule that binds to a protein on the surface of a cell present in the microenvironment of the tumor; and c) irradiating an area proximal to a tumor at a wavelength of 500 nm to 900 nm at a dose of at least 1 J $cm^{-2}$ or 1 J/cm of fiber length; and d) if the level of expression of the at least one biomarker(s) is at or below the threshold, further administering an additional therapeutic agent, e.g., an immune modulating agent or an anti-cancer agent, to the subject; thereby improving the efficacy of the tumor treatment.

In some embodiments, also provided are methods for selecting a subject for treatment with an additional therapeutic agent, such as those described in herein. In some aspects, the methods involve a) administering to a subject a conjugate comprising a phthalocyanine dye linked to a targeting molecule capable of binding to a molecule on the surface of a cell present in the microenvironment of the tumor; b) irradiating an area proximal to a tumor at a wavelength of 500 nm to 900 nm at a dose of at least 1 J $cm^{-2}$ or 1 J/cm of fiber length; and c) measuring the level of expression of at least one biomarker(s) in a sample from a subject; and d) if the level of expression of the at least one biomarker(s) is at or above a threshold level, selecting the subject for treatment with an additional therapeutic agent, e.g., an immune modulating agent or an anti-cancer agent.

In some embodiments, the additional therapeutic agent or agents can be administered at a sufficient time prior to performing the irradiation so that a therapeutic effect on treating the tumor is increased. In some embodiments, prior to irradiation in the method of photoimmunotherapy, one or more other therapeutic agents, such as an immune modulating agent (e.g., immune checkpoint inhibitor) or anti-cancer agent (e.g., antimetabolite), are administered to the subject. In one embodiment, an immune modulating agent can be administered a sufficient time prior to the irradiation, such as generally at least 12 hours prior to the irradiation, to render the immune system responsive to tumor-associated agents released upon tumor cell lysis after photoimmunotherapy. In another embodiment, an anti-cancer agent can be administered a sufficient time prior to the irradiation, such as generally at least 5 minutes prior to the irradiation, to achieve systemic availability of the anti-cancer agent so that it can be immediately delivered into the tumor upon changes in vascular permeability after photoimmunotherapy.

The one or more additional agents, such as an immune modulating agent or an anti-cancer agent, can be administered prior to, simultaneous with, subsequent to or intermittently with the phthalocyanine dye-targeting molecule conjugate. In some embodiments, the activation of the phthalocyanine dye photosensitizer of the conjugate by irradiation with light is not effected until a time after the administration of the additional therapeutic agent, such as described herein. In some embodiments, the activation of the phthalocyanine dye photosensitizer of the conjugate by irradiation with light is carried out before the administration of the additional therapeutic agent, such as described herein. In some cases, the one or more other therapies can be administered prior to, during, or following administration of the phthalocyanine dye-targeting molecule conjugate (e.g., IR700-antibody conjugate).

In some embodiments, the additional therapeutic agent can be administered after or following administration of the phthalocyanine dye-targeting molecule conjugate. For example, in some embodiments, the conjugate is administered prior to the one or more additional therapies and the conjugate and one or more additional therapies are each administered prior to irradiating the tumor. In some embodiments, the conjugate is administered subsequent to the one or more additional therapies and the conjugate and one or more additional therapies are each administered prior to irradiating the tumor. In some embodiments, the irradiation is carried out after administration of the additional therapeutic and the phthalocyanine dye-targeting molecule conjugate.

In some embodiments, the irradiation is carried out or effected after administration of the additional therapeutic agent and the phthalocyanine dye-targeting molecule conjugate. In some embodiments, the irradiation is effected after administration of the phthalocyanine dye-targeting molecule conjugate.

In some embodiments, the combination therapy includes two irradiations or illuminations. In some embodiments, the combination therapy involves a first irradiation of the tumor after administering the phthalocyanine dye-targeting molecule conjugate and a second irradiation of the tumor after administering the additional therapeutic agent. In some embodiments, the additional therapeutic agent is a second conjugate comprising a phthalocyanine dye and a targeting molecule. In some embodiments, each irradiation is performed within 6 to 48 hours after administering the respective conjugate, such as generally at least about 6 hours, 12 hours, 24 hours or 36 hours after administration of each conjugate.

In some embodiments, the combined effect of the photoimmunotherapy in combination with the one or more other agents can be synergistic compared to treatments involving only photoimmunotherapy with the phthalocyanine dye-targeting molecule conjugate or monotherapy with the other therapeutic agent. In some embodiments, the methods provided herein result in an increase or an improvement in a desired anti-tumor therapeutic effect, such as an increased or an improvement in the reduction or inhibition of one or more symptoms associated with cancer, than photoimmunotherapy or monotherapy alone.

Treatments with a phthalocyanine dye-targeting molecule conjugate, and, optionally, an additional therapeutic agent, can each independently be completed in a single day, or may be done repeatedly on multiple days with the same or a different dosage. Repeated treatments may be done on the same day, on successive days, or every 1-3 days, every 3-7 days, every 1-2 weeks, every 2-4 weeks, every 1-2 months, or at even longer intervals.

In some embodiments, the combination therapy includes administering to a subject a therapeutically effective amount of the additional therapeutic agent. The additional therapeutic agent in an amount that is from or from about 0.01 mg to 1000 mg, such as at a dose of at least 0.01 mg, 0.1 mg, 1 mg, 10 mg, 1000 mg, 2000 mg, 3000 mg or more. In an exemplary embodiment, an additional therapeutic agent may be administered at about 0.3 mg/kg to 10 mg/kg, or the maximum tolerated dose, such as at least 0.5 mg/kg, or at least 1 mg/kg, or at least 2 mg/kg, or at least 3 mg/kg, or at least 5 mg/kg, or at least 8 mg/kg. In some cases, the dose can be administered as a single dose or in a plurality of doses. Alternatively, the additional therapeutic agent may be administered by an escalating dosage regimen including administering a first dosage at about 3 mg/kg, a second dosage at about 5 mg/kg, and a third dosage at about 9 mg/kg. Alternatively, the escalating dosage regimen includes administering a first dosage of additional therapeutic agent at about 5 mg/kg and a second dosage at about 9 mg/kg. Another stepwise escalating dosage regimen may include administering a first dosage of additional therapeutic agent about 3 mg/kg, a second dosage of about 3 mg/kg, a third dosage of about 5 mg/kg, a fourth dosage of about 5 mg/kg, and a fifth dosage of about 9 mg/kg. In another aspect, a stepwise escalating dosage regimen may include administering a first dosage of 5 mg/kg, a second dosage of 5 mg/kg, and a third dosage of 9 mg/kg. In some embodiments, particular dosages can be administered twice weekly, once weekly, once every two weeks, once every three weeks or once a month or more. In some cases, the dosages can be administered over a course of a cycle that can be repeated, such as repeated for one month, two months, three months, six months, 1 year or more.

In some embodiments, the combination therapy includes administering to a subject a therapeutically effective amount of the anti-cancer agent, such as any described herein. In some embodiments, a therapeutically effective dose can be from or from about 0.01 mg to 1000 mg, such as a dose of at least 0.01 mg, 0.1 mg, 1 mg, 10 mg, 1000 mg, 2000 mg, 3000 mg or more. In some embodiments, a therapeutically effective dose of the anti-cancer agent is from or from about 0.01 mg/kg to about 50 mg/kg, such as about 0.1 mg/kg to about 20 mg/kg, about 0.1 to about 10 mg/kg, about 0.3 to about 10 mg/kg, about 0.5 mg/kg to about 5 mg/kg or about 0.5 mg/kg to about 1 mg/kg.

In some embodiments, the dose of the additional therapeutic agent is continued or repeated in accord with its clinically dosing schedule after PIT treatment. Thus, in some embodiments, in a dose schedule or cycle of administration in accord with the provided methods, the phthalocyanine dye conjugate (e.g. IR700 antibody conjugate) can be administered only one time, such as in a single dose or infusion, for PIT, whereas the administration of the immune modulating agent is continued or repeated more than one time, such as three times a week, two times a week, once a week, once every two weeks, once every three weeks or once a month during a dosing schedule or cycle of administration. In some embodiments, the dosing schedule or cycle of administration is or is about 28 days or 4 weeks.

1. Immune Modulating Agents

In some embodiments, the provided methods involve administering an additional therapeutic agent that is an immune modulating agent, based on the assessment of the biomarkers as described herein. In some aspects, the immune modulating agent can stimulate or promote the activity of immune cells, such as cells involved in the adaptive and innate immune systems. In some aspects, the immune modulating agents, such as checkpoint inhibitors, can help counter the immunosuppressive microenvironment of the tumor. In some aspects, as described herein, PIT-mediated cell killing also is associated with an increase in the levels of markers associated with immunosuppression, such as checkpoint pathway markers. In some aspects, administration of an additional therapeutic agent, such as an immune modulating agent, e.g., checkpoint inhibitor, can counter or reverse the immunosuppressive microenvironment, and improve or augment the efficacy of the PIT. Thus, the provided embodiments offer a method to improve the efficacy of the treatment of tumor by identifying subjects that would benefit from administration of an additional therapeutic agent, e.g., an immune modulating agent, based on the assessment of the one or more biomarkers.

In some aspects, the immune modulating agents that can be administered in combination with PIT methods employing phthalocyanine dye conjugates. Hence, the combination therapy provided herein, including combinations and methods of use thereof, include an immune modulating agent. In some aspects, immune modulating agents, or immunomodulators, are substances that either, directly or indirectly, suppress or activate the body's immune response. For example, immune modulating agents that stimulate immune response to tumors and/or pathogens may be used in combination with photoimmunotherapy. In some embodiments, the immune modulating agent can include cell-based (e.g. combination treatment with immune cells such as dendritic cells or T cells) or non-cell based immune modulating agents.

Generally, cancerous cells contain tumor-specific antigens that should be recognized by the immune system. Typically, in an active immune system, immune cells, such as cytotoxic T cells, attack and eradicate these cancerous cells. Under normal physiological conditions, the T cell-mediated immune response is initiated by antigen recognition by the T cell receptor (TCR) and is regulated by a balance of co-stimulatory and inhibitory signals (e.g. immune checkpoint proteins). In particular, CD4+ and CD8+ T cells expressing a TCR can become activated upon recognition of antigenic peptides presented on antigen-presenting cells on major histocompatibility complex (MHC) class I or class II molecules, respectively. In some aspects, activated CD8+ cells, or cytotoxic T cells, can kill tumor cells expressing the antigen, which can be helped by the presence of CD4+ T cells. In some embodiments, the immune cell is an antigen presenting cell. In some embodiments, the immune cell is a dendritic cell.

In the case of tumors, however, the tumor microenvironment has mechanisms to suppress the immune system, thereby evading immune recognition and preventing or reducing killing of tumor cells. For example, in some cases, immune checkpoint proteins can be dysregulated in tumors, thereby resulting in a suppression of the immune response in the tumor microenvironment as a mechanism of evading the immune system. In some cases, other mechanisms can act to inhibit access of immune cells to tumor antigens, thereby also contributing to the tumors ability to evade the immune system. The combination therapies provided herein address both of these evasion mechanisms, in order to provide a more robust immune response against the tumor while also killing tumor cells by photolytic mechanisms.

In some embodiments of the combination therapy methods provided herein, an immune modulating agent is administered to a subject in order to inhibit immunosuppressive signaling or enhance immunostimulant signaling. For example, inhibitory checkpoint protein antagonists and/or agonists of co-stimulatory receptors can stimulate a host's endogenous anti-tumor immune response by amplifying antigen-specific T cell responses. In aspects of the provided methods, photoimmunotherapy also can be performed, which can result in the killing of tumor cells, thereby releasing tumor-antigens. By performing photoimmunotherapy in combination with administration of an immune-modulating agent, the subsequent release of PIT-induced antigens can provide a source of antigenic stimuli for the T cells whose response has been amplified or stimulated by the immune modulating agent. Thus, in some aspects, the enhanced immune response that is generated upon therapy with an immune modulating agent is primed and ready to respond to tumor antigens that are exposed upon lysis of cells after PIT. Thus, in some aspects, the combination therapies provided herein address the natural evasion mechanisms that can be present in a tumor microenvironment, in order to provide a more robust immune response against the tumor while also killing tumor cells by photolytic mechanisms.

In some aspects, the selection of the immune modulating agent, dosage, frequency and relative timing of the administration, and selection of subjects to receive the immune modulating agent, can be based on the assessment of the one or more biomarkers, such as according to the methods provided herein.

In some embodiments, the immune modulating agent is itself a conjugate containing a phthalocyanine dye, such as a phthalocyanine dye linked to an antibody or antigen-binding fragment that is an immune modulating agent. In some embodiments, the immune modulating agent is an IR700-antibody conjugate that includes an immune modulating antibody (e.g. checkpoint inhibitor) that binds to a checkpoint protein on a tumor cell (e.g. PD-L1, PD-1, and CTLA4). In some embodiments, the immune modulating conjugate (e.g., IR700-antibody conjugate that is an immune modulating agent) is administered prior to administration of the phthalocyanine dye-targeting molecule conjugate, such as between 12 hours and 2 months, such as generally at least 12 hours, at least 24 hours, at least 48 hours, at least 96 hours, at least one week, at least two weeks, at least three weeks or at least one month prior to administration of the phthalocyanine dye-targeting molecule conjugate. In some embodiments, the immune modulating conjugate (e.g., IR700-antibody conjugate that is an immune modulating agent) is administered during or simultaneously with administration of the phthalocyanine dye-targeting molecule conjugate. In some embodiments, the immune modulating conjugate (e.g., IR700-antibody conjugate that is an immune modulating agent) is administered after administration of the phthalocyanine dye-targeting molecule conjugate, such as between 12 hours and 2 months, such as generally at least 12 hours, at least 24 hours, at least 48 hours, at least 96 hours, at least one week, at least two weeks, at least three weeks or at least one month after administration of the phthalocyanine dye-targeting molecule conjugate.

In some embodiments, irradiation the tumor is carried out either i) after administration of the immune modulating agent and after administration of the conjugate or ii) only after administration of the conjugate.

Exemplary dosage regimes and schedules for administering an immune modulating agent, phthalocyanine dye-conjugate (e.g., IR700-targeting molecule conjugate, such as an IR700-antibody dye conjugate) and for performing irradiation can be according to the methods provided herein, e.g., based on the assessment of one or more biomarkers as described in Sections I and II.

In some embodiments, the combination therapy methods can be performed with any immune modulating agent that can stimulate, amplify and/or otherwise enhance an anti-tumor immune response, such as by inhibiting immunosuppressive signaling or enhancing immunostimulant signaling. In some embodiments, the immune modulating agent is a peptide, protein or is a small molecule. In some embodiments, the protein can be a fusion protein or a recombinant protein. In some embodiments, the immune modulating agent binds to an immunologic target, such as a cell surface receptor expressed on immune cells, such a T cells, B cells or antigen-presenting cells. For example, in some embodiments, the immune modulating agent is an antibody or antigen-binding antibody fragment, a fusion protein, a small molecule or a polypeptide.

In some embodiments, the immune modulating agent inhibits an immune checkpoint pathway. The immune system has multiple inhibitory pathways that are involved in maintaining self-tolerance and for modulating immune responses. It is known that tumors can use certain immune-checkpoint pathways as a major mechanism of immune resistance, particularly against T cells that are specific for tumor antigens (Pardoll, 2012, Nature Reviews Cancer 12:252-264). Because many such immune checkpoints are initiated by ligand-receptor interactions, they can be readily blocked by antibodies against the ligands and/or their receptors.

Therefore, therapy with antagonistic molecules blocking an immune checkpoint pathway, such as small molecules, nucleic acid inhibitors (e.g., RNAi) or antibody molecules, are becoming promising avenues of immunotherapy for cancer and other diseases. In contrast to the majority of anti-cancer agents, checkpoint inhibitors do not necessarily target tumor cells directly, but rather target lymphocyte receptors or their ligands in order to enhance the endogenous antitumor activity of the immune system. (Pardoll, 2012, Nature Reviews Cancer 12:252-264).

As used herein, the term "immune checkpoint inhibitor" refers to molecules that totally or partially reduce, inhibit, interfere with or modulate one or more checkpoint proteins. Checkpoint proteins regulate T-cell activation or function. These proteins are responsible for co-stimulatory or inhibitory interactions of T-cell responses. Immune checkpoint proteins regulate and maintain self-tolerance and the duration and amplitude of physiological immune responses.

Immune checkpoint inhibitors include any agent that blocks or inhibits in a statistically significant manner, the inhibitory pathways of the immune system. Such inhibitors may include small molecule inhibitors or may include antibodies, or antigen binding fragments thereof, that bind to and block or inhibit immune checkpoint receptor ligands. Illustrative immune checkpoint molecules that may be targeted for blocking or inhibition include, but are not limited to, PD-1 (CD279), PD-L1 (CD274, B7-H1), PD-L2 (CD273, B7-DC), CTLA-4, LAG-3 (CD223), TIM-3, 4-1BB (CD137), 4-1BBL (CD137L), GITR (TNFRSF18, AITR), CD40, OX40 (CD134, TNFRSF4), CXCR2, tumor associated antigens (TAA), B7-H3, B7-H4, BTLA, HVEM, GAL9, VISTA, KIR, 2B4 (belongs to the CD2 family of molecules and is expressed on all NK, γδ, and memory CD8+ (αβ) T cells), CD160 (also referred to as BY55) and CGEN-15049. Immune checkpoint inhibitors include antibodies, or antigen binding fragments thereof, or other binding proteins, that bind to and block or inhibit the activity of one or more of PD-1, PD-L1, PD-L2, CTLA-4, LAG-3, TIM-3, 4-IBB, 4-IBBL, GITR, CD40, OX40, CXCR2, TAA, B7-H3, B7-H4, BTLA, HVEM, GAL9, VISTA, KIR, 2B4, CD160, and CGEN-15049. Illustrative immune checkpoint inhibitors include Tremelimumab (CTLA-4 blocking antibody), anti-OX40, PD-L1 monoclonal antibody (Anti-B7-H1; MEDI4736), MK-3475 (PD-1 blocker), nivolumab (anti-PD-1 antibody), CT-011 (anti-PD-1 antibody), BY55 monoclonal antibody, AMP224 (anti-PD-L1 antibody), BMS-936559 (anti-PD-L1 antibody), MPLDL3280A (anti-PD-L1 antibody), MSB0010718C (anti-PD-L1 antibody) and Yervoy/ipilimumab (anti-CTLA-4 checkpoint inhibitor antibody). Other exemplary checkpoint inhibitors are described below.

Programmed cell death 1 (PD-1) is an immune checkpoint protein that is expressed in B cells, NK cells, and T cells (Shinohara et al., 1995, Genomics 23:704-6; Blank et al., 2007, Cancer Immunol Immunother 56:739-45; Finger et al., 1997, Gene 197:177-87; Pardoll, 2012, Nature Reviews Cancer 12:252-264). The major role of PD-1 is to limit the activity of T cells in peripheral tissues during inflammation in response to infection, as well as to limit autoimmunity (Pardoll, 2012, Nature Reviews Cancer 12:252-264). PD-1 expression is induced in activated T cells and binding of PD-1 to one of its endogenous ligands acts to inhibit T-cell activation by inhibiting stimulatory kinases (Pardoll, 2012, Nature Reviews Cancer 12:252-264). PD-1 also acts to inhibit the TCR "stop signal" (Pardoll, 2012, Nature Reviews Cancer 12:252-264). PD-1 is highly expressed on Treg cells and may increase their proliferation in the presence of ligand (Pardoll, 2012, Nature Reviews Cancer 12:252-264). Anti-PD 1 antibodies have been used for treatment of melanoma, non-small-cell lung cancer, bladder cancer, prostate cancer, colorectal cancer, head and neck cancer, triple-negative breast cancer, leukemia, lymphoma and renal cell cancer (Topalian et al., 2012, N Engl J Med 366:2443-54; Lipson et al., 2013, Clin Cancer Res 19:462-8; Berger et al., 2008, Clin Cancer Res 14:3044-51; Gildener-Leapman et al., 2013, Oral Oncol 49:1089-96; Menzies & Long, 2013, Ther Adv Med Oncol 5:278-85). Exemplary anti-PD-1 antibodies include nivolumab (OPDIVO by BMS), pembrolizumab (Keytruda by Merck), pidilizumab (CT-011 by Cure Tech), lambrolizumab (MK-3475 by Merck), and AMP-224 (Merck). Other exemplary anti-PD-1 antibodies include AB122, AK105, AMG 404, AMP-224, AMP-514, BCD-100, BI 754091, Camrelizumab, Cemiplimab (LIBTAYO; REGN2810), Cetrelimab, CS1003, CX-188, Dostarlimab, F520, genolimzumab, GLS-010, HLX10, HX008, IBI308, JTX-4014, LZMO09, MGA012, PDR001, PF-06801591, REGN2810, SCT-Ii0A, SG001, Sintilimab, Spartalizumab, Sym021, Toripalimab, and TSR-042.

PD-L1 (also known as CD274 and B7-H1) and PD-L2 (also known as CD273 and B7-DC) are ligands for PD-1, found on activated T cells, B cells, myeloid cells, macrophages, and some types of tumor cells. Anti-tumor therapies have focused on anti-PD-L1 antibodies. The complex of PD-1 and PD-L1 inhibits proliferation of CD8+ T cells and reduces the immune response (Topalian et al., 2012, N Engl J Med 366:2443-54; Brahmer et al., 2012, N Eng J Med 366:2455-65). Anti-PD-L1 antibodies have been used for treatment of non-small cell lung cancer, melanoma, colorectal cancer, renal-cell cancer, pancreatic cancer, gastric cancer, ovarian cancer, breast cancer, and hematologic malignancies (Brahmer et al., N Eng J Med 366:2455-65; Ott et al., 2013, Clin Cancer Res 19:5300-9; Radvanyi et al., 2013, Clin Cancer Res 19:5541; Menzies & Long, 2013, Ther Adv Med Oncol 5:278-85; Berger et al., 2008, Clin Cancer Res 14:13044-51). Exemplary anti-PD-L1 antibodies include MDX-1105 (Medarex), MEDI4736 (Medimmune) MPDL3280A (Atezolizumab, Tecentriq, RG7446; Genentech), BMS-935559 (Bristol-Myers Squibb) and MSB0010718C. Other exemplary anti-PD-L1 antibodies include Avelumab (Bavencio, MSB0010718C; M7824), BCD-135, BGB-A333, CBT-502, Cosibelimab, CS1001, Durvalumab (Imfinzi, MEDI4736), FAZ053, HLX20, KN035, LDP, LY3300054, MSB2311, NM-01, REGN3504, SHR-1316 (HTI-1088), STI-3031 (IMC-001; STI-A1015), TG-1501, and ZKAB001 (STI-A1014).

Cytotoxic T-lymphocyte-associated antigen (CTLA-4), also known as CD152, is a co-inhibitory molecule that functions to regulate T-cell activation. CTLA-4 is a member of the immunoglobulin superfamily that is expressed exclusively on T-cells. CTLA-4 acts to inhibit T-cell activation and is reported to inhibit helper T-cell activity and enhance regulatory T-cell immunosuppressive activity (Pardoll, 2012, Nature Reviews Cancer 12:252-264). Although the precise mechanism of action of CTLA-4 remains under investigation, it has been suggested that it inhibits T cell activation by outcompeting CD28 in binding to CD80 and CD86, as well as actively delivering inhibitor signals to the T cell (Pardoll, 2012, Nature Reviews Cancer 12:252-264). Anti-CTLA-4 antibodies have been used in clinical trials for the treatment of melanoma, prostate cancer, small cell lung cancer, non-small cell lung cancer (Robert & Ghiringhelli, 2009, Oncologist 14:848-61; Ott et al., 2013, Clin Cancer Res 19:5300; Weber, 2007, Oncologist 12:864-72; Wada et al., 2013, J Transl Med 11:89). A significant feature of anti-CTLA-4 is the kinetics of anti-tumor effect, with a lag period of up to 6 months after initial treatment required for physiologic response (Pardoll, 2012, Nature Reviews Cancer 12:252-264). In some cases, tumors may actually increase in size after treatment initiation, before a reduction is seen (Pardoll, 2012, Nature Reviews Cancer 12:252-264). Exemplary anti-CTLA-4 antibodies include ipilimumab (YERVOY; Bristol-Myers Squibb) and tremelimumab (Pfizer). Other exemplary anti-CTLA-4 antibodies include ADG116, ADU-1604, AGEN1181, AGEN1884, BCD-145, BMS-986218, Ipilimumab, MK-1308, REGN4659, and Ticilimumab. Ipilimumab has recently received FDA approval for treatment of metastatic melanoma (Wada et al., 2013, J Transl Med 11:89). In some embodiments, the immune modulating agent is not an anti-CTLA-4 antibody.

Lymphocyte activation gene-3 (LAG-3), also known as CD223, is another immune checkpoint protein. LAG-3 has been associated with the inhibition of lymphocyte activity and in some cases the induction of lymphocyte anergy. LAG-3 is expressed on various cells in the immune system including B cells, NK cells, and dendritic cells. LAG-3 is a natural ligand for the MHC class II receptor, which is substantially expressed on melanoma-infiltrating T cells including those endowed with potent immune-suppressive activity. An exemplary anti-LAG-3 antibody is BMS-986016. IMP321 is a soluble version of the immune checkpoint molecule LAG-3, which activates dendritic cells, increasing antigen presentation.

T-cell immunoglobulin domain and mucin domain-3 (TIM-3), initially identified on activated Th1 cells, has been shown to be a negative regulator of the immune response. Blockade of TIM-3 promotes T-cell mediated anti-tumor immunity and has anti-tumor activity in a range of mouse tumor models. Combinations of TIM-3 blockade with other immunotherapeutic agents such as TSR-042, anti-CD137 antibodies and others, can be additive or synergistic in increasing anti-tumor effects. TIM-3 expression has been associated with a number of different tumor types including melanoma, NSCLC and renal cancer, and additionally, expression of intratumoral TIM-3 has been shown to correlate with poor prognosis across a range of tumor types including NSCLC, cervical, and gastric cancers. Blockade of TIM-3 is also of interest in promoting increased immunity to a number of chronic viral diseases. TIM-3 has also been shown to interact with a number of ligands including galectin-9, phosphatidylserine and HMGB1, although which of these, if any, are relevant in regulation of anti-tumor responses is not clear at present.

4-1BB, also known as CD137, is transmembrane glycoprotein belonging to the TNFR superfamily. 4-1BB receptors are present on activated T cells and B cells and monocytes. An exemplary anti-4-1BB antibody is urelumab (BMS-663513), which has potential immunostimulatory and antineoplastic activities.

Glucocorticoid-induced TNFR family related gene (GITR) is also a member of the TNFR superfamily. GITR is upregulated on activated T cells, which enhances the immune system. An exemplary anti-GITR antibody is TRX518.

Cluster of differentiation 40 (CD40) is also a member of the TNFR superfamily. CD40 is a costimulatory protein found on antigen-presenting cells and mediates a broad variety of immune and inflammatory responses. CD40 is also expressed on some malignancies, where it promotes proliferation. Exemplary anti-CD40 antibodies are dacetuzumab (SGN-40), lucatumumab (Novartis, antagonist), SEA-CD40 (Seattle Genetics), and CP-870,893.

Tumor necrosis factor receptor superfamily, member 4 (TNFRSF4), also known as OX40 and CD134, is another member of the TNFR superfamily. OX40 is not constitutively expressed on resting naïve T cells and acts as a secondary co-stimulatory immune checkpoint molecule. Exemplary anti-OX40 antibodies are MEDI6469 and MOXR0916 (RG7888, Genentech).

In some embodiments, the immune modulating agent is an antibody or antigen-binding antibody fragment thereof. Exemplary of such antibodies include, but are not limited to, Daclizumab (Zenapax), Bevacizumab (Avastin®), Basiliximab, Ipilimumab, Nivolumab, pembrolizumab, MPDL3280A, Pidilizumab (CT-011), MK-3475, BMS-936559, MPDL3280A (Atezolizumab), tremelimumab, IMP321, BMS-986016, LAG525, urelumab, PF-05082566, TRX518, MK-4166, dacetuzumab (SGN-40), lucatumumab (HCD122), SEA-CD40, CP-870, CP-893, MEDI6469, MEDI6383, MOXR0916, AMP-224, MSB0010718C (Avelumab), MEDI4736, PDR001, rHIgM12B7, Ulocuplumab, BKT140, Varlilumab (CDX-1127), ARGX-110, MGA271, lirilumab (BMS-986015, IPH2101), IPH2201, ARGX-115, Emactuzumab, CC-90002 and MNRP1685A or an antibody-binding fragment thereof.

CXCR2 is a chemokine receptor that is expressed on myeloid-derived suppressor cells (MDSCs). CXCR2s contribute to tumor immune escape. It has been shown that anti-CXCR2 monoclonal antibody therapy, enhanced an anti-PD-1 antibody-induced anti-tumor immune response and anti-tumor efficacy.

In some embodiments, the immune-modulating agent is cytokine. In some embodiments, the immune modulating agent is a cytokine or is an agent that induces increased expression of a cytokine in the tumor microenvironment. By "cytokine" is meant a generic term for proteins released by one cell population that act on another cell as intercellular mediators. Examples of such cytokines are lymphokines, monokines, and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-alpha and -beta; mullerian-inhibiting substance; mouse gonadotropin-associated peptide; inhibin; activin; vascular endothelial growth factor; integrin; thrombopoietin (TPO); nerve growth factors such as NGF-beta; platelet-growth factor; transforming growth factors (TGFs) such as TGF-alpha and TGF-beta; insulin-like growth factor-I and -II; erythropoietin (EPO); osteoinductive factors; interferons such as interferon-alpha, beta, and -gamma; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1alpha, IL-2, IL-3, IL-4, IL-5, IL-6, IL-7, IL-8, IL-9, IL-10, IL-11, IL-12; IL-15, a tumor necrosis factor such as TNF-alpha or TNF-beta; and other polypeptide factors including LIF and kit ligand (KL). As used herein, the term cytokine includes proteins from natural sources or from recombinant cell culture, and biologically active equivalents of the native sequence cytokines. For example, the immune modulating agent is a cytokine and the cytokine is IL-4, TNF-$\alpha$, GM-CSF or IL-2.

In some embodiments, the immune modulating agent is selected from among GM-CSF, CpG-ODN (CpG oligodeoxynucleotides), lipopolysaccharide (LPS), monophosphoryl lipid A (MPL), alum, recombinant Leishmania polyprotein, imiquimod, MF59, poly I:C, poly A:U, type 1 IFN, Pam3Cys, Pam2Cys, complete freund's adjuvant (CFA), alpha-galactosylceramide, RC-529, MDF2I3, Loxoribine, anti-CD40 agonist, SIRPa antagonist, ASO4, AS03, Flagellin, Resiquimod, DAP (diaminopimelic acid), MDP (muramyl dipeptide) and CAF01(cationic adjuvant formulation-01). In some embodiments, the immune modulating agent is a Toll-like receptor (TLR) agonist, an adjuvant or a cytokine. In some embodiments, the immune modulating agent is a TLR agonist and the TLR agonist is TLR agonist is a TLR4 agonist, a TLR7 agonist, a TLR8 agonist, or a TLR9 agonist. In some embodiments, the TLR agonist is selected from among triacylated lipoprotein, diacylated lipopeptide, lipoteichoic acid, peptidoglycan, zymosan, Pam3CSK4, dsRNA, poly(I:C), Poly G10, Poly G3, CpG, 3M003, flagellin, lipopolysaccharide (LPS) Leishmania homolog of eukaryotic ribosomal elongation and initiation factor 4a (LeIF), MEDI9197, SD-101, and imidazoquinoline TLR agonists.

In some embodiments, the immune modulating agent can contain one or more interleukins or other cytokines. For example, the interleukin can include leukocyte interleukin injection (Multikine), which is a combination of natural cytokines.

In some embodiments, the immune modulating agent is a Toll-like receptor (TLR) agonist. In some embodiments, such agonists can include a TLR4 agonist, a TLR8 agonist, or a TLR9 agonist. Such an agonist may be selected from peptidoglycan, poly(I:C), CpG, 3M003, flagellin, and Leishmania homolog of eukaryotic ribosomal elongation and initiation factor 4a (LeIF).

In some embodiments, the immune modulating agent can be one that enhances the immunogenicity of tumor cells such as patupilone (epothilone B), epidermal-growth factor receptor (EGFR)-targeting monoclonal antibody 7A7.27, histone deacetylase inhibitors (e.g., vorinostat, romidepsin, panobinostat, belinostat, and entinostat), the n3-polyunsaturated fatty acid docosahexaenoic acid, proteasome inhibitors (e.g., bortezomib), shikonin (the major constituent of the root of Lithospermum erythrorhizon,) and oncolytic viruses, such as T-Vec (Talimogene laherparepvec). In some embodiments, the immune modulating agent activates immunogenic cell death of the cancer or tumor, such as anthracyclines (doxorubicin, mitoxantrone), BK channel agonists, bortezomib, bortezomib plus mitomycin C plus hTERT-Ad, Cardiac glycosides plus non-ICD inducers, cyclophosphamide, GADD34/PP1 inhibitors plus mitomycin, LV-tS-MAC, and oxaliplatin. In some embodiments, the immune modulating agent can be an epigenetic therapy, such as DNA methyltransferase inhibitors (e.g., Decitabine, 5-aza-2'-deoxycytidine).

For example, in some embodiments, the immune modulating agent can be a DNA methyltransferase inhibitor, which can regulate expression of tumor associated antigens (TAA). TAAs are antigenic substances produced in tumor cells which triggers an immune response. TAAs are often down-regulated by DNA methylation in tumors to escape the immune system. Reversal of DNA methylation restores TAA expression, increasing the immunogenicity of tumor cells. For example, demethylating agents such as decitabine (5-aza-2'-deoxycytidine) can upregulate expression of TAAs in tumor cells and increase immune recognition of the cancerous cells. Photoimmunotherapy would further expose TAAs to the immune system by disrupting cells.

In some embodiments, the immune modulating agent itself can be an antibody conjugate containing a phthalocyanine dye linked to an antibody or antigen-binding antibody fragment that is an immune modulating agent, such as an immune checkpoint inhibitor. In some embodiments, the immune modulating agent is one that targets or binds to an immunosuppressive molecule, such as an immune checkpoint molecule, on the surface of tumor cells. For example, PD-L1 is an immunosuppressive molecule that is constitutively expressed or induced on many tumor cells and can prevent T cell activation through interactions with its receptor PD-1 expressed on immune cells. In some aspects, a phthalocyanine-dye conjugate containing an immune modulating agent that binds to an immunosuppressive molecule on a tumor cells (e.g., PD-L1) can be administered both to enhance an immune response and also to specifically kill cancer cells that express the immunosuppressive molecule, thereby reversing immune suppression in the tumor microenvironment. In particular, irradiation of tumor cells to which the conjugate binds can result in its activation to mediate PIT-induced cell killing of the PD-L1 cancer cells, which also would act to specifically eliminate the cancer cells in the tumor that control T-cell suppression in the tumor microenvironment.

Hence, provided herein is a conjugate containing a phthalocyanine dye (e.g., IR700) linked to an immune modulating agent that binds to an immunosuppressive molecule expressed on tumor cells. For example, in some embodiments, the immunosuppressive molecule expressed on tumor cells can be an immune checkpoint molecule. In some embodiments, the immune checkpoint molecule expressed on tumor cells is PD-L1. In some embodiments, the immune modulating agent that is part of the conjugate is an immune checkpoint inhibitor, such as an antibody or antigen-binding antibody fragment that binds to PD-L1. For example, provided herein is a conjugate containing a phthalocyanine dye (e.g., IR700) linked to an antibody or antigen-binding antibody fragment that binds to PD-L1. Exemplary immune checkpoint inhibitors, including antibodies or antigen-binding antibody fragments, against PD-L1 are described above, and any can be included in the provided conjugates. Exemplary anti-PD-L1 antibodies include, but are not limited to, BMS-935559, MEDI4736 (Durvalumab), MPDL3280A (Atezolizumab) and MSB0010718C (Avelumab), or an antigen-binding antibody fragment thereof. Exemplary conjugate molecules provided herein include, for example, IR700-BMS-935559, IR700-MEDI4736 (Durvalumab), IR700-MPDL3280A (Atezolizumab) and IR700-MSB0010718C (Avelumab). In some embodiments, such conjugates can be used in methods of photoimmunotherapy, for example, by irradiation with light at a wavelength sufficient to activate the dye. Such conjugates can be used in monotherapy-based photoimmunotherapy or can be used in combination therapy methods with other phthalocyanine dye conjugates.

For example, in some embodiments, combination therapy methods are provided in which a first conjugate containing a phthalocyanine dye (e.g., IR700) linked to an immune modulating agent that binds to an immunosuppressive molecule expressed on cells of a tumor (e.g., an anti-PD-L1 antibody, such as an IR700-anti-PD-L1 conjugate) is administered to a subject, and then a second conjugate containing a phthalocyanine dye linked to a targeting molecule is administered to the subject. Generally, the second conjugate can include any targeting molecule that is able to bind to a cell surface protein on a cell in a tumor, such as a cell present in a tumor microenvironment, such as any described above. In some embodiments, the first conjugate and the second conjugate bind to different proteins expressed on a cell in a tumor. In some embodiments, the second conjugate can include a phthalocyanine dye (e.g., IR700) linked to an antibody or antigen-binding antibody fragment that binds to a cell surface protein expressed on a cell in a tumor. Exemplary antibody or antigen-binding antibody fragments of the second conjugate can include, but are not limited to, bevacizumab, cetuximab, panitumumab, zalutumumab, nimotuzumab, Tositumomab (Bexxar®), Rituximab (Rituxan, MabThera), Ibritumomab tiuxetan (Zevalin), Daclizumab (Zenapax), Gemtuzumab (Mylotarg), Alemtuzumab, CEA-scan Fab fragment, OC125 monoclonal antibody, ab75705, B72.3, Bevacizumab (Avastin®), and Basiliximab, nivolumab, pembrolizumab, pidilizumab, MK-3475, BMS-936559, MPDL3280A (Atezolizumab), ipilimumab, tremelimumab, IMP321, BMS-986016, LAG525, urelumab, PF-05082566, TRX518, MK-4166, dacetuzumab, lucatumumab, SEA-CD40, CP-870, CP-893, MED16469, MEDI6383, MEDI4736, MOXR0916, AMP-224, PDR001, MSB0010718C (Avelumab), rHIgM12B7, Ulocuplumab, BKT140, Varlilumab (CDX-1127), ARGX-110, MGA271, lirilumab (BMS-986015, IPH2101), IPH2201, AGX-115, Emactuzumab, CC-90002 and MNRP1685A or is an antibody-binding fragment thereof.

In some embodiments, for example, if the treatment of the tumor with the conjugate followed by light irradiation increases the presence of immunosuppressive cells in the tumor or increases the expression of immunosuppressive markers at the tumor, a therapeutically effective amount of an immune modulating agent capable of reducing the amount or activity of immunosuppressive cells in the tumor or capable of blocking the activity of the immunosuppressive marker or reducing the activity of a tumor promoting cell in the tumor or capable of blocking the activity of the tumor promoting marker can be administered. For example, in some embodiments, a conjugate with a first dye that is a phthalocyanine dye is administered, in combination with an immune modulating agent includes a conjugate that includes a second phthalocyanine dye conjugated to an immune modulating agent capable of binding to the immunosuppressive cell or a tumor promoting cell, and modulating the activity of such cell. In some embodiments, the first and second phthalocyanine dye is the same or different.

In such aspects, the combination therapy methods generally include one or more irradiations with light at a wavelength sufficient to activate the dye of the first and/or second conjugate.

In some embodiments, at least two irradiations are performed, where at least a first irradiation is provided to activate the first conjugate and a second irradiation is provided to activate the second conjugate. In some embodiments, a first irradiation with light is provided to the tumor after administration of the first conjugate. For example, from or from about 12 hours to 48 hours, such as about or approximately within 24 hours, after administering the first conjugate, the tumor can be treated with light to kill cancer cells that express the immunosuppressive molecule, such as to kill tumor cells that express PD-L1. In some embodiments, the killing of such cells may permit re-activation of or amplification of T cell responses at the tumor. In some embodiments, subsequent to photoimmunotherapy of the first conjugate by administration and irradiation, the second phthalocyanine dye conjugate can be administered to the subject, followed by a second irradiation with light from or from about 12 hours to 48 hours, such as about or approximately within 24 hours, after administering the second conjugate. In some embodiments, the second irradiation achieves activation of the second conjugate, which can result in selective cell killing of tumor cells that express the tumor-targeted molecule recognized by the second conjugate, thereby releasing tumor antigens to induce a strong immunogenic response as the T cell in the tumor are no longer suppressed by the immunosuppressive molecule (e.g., PD-L1). In some embodiments, the first irradiation is performed prior to administration of the second conjugate, such as at least or about at least 1 minute, 5 minutes, 10 minutes, 30 minutes, 1 hour, 2 hours, 3 hours, 6 hours, 12 hours or 24 hours prior to administration of the second conjugate.

In some embodiments, a single irradiation can performed to effect activation of both the first conjugate and the second conjugate in order cause PIT-induced cell killing of tumor cells expressing the immunosuppressive molecule (e.g., PD-L1) recognized by the first conjugate and tumor cells expressing the tumor-targeted molecule recognized by the second conjugate. Hence, in such aspects, the one light irradiation of the tumor may induce both effects to selectively kill specific tumor cells, thereby releasing tumor antigens, as well as inducing a strong immunogenic response due to the killing of the immunosuppressive tumor cells, such as the tumor cells expressing PD-L1. In some embodiments, prior to the irradiation, the first conjugate can be administered prior, simultaneously, subsequently or intermittently from administration of the second conjugate. In some embodiments, the first conjugate is administered prior to the second conjugate, such as at least 5 minutes prior, and generally at least 12 hours or at least 24 hours prior. In some embodiments, the first and second conjugates are administered simultaneously. In some embodiments, the first and second conjugates are formulated separately. In some embodiments, the first and second conjugates are formulated together in the same composition.

2. Anti-Cancer Agents

Also provided herein are anti-cancer agents that can be administered in combination with photoimmunotherapy employing phthalocyanine dye-targeting molecule conjugates, based on the assessment of the one or more biomarkers prior to or subsequent to the photoimmunotherapy. In some embodiments, the one or more biomarkers can guide the use of additional therapeutic agents for combination therapies, such as with an anti-cancer agent. In some aspects, if the subject is determined as having a low likelihood of response based on the biomarkers in accordance with the methods provided herein, anti-cancer agents, such as those descried below, can be used as an additional therapeutic agent, for example, to improve the efficacy of the treatment. Hence, the combination therapy provided herein, including combinations and methods of use thereof, include an anti-cancer agent, which can include any agent whose use can reduce, arrest or prevent cancer in a subject. Optionally, an additional anti-cancer agent can be used in combination therapy with photoimmunotherapy using phthalocyanine dye-targeting molecule conjugates together with an immune modulating agent, for example to treat various cancers, based on the assessment of one or more biomarkers in accordance with the methods provided herein.

As described herein, photoimmunotherapy (PIT)-induced cell killing of tumor cells by administration of one or more phthalocyanine dye conjugates to a subject having a tumor in combination with irradiation can lead to increases in tumor permeability, such as increases in vascular permeability around the tumor space. It is believed herein that the increase in permeability can result in rapid leakage of systemically available molecules into the tumor space, thereby maximizing exposure of the tumor to such molecules. Thus, in some embodiments, in the combination therapy methods provided herein, an anti-cancer agent is administered to a subject a sufficient time prior to irradiation of an administered phthalocyanine dye-targeting molecule conjugate to render the anti-cancer agent systemically available, such as generally at least 5 minutes prior to irradiation, for example at least 10 minutes, 15 minutes, 30 minutes, 1 hour, 2 hours, 3 hours, 4 hours, 5 hours, 6 hours, 12 hours or 24 hours prior to irradiation. In such embodiments, following irradiation and PIT-induced killing of tumor cells, the systemically available anti-cancer agent can be immediately taken up into the tumor space where the agent can provide a therapeutic effect. Thus, in contrast to methods in which the anti-cancer agent is administered after irradiation, and hence after PIT-induced cell killing, in the instant methods there is no lag time in achieving a therapeutic effect because the anti-cancer agent is available for direct and immediate uptake into the tumor space. This can maximize therapeutic responses to the anti-cancer agent.

It is within the level of a skilled artisan to determine the appropriate timing of administration of a particular anti-cancer agent prior to performing irradiation to ensure sufficient systemic availability of the anti-cancer agent. In many cases, the pharmacokinetics of particular anti-cancer agents are well known. In some cases, pharmacokinetics can be assessed by measuring such parameters as the maximum (peak) plasma concentration ($C_{max}$), the peak time (i.e. when maximum plasma concentration occurs; $T_{max}$), the minimum plasma concentration (i.e. the minimum plasma concentration between doses of agent; $C_{min}$), the elimination half-life ($T_{1/2}$) and area under the curve (i.e. the area under the curve generated by plotting time versus plasma concentration of the agent; AUC), following administration. The concentration of a particular agent in the plasma following subcutaneous administration can be measured using any known methods suitable for assessing concentrations of agents in samples of blood. For example, an immunoassay, such as an ELISA, or chromatography/mass spectrometry-based assays can be used.

In some embodiments, the anti-cancer agent that is used in the combination therapy provided herein can refer to any agents, or compounds, used in anti-cancer treatment. These include any agents, when used alone or in combination with other compounds, that can alleviate, reduce, ameliorate, prevent, or place or maintain in a state of remission of clinical symptoms or diagnostic markers associated with tumors and cancer, and can be used in combinations and compositions provided herein. In some embodiments, the anti-cancer agent is one whose therapeutic effect is generally associated with penetration or delivery of the anti-cancer agent into the tumor microenvironment or tumor space. In some embodiments, the anti-cancer agent is an alkylating agent, a platinum drug, an antimetabolite, an anti-tumor antibiotic, a topoisomerase inhibitor, a mitotic inhibitor, a corticosteroid, a proteasome inhibitor, a kinase inhibitor, a histone-deacetylase inhibitor or an antibody or antigen-binding antibody fragment thereof. In some embodiments, the anti-cancer agent is a peptide, protein or small molecule drug.

In some embodiments, the anti-cancer agent is 5-Fluorouracil/leucovorin, oxaliplatin, irinotecan, regorafenib, ziv-aflibercept, capecitabine, cisplatin, paclitaxel, topotecan, carboplatin, gemcitabine, docetaxel, 5-FU, ifosfamide, mitomycin, pemetrexed, vinorelbine, carmustine wafer, temozolomide, methotrexate, capecitabine, lapatinib, etoposide, dabrafenib, vemurafenib, liposomal cytarabine, cytarabine, interferon alpha, erlotinib, vincristine, cyclophosphamide, lomustine, procarbazine, sunitinib, somatostatin, doxorubicin, pegylated liposomal encapsulated doxorubicin, epirubicin, eribulin, albumin-bound paclitaxel, ixabepilone, cotrimoxazole, taxane, vinblastine, temsirolimus, temozolomide, bendamustine, oral etoposide, everolimus, octreotide, lanreotide, dacarbazine, mesna, pazopanib, eribulin, imatinib, regorafenib, sorafenib, nilotinib, dasatinib, celecoxib, tamoxifen, toremifene, dactinomycin, sirolimus, crizotinib, ceritinib, enzalutamide, abiraterone acetate, mitoxantrone, cabazitaxel, fluoropyrimidine, oxaliplatin, leucovorin, afatinib, ceritinib, gefitinib, cabozantinib, oxaliplatin or pyrimidine aurora kinase inhibitor.

In some embodiments, the anti-cancer agent is an antibody or antigen-binding antibody fragment. In some embodiments, the anti-cancer agent can be any one or more of bevacizumab, cetuximab, panitumumab, ramucirumab, ipilimumab, rituximab, trastuzumab, ado-trastuzumab emtansine, pertuzumab, nivolumab, lapatinib, dabrafenib, vemurafenib, erlotinib, sunitinib, pazopanib, imatinib, regorafenib, sorafenib, nilotinib, dasantinib, celecoxib, crizotinib, certinib, afatinib, axitinib, bevacizumab, bosutinib, cabozantinib, afatinib, gefitinib, temsirolimus, everolimus, sirolimus, ibrutinib, imatinib, lenvatinib, olaparib, palbociclib, ruxolitinib, trametinib, vandetanib or vismodegib, or an antigen-binding antibody fragment thereof.

In some embodiments, the anti-cancer agent is an alkylating agent. Alkylating agents are compounds that directly damage DNA by forming covalent bonds with nucleic acids and inhibiting DNA synthesis. Exemplary alkylating agents include, but are not limited to, mechlorethamine, cyclophosphamide, ifosfamide, melphalan, chlorambucil, busulfan, and thiotepa as well as nitrosourea alkylating agents such as carmustine and lomustine.

In some embodiments, the anti-cancer agent is a platinum drug. Platinum drugs bind to and cause crosslinking of DNA, which ultimately triggers apoptosis. Exemplary platinum drugs include, but are not limited to, cisplatin, carboplatin, oxaliplatin, satraplatin, picoplatin, nedaplatin, triplatin, and lipoplatin.

In some embodiments, the anti-cancer agent is an antimetabolite. Antimetabolites interfere with DNA and RNA growth by substituting for the normal building blocks of RNA and DNA. These agents damage cells during the S phase, when the cell's chromosomes are being copied. In some cases, antimetabolites can be used to treat leukemias, cancers of the breast, ovary, and the intestinal tract, as well as other types of cancer. Exemplary antimetabolites include, but are not limited to, 5-fluorouracil (5-FU), 6-mercaptopurine (6-MP), capecitabine (Xeloda®), cytarabine (Ara-C®), floxuridine, fludarabine, gemcitabine (Gemzar®), hydroxyurea, methotrexate, and pemetrexed (Alimta®).

In some embodiments, the anti-cancer agent is an anti-tumor antibiotic. Anti-tumor antibiotics work by altering the DNA inside cancer cells to keep them from growing and multiplying. Anthracyclines are anti-tumor antibiotics that interfere with enzymes involved in DNA replication. These drugs generally work in all phases of the cell cycle. They can be widely used for a variety of cancers. Exemplary anthracyclines include, but are not limited to, daunorubicin, doxorubicin, epirubicin, and idarubicin. Other anti-tumor antibiotics include actinomycin-D, bleomycin, mitomycin-C, and mitoxantrone.

In some embodiments, the anti-cancer agent is a topoisomerase inhibitor. These drugs interfere with enzymes called topoisomerases, which help separate the strands of DNA so they can be copied during the S phase. Topoisomerase inhibitors can be used to treat certain leukemias, as well as lung, ovarian, gastrointestinal, and other cancers. Exemplary topoisomerase inhibitors include, but are not limited to, doxorubicin, topotecan, irinotecan (CPT-11), etoposide (VP-16), teniposide, and mitoxantrone.

In some embodiments, the anti-cancer agent is a mitotic inhibitor. Mitotic inhibitors are often plant alkaloids and other compounds derived from natural plant products. They work by stopping mitosis in the M phase of the cell cycle but, in some cases, can damage cells in all phases by keeping enzymes from making proteins needed for cell reproduction. Exemplary mitotic inhibitors include, but are not limited to, paclitaxel (Taxol®), docetaxel (Taxotere®), ixabepilone (Ixempra®), vinblastine (Velban®), vincristine (Oncovin®), vinorelbine (Navelbine®), and estramustine (Emcyt®).

In some embodiments, the anti-cancer agent is a corticosteroid. Corticosteroids, often simply called steroids, are natural hormones and hormone-like drugs that are useful in the treatment of many types of cancer. Corticosteroids can also be used before chemotherapy to help prevent allergic reactions as well as during and after chemotherapy to help prevent nausea and vomiting. Exemplary corticosteroids include, but are not limited to, prednisone, methylprednisolone (Solumedrol®), and dexamethasone (Decadron®).

In some embodiments, the anti-cancer agent is another type of chemotherapy drug, such as a proteasome inhibitor, a kinase inhibitor, or a histone-deacetylase inhibitor. In other embodiments, the anti-cancer agent is a biologic such as an antibody used in cancer therapy.

In some embodiments, the anti-cancer agent targets tumors associated with various cancers. The cancer can be any cancer located in the body of a subject, such as, but not limited to, cancers located at the head and neck, breast, liver, colon, ovary, prostate, pancreas, brain, cervix, bone, skin, eye, bladder, stomach, esophagus, peritoneum, or lung. For example, the anti-cancer agent can be used for the treatment of colon cancer, cervical cancer, cancer of the central nervous system, breast cancer, bladder cancer, anal carcinoma, head and neck cancer, ovarian cancer, endometrial cancer, small cell lung cancer, non-small cell lung carcinoma, neuroendocrine cancer, soft tissue carcinoma, penile cancer, prostate cancer, pancreatic cancer, gastric cancer, gall bladder cancer or esophageal cancer. In some cases, the cancer can be a cancer of the blood.

E. Exemplary Features

In some embodiments, a desired response of treatment according to the provided methods involving assessment of biomarkers, is to reduce or inhibit one or more symptoms associated with a tumor or a cancer, and/or improve the efficacy of the tumor treatment involving PIT. In some embodiments, the one or more symptoms do not have to be completely eliminated for the composition to be effective. In some embodiments, the provided methods results in a synergistic treatment effect compared to treatment by the conjugate alone, without using assessment of biomarkers to select subjects or types of treatment, In some aspects, by selecting subjects that exhibits a high likelihood of response to PIT, or administering additional therapeutic agents to subjects that may benefit from the additional treatment, the overall efficacy of treatment based on PIT can increase.

In some aspects, administration of a composition containing the phthalocyanine dye-targeting molecule conjugate followed by irradiation, according to the methods provided herein, e.g., based on biomarker assessment, can decrease the size of a tumor, such as the volume or weight of a tumor, or metastasis of a tumor, for example by at least 20%, at least 30%, at least 40%, at least 50%, at least 60%, at least 70%, at least 80%, at least 90%, at least 95%, at least 98%, or at least 100%, as compared to the tumor size, volume, weight, or metastasis in the absence of the conjugate. In some embodiments, the difference in tumor size, volume, weight or metastasis is evident after at least 7 days, at least 10 days, at least 14 days, at least 30 days, at least 60 days, at least 90 days, or at least 120 days after the treatment(s). In some embodiments, tumor size and volume can be monitored by radiography, ultrasound imaging, necropsy, by use of calipers, by micro-CT or by $^{18}$F-FDG-PET. Tumor size also can be assessed visually. In particular examples, tumor size (diameter) can be measured directly using calipers.

In some embodiments, combination therapy according to the methods provided herein, e.g., based on biomarker assessment, can result in a tumor size, volume, weight or metastasis that is less than the tumor size, volume, weight or metastasis would be if it were treated with either the phthalocyanine dye-targeting molecule conjugate /PIT alone or the additional therapy alone, that is, there is a synergistic effect. For example, the combination therapy provided herein can decrease the size of a tumor, such as the volume or weight of a tumor, or metastasis of a tumor, for example by at least 1.2-fold, 1.5-fold, 2-fold, 3-fold, 4-fold, 5-fold, 6-fold, 7-fold, 8-fold, 9-fold, 10-fold or more as compared to the tumor size, volume, weight, or metastasis achieved in therapy methods involving only photoimmunotherapy with a composition containing the phthalocyanine dye-targeting molecule conjugate followed by irradiation or in therapy methods involving monotherapy with the immune modulating agent or anti-cancer agent alone.

In some embodiments, a desired response of treatment according to the provided methods is to kill a population of cells by a desired amount, for example by killing at least 20%, at least 50%, at least 60%, at least 70%, at least 80%, at least 90%, at least 95%, at least 98%, or at least 100% of the cells, as compared to cell killing in the absence of the conjugate and irradiation. In some embodiments, the difference in tumor cell killing is evident after at least 1 hour, at least 2 hours, at least 6 hours, at least 12 hours, at least 1 day, at least 2 days, at least 3 days, at least 4 days, at least 5 days, at least 6 days, at least 7 days, at least 10 days, at least 14 days or at least 30 days, after the treatment(s). In some embodiments, cell killing activity can be assessed by a variety of techniques known including, but not limited to, cytotoxicity/cell viability assays that can be employed to measure cell necrosis and/or apoptosis, such as from a biopsy sample, following treatment(s), such as MTT (3-(4, 5-dimethylthiazol-2-yl)-2,5-diphenyltetrazolium bromide) assays and other related tetrazolium salt based assays (e.g., XTT, MTS or WST), ATP assays, apoptosis assays (e.g., using labeled annexin V), such as TUNEL staining of infected cells, DNA fragmentation assays, DNA laddering assays, and cytochrome C release assays. In some cases, imaging methods can be used, such as positron emission tomography (PET), including FDG-PET, single photon emission CT (SPECT), diffusion weighted imaging (DWI), dynamic susceptibility-weighted contrast-enhanced (DSC) MR imaging or dynamic contrast-enhanced (DCE) MR imaging, CT perfusion methods, magnetic resonance spectroscopy (MRS) Such assays and methods are well known.

In some embodiments, the combination therapy involving PIT performed according to the methods provided herein, e.g., based on biomarker assessment, can increase the killing of tumor cells, for example, by at least by at least 1.2-fold, 1.5-fold, 2-fold, 3-fold, 4-fold, 5-fold, 6-fold, 7-fold, 8-fold, 9-fold, 10-fold or more as compared to either of the single therapy.

In some embodiments, a desired response is to increase the survival time of a patient with a tumor, or who has had a tumor recently removed, by a desired amount, for example to increase survival by at least 20%, at least 50%, at least 60%, at least 70%, at least 80%, at least 90%, at least 95%, at least 98%, or at least 100%, as compared to the survival time in the absence of the conjugate and irradiation. In some embodiments, increased survival is evident by an increase in one or more survival indicators from among duration of median progression-free survival, duration of response, median overall survival or other survival-related clinical endpoint. In some embodiments, the difference in survival is evident after at least 7 days, at least 10 days, at least 14 days, at least 30 days, at least 60 days, at least 90 days, at least 120 days, at least 6 months, at least 12 months, at least 24 months, or at least 5 years or more after the treatment(s). In some embodiments, therapy involving PIT performed according to the methods provided herein, e.g., based on biomarker assessment, alone in accord with the methods herein, increases the duration of median progression-free survival, duration of response, median overall survival or other survival-related clinical endpoint by at least 3 months, at least 4 months, at least 5 months, at least 6 months, at least 7 months, at least 8 months, at least 9 months, at least 10 months, at least 11 months, at least 12 months, at least 18 months, at least 24 months, or at least 5 years or more compared to if a subject were treated with the corresponding targeting molecule that was not so conjugated. In some embodiments, the combination therapy involving PIT performed according to the methods provided herein, e.g., based on biomarker assessment, increases the duration of median progression-free survival, duration of response, median overall survival or other survival-related clinical endpoint by at least 3 months, at least 4 months, at least 5 months, at least 6 months, at least 7 months, at least 8 months, at least 9 months, at least 10 months, at least 11 months, at least 12 months, at least 18 months, at least 24 months, or at least 5 years or more compared to the single agents.

In some embodiments, the combination therapy involving PIT performed according to the methods provided herein, e.g., based on biomarker assessment, can increase the survival time of a treated subject, for example, by at least 1.2-fold, 1.5-fold, 2-fold, 3-fold, 4-fold, 5-fold, 6-fold, 7-fold, 8-fold, 9-fold, 10-fold or more as compared to the survival time in a subject receiving a therapy involving only photoimmunotherapy with a composition containing the phthalocyanine dye-targeting molecule conjugate followed by irradiation or in therapy methods involving monotherapy with the immune modulating agent or anti-cancer agent alone. In some embodiments, the combination therapy involving PIT performed according to the methods provided herein, e.g., based on biomarker assessment, increases the duration of median progression-free survival, duration of response, median overall survival or other survival-related clinical endpoint by at least 3 months, at least 4 months, at least 5 months, at least 6 months, at least 7 months, at least 8 months, at least 9 months, at least 10 months, at least 11 months, at least 12 months, at least 18 months, at least 24 months, or at least 5 years or more compared to if it were treated with either the phthalocyanine dye-targeting molecule conjugate /PIT alone or the additional therapy alone.

In one aspect, the response to treatment is characterized utilizing Response Evaluation Criteria in Solid Tumors (RECIST) criteria, which is the recommended guideline for assessment of tumor response by the National Cancer Institute (see Therasse et al., J. Natl. Cancer Inst. 92:205-216, 2000). In some embodiments, patients can be assessed for response to the therapy using RECIST criteria as outlined in the revised version 1.1 guidelines (RECIST 1.1, see Eisenhauer et al. (2009) European Journal of Cancer, 45:228-247). The criteria for objective status are required for protocols to assess solid tumor response. Representative criteria include the following: (1) Complete Response (CR), defined as complete disappearance of all measurable disease; no new lesions; no disease related symptoms; no evidence of non-measurable disease; (2) Partial Response (PR) defined as 30% decrease in the sum of the longest diameter of target lesions (e.g., tumor); (3) Progressive Disease (PD), defined as 20% increase in the sum of the longest diameter of target lesions or appearance of any new lesion; (4) Stable or No Response, defined as not qualifying for CR, PR, or PD. (See Therasse et al., supra.) In some embodiments, the objective response rate (ORR) can be determined, which is the percentage of subjects in which a CR or PR response is observed. ORR is commonly used to measure tumor response to treatment in oncology clinical trials.

In some embodiments, administration of the phthalocyanine dye-targeting molecule conjugate in accord with the provided methods, either as a monotherapy or in a combination therapy, achieves a reduction in the size or volume of the tumor by at least 30%, at least 40%, at least 50%, at least 60%, at least 70%, at least 80% at least 90% or more within two weeks or one month of the irradiation compared to the size or volume of the tumor prior to the administration and irradiation.

In some embodiments, in a population of treated subjects, effects an improvement of a tumor-related parameter compared to a similarly situated population of subjects that have not been treated with the method, wherein the parameter is selected from one or more of: a) objective response rate (ORR); b) progression free survival (PFS); c) overall survival (OS); d) reduction in toxicity; e) tumor response; f) quality of life; g) symptom endpoint; h) disease-free survival; h) complete response (CR); or i) time to progression. In some embodiments, the parameter is improved by at least 10%, at least 20%, at least 30%, at least 40%, at least 50%, at least 60%, at least 70%, at least 80%, at least 90%, at least 100% or more.

In some embodiments, in a population of treated subjects, administration of the phthalocyanine dye-targeting molecule conjugate in accord with the provided methods, either as a monotherapy or in a combination therapy, results in a PR in at least 50%, 60%, 70%, 80%, 90%, 95% or 100% of the treated subjects. In some embodiments, in a population of treated subjects, administration of the phthalocyanine dye-targeting molecule conjugate in accord with the provided methods results in a CR in at least 10%, 20%, 30%, 40%, 50%, 60%, 70%, 80%, 90%, 95% or 100% of the treated subjects.

In some embodiments, in a population of treated subjects, administration of the phthalocyanine dye-targeting molecule conjugate in accord with the provided methods, either as a monotherapy or in a combination therapy, results in an ORR that is greater than about 13%, for example greater than about 15%, greater than about 20%, greater than about 30%, greater than about 40%, greater than about 50%, greater than about 60%, greater than about 70%, greater than about 80%, greater than about 95%, or greater than about 99%.

In some embodiments, the combination therapy provided herein, such as therapies that employing an immune modulating agent, can be used to stimulate an immune response in a cancer patient. Typically, immune responses may be detected by any of a variety of well-known parameters, including but not limited to in vivo or in vitro determination of: soluble immunoglobulins or antibodies; soluble mediators such as cytokines, lymphokines, chemokines, hormones, growth factors and the like as well as other soluble small peptide, carbohydrate, nucleotide and/or lipid mediators; cellular activation state changes as determined by altered functional or structural properties of cells of the immune system, for example cell proliferation, altered motility, induction of specialized activities such as specific gene expression or cytolytic behavior; cellular differentiation by cells of the immune system, including altered surface antigen expression profiles or the onset of apoptosis (programmed cell death); an increase in cytotoxic T-cells, activated macrophages or natural killer cells; or any other criterion by which the presence of an immune response may be detected.

Procedures for performing these and similar assays are widely known and may be found, for example in Lefkovits (Immunology Methods Manual: The Comprehensive Sourcebook of Techniques, 1998; see also Current Protocols in Immunology; see also, e.g., Weir, Handbook of Experimental Immunology, 1986 Blackwell Scientific, Boston, Mass.; Mishell and Shigii (eds.) Selected Methods in Cellular Immunology, 1979 Freeman Publishing, San Francisco, Calif.; Green and Reed, 1998 Science 281:1309 and references cited therein.).

Detection of the proliferation of tumor-reactive T cells may be accomplished by a variety of known techniques. For example, T cell proliferation can be detected by measuring the rate of DNA synthesis, and tumor specificity can be determined by controlling the stimuli (such as, for example, a specific desired tumor- or a control antigen-pulsed antigen presenting cells) to which candidate tumor-reactive T cells are exposed. T cells which have been stimulated to proliferate exhibit an increased rate of DNA synthesis. A typical way to measure the rate of DNA synthesis is, for example, by pulse-labeling cultures of T cells with tritiated thymidine, a nucleoside precursor which is incorporated into newly synthesized DNA. The amount of tritiated thymidine incorporated can be determined using a liquid scintillation spectrophotometer. Other ways to detect T cell proliferation include measuring increases in interleukin-2 (IL-2) production, $Ca^{2+}$ flux, or dye uptake, such as 3-(4,5-dimethylthiazol-2-yl)-2,5-diphenyl-tetrazolium Alternatively, synthesis of lymphokines (such as interferon-gamma) can be measured or the relative number of T cells that can respond to a particular antigen may be quantified.

Detection of antibody production (e.g., tumor specific antibody production) may be achieved, for example, by assaying a sample (e.g., an immunoglobulin containing sample such as serum, plasma or whole blood) from a host treated with a composition according to the present invention using in vitro methodologies such as radioimmunoassay (RIA), enzyme linked immunosorbent assays (ELISA), equilibrium dialysis or solid phase immunoblotting including Western blotting. In preferred embodiments ELISA assays may further include tumor antigen-capture immobilization of a target tumor antigen with a solid phase monoclonal antibody specific for the antigen, for example, to enhance the sensitivity of the assay. Elaboration of soluble mediators (e.g., cytokines, chemokines, lymphokines, prostaglandins, etc.) may also be readily determined by enzyme-linked immunosorbent assay (ELISA), for example, using methods, apparatus and reagents that are readily available from commercial sources (e.g., Sigma, St. Louis, Mo.; see also R & D Systems 2006 Catalog, R & D Systems, Minneapolis, Minn.).

Any number of other immunological parameters may be monitored using routine assays that are well known. These may include, for example, antibody dependent cell-mediated cytotoxicity (ADCC) assays, secondary in vitro antibody responses, flow immunocytofluorimetric analysis of various peripheral blood or lymphoid mononuclear cell subpopulations using well established marker antigen systems, immunohistochemistry or other relevant assays. These and other assays may be found, for example, in Rose et al. (Eds.), Manual of Clinical Laboratory Immunology, 5th Ed., 1997 American Society of Microbiology, Washington, D.C.

IV. PHTHALOCYANINE DYE CONJUGATES

In some embodiments, the methods and uses provided herein include a component of photoimmunotherapy (PIT) and/or a combination therapy based on the expression of one or more biomarkers. In some embodiments, the photoimmunotherapy involves administering a conjugate containing a photosensitizer, such as a phthalocyanine dye, for example IR700, and a targeting molecule (e.g., antibody or an antigen binding fragment of an antibody) that binds to a cell surface protein. In some aspects, based on the assessment of one or more biomarkers, subjects can be identified for treatment with the conjugate containing a targeting molecule and a phthalocyanine dye. In some embodiments, the provided methods can be used to assess the likelihood of response to a photoimmunotherapy and/or a combination therapy that includes administering the phthalocyanine dye conjugate. In some cases, photoimmunotherapy employed in the provided methods includes administration of a conjugate containing the phthalocyanine dye and targeting molecule, such as an antibody or an antigen-binding fragment thereof.

In some embodiments, binding of the targeting molecule that is conjugated to the photosensitizer, such as a phthalocyanine dye (e.g., IR700), to the cell surface protein permits the targeting of the conjugate to cells involved in a disease or condition, such as a tumor or cancer, infection, inflammatory disease or condition, neuronal disease or condition or other diseases or conditions. In some embodiments, the targeted cells (e.g., cells expressing the cell surface protein capable of being bound by the targeting molecule) are present in the microenvironment of a lesion associated with the disease or condition, for example, the cells are present in a tumor microenvironment. In some embodiments, cell targeting increases the efficacy of photoimmunotherapy induced upon local irradiation of the lesion (e.g., tumor) of the subject at a wavelength that is absorbed by the phthalocyanine dye (e.g., a near-infrared (NIR) wavelength), since cell killing is selective to those cells in which the dye-targeting molecule conjugate is bound.

In some embodiments, the phthalocyanine dye conjugates for use in the combination therapy provided herein include a dye molecule conjugated to a targeting molecule via a linker group. In one aspect, the conjugate is of Formula I:

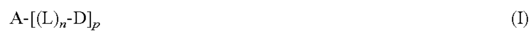

$$A\text{-}[(L)_n\text{-}D]_p \qquad (I)$$

wherein:

A is a targeting molecule that can bind to cells or tissues;

L is an independently selected linker for each p;

n is 1 or 2;

D is an independently selected hydrophilic phthalocyanine dye for each p; and p is independently 1, 2, 3, 4, 5 or greater than 5, such as up to 1000. For example, p can be 1 to 1000, such as generally 1 to 10 or 2 to 5.

In some embodiments, the phthalocyanine dye conjugate is produced by a method or process in which the phthalocyanine dye-targeting molecule conjugate, such as an IR700-targeting molecule (e.g., IR700-antibody) conjugate, is prepared under light-protected conditions. In some embodiments, the method includes 1) preparing or providing a phthalocyanine dye and a targeting molecule; 2) contacting the targeting molecule and phthalocyanine dye under conditions to generate the conjugate with minimal exposure of the dye; and 3) formulating, purifying and/or isolating the conjugate to produce a composition containing the drug substance, where one or more of the steps, such as in some cases all of the steps, are performed with minimal exposure of the dye or the conjugate containing the dye to environmental light. In some embodiments, the phthalocyanine dye-targeting molecule conjugate, such as an IR700-targeting molecule (e.g., IR700-antibody) conjugate, is a conjugate, or is prepared using methods for producing a conjugate, as described in WO 2017/031363 which is incorporated by reference herein. Exemplary conjugates for photoimmunotherapy employed in the methods described herein, include those described in, for example, U.S. Pat. No. 8,524,239 or U.S. publication No. US2014/0120119 and WO 2017/031367.

A. Phthalocyanine Dye

Phthalocyanines are a group of photo sensitizer compounds having the phthalocyanine ring system. Phthalocyanines are azaporphyrins that contain four benzoindole groups connected by nitrogen bridges in a 16-membered ring of alternating carbon and nitrogen atoms (i.e., $C_{32}H_{16}N_8$) which form stable chelates with metal and metalloid cations. In these compounds, the ring center is occupied by a metal ion (either a diamagnetic or a paramagnetic ion) that may, depending on the ion, carry one or two ligands. In addition, the ring periphery may be either unsubstituted or substituted. The synthesis and use of a wide variety of phthalocyanines in photodynamic therapy are described in International Publication WO 2005/099689 and U.S. Pat. No. 7,005,518.

In some embodiments, phthalocyanines strongly absorb red or near IR radiation with absorption peaks falling between about 600 nm and 810 nm, which, in some cases, allow deep penetration of tissue by the light. Phthalocyanines are generally photostable. This photostability is typically advantageous in pigments and dyes and in many of the other applications of phthalocyanines.

In some embodiments, the phthalocyanine dye contains a linker, i.e., is a linker-phthalocyanine dye moiety (L-D). In some embodiments, the linker contains a reactive group. In some embodiments, the phthalocyanine dye is of Formula Ia:

(Ia)

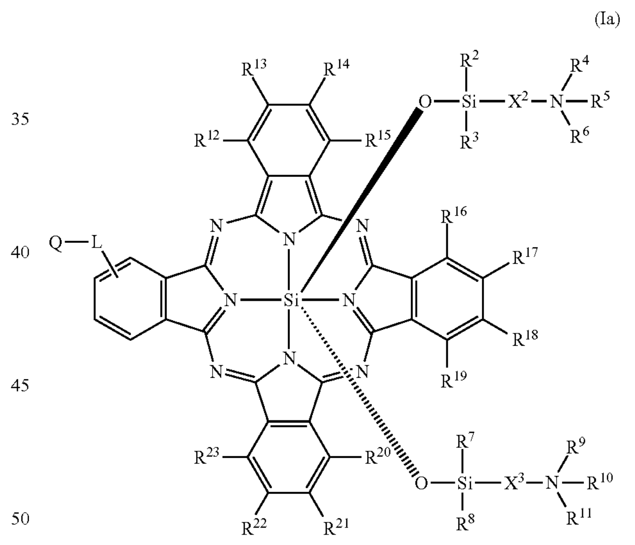

wherein

L is selected from a direct link, or a covalent linkage;

Q is a reactive group or an activatable group that can be part of the linker L, and is any group that can react to form a bond between L and the targeting molecule A;

$R^2$, $R^3$, $R^7$, and $R^8$ are each independently selected from optionally substituted alkyl and optionally substituted aryl;

$R^4$, $R^5$, $R^6$, $R^9$, $R^{10}$, and $R^{11}$, if present, are each independently selected from hydrogen, optionally substituted alkyl, optionally substituted alkanoyl, optionally substituted alkoxycarbonyl, optionally substituted alkylcarbamoyl, or a chelating ligand, wherein at least one of $R^4$, $R^5$, $R^6$, $R^9$, $R^{10}$, and $R^{11}$ comprises a water soluble group;

$R^{12}$, $R^{13}$, $R^{14}$, $R^{15}$, $R^{16}$, $R^{17}$, $R^{18}$, $R^{19}$, $R^{20}$, $R^{21}$, $R^{22}$, and $R^{23}$ are each functional groups that can be independently selected from hydrogen, halogen, optionally substituted alkylthio, optionally substituted alkylamino or optionally substituted alkoxy;

or in an alternative embodiment, at least one of i) $R^{13}$ and $R^{14}$, and the carbons to which they are attached, or ii) $R^{17}$ and $R^{18}$, and the carbons to which they are attached, or iii) $R^{21}$ and $R^{22}$, and the carbons to which they are attached, join to form a fused ring; and $X^2$ and $X^3$ are each independently $C_1$-$C_{10}$ alkylene, optionally interrupted by a heteroatom.

In some embodiments, the phthalocyanine dye is of Formula Ib:

(Ib)

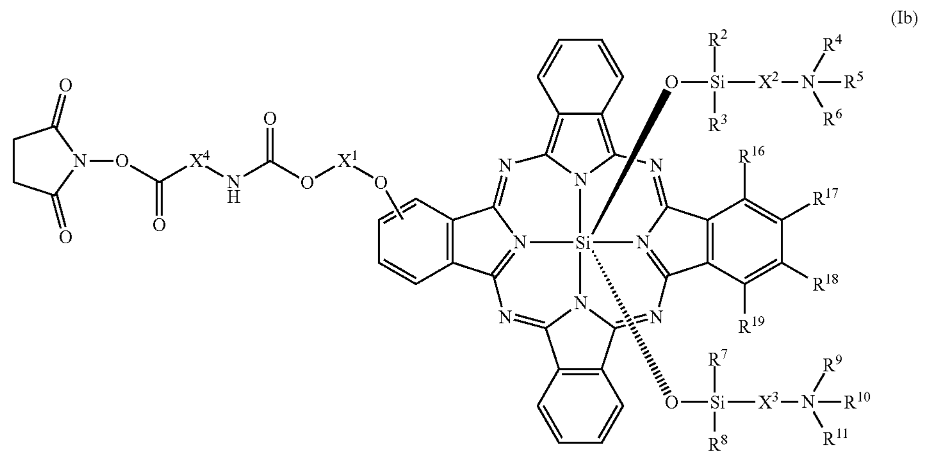

wherein $X^1$ and $X^4$ are each independently a $C_1$-$C_{10}$ alkylene optionally interrupted by a heteroatom; and $R^2$, $R^3$, $R^4$, $R^5$, $R^6$, $R^7$, $R^8$, $R^9$, $R^{10}$, $R^{11}R^{16}$, $R^{17}$, $R^{18}$, $R^{19}$, $X^2$, and $X^3$ are as defined herein.

In some embodiments, the phthalocyanine dye has a maximum light absorption in the near infrared (NIR range). In some embodiments, the phthalocyanine dye has a maximum light absorption wavelength between 400 nm and 900 nm, such as between 600 nm and 850 nm, such as between 680 nm and 850 nm, for example at approximately 690 nm±50 nm or 690±20 nm. In some embodiments, the phthalocyanine dye can be excited efficiently by commercially available laser diodes that emit light at these wavelengths.

In some embodiments of the methods provided herein, the conjugate administered for photoimmunotherapy and/or the combination therapy, according to the methods provided herein, include a phthalocyanine dye containing the reactive group is IR700 NHS ester, such as IRDye 700DX NHS ester (Li-Cor 929-70010, 929-70011). Thus, in some embodiments, the dye is a compound having the following formula:

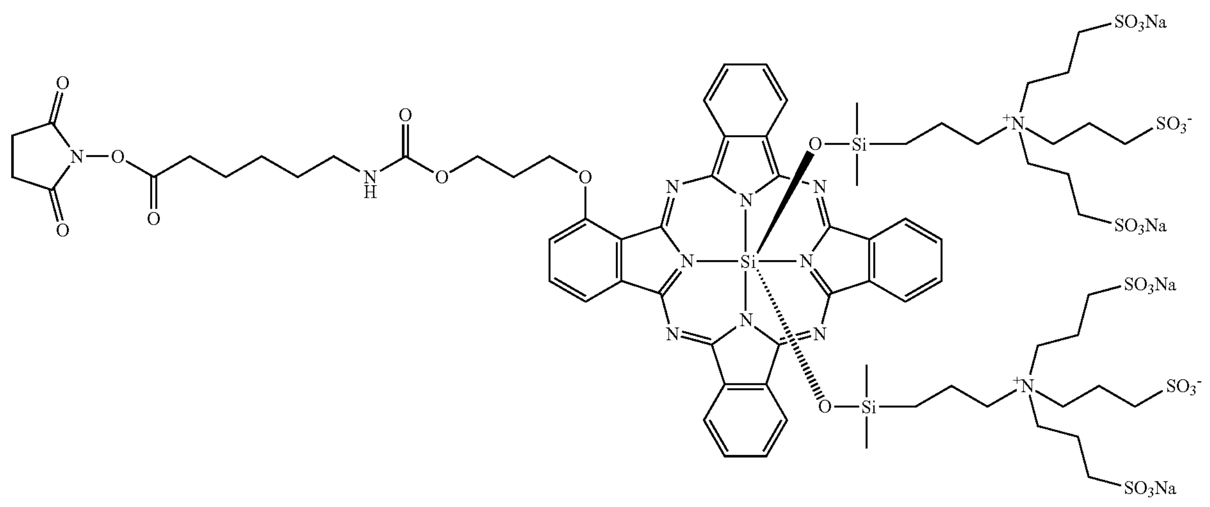

Chemical Formula: $C_{74}H_{96}N_{12}Na_4O_{27}S_6Si_3$
Exact Mass: 1952.37
Molecular Weight: 1954.22
IRDye 700DX NHS Ester For purposes herein, the term "IR700," "IRDye 700DX," or variations thereof refer to the above formula when the dye is conjugated to a targeting molecule via its reactive group. Generally, IR700 has several favorable chemical properties. Amino-reactive IR700 is a relatively hydrophilic dye and can be covalently conjugated with an antibody using the NHS ester of IR700. Typically, IR700 also has more than 5-fold higher extinction coefficient ($2.1\times10^5$ $M^{-1}$ $cm^{-1}$ at the absorption maximum of 689 nm), than conventional photosensitizers such as the hematoporphyrin derivative Photofrin® ($1.2\times10^3$ $M^{-1}$ $cm^{-1}$ at 630 nm), meta-tetra(hydroxyphenyl)chlorin; Foscan® ($2.2\times10^4$ $M^{-1}$ $cm^{-1}$ at 652 nm), and mono-L-aspartyl chlorin e6; NPe6/Laserphyrin® ($4.0\times10^4$ $M^{-1}$ $cm^{-1}$ at 654 nm).

The phthalocyanine dyes described herein can be made with commercially available starting material. The core structure is synthesized by condensation of two or more different diiminoisoindolines. Synthetic strategies using different dinitriles or diiminoisoindolines can lead to various degrees of substitution of the phthalocyanine and/or distribution of regioisomers. Exemplary synthetic schemes for generating the dyes are described in U.S. Pat. No. 7,005,518.

In some embodiments, in any of the methods provided herein, the targeting molecule (e.g. antibody) is linked directly or indirectly to the phthalocyanine dye (e.g. IR700). In some embodiments, the targeting molecule (e.g. antibody) is linked, directly or indirectly, to the phthalocyanine dye (e.g. IR700) via a covalent bond or a non-covalent interaction. In some embodiments, the covalent or non-covalent interactions or linkage is direct or indirect. In some embodiments, the attachment includes an indirect link, such as through a linker (e.g. such as any of the exemplary linkers described above), binding moiety or domain or reactive group. In some embodiments, the linkage includes a direct interaction between the targeting molecule and a phthalocyanine dye (e.g., IR700). In other embodiments, one or both of the targeting molecule and the phthalocyanine dye are linked to one or more linkers, and the interaction is indirect, e.g., between a linker attached to one of the molecules and another molecule, or between two linkers, each attached to the targeting molecule or the phthalocyanine dye.

B. Targeting Molecules, e.g., Antibodies

In some embodiments, the photoimmunotherapy employed in the provided methods and uses, involves administering a conjugate containing a targeting molecule (e.g., antibody or an antigen binding fragment of an antibody) that binds to a cell surface protein, such as a cell surface protein associated with a disease or condition to be treated in accordance with the provided methods, such as a tumor. In some aspects, the conjugate contains a photosensitizer such as a phthalocyanine dye, as described herein. In some aspects, the provided methods can be applied to identify or select subjects for treatment with the photoimmunotherapy using particular targeting molecules to target and treat a disease or condition such as a tumor, based on the expression of one or more biomarkers. In some embodiments, the phthalocyanine dye is conjugated to a targeting molecule via a reactive group of the dye molecule. In some embodiments, the targeting molecule is one that is able to target the conjugate to a cell, for example, by binding to a cell surface molecule (e.g. cell surface receptor) on the cell. In some embodiments, the targeting molecule, e.g., a macromolecule, can selectively bind to a desired cell type, cells with a particular phenotype, or cells displaying one or more cell surface markers or antigens. In some cases, the targeting molecule binds to a cell that is a cancer cell, a tumor cell, an inflammatory cell, an immune cell, a neuron, a stem cell, a proliferating cell, or a cell in a hyperplasia. In some embodiments, the cell is an inflammatory cell, such a leukocyte, for example, a neutrophil, an eosinophil, a basophil, a lymphocyte, or a monocyte. In some embodiments, the cell is an immune cell, such as a T cell, a B cell, a Natural Killer (NK) cell, a dendritic cell, a macrophage or a neutrophil.

In some embodiments, the targeting molecule (e.g., antibody) of the phthalocyanine dye conjugate bind to a protein on the surface of a cell or cells present in a microenvironment of a lesion, such as a tumor, that is associated with or present as a result of a disease or condition. For example, in some embodiments, the conjugate binds to a protein on the surface of a cell or cells present in a tumor microenvironment associated with or present in a tumor. In some embodiments, the conjugate binds to a protein present the extracellular matrix in the microenvironment of the tumor.

As used herein, a "cell present in the microenvironment of a lesion" refers to any cell present in the cellular environment associated with a lesion, a disease or a disorder, such as any cell present in or immediately adjacent to a tumor, such as cells present in a tumor microenvironment, or the extracellular matrix in the tumor microenvironment.

As used herein, a "cell present in a tumor microenvironment" refers to any cell present in the cellular environment in which the tumor exists, such as any cell present in or immediately adjacent to the tumor, including the proliferating tumor cells (e.g., cancer cells), the tumor stroma, blood vessels, infiltrating inflammatory cells (e.g., immune cells) and a variety of associated tissue cells (e.g., fibroblasts). Thus, it is understood that reference to the tumor refers not only to the tumor cells, which can include malignant or cancer cells, but also to other cells present in the tumor microenvironment that regulate the growth of the tumor, including immune cells. In some cases, immune cells present in a tumor microenvironment can include T lymphocytes, including regulatory T lymphocytes (Treg), dendritic cells (DCs), natural killer (NK) cells, B cells, macrophages and other immune cells (Whiteside (2008) Oncogene, 27:5904-5912). It is recognized that, in some aspects, many non-cancerous cells present in and around the tumor can regulate the proliferation, angiogenesis, invasion and/or metastasis of tumor cells, thereby promoting the growth of the tumor. Thus, in some cases, targeting such non-cancerous cells, such as immune cells (e.g., T cells, such as regulatory T cells), present in a tumor can be an effective therapy for killing a tumor by PIT.

Generally, cancerous cells contain antigens associated with a tumor that should be recognized by the immune system. Typically, in an active immune system, immune cells, such as cytotoxic T cells, attack and eradicate these cancerous cells. Under normal physiological conditions, the T cell-mediated immune response is initiated by antigen recognition by the T cell receptor (TCR) and is regulated by a balance of co-stimulatory and inhibitory signals (e.g., immune checkpoint proteins). In particular, CD4+ and CD8+ T cells expressing a TCR can become activated upon recognition of antigenic peptides presented on antigen-presenting cells on major histocompatibility complex (MHC) class I or class II molecules, respectively. In some aspects, activated CD8+ cells, or cytotoxic T cells, can kill tumor cells expressing the antigen, which can be helped by the presence of CD4+ T cells.

In the case of tumors, however, the tumor microenvironment has mechanisms to suppress the immune system, thereby evading immune recognition and preventing or reducing killing of tumor cells. For example, in some cases, immune checkpoint proteins can be dysregulated in tumors, thereby resulting in a suppression of the immune response in the tumor microenvironment as a mechanism of evading the immune system. In some cases, tumor-infiltrating lymphocytes can include Tregs (e.g., CD4+CD25+ T cells), which are cells that are capable of suppressing proliferation of other T cells in the microenvironment (Whiteside, T L (2008) Oncogene, 27:5904-5912). In some cases, other mechanisms can act to inhibit access of immune cells to tumor antigens, thereby also contributing to the tumors ability to evade the immune system.

In some embodiments, the targeting molecule is a targeting molecule that binds to a cell surface protein on a tumor or cancer cell. In some embodiments, the targeting molecule binds to a cell surface protein on an immune cell or other non-cancerous cell present in a tumor microenvironment. In some embodiments, the targeting molecule binds to a cell surface protein on the surface of a T lymphocyte, such as a Treg, a dendritic cell, a natural killer (NK) cell, a B cell, a macrophage or other immune cell that is present in a tumor microenvironment. In some cases, the tumor or cancer is located at the head and neck, breast, liver, colon, ovary, prostate, pancreas, brain, cervix, bone, skin, eye, bladder, stomach, esophagus, peritoneum, or lung.

Exemplary of targeting molecules, such as targeting molecules that target a tumor or cancer, include, but are not limited to, any as described in published international PCT appl. Nos. WO02014120974, WO2014176284, WO2015042325, U.S. Pat. No. 8,524,239 or U.S. patent publication No. US20140120119.

Exemplary targeting molecules include, but are not limited to, a protein, a glycoprotein, an antibody, an antibody fragment, an antigen, an antigen binding fragment, a peptide, a polypeptide, a small molecule, a polymeric synthetic molecule, a polymeric nanoparticle, a liposome, an enzyme substrate, a hormone, a neurotransmitter, a cell metabolite, a viral particle, a viral capsid, a viral nanoparticle, a bacterial particle, a marker, a cell, a hapten, an avidin, a streptavidin, a monomeric streptavidin, a biotin, a carbohydrate, an oligosaccharide, a polysaccharide, a nucleic acid, a deoxy nucleic acid, a fragment of DNA, a fragment of RNA, nucleotide triphosphates, acyclo terminator triphosphates, or PNA. In some embodiments, the targeting molecule is an amino acid, peptide, protein, tyramine, polysaccharide, ion-complexing moiety, nucleoside, nucleotide, oligonucleotide, psoralen, drug, hormone, lipid, lipid assembly, polymer, polymeric microparticle, a biological cell, or virus.

In some embodiments, the targeting molecule targets or binds to an antigen, such as any structural substance that serves as a target capable of being bound by the targeting molecule. In some embodiments, the antigen is or is comprised as part of a cell surface molecule, such as a protein, e.g., a receptor, that is expressed on a cell surface. In some embodiments, for example, the antigen is or is comprised as part of a molecule expressed on the surface of a cell present in a tumor, including any cell present in the tumor microenvironment. Examples of cell surface molecules include, but are not limited to, an antigen, peptides, lipids, polysaccharides, carbohydrate, or nucleic acids containing antigenic determinants, such as those recognized by an immune cell. In some examples, an antigen includes a tumor-specific peptide (such as one found on the surface of a cancer cell) or immunogenic fragment thereof. In some embodiments, the targeting molecule is an antibody or an antigen-binding antibody fragment thereof.

In some embodiments, the targeting molecule can bind to a cell surface molecule or protein on an immune cell to either suppress or activate the body's immune response. In some embodiments, binding of the immune modulating agent to the cell surface molecule or protein can stimulate an immune response to a tumor, such as by inhibiting immune suppression or by enhancing immunostimulation. In some embodiments, the cell surface molecule or protein can be CD25, PD-1 (CD279), PD-L1 (CD274, B7-H1), PD-L2 (CD273, B7-DC), CTLA-4, LAG-3 (CD223), TIM-3 (HAVCR2), 4-1BB (CD137, TNFRSF9), CXCR2, CXCR4 (CD184), CD27, CEACAM1, Galectin 9, BTLA, CD160, VISTA (PD-1 homologue), B7-H4 (VCTN1), CD80 (B7-1), CD86 (B7-2), CD28, HHLA2 (B7-H7), CD28H, CD155, CD226, TIGIT, CD96, Galectin 3, CD40, CD40L, CD70, LIGHT (TNFSF14), HVEM (TNFRSF14), B7-H3 (CD276), Ox40L (TNFSF4), CD137L (TNFSF9, GITRL), B7RP1, ICOS (CD278), ICOSL, KIR, GALS, NKG2A (CD94), GARP, TL1A, TNFRSF25, TMIGD2, BTNL2, Butyrophilin family, CD48, CD244, Siglec family, CD30, CSF1R, MICA (MHC class I polypeptide-related sequence A), MICB (MHC class I polypeptide-related sequence B), NKG2D, KIR family (Killer-cell immunoglobulin-like receptor, LILR family (Leukocyte immunoglobulin-like receptors, CD85, ILTs, LIRs), SIRPA (Signal regulatory protein alpha), CD47 (IAP), Neuropilin 1 (NRP-1), a VEGFR or VEGF. In some example, the targeting molecule is an antibody or antigen-binding fragment that binds a cell surface protein involved in immune modulation, such as an immune checkpoint protein. In some embodiments, the cell surface molecule can be HER1/EGFR, HER2/ERBB2, CD20, CD25 (IL-2Ra receptor), CD33, CD52, CD133, CD206, CEA, CEACAM1, CEACAM3, CEACAM5, CEACAM6, cancer antigen 125 (CA125), alpha-fetoprotein (AFP), Lewis Y, TAG72, Caprin-1, mesothelin, PDGF receptor, PD-1, PD-L1, CTLA-4, IL-2 receptor, vascular endothelial growth factor (VEGF), CD30, EpCAM, EphA2, Glypican-3, gpA33, mucins, CAIX, PSMA, folate-binding protein, gangliosides (such as GD2, GD3, GM1 and GM2), VEGF receptor (VEGFR), integrin $\alpha V\beta 3$, integrin $\alpha 5\beta 1$, ERBB3, MET, IGF1R, EPHA3, TRAILR1, TRAILR2, RANKL, FAP, tenascin, AFP, BCR complex, CD3, CD18, CD44, CTLA-4, gp72, HLA-DR 10β, HLA-DR antigen, IgE, MUC-1, nuC242, PEM antigen, metalloproteinases, Ephrin receptor, Ephrin ligands, HGF receptor, CXCR4, CXCR4, Bombesin receptor, or SK-1 antigen.

In some embodiments, the targeting molecule is an antibody or an antigen-binding antibody fragment that specifically binds to an antigen that is or is part of a cell surface molecule expressed on the surface of a cell. Included among such antibodies are antibodies or antigen-binding antibody fragments capable of binding to a cell surface molecule, such as a cell surface protein, e.g., cell surface receptor, described herein. In some cases, the antibody can bind to an antigen of a protein expressed on a cell in a tumor, including a tumor-specific protein.

In some embodiments, the targeting molecule binds to an antigen or protein directly or indirectly. For example, in some embodiments, the targeting molecule is a second binding molecule that binds to a first binding molecule which is capable of binding to the antigen or protein. For example, the targeting molecule is a secondary antibody, which binds to a first binding molecule, e.g., a primary antibody, capable of binding the protein or antigen, e.g., a cell surface protein or a cell surface receptor. Thus, in some embodiments, the dye is conjugated to a secondary antibody.

An "antibody" is a polypeptide ligand comprising at least a light chain and/or heavy chain immunoglobulin variable region that specifically recognizes and binds an epitope of an antigen. Generally, antibodies are composed of a heavy and a light chain, each of which has a variable region, termed the variable heavy ($V_H$) region and the variable light ($V_L$) region. Together, the $V_H$ region and the $V_L$ region are responsible for binding the antigen recognized by the antibody. The term antibody includes intact antibodies and antigen-binding antibody fragments that exhibit antigen-binding, such as Fab fragments, Fab' fragments, $F(ab)'_2$ fragments, single chain Fv proteins ("scFv"), and disulfide stabilized Fv proteins ("dsFv"). An scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes genetically engineered forms such as modified forms of immunoglobulins, chimeric antibodies, for example, humanized murine antibodies, and heteroconjugate antibodies, such as bispecific antibodies. See also, *Pierce Catalog and Handbook,* 1994-1995 (Pierce Chemical Co., Rockford, Ill.); Kuby, J., *Immunology,* 3rd Ed., W.H. Freeman & Co., New York, 1997.

Typically, a naturally occurring immunoglobulin has heavy (H) chains and light (L) chains interconnected by disulfide bonds. There are two types of light chain, lambda (λ) and kappa (k). There are five main heavy chain classes, or isotypes, which determine the functional activity of an antibody molecule: IgM, IgD, IgG, IgA and IgE.

Each heavy and light chain contains a constant region and a variable region, also known as "domains." In combination, the heavy and the light chain variable regions generally specifically bind the antigen. Light and heavy chain variable regions may contain a "framework" region interrupted by three hypervariable regions, also called "complementarity-determining regions" or "CDRs." The extent of the framework region and CDRs has been defined (see, Kabat et al., *Sequences of Proteins of Immunological Interest*, U.S. Department of Health and Human Services, 1991, which is hereby incorporated by reference). The Kabat database is now maintained online. The sequences of the framework regions of different light or heavy chains are relatively conserved within a species, such as humans. The framework region of an antibody, that is the combined framework regions of the constituent light and heavy chains, serves to position and align the CDRs in three-dimensional space.

The CDRs are typically responsible for binding to an epitope of an antigen. The CDRs of each chain are typically referred to as CDR1, CDR2, and CDR3, numbered sequentially starting from the N-terminus, and are also generally identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found. Antibodies with different specificities, such as different combining sites for different antigens, have different CDRs. Although it is the CDRs that vary from antibody to antibody, only a limited number of amino acid positions within the CDRs are directly involved in antigen binding. These positions within the CDRs are called specificity determining residues (SDRs).

References to "$V_H$" or "VH" refer to the variable region of an immunoglobulin heavy chain, including that of an Fv, scFv, dsFv or Fab. References to "$V_L$" or "VL" refer to the variable region of an immunoglobulin light chain, including that of an Fv, scFv, dsFv or Fab.

Among the provided antibodies are antibody fragments. An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, $F(ab')_2$; diabodies; linear antibodies; single-chain antibody molecules (e.g., scFv); and multispecific antibodies formed from antibody fragments. Other antibody fragments or multispecific antibodies formed from antibody fragments include a multivalent scFv, a bispecific scFv or an scFv-CH3 dimer. Antibody fragments can be made by various techniques, including but not limited to proteolytic digestion of an intact antibody as well as production by recombinant host cells.

A "monoclonal antibody" is an antibody produced by a single clone of B lymphocytes or by a cell into which the light and heavy chain genes of a single antibody have been transfected. Monoclonal antibodies are produced by methods known to a skilled person, for instance by making hybrid antibody-forming cells from a fusion of myeloma cells with immune spleen cells. Monoclonal antibodies include humanized monoclonal antibodies.

A "chimeric antibody" has framework residues from one species, such as human, and CDRs, which generally confer antigen binding, from another species, such as a murine antibody that specifically binds mesothelin.

A "humanized" immunoglobulin is an immunoglobulin including a human framework region and one or more CDRs from a non-human (for example a mouse, rat, or synthetic) immunoglobulin. The non-human immunoglobulin providing the CDRs is termed a "donor," and the human immunoglobulin providing the framework is termed an "acceptor." In some embodiments, the CDRs are from the donor immunoglobulin in a humanized immunoglobulin. Constant regions need not be present, but if they are, they may be substantially identical to human immunoglobulin constant regions, such as at least about 85-90%, such as about 95% or more identical. Hence, parts of a humanized immunoglobulin, except possibly the CDRs, are substantially identical to corresponding parts of natural human immunoglobulin sequences. A "humanized antibody" is an antibody comprising a humanized light chain and a humanized heavy chain immunoglobulin. A humanized antibody binds to the same antigen as the donor antibody that provides the CDRs. The acceptor framework of a humanized immunoglobulin or antibody may have a limited number of substitutions by amino acids taken from the donor framework. Humanized or other monoclonal antibodies can have additional conservative amino acid substitutions which have substantially no effect on antigen binding or other immunoglobulin functions. Humanized immunoglobulins can be constructed by means of genetic engineering (see for example, U.S. Pat. No. 5,585,089).

A "human" antibody (also called a "fully human" antibody) is an antibody that includes human framework regions and CDRs from a human immunoglobulin. In some embodiments, the framework and the CDRs are from the same originating human heavy and/or light chain amino acid sequence. However, frameworks from one human antibody can be engineered to include CDRs from a different human antibody. Parts of a human immunoglobulin may be substantially identical to corresponding parts of natural human immunoglobulin sequences.

"Specifically binds" refers to the ability of a molecule, such as an antibody or antigen-binding fragment, to specifically bind an antigen, such as a tumor-specific antigen, relative to binding to unrelated proteins, such as non-tumor proteins, for example β-actin. In some embodiments, a molecule, such as an antibody or fragment, including a molecule, such as an antibody or fragment, attached to a phthalocyanine dye molecule, specifically binds to a target, such as a cell surface protein, with a binding constant that is at least $10^3$ $M^{-1}$ greater, $10^4 M^{-1}$ greater or $10^5 M^{-1}$ greater than a binding constant for other molecules in a sample or subject. In some embodiments, a molecule, such as an antibody or fragments thereof, has an equilibrium association constant ($K_A$) of greater than or equal to about $10^6$ $M^{-1}$, greater than or equal to about $10^7$ $M^{-1}$, greater than or equal to about $10^8$ $M^{-1}$, or greater than or equal to about $10^9$ $M^{-1}$, $10^{10} M^{-1}$, $10^{11}$ $M^{-1}$ or $10^{12}$ $M^{-1}$. Antibodies also can be characterized by an equilibrium dissociation constant ($K_D$) of $10^{-6}$ M, $10^{-7}$ M, $10^{-8}$ M, $10^{-10}$ M, $10^{-11}$ M or $10^{-12}$ M or lower. In some embodiments, an equilibrium dissociation constant ($K_D$) can be 1 nM or less Affinity constants, such as $K_D$ or $K_A$, can be estimated empirically or affinities can be determined comparatively, e.g. by comparing the affinity of one antibody and another antibody for a particular antigen. For example, such affinities can be readily determined using techniques known, such as, for example, by competitive ELISA (enzyme-linked immunosorbent assay) or using a surface-plasmon resonance device, such as the Biacore T100 (available from Biacore, Inc., Piscataway, N.J.), a radioimmunoassay using radiolabeled target antigen, or by another method known to the skilled artisan.

In some embodiments, the phthalocyanine dye (e.g., IR700) is conjugated to an antibody or an antigen-binding antibody fragment. For example, in some aspects, the phthalocyanine dye-targeting molecule conjugate is an IR700-antibody conjugate. Exemplary antibodies to which the phthalocyanine dye (e.g., IR700) can be conjugated to include, but are not limited to, cetuximab, panitumumab, zalutumumab, nimotuzumab, trastuzumab, Ado-trastuzumab emtansine, Tositumomab (Bexxar®), Rituximab (Rituxan, MabThera), Ibritumomab tiuxetan (Zevalin), Daclizumab (Zenapax), Gemtuzumab (Mylotarg), Alemtuzumab, CEA-scan Fab fragment, OC125 monoclonal antibody, ab75705, B72.3, Bevacizumab (Avastin®), Afatinib, Axitinib, Bosutinib, Cabozantinib, Ceritinib, Crizotinib, Dabrafenib, Dasatinib, Erlotinib, Everolimus, Ibrutinib, Imatinib, Lapatinib, Lenvatinib, Nilotinib, Olaparib, Palbociclib, Pazopanib, Pertuzumab, Ramucirumab, Regorafenib, Ruxolitinib, Sorafenib, Sunitinib, Temsirolimus, Trametinib, Vandetanib, Vemurafenib, Vismodegib, Basiliximab, Ipilimumab, Nivolumab, pembrolizumab, MPDL3280A (Atezolizumab), Pidilizumab (CT-011), MK-3475, BMS-936559, MPDL3280A, tremelimumab, IMP321, BMS-986016, LAG525, urelumab, PF-05082566, TRX518, MK-4166, dacetuzumab, lucatumumab, SEQ-CD40, CP-870, CP-893, MEDI6469, MEDI6383, MOXR0916, AMP-224, MSB0010718C (Avelumab), MEDI4736, PDR001, rHIgM12B7, Ulocuplumab, BKT140, Varlilumab (CDX-1127), ARGX-110, MGA271, lirilumab (BMS-986015, IPH2101), IPH2201, AGX-115, Emactuzumab, CC-90002 and MNRP1685A or an antibody-binding fragment thereof.

In some embodiments, the conjugate contains a number of dye residues per targeting molecule that is from or from about 1 to about 1000, such as from or from about 1 to about 100, from or from about 1 to about 50, from or from about 1 to about 25, from or from about 1 to about 10, from or from about 1 to about 5. In some embodiments, the ratio of dye molecules to targeting molecule is or is about 2:1, 3:1, 4:1, 5:1, 10:1, 15:1, 20:1, 25:1, 50:1, 75:1, 100:1, 150:1, 200:1, 250:1, 300:1, 350:1, 400:1, 450:1, 500:1, 550:1, 600:1, 650:1, 700:1, 750:1, 800:1, 850:1, 900:1, 950:1 or 1000:1, or is between or between about any two of such values. In some embodiments, the targeting molecule may contain up to 2, 3, 4, 5, 6, 7, 8, 9, 10, 15, 20, 50, 75, 100, 150, 200, 250, 300, 350, 400, 450, 500, 550, 600, 650, 700, 750, 800, 850, 900, 950 or 1000 dye molecules. In some embodiments, the targeting molecule may contain more than 1000 dye molecules or less than 10 dye molecules.

In some embodiments, such as when the targeting molecule is a polypeptide, such as an antibody or antigen-binding antibody fragment, the number of dye molecule per targeting molecule can be from or from about 2 to about 5, such as from or from about 2 to about 4, for example about 3 or 3. Thus, in some embodiments, the targeting molecule may contain about 10 to about 1000 dye molecules.

C. Pharmaceutical Compositions and Articles of Manufacture

In some aspects, pharmaceutical compositions containing a phthalocyanine-dye targeting molecule conjugate (e.g., IR700-antibody conjugate) are employed in the methods provided herein. In some embodiments, the compositions can be used in methods provided herein that involve photoimmunotherapy and/or a combination therapy, for example based on the assessment of one or more biomarkers. The phthalocyanine dye-targeting molecule conjugate, for example, IR700-antibody conjugate. In some embodiments, the compositions can be provided in combination with an additional therapeutic agent, such as an immune modulating agent or anti-cancer agent, for use according to the methods provided herein. In some embodiments, the phthalocyanine dye-targeting molecule conjugate and other therapeutic agent, such as one or both of an immune modulating agent or anti-cancer agent, can be packaged as an article of manufacture as separate compositions for administration together, sequentially or intermittently. The combinations can be packaged as a kit. Exemplary compositions, formulations, dosage forms, packaging and articles of manufacture include those described in, for example, U.S. Pat. No. 8,524,239 or U.S. publication No. US2014/0120119, WO 2017/031367 and WO 2017/031363. In some embodiments, the kits and articles of manufacture also contain reagents required for assessing the level, concentration and/or amount of the one or more biomarker(s), and instructions for carrying out the methods provided herein.

V. DEFINITIONS

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

As used herein, the singular forms “a,” “an,” and “the” include plural referents unless the context clearly dictates otherwise. For example, “a” or “an” means “at least one” or “one or more.” It is understood that aspects and variations described herein include “consisting” and/or “consisting essentially of” aspects and variations.

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

The term “about” as used herein refers to the usual error range for the respective value readily known to the skilled person in this technical field. Reference to “about” a value or parameter herein includes (and describes) embodiments that are directed to that value or parameter per se. For example, description referring to “about X” includes description of “X”.

As used herein, a “conjugate” refers to a polypeptide linked directly or indirectly to one or more other polypeptides or chemical moieties. Such conjugates include fusion proteins, those produced by chemical conjugates and those produced by any other methods. For example, a conjugate can refer to a phthalocyanine dye, such as an IR700 molecule, linked directly or indirectly to one or more other polypeptides or chemical moieties, such as to a targeting molecule that binds to or targets to a cell surface protein.

As used herein, a composition refers to any mixture of two or more products, substances, or compounds, including cells. It may be a solution, a suspension, liquid, powder, a paste, aqueous, non-aqueous or any combination thereof.

As used herein, a “pharmaceutical composition” or “pharmaceutical formulation” refers to a preparation which is in such form as to permit the biological activity of an active ingredient contained therein to be effective, and which contains no additional components which are unacceptably toxic to a subject to which the formulation would be administered.

As used herein, a “pharmaceutically acceptable carrier” refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, a combination refers to any association between or among two or more items. The combination can be two or more separate items, such as two compositions or two collections, can be a mixture thereof, such as a single mixture of the two or more items, or any variation thereof. The elements of a combination are generally functionally associated or related.

As used herein, a derivative refers to a form of a drug that has undergone change or modification from a reference drug or agent, but still retains activity (e.g., exhibits increased or decreased activity) compared to the reference drug or agent. Typically, a derivative form of a compound means that a side chain of the compound has been modified or changed.

As used herein, an analogue or analog of a drug or agent is a drug or agent that is related to a reference drug, but whose chemical and biological activities can be different. Typically, analogues exhibit similar activities to a reference drug or agent, but the activity can be increased or decreased or otherwise improved. Typically, an analogue form of a compound or drug means that the backbone core of the structure is modified or changed compared to a reference drug.

As used herein, a kit is a packaged combination that optionally includes other elements, such as additional reagents and instructions for use of the combination or elements thereof.

The term “package insert” is used to refer to instructions customarily included in commercial packages of therapeutic products, that contain information about the indications, usage, dosage, administration, combination therapy, contraindications and/or warnings concerning the use of such therapeutic products.

As used herein, an "article of manufacture" is a product that is made and, in some cases, that can be sold. In some embodiments, the term can refer to compositions contained in articles of packaging, such as in a container.

As used herein, "combination therapy" refers to a treatment in which a subject is given two or more therapeutic agents, such as at least two or at least three therapeutic agents, for treating a single disease. In some embodiments, each therapy can result in an independent pharmaceutical effect, and together can result in an additive or synergistic pharmaceutical effect. In particular aspects, "combination therapy" refers to a treatment in which the subject is given photoimmunotherapy (PIT), in combination with an additional therapeutic agent, such as an immune modulating agent or an anti-cancer agent. In some aspects, as used herein, "combination therapy" refers to administration of a targeting molecule-phthalocyanine dye conjugate and light treatment, in combination with an additional therapeutic agent, such as an immune modulating agent.

As used herein, "disease or disorder" refers to a pathological condition in an organism resulting from cause or condition including, but not limited to, infections, acquired conditions, genetic conditions, and characterized by identifiable symptoms.

As used herein, "treating" a subject with a disease or condition means that the subject's symptoms are partially or totally alleviated, or remain static, following treatment. Hence treating encompasses prophylaxis, therapy and/or cure. Prophylaxis refers to prevention of a potential disease and/or a prevention of worsening of symptoms or progression of a disease.

As used herein, "treatment" means any manner in which the symptoms of a condition, disorder or disease or other indication, are ameliorated or otherwise beneficially altered.

As used herein, "therapeutic effect" means an effect resulting from treatment of a subject that alters, typically improves or ameliorates the symptoms of a disease or condition or that cures a disease or condition.

As used herein, a "therapeutically effective amount" or a "therapeutically effective dose" refers to the quantity of an agent, compound, material, or composition containing a compound that is at least sufficient to produce a therapeutic effect. Hence, it is the quantity necessary for preventing, curing, ameliorating, arresting or partially arresting a symptom of a disease or disorder.

As used herein, amelioration of the symptoms of a particular disease or disorder by a treatment, such as by administration of a pharmaceutical composition or other therapeutic, refers to any lessening, whether permanent or temporary, lasting or transient, of the symptoms that can be attributed to or associated with administration of the composition or therapeutic.

As used herein, the term "subject" refers to an animal, including a mammal, such as a human being.

As used herein, "optional" or "optionally" means that the subsequently described event or circumstance does or does not occur, and that the description includes instances where said event or circumstance occurs and instances where it does not. For example, an optionally substituted group means that the group is unsubstituted or is substituted.

All publications, including patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The section headings used herein are for organizational purposes only and are not to be construed as limiting the subject matter described.

VI. EXEMPLARY EMBODIMENTS

Among the provided embodiments are:

1. A method of treating a tumor in a subject, the method comprising:

a) administering to a subject having a tumor a conjugate comprising a phthalocyanine dye linked to a targeting molecule that binds to a protein on the surface of a cell present in the microenvironment of the tumor;

b) measuring in a sample from the subject the level of expression of at least one biomarker(s);

c) irradiating an area proximal to a tumor at a wavelength of 500 nm to 900 nm at a dose of at least 1 J $cm^{-2}$ or 1 J/cm of fiber length;

d) measuring the level of expression of the at least one biomarker(s) after the irradiation and determining whether the level of the at least biomarker is increased in the subject relative to the level measured prior to the irradiation; and e) if the level is increased, administering an immune modulating agent to the subject, thereby treating the tumor.

2. A method of improving the efficacy of a tumor treatment, the method comprising:

a) measuring in sample from a subject having a tumor the level of expression of at least one biomarker(s) and determining whether the level of expression of the at least one biomarker(s) is at or above a threshold;

b) administering to the subject a conjugate comprising a phthalocyanine dye linked to a targeting molecule that binds to a protein on the surface of a cell present in the microenvironment of the tumor;

c) irradiating an area proximal to a tumor at a wavelength of 500 nm to 900 nm at a dose of at least 1 J $cm^{-2}$ or 1 J/cm of fiber length; and d) if the level of expression of the at least one biomarker(s) is at or above the threshold, further administering an immune modulating agent to the subject; thereby improving the efficacy of the tumor treatment.

3. A method of improving the efficacy of a tumor treatment, the method comprising:

a) measuring in sample from a subject having a tumor the level of expression of at least one biomarker(s) and determining whether the level of expression of the at least one biomarker(s) is at or below a threshold;

b) administering to the subject a conjugate comprising a phthalocyanine dye linked to a targeting molecule that binds to a protein on the surface of a cell present in the microenvironment of the tumor;

c) irradiating an area proximal to a tumor at a wavelength of 500 nm to 900 nm at a dose of at least 1 J $cm^{-2}$ or 1 J/cm of fiber length; and d) if the level of expression of the at least one biomarker(s) is at or below the threshold, further administering an immune modulating agent to the subject; thereby improving the efficacy of the tumor treatment.

4. A method of improving the efficacy of a tumor treatment, the method comprising:

a) measuring in sample from a subject having a tumor the level of expression of at least one checkpoint pathway marker(s) and determining whether the level of expression of the at least one checkpoint pathway marker(s) is at or above a threshold;

b) administering to the subject a conjugate comprising a phthalocyanine dye linked to a targeting molecule that binds to a protein on the surface of a cell present in the microenvironment of the tumor;

c) irradiating an area proximal to a tumor at a wavelength of 500 nm to 900 nm at a dose of at least 1 J $cm^{-2}$ or 1 J/cm of fiber length; and d) if the level of expression of the at least one checkpoint pathway marker(s) is at or above the threshold, further administering checkpoint inhibitor to the subject; thereby improving the efficacy of the tumor treatment.

5. A method of treating subjects having a high likelihood of response within a population of subjects having a tumor comprising:

a) measuring in a sample from each of the subjects in the population the level of expression of at least one biomarker(s);

b) identifying the subject as having a high likelihood of response if the expression of the at least one biomarker(s) is at or above a threshold;

c) administering to the subjects identified as having a high likelihood of response a conjugate comprising a phthalocyanine dye linked to a targeting molecule that binds to a protein on the surface of a cell present in the microenvironment of the tumor; and d) irradiating an area proximal to a tumor at a wavelength of 500 nm to 900 nm at a dose of at least 1 J $cm^{-2}$ or 1 J/cm of fiber length, thereby treating the tumor in the subjects identified as having a high likelihood of response.

6. The method of embodiment 5, further comprising:

e) measuring in a sample from the subject the level of expression of the at least one biomarker(s) after the irradiation and determining whether the level of the at least one at least one biomarker(s) is increased in the subject compared to the level measured prior to the irradiation; and f) if the level is increased, administering an immune modulating agent to the subject.

7. A method of treating a tumor in a subject, the method comprising:

a) measuring in a sample from each of the subjects in the population the level of expression of at least one biomarker(s);

b) selecting the subject for treatment if the expression of the at least one biomarker(s) is at or above a threshold;

c) administering to the selected subject a conjugate comprising a phthalocyanine dye linked to a targeting molecule that binds to a protein on the surface of a cell present in the microenvironment of the tumor; and d) irradiating an area proximal to a tumor at a wavelength of 500 nm to 900 nm at a dose of at least 1 J $cm^{-2}$ or 1 J/cm of fiber length, thereby treating the tumor.

8. The method of embodiment 7, further comprising:

e) measuring in a sample from the subject the level of expression of the at least one biomarker(s) after the irradiation and determining whether the level of the at least one at least one biomarker(s) is increased in the subject compared to the level measured prior to the irradiation; and f) if the level is increased, administering an immune modulating agent to the subject.

9. The method of embodiment 7, further comprising:

e) measuring in a sample from the subject the level of expression of the at least one biomarker(s) after the irradiation and determining whether the level of the at least one at least one biomarker(s) is increased in the subject compared to the level measured prior to the irradiation; and f) if the level is decreased, administering an immune modulating agent to the subject.

10. A method of increasing expression of at least one biomarker(s) in a subject having a tumor, the method comprising:

a) administering to a subject having a tumor, a conjugate comprising a phthalocyanine dye linked to a targeting molecule that binds to a protein on the surface of a cell present in the microenvironment of the tumor; and b) after administering the conjugate, irradiating an area proximal to a tumor at a wavelength of 500 nm to 900 nm at a dose of at least 1 J $cm^{-2}$ or 1 J/cm of fiber length;

thereby increasing the expression of the at least one biomarker(s) compared to the expression of the at least one biomarker(s) without the irradiation.

11. A method of selecting subjects for treatment with an immune modulating agent, the method comprising:

a) administering to a subject a conjugate comprising a phthalocyanine dye linked to a targeting molecule capable of binding to a molecule on the surface of a cell present in the microenvironment of the tumor;

b) irradiating an area proximal to a tumor at a wavelength of 500 nm to 900 nm at a dose of at least 1 J $cm^{-2}$ or 1 J/cm of fiber length;

c) measuring the level of expression of at least one biomarker(s) in a sample from a subject; and d) if the level of expression of the at least one biomarker(s) is at or above a threshold level, selecting the subject for treatment with an immune modulating agent.

12. The method of embodiment 11, further comprising administering to the selected subject a therapeutically effective amount of the immune modulating agent.

13. A method of selecting subjects for treatment with a conjugate comprising a phthalocyanine dye linked to a targeting molecule, the method comprising:

a) measuring the level of expression of at least one biomarker(s) in a sample from a subject; and b) if the level of expression of the at least one biomarker(s) is at or above a threshold level, selecting the subject for treatment with a conjugate comprising a phthalocyanine dye linked to a targeting molecule capable of binding to a molecule on the surface of a cell present in the microenvironment of the tumor.

14. A method of assessing the likelihood of response to treatment with a conjugate comprising a phthalocyanine dye linked to a targeting molecule, the method comprising:

a) measuring the level of expression of at least one biomarker(s) in a sample from a subject; and b) identifying the subject as having a high likelihood of response to treatment with a conjugate comprising a phthalocyanine dye linked to a targeting molecule capable of binding to a molecule on the surface of a cell present in the microenvironment of the tumor if the level of expression of the at least one biomarker(s) is at or above a threshold level.

15. A method of selecting subjects for treatment with a conjugate comprising a phthalocyanine dye linked to a targeting molecule, the method comprising:

a) measuring the level of expression of at least one biomarker(s) in a sample from a subject; and b) selecting the subject for treatment with a conjugate comprising a phthalocyanine dye linked to a targeting molecule capable of binding to a molecule on the surface of a cell present in the microenvironment of the tumor and an immune modulating agent if the level of expression of the at least one biomarker(s) is at or below a threshold level.

16. A method of assessing the likelihood of response to treatment with a conjugate comprising a phthalocyanine dye linked to a targeting molecule, the method comprising:

a) measuring the level of expression of at least one biomarker(s) in a sample from a subject; and b) identifying the subject as having a low likelihood of response to treatment with a conjugate comprising a phthalocyanine dye linked to a targeting molecule capable of binding to a molecule on the surface of a cell present in the microenvironment of the tumor if the level of expression of the at least one biomarker(s) is at or below a threshold level.

17. The method of any of embodiments 13-16, further comprising administering to the selected subject a therapeutically effective amount of the conjugate.

18. The method of embodiment 17, further comprising irradiating an area proximal to a tumor at a wavelength of 500 nm to 900 nm at a dose of at least 1 J $cm^{-2}$ or 1 J/cm of fiber length.

19. The method of any of embodiments 16-18, wherein if the subject is identified as having a low likelihood of response, further administering to the subject a therapeutically effective amount of an immune modulating agent.

20. A method of monitoring a response to treatment with a conjugate comprising a phthalocyanine dye linked to a targeting molecule, the method comprising:

a) administering to a subject a conjugate comprising a phthalocyanine dye linked to a targeting molecule capable of binding to a molecule on the surface of a cell present in the microenvironment of the tumor;

b) irradiating an area proximal to a tumor at a wavelength of 500 nm to 900 nm at a dose of at least 1 J $cm^{-2}$ or 1 J/cm of fiber length; and c) measuring the level of expression of at least one biomarker(s) in a sample from a subject; wherein the subject is identified as having a high likelihood of response if the level of expression of the at least one biomarker(s) is at or above a threshold level.

21. A method of monitoring a response to treatment with a conjugate comprising a phthalocyanine dye linked to a targeting molecule, the method comprising:

a) administering to a subject a conjugate comprising a phthalocyanine dye linked to a targeting molecule capable of binding to a molecule on the surface of a cell present in the microenvironment of the tumor;

b) irradiating an area proximal to a tumor at a wavelength of 500 nm to 900 nm at a dose of at least 1 J $cm^{-2}$ or 1 J/cm of fiber length; and c) measuring the level of expression of at least one biomarker(s) in a sample from a subject; wherein the subject is identified as having a high likelihood of response if the level of expression of the at least one biomarker(s) is at or below a threshold level.

22. A method of treating a tumor in a subject, the method comprising:

a) administering to a subject a conjugate comprising a phthalocyanine dye linked to a targeting molecule capable of binding to a molecule on the surface of a cell present in the microenvironment of the tumor;

b) irradiating an area proximal to a tumor at a wavelength of 500 nm to 900 nm at a dose of at least 1 J $cm^{-2}$ or 1 J/cm of fiber length, wherein the treatment of the tumor with the conjugate followed by light irradiation primes activation of immune cells;

c) measuring the level of expression of at least one biomarker(s) in a sample from a subject;

d) if the level of expression of the at least one biomarker is at or above a threshold level, administering to the subject a therapeutically effective amount of an immune modulating agent; thereby treating the tumor.

23. A method of treating a tumor in a subject, the method comprising:

a) administering to a subject a conjugate comprising a phthalocyanine dye linked to a targeting molecule capable of binding to a molecule on the surface of a cell present in the microenvironment of the tumor;

b) irradiating an area proximal to a tumor at a wavelength of 500 nm to 900 nm at a dose of at least 1 J $cm^{-2}$ or 1 J/cm of fiber length, wherein the treatment of the tumor with the conjugate followed by light irradiation primes activation of immune cells;

c) measuring the level of expression of at least one biomarker(s) in a sample from a subject;

d) if the level of expression of the at least one biomarker is below a threshold level, administering to the subject one or more additional doses of the conjugate and irradiating the area proximal to the tumor; thereby treating the tumor.

24. The method of any of embodiments 1-3, 6, 8, 9, 12, 15, 19 and 22, wherein the method provides a synergistic treatment effect compared to treatment by the conjugate alone or the immune modulating agent alone.

25. The method of embodiment 4, wherein the method provides a synergistic treatment effect compared to treatment by the conjugate alone or the checkpoint inhibitor alone.

26. The method of any of embodiments 1-12 and 18-25, wherein the administration of the conjugate followed by irradiation primes activation of immune cells.

27. The method of any of embodiments 1-3 and 5-26, wherein the at least one biomarker(s) comprises a cell surface marker.

28. The method of any of embodiments 1-3 and 5-27, wherein the cell surface marker is an immune cell surface marker.

29. The method of embodiment 27 or embodiment 28, wherein the cell surface marker is an antigen presenting cell marker.

30. The method of any of embodiments 27-29, wherein the cell surface marker is a dendritic cell marker.

31. The method of any of embodiments 27-30, wherein the cell surface marker is selected from among one or more of CD86, CD80 or MHCII.

32. The method of any of embodiments 27-29, wherein the cell surface marker is a macrophage marker.

33. The method of embodiment 27 or embodiment 28, wherein the cell surface marker is a natural killer cell marker.
34. The method of any of embodiments 27, 28 and 33, wherein the cell surface marker is selected from among one or more of CD69 or CD107a.
35. The method of embodiment 27, wherein the cell surface marker is a checkpoint pathway marker.
36. The method of embodiment 27 or embodiment 35, wherein the cell surface marker is selected from among one or more of PD-1, PD-L1 or CTLA-4.
37. The method of embodiment 27, wherein the cell surface marker is an immunogenic cell death marker.
38. The method of embodiment 27 or embodiment 37, wherein the cell surface marker is selected from among one or more of heat shock protein 70 (Hsp70), Hsp90 and calreticulin (CRT).
39. The method of any of embodiments 1-3 and 5-26, wherein the at least one biomarker(s) comprises a soluble marker or a serum marker.
40. The method of embodiment 39, wherein the soluble marker is a cytokine or a chemokine.
41. The method of embodiment 40, wherein the cytokine or the chemokine is selected from among one or more of tumor necrosis factor alpha (TNF-α), IFN-γ-Inducible Protein 10 (IP-10)/CXCL10, MIP-1α (Macrophage Inflammatory Protein-1 alpha)/CCL3, MIP-1β (Macrophage Inflammatory Protein-1 beta)/CCL4, interleukin-1 beta (IL-1β), interleukin-8 (IL-8)/CXCL8, 6CKine, BCA-1, CTACK, EGF, ENA-78, Eotaxin/CCL11, Eotaxin-2, Eotaxin-3, FGF-2, Flt-3 ligand, Fractalkine, G-CSF, GM-CSF, GRO, GRO alpha/CXCL1, 1-309, ICAM-1/CD54, IFN alpha (IFN-α), IFN gamma (IFN-γ), IFN-α2, IFN-γ, IL-1 alpha (IL-1α), IL-10, IL-12 p40, IL-12p70, IL-13, IL-15, IL-16, IL-17A, IL-17A/CTLA-8, IL-18, IL-2, IL-20, IL-21, IL-22, IL-23, IL-27, IL-28A, IL-3, IL-31, IL-33, IL-4, IL-5, IL-6, IL-7, IL-9, interleukin-1 receptor antagonist (IL-1ra), IP-10, LIF, MCP-1, MCP-1/CCL2, MCP-2, MCP-3, MCP-4, MDC (CCL22), MIP-1d, PDGF-AA, PDGF-AB/BB, RANTES/CCL5, sCD40L, SCF, SDF-1α/CXCL12, SDF-1a+B, sE-Selectin, sP-Selectin, TARC, TGFα, tumor necrosis factor beta (TNF-β)/LTA, TPO, TRAIL, TSLP or VEGF.
42. The method of embodiment 40 or embodiment 41, wherein the cytokine or the chemokine is selected from among one or more of tumor necrosis factor alpha (TNF-α), IFN-γ-Inducible Protein 10 (IP-10)/CXCL10, MIP-1α (Macrophage Inflammatory Protein-1 alpha)/CCL3, MIP-1β (Macrophage Inflammatory Protein-1 beta)/CCL4, interleukin-1 beta (IL-1β), interleukin-8 (IL-8)/CXCL8, Eotaxin/CCL11, GRO alpha/CXCL1, GM-CSF, IFN alpha (IFN-α), IFN gamma (IFN-γ), IL-1 alpha (IL-1α), interleukin-1 receptor antagonist (IL-1ra), IL-2, IL-4, IL-5, IL-6, IL-7, IL-9, IL-10, IL-12p70, IL-13, IL-15, IL-17A/CTLA-8, IL-18, IL-21, IL-22, IL-23, IL-27, IL-31, MCP-1/CCL2, RANTES/CCL5, SDF-1α/CXCL12, and tumor necrosis factor beta (TNF-β)/LTA.
43. The method of any of embodiments 40-42, wherein the cytokine or the chemokine is selected from among one or more of tumor necrosis factor alpha (TNF-α), IFN-γ-Inducible Protein 10 (IP-10), MIP-1α (Macrophage Inflammatory Protein-1 alpha), MIP-1β (Macrophage Inflammatory Protein-1 beta), interleukin-1 beta (IL-1β) and interleukin-8 (IL-8)/CXCL8.
44. The method of embodiment 39, wherein the soluble marker is a danger associated molecular patterns (DAMPs) marker.
45. The method of embodiment 44, wherein the DAMPs marker is high-mobility group-box protein (HMGB1).
46. The method of any of embodiments 1-45, wherein the at least biomarker(s) is 2, 3, 4, 5, 6, 7 or more biomarkers.
47. The method of embodiment 46, wherein the at least biomarker(s) is 2 biomarkers.
48. The method of embodiment 46, wherein the at least biomarker(s) is 3 biomarkers.
49. The method of embodiment 46, wherein the at least biomarker(s) is 4 biomarkers.
50. The method of embodiment 46, wherein the at least biomarker(s) is 5 biomarkers.
51. The method of any of embodiments 1-50, wherein the sample is a tumor sample and/or the sample comprises or is likely to comprise tumor cells.
52. The method of any of embodiments 1-51, wherein the sample comprises a tumor biopsy.
53. The method of any of embodiments 1-52, wherein the sample is or comprises a blood sample, a plasma sample, a serum sample, a lymph node sample, a bone marrow sample, a buccal swab, a fecal sample or a urine sample.
54. The method of any of embodiments 1-12 and 18-53, wherein the irradiation is at a wavelength of 600 nm to 850 nm at a dose of from at or about 25 J $cm^{-2}$ to at or about 400 J $cm^{-2}$ or from at or about 25 J/cm of fiber length to at or about 500 J/cm of fiber length.
55. The method of any of embodiments 1-12 and 18-54, wherein the irradiation is at a wavelength of at or about 660 nm to at or about 740 nm.
56. The method of any of embodiments 1-12 and 18-54, wherein the irradiation is at a wavelength of at or about 690±50 nm or at a wavelength of at or about 690±20 nm.
57. The method of any of embodiments 1-12 and 18-56, wherein the irradiation is at a dose of at or about 2 J $cm^{-2}$ to at or about 400 J $cm^{-2}$ or from at or about 2 J/cm fiber length to at or about 500 J/cm fiber length.
58. The method of any of embodiments 1-12 and 18-57, wherein: the irradiation is at a dose of at least at or about 2 J $cm^{-2}$, 5 J $cm^{-2}$, 10 J $cm^{-2}$, 25 J $cm^{-2}$, 50 J $cm^{-2}$, 75 J $cm^{-2}$, 100 J $cm^{-2}$, 150 J $cm^{-2}$, 200 J $cm^{-2}$, 300 J $cm^{-2}$, 400 J $cm^{-2}$, or 500 J $cm^{-2}$; or the irradiation is at a dose of at least at or about 2 J/cm fiber length, 5 J/cm fiber length, 10 J/cm fiber length, 25 J/cm fiber length, 50 J/cm fiber length, 75 J/cm fiber length, 100 J/cm fiber length, 150 J/cm fiber length, 200 J/cm fiber length, 250 J/cm fiber length, 300 J/cm fiber length, 400 J/cm fiber length or 500 J/cm fiber length.
59. The method of any of embodiments 1-58, wherein the phthalocyanine dye has a maximum absorption wavelength from at or about 600 nm to at or about 850 nm.
60. The method of any of embodiments 1-59, wherein the phthalocyanine dye is linked directly or indirectly to the targeting molecule.
61. The method of any of embodiments 1-60, wherein the phthalocyanine dye comprises the formula:

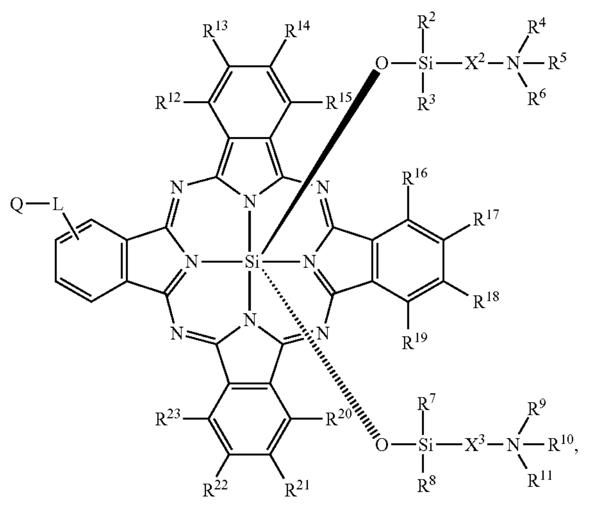

wherein:

L is a linker;

Q is a reactive group for attachment of the dye to the targeting molecule;

$R^2$, $R^3$, $R^7$, and $R^8$ are each independently selected from optionally substituted alkyl and optionally substituted aryl;

$R^4$, $R^5$, $R^6$, $R^9$, $R^{10}$, and $R^{11}$ are each independently selected from hydrogen, optionally substituted alkyl, optionally substituted alkanoyl, optionally substituted alkoxycarbonyl, optionally substituted alkylcarbamoyl, and a chelating ligand, wherein at least one of $R^4$, $R^5$, $R^6$, $R^9$, $R^{10}$, and $R^{11}$ comprises a water soluble group;

$R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ are each independently selected from hydrogen, halogen, optionally substituted alkylthio, optionally substituted alkylamino and optionally substituted alkoxy; and $X^2$ and $X^3$ are each independently $C_1$-$C_{10}$ alkylene, optionally interrupted by a heteroatom.

62. The method of any of embodiments 1-60, wherein the phthalocyanine dye comprises the formula:

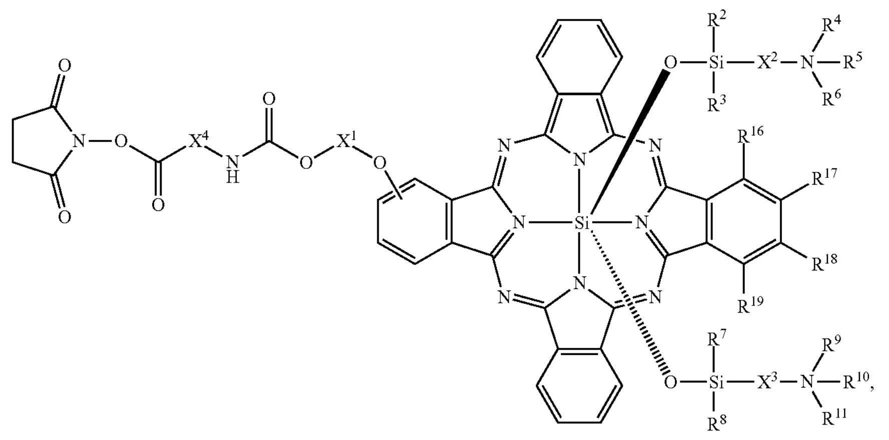

wherein:

$X^1$ and $X^4$ are each independently a $C_1$-$C_{10}$ alkylene optionally interrupted by a heteroatom;

$R^2$, $R^3$, $R^7$, and $R^8$ are each independently selected from optionally substituted alkyl and optionally substituted aryl;

$R^4$, $R^5$, $R^6$, $R^9$, $R^{10}$, and $R^{11}$ are each independently selected from hydrogen, optionally substituted alkyl, optionally substituted alkanoyl, optionally substituted alkoxycarbonyl, optionally substituted alkylcarbamoyl, and a chelating ligand, wherein at least one of $R^4$, $R^5$, $R^6$, $R^9$, $R^{10}$, and $R^{11}$ comprises a water soluble group; and $R^{16}$, $R^{17}$, $R^{18}$ and, $R^{19}$ are each independently selected from hydrogen, halogen, optionally substituted alkylthio, optionally substituted alkylamino and optionally substituted alkoxy.

63. The method of any of embodiments 1-62, wherein the phthalocyanine dye comprises IRDye 700DX (IR700).

64. The method of any of embodiments 1-63, wherein the targeting molecule is an antibody or an antigen-binding antibody fragment.

65. The method of embodiment 64, wherein the antibody is an antigen-binding antibody fragment that is a Fab, single $V_H$ domain, a single chain variable fragment (scFv), a multivalent scFv, a bispecific scFv or an scFv-$C_H3$ dimer.

66. The method of any of embodiments 1-65, wherein the targeting molecule binds to a protein selected from among HER1/EGFR, HER2/ERBB2, CD20, CD25 (IL-2Ra receptor), CD33, CD52, CD133, CD206, CEA, CEACAM1, CEACAM3, CEACAM5, CEACAM6, cancer antigen 125 (CA125), alpha-fetoprotein (AFP), Lewis Y, TAG72, Caprin-1, mesothelin, PDGF receptor, PD-1, PD-L1, CTLA-4, IL-2 receptor, vascular endothelial growth factor (VEGF), CD30, EpCAM, EphA2, Glypican-3, gpA33, mucins, CAIX, PSMA, folate-binding protein, gangliosides (such as GD2, GD3, GM1 and GM2), VEGF receptor (VEGFR), integrin αVβ3, integrin α5β1, ERBB3, MET, IGF1R, EPHA3, TRAILR1, TRAILR2, RANKL, FAP, tenascin, AFP, BCR complex, CD3, CD18, CD44, CTLA-4, gp72, HLA-DR 10 β, HLA-DR antigen, IgE, MUC-1, nuC242, PEM antigen, metalloproteinases, Ephrin receptor, Ephrin ligands, HGF receptor, CXCR4, CXCR4, Bombesin receptor, and SK-1 antigen.

67. The method of any of embodiments 1-66, wherein the targeting molecule binds to a protein selected from among CD25, PD-1 (CD279), PD-L1 (CD274, B7-H1), PD-L2 (CD273, B7-DC), CTLA-4, LAG3 (CD223), TIM3 (HAVCR2), 4-1BB (CD137, TNFRSF9), CXCR2, CXCR4 (CD184), CD27, CEACAM1, Galectin 9, BTLA, CD160, VISTA (PD1 homologue), B7-H4 (VCTN1), CD80 (B7-1), CD86 (B7-2), CD28, HHLA2 (B7-H7), CD28H, CD155, CD226, TIGIT, CD96, Galectin 3, CD40, CD40L, CD70, LIGHT (TNFSF14), HVEM (TNFRSF14), B7-H3 (CD276), Ox40L (TNFSF4), CD137L (TNFSF9, GITRL), B7RP1, ICOS (CD278), ICOSL, KIR, GALS, NKG2A (CD94), GARP, TL1A, TNFRSF25, TMIGD2, BTNL2, Butyrophilin family, CD48, CD244, Siglec family, CD30, CSF1R, MICA (MHC class I polypeptide-related sequence A), MICB (MHC class I polypeptide-related sequence B), NKG2D, KIR family (Killer-cell immunoglobulin-like receptor, LILR family (Leukocyte immunoglobulin-like receptors, CD85, ILTs, LIRs), SIRPA (Signal regulatory protein alpha), CD47 (IAP), Neuropilin 1 (NRP-1), a VEGFR, and VEGF.
68. The method of any of embodiments 64-67, wherein the antibody or an antigen-binding antibody fragment is selected from among cetuximab, panitumumab, zalutumumab, nimotuzumab, Tositumomab (Bexxar®), Rituximab (Rituxan, MabThera), Ibritumomab tiuxetan (Zevalin), Daclizumab (Zenapax), Gemtuzumab (Mylotarg), Alemtuzumab, CEA-scan Fab fragment, OC125 monoclonal antibody, ab75705, B72.3, Bevacizumab (Avastin®), Basiliximab, nivolumab, pembrolizumab, pidilizumab, MK-3475, BMS-936559, MPDL3280A, ipilimumab, tremelimumab, IMP321, BMS-986016, LAG525, urelumab, PF-05082566, TRX518, MK-4166, dacetuzumab, lucatumumab, SEA-CD40, CP-870, CP-893, MED16469, MEDI6383, MEDI4736, MOXR0916, AMP-224, PDR001, MSB0010718C, rHIgM12B7, Ulocuplumab, BKT140, Varlilumab (CDX-1127), ARGX-110, MGA271, lirilumab (BMS-986015, IPH2101), IPH2201, AGX-115, Emactuzumab, CC-90002 and MNRP1685A or is an antigen-binding antibody fragment thereof.
69. The method of any of embodiments 1-68, wherein the conjugate is selected from among cetuximab-IR700, panitumumab-IR700, zalutumumab-IR700, nimotuzumab-IR700, Tositumomab-IR700, Rituximab-IR700, Ibritumomab tiuxetan-IR700, Daclizumab-IR700, Gemtuzumab-IR700, Alemtuzumab-IR700, CEA-scan Fab fragment-IR700, OC125-IR700, ab75705-IR700, B72.3-IR700, Bevacizumab-IR700, Basiliximab-IR700, nivolumab-IR700, pembrolizumab-IR700, pidilizumab-IR700, MK-3475-IR700, BMS-936559-IR700, MPDL3280A-IR700, ipilimumab-IR700, tremelimumab-IR700, IMP321-IR700, BMS-986016-IR700, LAG525-IR700, urelumab-IR700, PF-05082566-IR700, TRX518-IR700, MK-4166-IR700, dacetuzumab-IR700, lucatumumab-IR700, SEA-CD40-IR700, CP-870-IR700, CP-893-IR700, MED16469-IR700, MED16383-IR700, MED14736-IR700, MOXR0916-IR700, AMP-224-IR700, PDR001-IR700, MSB0010718C-IR700, rHIgM12B7-IR700, Ulocuplumab-IR700, BKT140-IR700, Varlilumab-IR700, ARGX-110-IR700, MGA271-IR700, lirilumab-IR700, IPH2201-IR700, AGX-115-IR700, Emactuzumab-IR700, CC-90002-IR700 and MNRP1685A-IR700.
70. The method of embodiment 69, wherein the targeting molecule is an antibody that is cetuximab or is an antigen-binding antibody fragment thereof or the conjugate is cetuximab-IR700.
71. The method of any of embodiments 1-70, wherein the conjugate is administered systemically.
72. The method of any of embodiments 1-70, wherein the conjugate is administered intravenously.
73. The method of any of embodiments 1-12 and 18-72, wherein the irradiation is carried out 24 hours±3 hours after administering the conjugate.
74. The method of any of embodiments 1-73, wherein the tumor is a superficial tumor.
75. The method of embodiment 74, wherein the tumor is less than 10 mm thick.
76. The method of embodiment 74 or embodiment 75, wherein the irradiation is carried out using a microlens-tipped fiber for surface illumination.
77. The method of any of embodiments 74-76, wherein the irradiation dose is from or from about 5 $J/cm^{-2}$ to about 200 $J/cm^{-2}$.
78. The method of any of embodiments 1-73, wherein the lesion is a tumor that is an interstitial tumor.
79. The method of embodiment 78, wherein the tumor is greater than 10 mm deep or is a subcutaneous tumor.
80. The method of embodiment 78 or embodiment 79, wherein the irradiation is carried out using cylindrical diffusing fibers comprising a diffuser length of 0.5 cm to 10 cm and spaced 1.8±0.2 cm apart.
81. The method of any of embodiments 78-80, wherein the light irradiation dose is from or from about 20 J/cm fiber length to about 500 J/cm fiber length.
82. The method of any of embodiments 1-3 and 5-81, wherein the immune modulating agent is capable of increasing the activity of the immune cell.
83. The method of any of embodiments 1-3 and 5-82, wherein the immune modulating agent is selected from among GM-CSF, CpG-ODN (CpG oligodeoxynucleotides), lipopolysaccharide (LPS), monophosphoryl lipid A (MPL), alum, recombinant Leishmania polyprotein, imiquimod, MF59, poly I:C, poly A:U, type 1 IFN, Pam3Cys, Pam2Cys, complete freund's adjuvant (CFA), alpha-galactosylceramide, RC-529, MDF2β, Loxoribine, anti-CD40 agonist, SIRPa antagonist, AS04, AS03, Flagellin, Resiquimod, DAP (diaminopimelic acid), MDP (muramyl dipeptide) CAF01 (cationic adjuvant formulation-01), anthracyclines (doxorubicin, mitoxantrone), BK channel agonists, bortezomib, bortezomib plus mitomycin C plus hTERT-Ad, Cardiac glycosides plus non-Immunogenic cell death inducers, cyclophosphamide, GADD34/PP1 inhibitors plus mitomycin, LV-tSMAC, and oxaliplatin.
84. The method of any of embodiments 1-3 and 5-84, wherein the immune modulating agent is a Toll-like receptor (TLR) agonist, an adjuvant or a cytokine or a chemokine.
85. The method of embodiment 84, wherein the immune modulating agent is a TLR agonist and the TLR agonist is TLR agonist is a TLR4 agonist, a TLR7 agonist, a TLR8 agonist, or a TLR9 agonist.
86. The method of embodiment 84 or embodiment 85, wherein the TLR agonist is selected from among triacylated lipoprotein, diacylated lipopeptide, lipoteichoic acid, peptidoglycan, zymosan, Pam3CSK4, dsRNA, poly(I:C), Poly G10, Poly G3, CpG, 3M003, flagellin, lipopolysaccharide (LPS) Leishmania homolog of eukaryotic ribosomal elongation and initiation factor 4a (LeIF), MEDI9197, SD-101, and imidazoquinoline TLR agonists.

87. The method of any of embodiments 1-3 and 5-81, wherein the immune modulating agent is a cytokine and the cytokine is IL-4, TNF-α, GM-CSF or IL-2.

88. The method of 1-3 and 5-81, wherein the immune modulating agent is an immune checkpoint inhibitor.

89. The method of any of embodiments 1-81 and 88, wherein the immune modulating agent comprises an antibody or antigen binding fragment thereof that specifically binds a molecule selected from among CD25, PD-1, PD-L1, PD-L2, CTLA-4, LAG-3, TIM-3, 4-1BB, GITR, CD40, CD40L, OX40, OX40L, CXCR2, B7-H3, B7-H4, BTLA, HVEM, CD28 and VISTA.

90. The method of any of embodiments 1-81, 88 and 89, wherein the immune modulating agent is selected from among nivolumab, pembrolizumab, pidilizumab, MK-3475, BMS-936559, MPDL3280A, ipilimumab, tremelimumab, IMP31, BMS-986016, urelumab, TRX518, dacetuzumab, lucatumumab, SEQ-CD40, CP-870, CP-893, MED16469, MED14736, MOXR0916, AMP-224, and MSB001078C, or is an antigen-binding fragment thereof of any of the foregoing.

91. The method of any of embodiments 1-81 and 88-90, wherein the immune modulating agent is an antibody or antibody fragment that binds to PD-L1.

92. The method of any of embodiments 1-81 and 88-91, wherein the immune modulating agent is an antibody selected from BMS-935559, MEDI4736, MPDL3280A and MSB0010718C, or an antigen-binding fragment thereof.

93. The method of any of embodiments 1-81 and 88-90, wherein the immune modulating agent is an antibody or antibody fragment that binds to PD-1.

93. The method of any of embodiments 1-81, 88-91 and 93, wherein the immune modulating agent is an antibody selected from nivolumab, pembrolizumab, pidilizumab, lambrolizumab or AMP-224, or an antigen-binding fragment thereof.

94. The method of any of embodiments 88-93, wherein the immune modulating agent further comprises a second phthalocyanine dye.

95. The method of embodiment 94, wherein the second phthalocyanine dye comprises IRDye 700DX (IR700).

96. The method of any of embodiments 1-3 and 5-95, wherein the immune modulating agent is administered greater than or greater than about 30 minutes, 1 hour, 2 hours, 6 hours, 12 hours, 24 hours, 48 hours, 96 hours, one week, two weeks, three weeks or one month prior to irradiating the area proximal to the tumor.

97. The method of any of embodiments 1-3 and 5-96, wherein the method comprises continued administration of the immune modulating agent subsequent to the irradiation three times a week, two times a week, once every week, once every two weeks, once every three weeks or once a month.

98. The method of any of embodiments 1-12 and 18-97, wherein the irradiation is carried out either i) after administration of the immune modulating agent and after administration of the conjugate or ii) only after administration of the conjugate.

99. The method of any of embodiments 1-3 and 5-98, wherein the conjugate is administered prior to, simultaneously or subsequently to administration of the immune modulating agent.

100. The method of any of embodiments 1-3 and 5-99, wherein the immune modulating agent is administered after the irradiation.

101. The method of any of embodiments 1-3 and 5-99, wherein the conjugate is administered from or from about 12 hours to 48 hours prior to the irradiation and the immune modulating agent is administered from or from about 12 hours to about 1 month after irradiating the tumor.

102. The method of any of embodiments 1-3 and 5-99, wherein the conjugate is administered after administering the immune modulating agent but prior to the irradiation.

103. The method of any of embodiments 1-3, 5-99 and 102, wherein the conjugate is administered from or from about 12 hours to 48 hours prior to the irradiation and the immune modulating agent is administered from or from about 12 hours to about 1 month prior to irradiating the tumor.

104. The method of any of embodiments 1-103, wherein the tumor is a cancer.

105. The method of embodiment 104, wherein the cancer is a cancer located at the head and neck, breast, liver, colon, ovary, prostate, pancreas, brain, cervix, bone, skin, eye, bladder, stomach, esophagus, peritoneum, or lung.

106. The method of any of embodiments 1-105, wherein the tumor is a sarcoma or carcinoma.

107. The method of any of embodiments 1-106, wherein the tumor is a carcinoma that is a squamous cell carcinoma, basal cell carcinoma or adenocarcinoma.

108. The method of embodiment 107, wherein the tumor is a carcinoma that is a carcinoma of the bladder, pancreas, colon, ovary, lung, breast, stomach, prostate, cervix, esophagus or head and neck.

109. The method of any of embodiments 1-108, wherein the method reduces the size or volume of the tumor by at least 30%, at least 40%, at least 50%, at least 60%, at least 70%, at least 80% at least 90% or more within one month of the irradiation compared to the size or volume of the tumor prior to the administration and irradiation.

110. The method of any of embodiments 1-109, wherein, in a population of treated subjects, effects an improvement of a tumor-related parameter compared to a similarly situated population of subjects that have not been treated with the method, wherein the parameter is selected from one or more of: a) objective response rate (ORR); b) progression free survival (PFS); c) overall survival (OS); d) reduction in toxicity; e) tumor response; f) quality of life; g) symptom endpoint; h) disease-free survival; h) complete response (CR); or i) time to progression.

111. The method of embodiment 110, wherein the parameter is improved by at least 10%, at least 20%, at least 30%, at least 40%, at least 50%, at least 60%, at least 70%, at least 80%, at least 90%, at least 100% or more.

112. The method of any of embodiments 1-111, wherein, in a population of treated subjects, effects an objective response rate (ORR) of at least 15%, at least 25%, at least 50%, at least 55%, at least 60%, at least 65%, at least 70%, at least 75%, at least 80%, at least 85%, at least 90%, at least 95% or more.

113. A method of treating a tumor in a subject, the method comprising:

a) measuring in a sample from the subject having a tumor a first level of an immune checkpoint biomarker;

b) comparing the first level from the subject to a first threshold level; and c) if the first level from the subject is lower than the first threshold level, administering a photoimmunotherapy (PIT) treatment to the subject, thereby treating the tumor.

114. A method of selecting a subject for treatment, the method comprising:

a) measuring in a sample from the subject having a tumor a first level of an immune checkpoint biomarker;

b) comparing the first level from the subject to a first threshold level; and c) if the first level from the subject is lower than the first threshold level, selecting the subject for a photoimmunotherapy (PIT) treatment.

115. A method of assessing the likelihood for response to a treatment in a subject, the method comprising:

a) measuring in a sample from the subject having a tumor a first level of an immune checkpoint biomarker;

b) comparing the first level from the subject to a first threshold level; and c) if the first level from the subject is lower than the first threshold level, identifying the subject as having a high likelihood for response to a photoimmunotherapy (PIT) treatment.

116. A method of selecting a subject for treatment, the method comprising:

a) measuring in a sample from the subject having a tumor a first level of an immune checkpoint biomarker;

b) comparing the first level from the subject to a first threshold level; and c) if the first level from the subject is higher than the first threshold level, selecting the subject for treatment with an immune checkpoint inhibitor prior to a photoimmunotherapy (PIT) treatment.

117. A composition comprising a conjugate comprising a silicon phthalocyanine dye for use in a treatment of a tumor in a subject, wherein the treatment comprises:

a) measuring in a sample from the subject having a tumor a first level of an immune checkpoint biomarker;

b) comparing the first level from the subject to a first threshold level; and c) if the first level from the subject is lower than the first threshold level, administering a photoimmunotherapy (PIT) treatment comprising administering the composition to the subject, thereby treating the tumor.

118. A composition comprising an agent for measuring a level of an immune checkpoint biomarker for use in a method of selecting a subject for treatment, wherein the method comprises:

a) measuring with the composition comprising the agent in a sample from the subject having a tumor a first level of an immune checkpoint biomarker;

b) comparing the first level from the subject to a first threshold level; and c) if the first level from the subject is lower than the first threshold level, selecting the subject for a photoimmunotherapy (PIT) treatment.

119. A composition comprising an agent for measuring a level of an immune checkpoint biomarker for use in a method of assessing the likelihood for response to a treatment in a subject, wherein the method comprises:

a) measuring with the composition comprising the agent in a sample from the subject having a tumor a first level of an immune checkpoint biomarker;

b) comparing the first level from the subject to a first threshold level; and c) if the first level from the subject is lower than the first threshold level, identifying the subject as having a high likelihood for response to a photoimmunotherapy (PIT) treatment.

120. A composition comprising an agent for measuring a level of an immune checkpoint biomarker for use in a method of selecting a subject for treatment, wherein the method comprises:

a) measuring with the composition comprising the agent in a sample from the subject having a tumor a first level of an immune checkpoint biomarker;

b) comparing the first level from the subject to a first threshold level; and c) if the first level from the subject is higher than the first threshold level, selecting the subject for treatment with an immune checkpoint inhibitor prior to a photoimmunotherapy (PIT) treatment.

121. A composition comprising an immune checkpoint inhibitor for use in combination with a photoimmunotherapy (PIT) in a treatment of a tumor in a subject, wherein the treatment comprises:

a) measuring in a sample from the subject having a tumor a first level of an immune checkpoint biomarker;

b) comparing the first level from the subject to a first threshold level; and c) if the first level from the subject is higher than the first threshold level, administering the composition to the subject prior to the photoimmunotherapy (PIT) treatment.

122. Use of a composition comprising a conjugate comprising a silicon phthalocyanine dye in the manufacture of a medicament for the treatment of a tumor in a subject, wherein the treatment comprises:

a) measuring in a sample from the subject having a tumor a first level of an immune checkpoint biomarker;

b) comparing the first level from the subject to a first threshold level; and c) if the first level from the subject is lower than the first threshold level, administering a photoimmunotherapy (PIT) comprising administering the composition to the subject, thereby treating the tumor.

123. Use of an immune checkpoint inhibitor in the manufacture of a medicament for the treatment of a tumor in a subject in combination with a photoimmunotherapy (PIT) treatment, wherein the treatment comprises:

a) measuring in a sample from the subject having a tumor a first level of an immune checkpoint biomarker;

b) comparing the first level from the subject to a first threshold level; and c) if the first level from the subject is higher than the first threshold level, administering the immune checkpoint inhibitor to the subject prior to the photoimmunotherapy (PIT) treatment, thereby treating the tumor.

124. The method, the composition for use or the use of any of embodiments 113-123, wherein the immune checkpoint biomarker is selected from the group consisting of PD-L1, PD-1, and PD-L1:PD-1 ratio.

125. A method of selecting a subject for treatment, the method comprising:

a) measuring in a sample from the subject having a tumor a first level of a first biomarker;

b) comparing the first level from the subject to a first threshold level of the first biomarker; and c) if the first level of the first biomarker from the subject is lower than a first threshold level of the first biomarker, selecting the subject for a photoimmunotherapy (PIT) treatment.

126. A method of assessing the likelihood for response to a treatment in a subject, the method comprising:

a) measuring in a sample from the subject having a tumor a first level of a first biomarker;

b) comparing the first level from the subject to a first threshold level of the first biomarker; and c) if the first level of the first biomarker from the subject is lower than a first threshold level of the first biomarker, identifying the subject as having a high likelihood for response to a photoimmunotherapy (PIT) treatment.

127. A method of selecting a subject for treatment, the method comprising:

a) measuring in a sample from the subject having a tumor a first level of a first biomarker;

b) comparing the first level from the subject to a first threshold level of the first biomarker; and c) if the first level of the first biomarker from the subject is higher than a first threshold level of the first biomarker, selecting the subject for a photoimmunotherapy (PIT) treatment.

128. A method of assessing the likelihood for response to a treatment in a subject, the method comprising:

a) measuring in a sample from the subject having a tumor a first level of a first biomarker;

b) comparing the first level from the subject to a first threshold level of the first biomarker; and c) if the first level of the first biomarker from the subject is higher than a first threshold level of the first biomarker, identifying the subject as having a high likelihood for response to a photoimmunotherapy (PIT) treatment.

129. A composition comprising an agent for measuring a level of a first biomarker for use in a method of selecting a subject for treatment, wherein the method comprises:

a) measuring with the composition comprising the agent in a sample from the subject having a tumor a first level of a first biomarker;

b) comparing the first level from the subject to a first threshold level of the first biomarker; and c) if the first level of the first biomarker from the subject is lower than a first threshold level of the first biomarker, selecting the subject for a photoimmunotherapy (PIT) treatment.

130. A composition comprising an agent for measuring a level of a first biomarker for use in a method of assessing the likelihood for response to a treatment in a subject, wherein the method comprises:

a) measuring in a sample from the subject having a tumor a first level of a first biomarker;

b) comparing the first level from the subject to a first threshold level of the first biomarker; and c) if the first level of the first biomarker from the subject is lower than a first threshold level of the first biomarker, identifying the subject as having a high likelihood for response to a photoimmunotherapy (PIT) treatment.

131. A composition comprising an agent for measuring a level of a first biomarker for use in a method of selecting a subject for treatment, wherein the method comprises:

a) measuring with the composition comprising the agent in a sample from the subject having a tumor a first level of a first biomarker;

b) comparing the first level from the subject to a first threshold level of the first biomarker; and c) if the first level of the first biomarker from the subject is higher than a first threshold level of the first biomarker, selecting the subject for a photoimmunotherapy (PIT) treatment.

132. A composition comprising an agent for measuring a level of a first biomarker for use in a method of assessing the likelihood for response to a treatment in a subject, wherein the method comprises:

a) measuring with the composition comprising the agent in a sample from the subject having a tumor a first level of a first biomarker;

b) comparing the first level from the subject to a first threshold level of the first biomarker; and c) if the first level of the first biomarker from the subject is higher than a first threshold level of the first biomarker, identifying the subject as having a high likelihood for response to a photoimmunotherapy (PIT) treatment.

133. The method, the composition for use or the use of any of embodiments 114-132, wherein the method or the treatment further comprises administering a PIT treatment to the selected or the identified subject, thereby treating the tumor.

134. The method, the composition for use or the use of any of embodiments 113-133, wherein the PIT treatment comprises administering a conjugate comprising a silicon phthalocyanine dye, and a targeting molecule.

135. The method, the composition for use or the use of embodiment 134, wherein the targeting molecule comprises an EGFR binding molecule.

136. The method, the composition for use or the use of any of embodiments 113-135, wherein the PIT treatment comprises irradiating an area proximal to the tumor at a wavelength of at or about 500 nm to at or about 900 nm.

137. The method, the composition for use or the use of embodiment 136, wherein the irradiation is at a wavelength of at or about 660 nm to at or about 740 nm.

138. The method, the composition for use or the use of any of embodiments 113-137, w herein the PIT treatment comprises irradiating an area proximal to the tumor at a dose of at least at or about 1 J $cm^{-2}$ or at or about 1 J/cm of fiber length.

139. The method, the composition for use or the use of embodiment 138, wherein the irradiation is at a dose of at or about 25 J $cm^{-2}$ to at or about 400 J $cm^{-2}$ or at or about 25 J/cm of fiber length to at or about 500 J/cm of fiber length.

140. A method of treating a tumor in a subject, the method comprising:

a) measuring in a sample from the subject having a head and neck cancer, a first level of PD-L1;

b) comparing the first level of PD-L1 from the subject to a first threshold level; and c) if the first level from the subject is lower than the first threshold level, administering a photoimmunotherapy (PIT) treatment comprising administering a conjugate comprising a silicon phthalocyanine dye, and an EGFR binding molecule to the subject, and irradiating an area proximal to the tumor at a wavelength of at or about 660 nm to at or about 740 nm at a dose of at or about 25 J $cm^{-2}$ to at or about 400 J $cm^{-2}$ or at or about 25 J/cm of fiber length to at or about 500 J/cm of fiber length, thereby treating the tumor.

141. A method of selecting a subject for treatment, the method comprising:

a) measuring in a sample from the subject having a head and neck cancer, a first level of PD-L1;

b) comparing the first level of PD-L1 from the subject to a first threshold level; and c) if the first level from the subject is lower than the first threshold level, selecting the subject for a photoimmunotherapy (PIT) treatment comprising administering a conjugate comprising a silicon phthalocyanine dye, and an EGFR binding molecule to the subject, and irradiating an area proximal to the tumor at a wavelength of at or about 660 nm to at or about 740 nm at a dose of at or about 25 J $cm^{-2}$ to at or about 400 J $cm^{-2}$ or at or about 25 J/cm of fiber length to at or about 500 J/cm of fiber length.

142. A method of assessing the likelihood for response to a treatment in a subject, the method comprising:

a) measuring in a sample from the subject having a head and neck cancer, a first level of PD-L1;

b) comparing the first level of PD-L1 from the subject to a first threshold level; and c) if the first level from the subject is lower than the first threshold level, identifying the subject as having a high likelihood for response to a photoimmunotherapy (PIT) treatment comprising administering a conjugate comprising a silicon phthalocyanine dye, and an EGFR binding molecule to the subject, and irradiating an area proximal to the tumor at a wavelength of at or about 660 nm to at or about 740 nm at a dose of at or about 25 J $cm^{-2}$ to at or about 400 J $cm^{-2}$ or at or about 25 J/cm of fiber length to at or about 500 J/cm of fiber length.

143. A method of selecting a subject for treatment, the method comprising:

a) measuring in a sample from the subject having a head and neck cancer, a first level of PD-L1;

b) comparing the first level of PD-L1 from the subject to a first threshold level; and c) if the first level from the subject is higher than the first threshold level, selecting the subject for treatment with an immune checkpoint inhibitor prior to a photoimmunotherapy (PIT) treatment comprising administering a conjugate comprising a silicon phthalocyanine dye, and an EGFR binding molecule to the subject, and irradiating an area proximal to the tumor at a wavelength of at or about 660 nm to at or about 740 nm at a dose of at or about 25 J $cm^{-2}$ to at or about 400 J $cm^{-2}$ or at or about 25 J/cm of fiber length to at or about 500 J/cm of fiber length.

144. A composition comprising a conjugate comprising a silicon phthalocyanine dye, and an EGFR binding molecule for use in a treatment of a tumor in a subject, wherein the treatment comprises:

a) measuring in a sample from the subject having a head and neck cancer, a first level of PD-L1;

b) comparing the first level of PD-L1 from the subject to a first threshold level; and c) if the first level from the subject is lower than the first threshold level, administering a photoimmunotherapy (PIT) treatment comprising administering the composition to the subject, and irradiating an area proximal to the tumor at a wavelength of at or about 660 nm to at or about 740 nm at a dose of at or about 25 J $cm^{-2}$ to at or about 400 J $cm^{-2}$ or at or about 25 J/cm of fiber length to at or about 500 J/cm of fiber length, thereby treating the tumor.

145. Use of a conjugate comprising a silicon phthalocyanine dye, and an EGFR binding molecule in the manufacture of a medicament for the treatment of a tumor in a subject, wherein the treatment comprises:

a) measuring in a sample from the subject having a head and neck cancer, a first level of PD-L1;

b) comparing the first level of PD-L1 from the subject to a first threshold level; and c) if the first level from the subject is lower than the first threshold level, administering a photoimmunotherapy (PIT) treatment comprising administering the composition to the subject, and irradiating an area proximal to the tumor at a wavelength of at or about 660 nm to at or about 740 nm at a dose of at or about 25 J $cm^{-2}$ to at or about 400 J $cm^{-2}$ or at or about 25 J/cm of fiber length to at or about 500 J/cm of fiber length, thereby treating the tumor.

146. Use of an immune checkpoint inhibitor in the manufacture of a medicament for the treatment of a tumor in a subject in combination with a photoimmunotherapy (PIT) treatment, wherein the treatment comprises:

a) measuring in a sample from the subject having a head and neck cancer, a first level of PD-L1;

b) comparing the first level of PD-L1 from the subject to a first threshold level; and c) if the first level from the subject is higher than the first threshold level, administering the immune checkpoint inhibitor to the subject prior to the photoimmunotherapy (PIT) treatment that comprises administering the composition to the subject, and irradiating an area proximal to the tumor at a wavelength of at or about 660 nm to at or about 740 nm at a dose of at or about 25 J $cm^{-2}$ to at or about 400 J $cm^{-2}$ or at or about 25 J/cm of fiber length to at or about 500 J/cm of fiber length, thereby treating the tumor.

147. A composition comprising an agent for measuring a level of PD-L1 for use in a method of selecting a subject for treatment, wherein the method comprises:

a) measuring with the composition comprising the agent in a sample from the subject having a head and neck cancer, a first level of PD-L1;

b) comparing the first level of PD-L1 from the subject to a first threshold level; and c) if the first level from the subject is lower than the first threshold level, selecting the subject for a photoimmunotherapy (PIT) treatment comprising administering a conjugate comprising a silicon phthalocyanine dye, and an EGFR binding molecule to the subject, and irradiating an area proximal to the tumor at a wavelength of at or about 660 nm to at or about 740 nm at a dose of at or about 25 J $cm^{-2}$ to at or about 400 J $cm^{-2}$ or at or about 25 J/cm of fiber length to at or about 500 J/cm of fiber length.

148. A composition comprising an agent for measuring a level of PD-L1 for use in method of assessing the likelihood for response to a treatment in a subject, wherein the method comprises:

a) measuring with the composition comprising the agent in a sample from the subject having a head and neck cancer, a first level of PD-L1;

b) comparing the first level of PD-L1 from the subject to a first threshold level; and c) if the first level from the subject is lower than the first threshold level, identifying the subject as having a high likelihood for response to a photoimmunotherapy (PIT) treatment comprising administering a conjugate comprising a silicon phthalocyanine dye, and an EGFR binding molecule to the subject, and irradiating an area proximal to the tumor at a wavelength of at or about 660 nm to at or about 740 nm at a dose of at or about 25 J $cm^{-2}$ to at or about 400 J $cm^{-2}$ or at or about 25 J/cm of fiber length to at or about 500 J/cm of fiber length.

149. A composition comprising an agent for measuring a level of PD-L1 for use in a method of selecting a subject for treatment, wherein the method comprises:

a) measuring with the composition comprising the agent in a sample from the subject having a head and neck cancer, a first level of PD-L1;

b) comparing the first level of PD-L1 from the subject to a first threshold level; and c) if the first level from the subject is higher than the first threshold level, selecting the subject for treatment with an immune checkpoint inhibitor prior to a photoimmunotherapy (PIT) treatment comprising administering a conjugate comprising a silicon phthalocyanine dye, and an EGFR binding molecule to the subject, and irradiating an area proximal to the tumor at a wavelength of at or about 660 nm to at or about 740 nm at a dose of at or about 25 J $cm^{-2}$ to at or about 400 J $cm^{-2}$ or at or about 25 J/cm of fiber length to at or about 500 J/cm of fiber length.

150. The method, the composition for use or the use of any of embodiments 135-149, wherein the EGFR binding molecule is an anti-EGFR antibody, antibody fragment or antibody-like molecule.

151. The method, the composition for use or the use of any of embodiments 135-150, wherein the EGFR binding molecule is cetuximab or a fragment thereof.

152. The method, the composition for use or the use of any of embodiments 136-151, wherein the irradiation is at a wavelength of at or about 690±20 nm.

153. The method, the composition for use or the use of any of embodiments 136-152, wherein the irradiation is at a dose of at or about 50 J $cm^{-2}$ or 100 J/cm of fiber length.

154. The method, the composition for use or the use of any of embodiments 125-153, wherein the first biomarker is a protein, a cell, or an mRNA.

155. The method, the composition for use or the use of any of embodiments 125-154, wherein the first biomarker is an immune cell, CD11c, CD14, CD68, CD163, or PD-L1.

156. The method, the composition for use or the use of embodiment 154 or 155, wherein the cell expresses CD3, CD4, and PD-1.

157. The method, the composition for use or the use of any of embodiments 125, 126, 129, 130, and 133-156, wherein the first biomarker is an mRNA selected from among an mRNA of APOE, BATF3, BCL6B, CASP9, CCND1, COL11A2, CSF2, CSF3, CTNNB1, DLL4, EGF, EIF2B4, ESR1, GLS, HDAC5, HSD11B1, IL11RA, IL32, MAP3K12, NLRP3, NOTCH2, P4HA1, PF4, PGPEP1, PLOD2, RIPK2, RPTOR, SF3A1, SNAI1, SPP1, SRP54, STC1, TMEM140, TNFSF12, and VEGFA.

158. The method, the composition for use or the use of any of embodiments 127, 128, and 131-156, wherein the first biomarker is an mRNA selected from among an mRNA of ANGPT1, CPA3, CXCL14, IL18, KIT, MAP3K5, OAZ1, RB1, STAT3, SYK, TICAM1, and TPSAB1/B2.

159. The method, the composition for use or the use of any of embodiments 113-158, wherein the sample is a tumor sample.

160. The method, the composition for use or the use of any of embodiments 113-159, wherein the sample is a tumor biopsy sample.

161. The method, the composition for use or the use of any of embodiments 113-160, wherein the immune checkpoint biomarker, the first biomarker or PD-L1 is measured in the whole tissue of the sample or a tumor region of the sample.

162. The method, the composition for use or the use of any of embodiments 113-161, wherein the level of the immune checkpoint biomarker, the first biomarker or PD-L1 is measured using a bioassay; and/or wherein the agent for measuring the level of the immune checkpoint biomarker, the first biomarker or PD-L1 is comprised in a bioassay.

163. The method, the composition for use or the use of embodiment 162, wherein the bioassay is selected from one or more of the group consisting of immunofluorescence, fluorescence in-situ hybridization, immunohistochemistry and/or high-throughput nucleic acid sequencing.

164. The method, the composition for use or the use of any of embodiments 113-163, wherein the level of the immune checkpoint biomarker, the first biomarker or PD-L1 is measured using a multiplexed bioassay; and/or wherein the agent for measuring the level of the immune checkpoint biomarker, the first biomarker or PD-L1 is comprised in a multiplexed bioassay.

165. The method, the composition for use or the use of embodiment 164, wherein the multiplexed bioassay comprises one or more assays selected from immunofluorescence, fluorescence in-situ hybridization, immunohistochemistry and/or high-throughput nucleic acid sequencing.

166. The method, the composition for use or the use of any of embodiments 113-165, wherein the first level and/or the threshold level(s) is/are measured as a Combined Positive Score (CPS) equal to the number of cells staining positive for the immune checkpoint biomarker, the first biomarker or PD-L1 divided by the total number of tumor cells, multiplied by 100.

167. The method, the composition for use or the use of any of embodiments 113-165, wherein the first level and/or the threshold level(s) is/are measured as a Tumor Proportion Score (TPS) equal to the number of tumor cells staining positive for the immune checkpoint biomarker, the first biomarker or PD-L1 divided by the total number of tumor cells, multiplied by 100.

168. The method, the composition for use or the use of any of embodiments 113-167, wherein the tumor comprises EGFR expressing cells in the tumor or tumor microenvironment.

169. The method, the composition for use or the use of any of embodiments 113-139 and 150-168, wherein the tumor is a head and neck cancer.

170. The method, the composition for use or the use of any of embodiments 113-169, wherein the phthalocyanine dye comprises the formula:

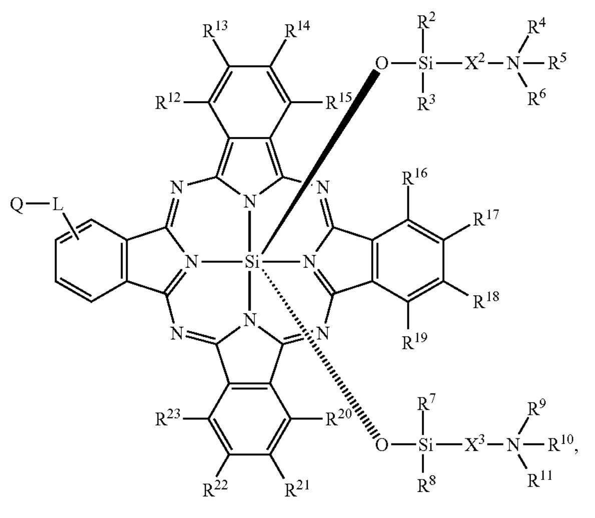

wherein:

L is a linker;

Q is a reactive group for attachment of the dye to the targeting molecule;

$R^2$, $R^3$, $R^7$, and $R^8$ are each independently selected from optionally substituted alkyl and optionally substituted aryl;

$R^4$, $R^5$, $R^6$, $R^9$, $R^{10}$, and $R^{11}$ are each independently selected from hydrogen, optionally substituted alkyl, optionally substituted alkanoyl, optionally substituted alkoxycarbonyl, optionally substituted alkylcarbamoyl, and a chelating ligand, wherein at least one of $R^4$, $R^5$, $R^6$, $R^9$, $R^{10}$, and $R^{11}$ comprises a water soluble group;

$R^{12}$, $R^{13}$, $R^{14}$, $R^5$, $R^{16}$, $R^{17}$, $R^{18}$, $R^{19}$, $R^{20}$, $R^{21}$, $R^{22}$ and $R^{23}$ are each independently selected from hydrogen, halogen, optionally substituted alkylthio, optionally substituted alkylamino and optionally substituted alkoxy; and $X^2$ and $X^3$ are each independently $C_1$-$C_{10}$ alkylene, optionally interrupted by a heteroatom.

171. The method, the composition for use or the use of any of embodiments 113-170, wherein the phthalocyanine dye comprises the formula:

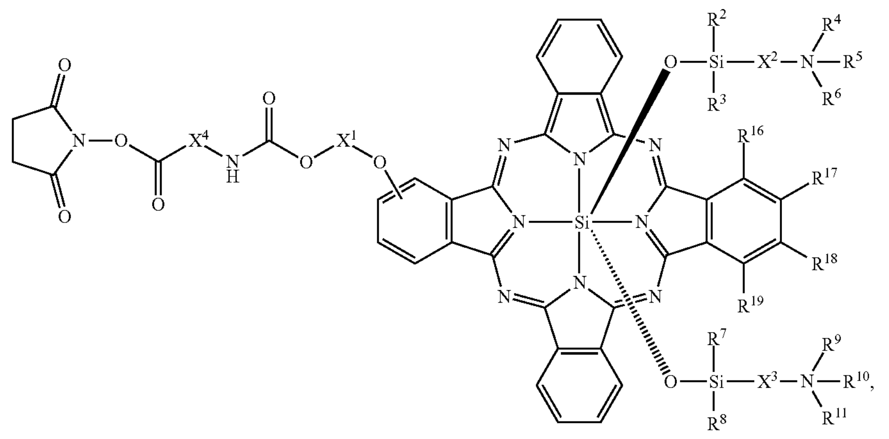

wherein:

$X^1$ and $X^4$ are each independently a $C_1$-$C_{10}$ alkylene optionally interrupted by a heteroatom;

$R^2$, $R^3$, $R^7$, and $R^8$ are each independently selected from optionally substituted alkyl and optionally substituted aryl;

$R^4$, $R^5$, $R^6$, $R^9$, $R^{10}$, and $R^{11}$ are each independently selected from hydrogen, optionally substituted alkyl, optionally substituted alkanoyl, optionally substituted alkoxycarbonyl, optionally substituted alkylcarbamoyl, and a chelating ligand, wherein at least one of $R^4$, $R^5$, $R^6$, $R^9$, $R^{10}$, and $R^{11}$ comprises a water soluble group; and $R^{16}$, $R^{17}$, $R^{18}$ and $R^{19}$ are each independently selected from hydrogen, halogen, optionally substituted alkylthio, optionally substituted alkylamino and optionally substituted alkoxy.

172. The method, the composition for use or the use of any of embodiments 113-171, wherein the silicon phthalocyanine dye is IR700 dye.

173. The method, the composition for use or the use of any of embodiments 113-172, wherein if the first level of the immune checkpoint biomarker, the first biomarker or PD-L1 from the subject is equal to or higher than the first threshold level, the method or the treatment further comprises administering an immune checkpoint inhibitor to the subject.

174. The method, the composition for use or the use of embodiment 173, wherein the method or the treatment further comprises administering a photoimmunotherapy (PIT) treatment to the subject subsequent to the administration of the immune checkpoint inhibitor.

175. The method, the composition for use or the use of any of embodiments 113-174, wherein the method further comprises administering an immune checkpoint inhibitor to the subject subsequent to the administration of the PIT treatment.

176. The method, the composition for use or the use of any of embodiments 113-175, wherein the method further comprises:

measuring a second level of the immune checkpoint biomarker, the first biomarker or PD-L1 in a second sample from the subject after PIT treatment;

determining whether the second level of the immune checkpoint biomarker, the first biomarker or PD-L1 is increased in the subject relative to the first level measured prior to the PIT treatment;

and if the second level is increased relative to the first level, administering an immune checkpoint inhibitor to the subject.

177. The method, the composition for use or the use of any of embodiments 113-176, wherein the method further comprises measuring a third level of immune cells positive for CD3, CD4, and PD-1 from a non-tumor region sample from the subject prior to the PIT treatment, comparing the third level to a third threshold, and wherein if the third level is higher than the third threshold, selecting the subject for treatment with PIT.

178. A method of assessing the response of a subject to photoimmunotherapy (PIT) treatment comprising:

a) measuring a first level of expression of a biomarker in a first sample from the subject prior to a PIT treatment;

b) administering the PIT treatment to the subject; and c) measuring a second level of expression of the biomarker in a second sample from the subject subsequent to the PIT treatment;

wherein if the first level is lower than the second level, identifying the subject as responding to the PIT treatment.

179. A composition comprising an agent for measuring of a biomarker for use in a method of assessing the response of a subject to photoimmunotherapy (PIT) treatment, wherein the method comprises:

a) measuring with the composition comprising the agent a first level of expression of a biomarker in a first sample from the subject prior to a PIT treatment;

b) administering the PIT treatment to the subject; and c) measuring with the composition comprising the agent a second level of expression of the biomarker in a second sample from the subject subsequent to the PIT treatment;

wherein if the first level is lower than the second level, identifying the subject as responding to the PIT treatment.

180. A method of assessing the response of a subject to photoimmunotherapy (PIT) treatment comprising:

a) measuring a first level of expression of a biomarker in a first sample from the subject prior to a PIT treatment;

b) administering the PIT treatment to the subject; and c) measuring a second level of expression of the biomarker in a second sample from the subject subsequent to the PIT treatment;

wherein if the first level is higher than the second level, identifying the subject as responding to the PIT treatment.

181. A composition comprising an agent for measuring of a biomarker for use in a method of assessing the response of a subject to photoimmunotherapy (PIT) treatment, wherein the method comprises:

a) measuring with the composition comprising the agent a first level of expression of a biomarker in a first sample from the subject prior to a PIT treatment;

b) administering the PIT treatment to the subject; and c) measuring with the composition comprising the agent a second level of expression of the biomarker in a second sample from the subject subsequent to the PIT treatment;

wherein if the first level is higher than the second level, identifying the subject as responding to the PIT treatment.

182. The method, the composition for use or the use of any of embodiments 178-181, wherein the biomarker is selected from the group consisting of FoxP3, CD11c, CD14, or CD68, and CD163.

183. The method, the composition for use or the use of any of embodiments 178-182, wherein the biomarker expression in first, and second samples are measured in whole tissue or a tumor region of the samples.

184. The method, the composition for use or the use of any of embodiments 178-183, wherein if the first level is lower than the second level after a first administration of the PIT treatment to the subject, the method or treatment further comprises administering a second PIT treatment and/or an immune checkpoint inhibitor to the subject.

185. The method, the composition for use or the use of any of embodiments 116, 120, 121, 123, 124, 133-139, 143-177 and 184, wherein the immune checkpoint inhibitor is an inhibitor of PD-L1, PD-1, or CTLA4.

186. The method, the composition for use or the use of any of embodiments 116, 120, 121, 123, 124, 133-139, 143-177, 184, and 185, wherein the immune checkpoint inhibitor comprises an antibody, antibody fragment or antibody-like molecule.

187. The method, the composition for use or the use of embodiment 185 or 186, wherein the immune checkpoint inhibitor is an antibody selected from BMS-935559, MEDI4736, MPDL3280A, MSB0010718C, nivolumab, pembrolizumab, pidilizumab, lambrolizumab or AMP-224, or an antigen-binding fragment thereof.

188. A kit comprising:

(1) a conjugate comprising a phthalocyanine dye linked to a targeting molecule; and (2) instructions for performing the method of, or according to the treatment in the composition for use or the use of any one of embodiments 1-187, and optionally (3) an agent for measuring a level of the biomarker, the immune checkpoint biomarker, the first biomarker or PD-L1.

189. A kit comprising:

(1) an agent for measuring a level of the biomarker, the immune checkpoint biomarker, the first biomarker or PD-L1;

(2) instructions for performing the method of, or according to the treatment in the composition for use or the use of any one of embodiments 1-187, and optionally (3) a conjugate comprising a phthalocyanine dye linked to a targeting molecule.

VII. EXAMPLES

The following examples are included for illustrative purposes only and are not intended to limit the scope of the invention.

Example 1

Target Cell Surface Protein Binding and Killing of Target Cells by Photoimmunotherapy (PIT) In Vitro Using Antibody-IR700 Conjugate The ability of an exemplary antibody-phthalocyanine dye conjugate to bind the target cell surface protein and to kill target cells via photoimmunotherapy (PIT) was assessed using exemplary in vitro assays. The assays were performed using a cetuximab-IRDye 700DX conjugate, which specifically binds to the cell surface protein epidermal growth factor receptor (EGFR) via the anti-EGFR antibody cetuximab. Similar in vitro assays are within the level of a skilled artisan to assess other IRDye 700DX-targeting molecule conjugates, e.g., IRDye 700DX-antibody conjugates, using cell lines that express the protein to which the targeting molecule (e.g., antibody) binds and/or assays that assess a functional activity induced upon such binding.

To assess target cell binding by cetuximab-IRDye 700DX (CTX-IR700), BxPC3 cells (#CRL-1687, ATCC, Manassas VA), expressing epidermal growth factor receptor (EGFR), were incubated with or without CTX-IR700, and assessed using standard flow cytometric techniques to detect the intrinsic fluorescence of IR700. For a competition assay, a 100-fold molar excess of unconjugated cetuximab was incubated with the CTX-IR700 and BxPC3 cells.

To evaluate PIT-mediated target cell killing by CTX-IR700, BxPC3 cells were incubated for one hour with cetuximab-IRDye 700DX in culture media, and then washed one time with the culture media to remove unbound cetuximab-IRDye 700DX. The cells were then illuminated with a 690 nm laser emitting non-thermal red light at varying fluences between approximately 0.5 $J/cm^{-2}$ and 100 $J/cm^{-2}$, or as control, not subject to light treatment. Cell death was measured 24 hours after light illumination using the fluorescent stain CellTox Green (Cat No: G8731, Promega, Madison, WI), a non-permeable fluorescent dye that exhibits increased fluorescence upon binding to DNA. Only cells that have compromised plasma membranes exhibit strong CellTox Green staining. The CellTox Green fluorescence signal was measured using a fluorescence plate reader. The cells were then lysed with Triton-based Lysis Buffer (Promega), and the CellTox Green fluorescence signal was measured again post lysis. Percent cell death was calculated based on (CellTox Green value after PIT treatment)/(CellTox Green value after complete lysis).

As shown in FIG. 1A, CTX-IR700 bound the surface of EGFR-expressing BxPC3 tumor cells, as detected by the intrinsic fluorescence from IR700. The addition of excess unconjugated cetuximab out-competed CTX-IR700 binding, showing the specificity of binding of the CTX-IR700 to EGFR. The results showed that CTX-IR700 bound to BxPC3 cells in an EGFR-dependent manner.

As shown in FIG. 1B, the percent of cell death at 24 hours after PIT increased with the fluence of light applied. The results showed a light fluence-dependent PIT-mediated cell killing by the exemplary antibody-IRDye 700DX conjugate CTX-IR700.

Example 2

Immunogenic Cell Death of Target Cells after PIT Using Antibody-IR700 Conjugate Expression of immunogenic cell death (ICD) markers was evaluated after PIT by incubation with an exemplary antibody-IR700 conjugate and light treatment, to assess whether immune stimulatory changes may result from PIT-treated cells. Immunogenic cell death is a specific type of cell death exhibited by necrotic cells and is characterized by increased presentation and release of immune stimulatory markers. Cells exhibiting ICD display membrane changes such as elevated surface expression of heat shock protein 90, and secretion of soluble, intracellular and/or nuclear markers known as danger associated molecular patterns (DAMPs), such as ATP and high-mobility group-box protein (HMGB1) (Kromer et al. (2013) Annual Review of Immunology, 31:51-72).

EGFR-expressing A-431 (ATCC® CRL1555™) epidermoid carcinoma and FaDu (ATCC® HTB-43™) squamous cell carcinoma cells were incubated with cetuximab-IRDye 700DX (CTX-IR700). A-431 cells were illuminated at 6 $J/cm^2$ and FaDu cells were illuminated at 12 $J/cm^2$, with a 690 nm laser. Cell surface expression of ICD markers, including Hsp70, Hsp90 and calreticulin (CRT), were measured by flow cytometry after staining with antibodies specific for each protein. The tumor cells were also illuminated at 32 $J/cm^2$ for PIT-mediated killing of target cells, and the culture supernatants from various groups were assessed for secretion of HMGB1 using an enzyme-linked immunosorbent assay (ELISA). The controls represented cells not treated with light.

As shown in FIGS. 2A-2B, PIT treatment after incubation of EGFR-expressing A-431 and FaDu cells with CTX-IR700 exhibited increased expression of exemplary ICD markers Hsp70, Hsp90 and calreticulin (CRT) compared to control groups that did not receive light treatment.

As shown in FIG. 2C, PIT treatment after incubation of EGFR-expressing A-431 and FaDu cells with CTX-IR700 resulted in a large increase of release of the nuclear DAMP ICD marker HMGB1 into the supernatant of the culture, compared to the control groups that did not receive light treatment.

The results showed that expression or release of various ICD markers were increased upon PIT-mediated target cell death after incubation with the exemplary CTX-IR700 conjugate and light treatment, consistent with PIT-treated cells exhibiting markers characteristic of ICD and having the potential to activate immune cells.

Example 3

Activation of Dendritic Cells Upon Killing of Target Cells after PIT Using Antibody-IR700 Conjugate Activation of dendritic cells (DCs) was assessed after exposure to PIT-treated tumor cells. As described in Example 2 above, PIT-treated cells undergo immunogenic cell death, exhibiting elevated release of HMGB1, and can enhance stimulation or activation of immune cells such as DCs. As DCs become activated, surface expression of DC maturation/activation markers, such as cluster of differentiation 86 (CD86) and major histocompatibility complex II (MHCII), can be elevated, and can result in production of pro-inflammatory cytokines.

Human DCs were exposed to target cancer cells incubated with the exemplary cetuximab-IRDye 700DX (CTX-IR700) conjugate, with or without light treatment, generally as described in Example 2 above. The DCs were assessed by flow cytometry for expression of activation markers CD86 and MHCII, and production of pro-inflammatory cytokines such as tumor necrosis factor (TNF), IFN-γ-Inducible Protein 10 (IP-10), MIP-1α (Macrophage Inflammatory Protein-1 alpha), MIP-1β (Macrophage Inflammatory Protein-1 beta), interleukin-1 beta (IL-1β) and interleukin-8 (IL-8) was assessed using a multiplexed immunoassay.

Figures 3A, 3B:
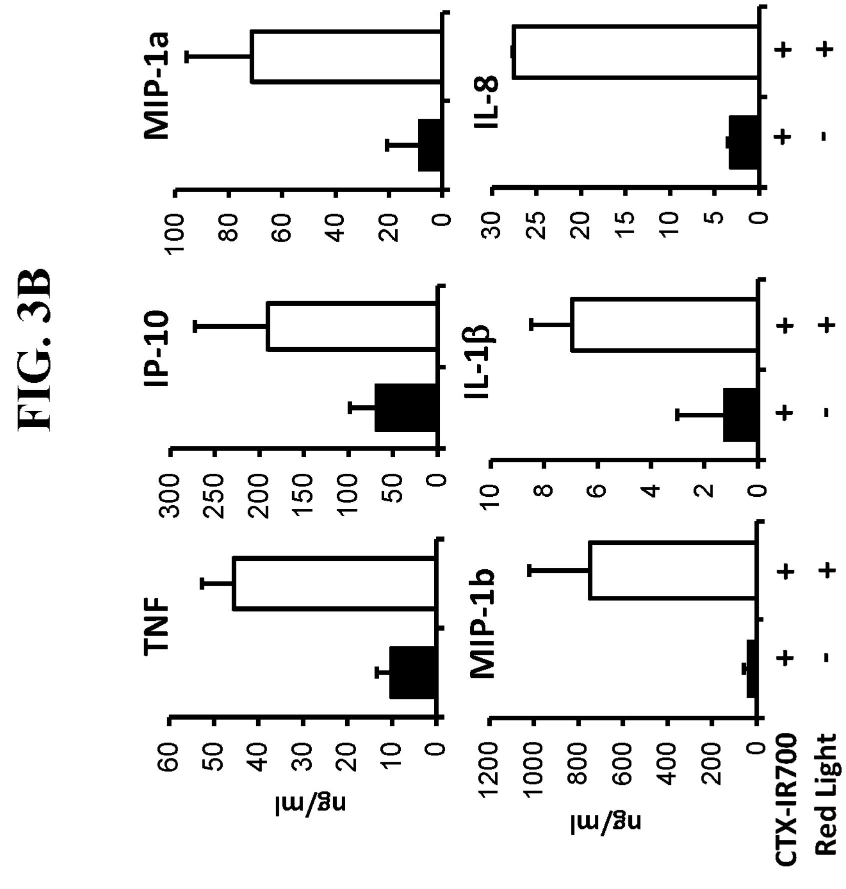
FIG. 3A shows the expression of dendritic cell (DC) activation markers cluster of differentiation 86 (CD86) and major histocompatibility complex II (MHCII) assessed by flow cytometry, in human DCs exposed to PIT treated tumor cells (after incubation with CTX-IR700 and with (+) light treatment or without (−) light treatment as control;*: p-value <0.05).
FIG. 3B shows the level of pro-inflammatory cytokines tumor necrosis factor (TNF), IFN-γ-Inducible Protein 10 (IP-10), MIP-1α (Macrophage Inflammatory Protein-1 alpha), MIP-1β (Macrophage Inflammatory Protein-1 beta), interleukin-1 beta (IL-1β) and interleukin-8 (IL-8) produced by DCs after exposure to PIT-treated tumor cells, using a multiplexed immunoassay.

As shown in FIG. 3A, human DCs exposed to PIT-treated tumor cells exhibited higher expression of dendritic cell activation markers CD86 and MHCII, compared to DCs exposed to supernatant from control cells without light treatment. As shown in FIG. 3B, human DCs produced higher amounts of several pro-inflammatory cytokines, including TNF, IP-10, MIP-1α, MIP-1β, IL-1β and IL-8, after exposure to PIT-treated tumor cells. The results showed that immune cells, such as DCs, can be activated and secrete pro-inflammatory cytokines upon exposure to cancer cells killed by PIT using antibody-IR700 conjugates. Combination treatment with PIT with an immune-modulating agent may further enhance the immune activating potential of PIT.

Example 4

Assessment of In Vivo Anti-Cancer Activity of PIT Using Antibody-IR700 Conjugate and Activation of Innate and Adaptive Immunity Anti-cancer activity of PIT with an exemplary antibody-IR700 conjugate and the effect of PIT-treated tumor cells in activating innate and adaptive immunity was evaluated in vivo using a mouse tumor model system. As described in Examples 2 and 3 above, PIT-treated cancer cells can lead to activation of immune cells, such as DCs, in the tumor microenvironment.

To assess the anti-cancer activity and determine whether immune activation occurs after tumor killing by PIT in vivo, CT26 murine colon carcinoma cells were engineered to express the murine antigen Ephrin type-A receptor 2 (EphA2) (CT26-EphA2) and implanted into immunocompetent BALB/c mice to generate a mouse tumor model. The level of expression of EphA2 on the engineered CT26-EphA2 cells was assessed by flow cytometry. Approximately 6 days after tumor implantation, a conjugate containing IRDye 700Dx attached to an antibody that specifically binds to EphA2 (anti-EphA2-IR700) was systemically administered to the mice. Accumulation of the conjugates into CT26-EphA2 tumors was detected by fluorescence imaging after systemic administration of the conjugate. The tumor was illuminated with red light 24 hours following administration of the anti-EphA2-IR700 conjugate at 100 $J/cm^{-2}$ using 150 $mW/cm^{-2}$ light fluence. As a control, CT26-EphA2 tumor implanted mice were administered the anti-EphA2-IR700 conjugate but were not subject to light treatment. To determine whether intratumoral immune cells were activated after tumor cell killing by PIT, CT26-EphA2 tumors were excised either 1 or 8 days after light treatment, dissociated into single cells, and assessed for expression of various immune cell and activation markers by flow cytometry.

Figures 4A, 4B, 4C:
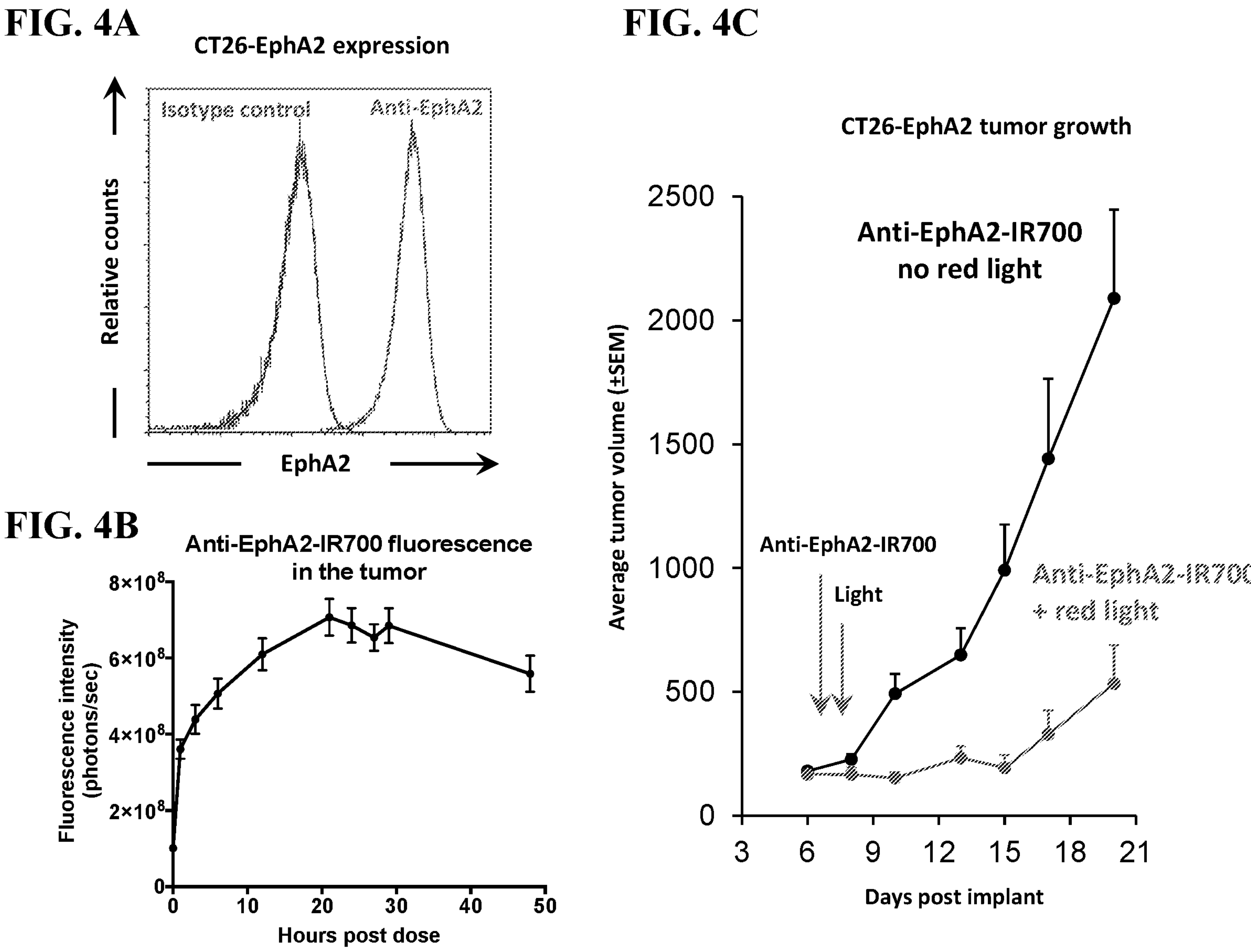
FIG. 4A shows the level of expression of Ephrin type-A receptor 2 (EphA2) on CT26 murine colon carcinoma cells engineered to express EphA2 (CT26-EphA2), as assessed by flow cytometry.
FIG. 4B shows the fluorescence intensity (photons/sec) of the tumor area over time between approximately 0 to 50 hours after administration of the anti-EphA2-IR700 conjugate in a mouse tumor model (CT26-EphA2 cells implanted into immunocompetent BALB/c mice), as detected by flow cytometry of the intrinsic fluorescence of IRDye 700DX.
FIG. 4C shows the average tumor volume changes over time (between approximately 5 to 21 days after tumor implantation) in the CT26-EphA2 mouse model that had been administered an anti-EphA2-IR700 conjugate and illuminated with red light at 690 nm, 24 hours after administration of the conjugate (+ red light), or without light treatment as control (no red light).

As shown in FIG. 4A, CT26-EphA2 cells exhibited stable cell surface expression of EphA2, as detected by flow cytometry. As shown in FIG. 4B, the anti-EphA2-IR700 conjugates were shown to accumulate in the CT26-EphA2 tumors after systemic administration, as measured by an increase of fluorescence intensity in the tumor area, demonstrating the localization of the conjugate to the tumor cells expressing the EphA2 antigen. As shown in FIG. 4C, PIT treatment by administering an exemplary anti-EphA2-IR700 conjugate and light illumination resulted in a substantial tumor growth inhibition compared to control mice that were administered the conjugate but were not subject to light treatment.

Figures 5A, 5B:
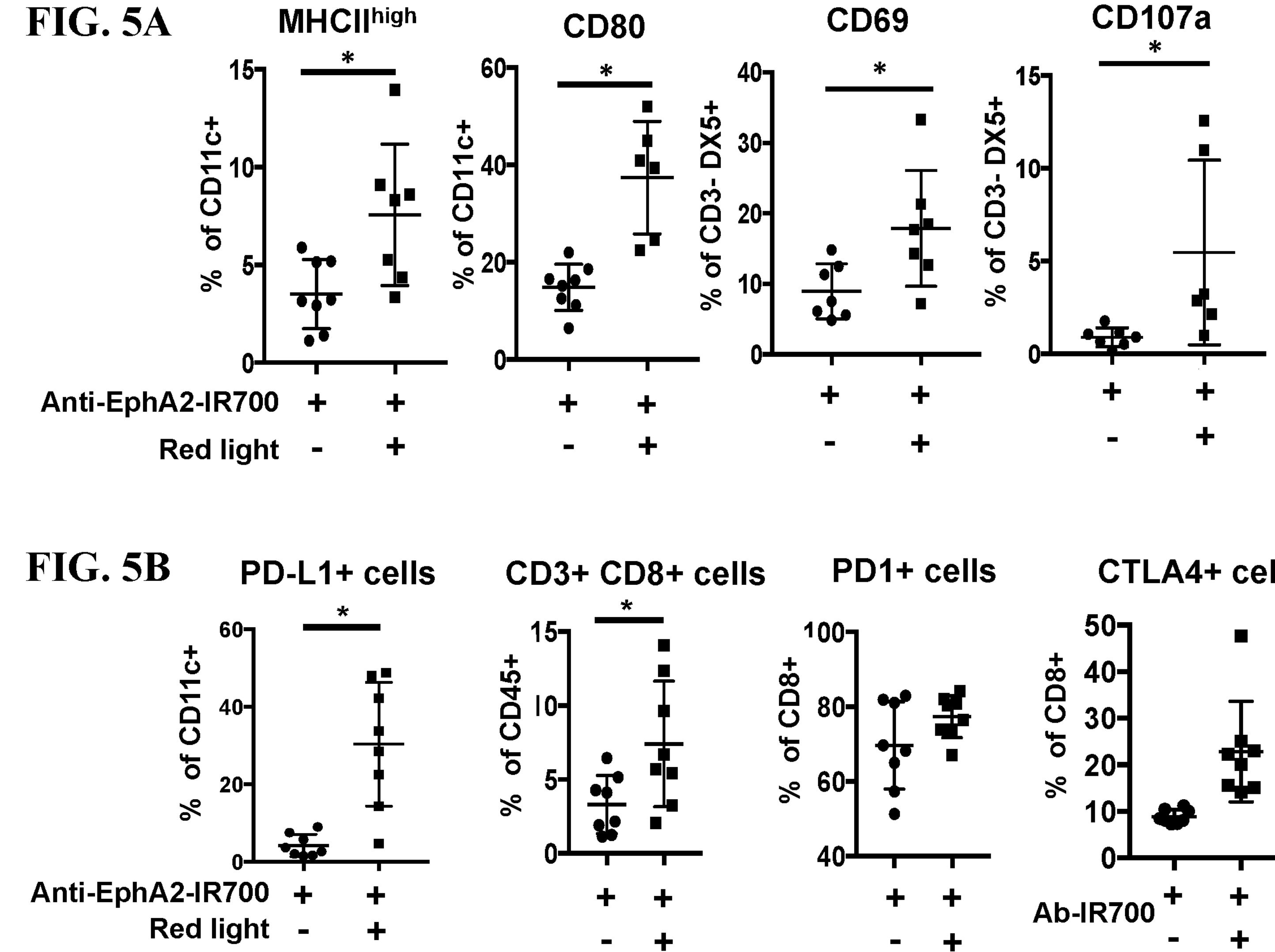
FIG. 5A shows the percentage of intratumoral CD11c+ dendritic cells expressing the activation markers $MHCII^{high}$ and CD80 and the percentage of intratumoral CD3-DX5+ (CD3-CD49b+) natural killer cells expressing the markers of cytotoxic activity, CD69 and CD107a, assessed in the tumor one day after light treatment (*: $p<0.05$).
FIG. 5B shows the percentage of CD11c+ dendritic cells expressing PD-L1, the percentage of CD3+CD8+ T cells, and the percentage of PD-1 and CTLA-4-expressing cells among intratumoral CD3+CD8+ T cells, 8 days after light treatment (*: $p<0.05$).

FIG. 5A shows the percentage of intratumoral dendritic cells or natural killer cells expressing markers indicative of activation or cytotoxic activity, one day after PIT treatment. As shown, the percentage of intratumoral CD11c+ dendritic cells expressing the activation markers $MHCII^{high}$ and CD80 was substantially higher in the CT26-EphA2 tumors treated with PIT, compared to the percentage in the control group not subject to light treatment (*p <0.05). In addition, the percentage of intratumoral CD3-DX5+ (monoclonal antibody DX5 recognizing the cell surface marker CD49b) natural killer cells expressing the markers of cytotoxic activity, CD69 and CD107a, was substantially higher in the CT26-EphA2 tumors treated with PIT, compared to the percentage in the control group not subject to light treatment (*p<0.05).

FIG. 5B shows the percentage of dendritic cells and T cells expressing markers related to checkpoint inhibition, 8 days after PIT treatment. As shown, the percentage of CD11c+ dendritic cells expressing PD-L1 was substantially higher in the PIT-treated tumor compared to the control group not subject to light treatment (*p<0.05). The percentage of CD3+CD8+ T cells was also substantially higher in the PIT-treated tumor compared to control group not subject to light treatment (*p<0.05). Among the intratumoral CD3+ CD8+ T cells, a higher percentage of PD-1 and CTLA-4-expressing cells was also observed in the PIT-treated tumor compared to the control group not subject to light treatment.

Taken together, the results showed that expression of activation markers for innate and adaptive immunity increased in the tumor after PIT treatment, consistent with the activation of the innate and adaptive immune response in the tumor microenvironment after death of the target cancer cells via PIT. The increase of expression of PD-1, PD-L1 and CTLA-4 after PIT treatment supports a treatment regimen with an additional immune modulating agent, such as with an immune checkpoint inhibitor, e.g., agents targeting PD-1, PD-L1 or CTLA-4, to synergistically enhance the anticancer effects of antibody-IR700 conjugates.

Example 5

Clinical Study Evaluation and Expression of PD-L1

This example describes an open label, Phase 1/2a clinical study of treatment with an anti-EGFR antibody-IRDye 700DX conjugate followed by illumination to induce photoimmunotherapy (PIT) in head and neck squamous cell carcinoma (HNSCC) patients who have failed prior treatments.

Figures 6A, 6B:
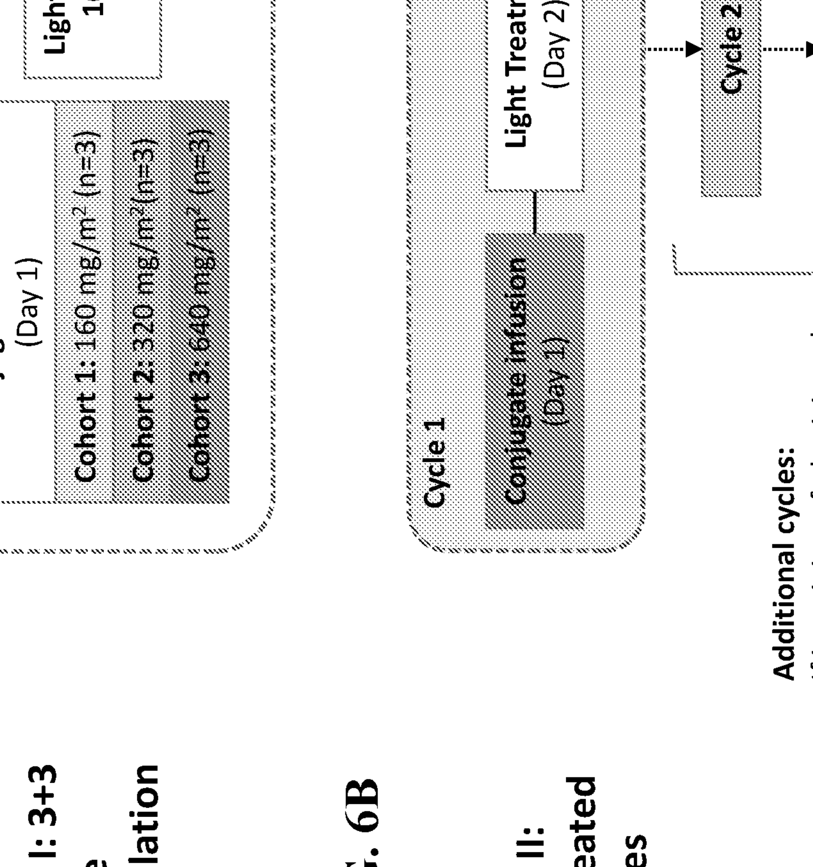
FIGS. 6A-6B show the treatment schema for a clinical study for treatment using clinical study of treatment with an anti-EGFR antibody-IRDye 700DX conjugate followed by illumination to induce photoimmunotherapy (PIT) in patients having head and neck squamous cell carcinoma (HNSCC).

The clinical study included 41 individual patients with histologically confirmed recurrent HNSCC who, in the opinion of their treating physician, could not be satisfactorily treated with surgery, radiation or platinum chemotherapy. The study schema is shown in FIGS. 6A-6B. In part I of the study (FIG. 6A), patients were grouped into 3 cohorts. On Day 1, Cohort 1 was infused with an anti-EGFR-IR700 dye conjugate at a dose of 160 $mg/m^{-2}$; Cohort 2 was infused at a dose of 320 $mg/m^{-2}$; and Cohort 3 infused at a dose of 640 $mg/m^{-2}$. On Day 2, photoimmunotherapy (PIT) was applied locoregionally at a light dose of 50 $J/cm^{-2}$ for superficial lesions and 100 J/cm for interstitial lesions using a wavelength of 690 nm. Patients in each cohort were followed for one month post-treatment. For patients participating in part II of the study (30 individuals; FIG. 6B), the initial treatment was the same as part I, but only the 640 $mg/m^{-2}$ dose was used in each cycle; following this first cycle of treatment, at physician's discretion, the cycle of conjugate infusion and PIT was repeated for up to 4 cycles.

Figure 11:
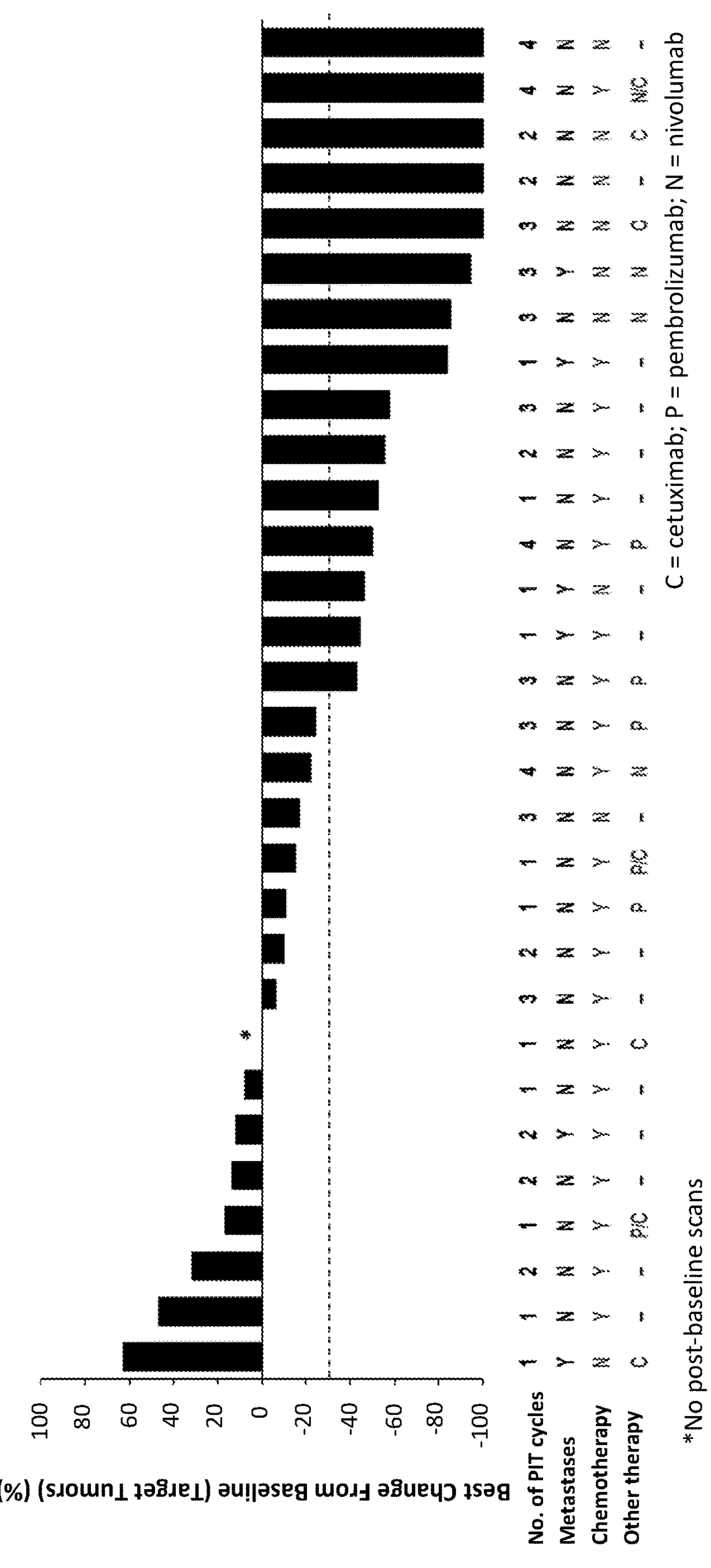
FIG. 11 summarizes the changes in tumor size for patients (subject) treated with anti-EGFR-IR700 PIT treatment in the phase II trial. Patients having tumors that decreased in size by 30% or more were considered to be "responders" to treatment. Also indicated are the presence of metastases, pre-treatment chemotherapy or other therapy (immunotherapy with cetuximab, pembrolizumab, and/or nivolumab) for each patient.
Figures 12A, 12B, 12C, 12D:
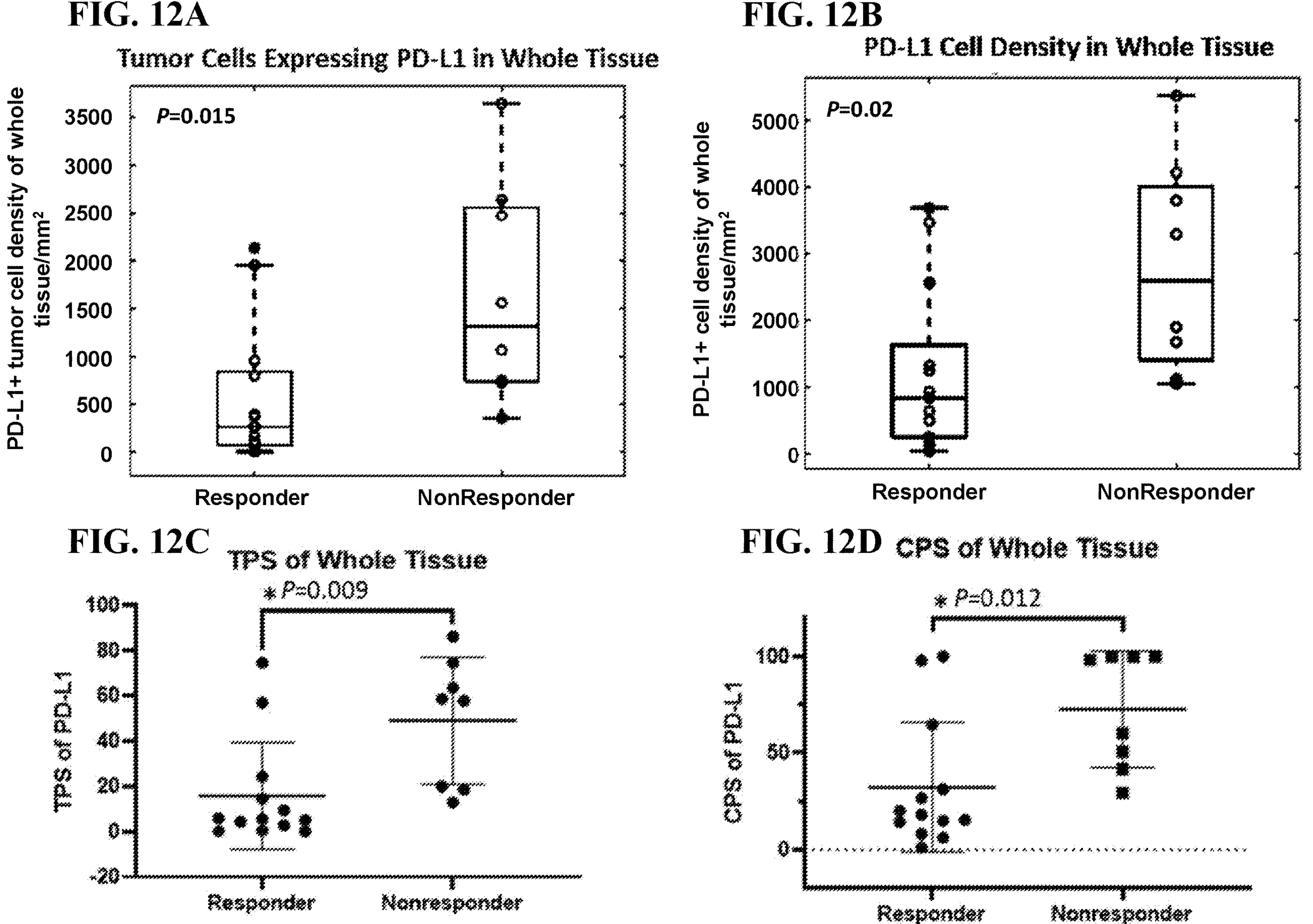
FIGS. 12A-12D compare the pretreatment levels of tumor cells expressing PD-L1 (FIG. 12A), PD-L1 cell density (FIG. 12B), and PD-L1 TPS (FIG. 12C), and PD-L1 CPS (FIG. 12D) in whole tissue biopsies of "responder" and "non-responder" patients (subjects).
Figures 13A, 13B, 13C, 13D:
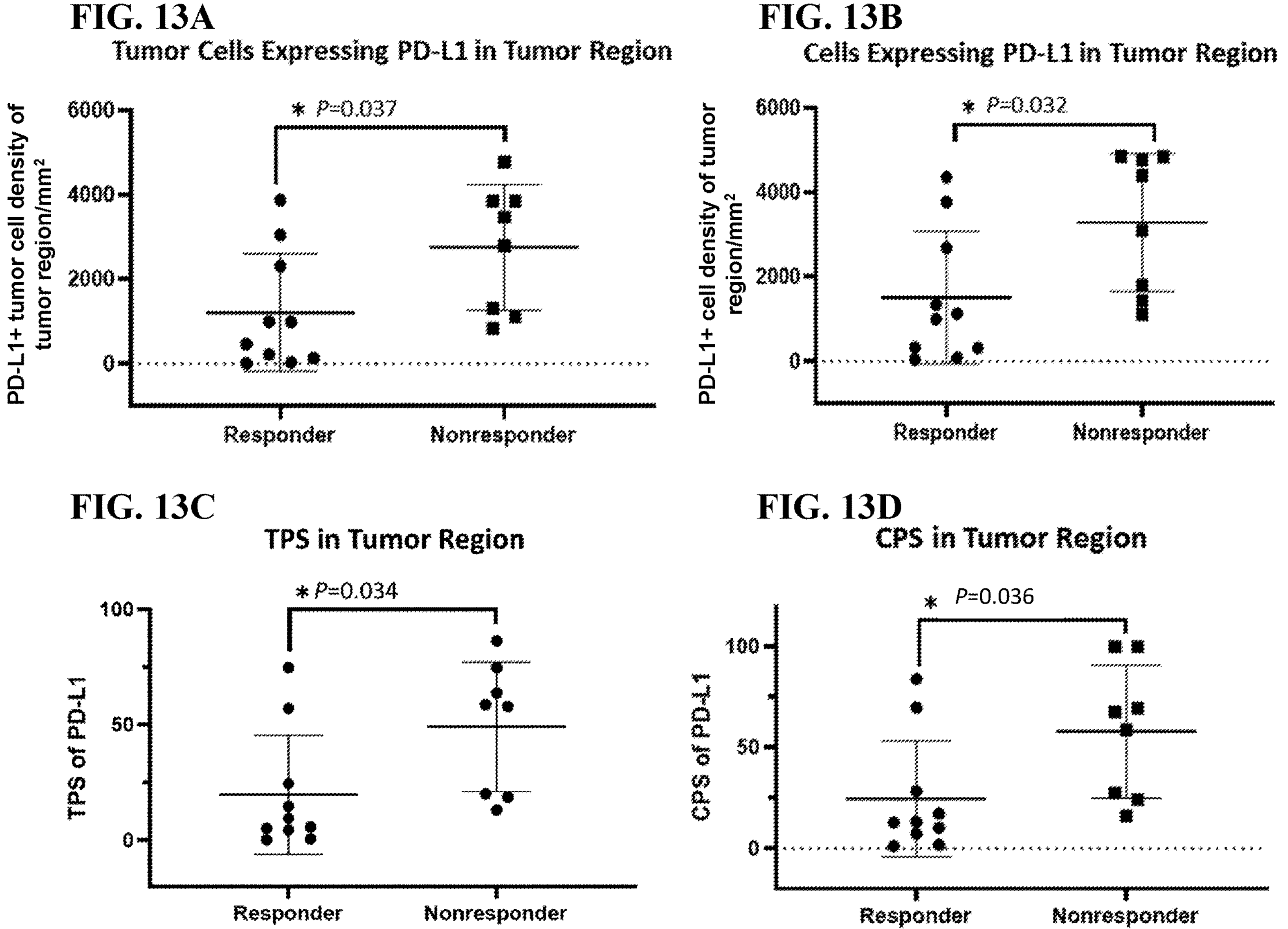
FIGS. 13A-13D depict the pretreatment levels of tumor cells expressing PD-L1 (FIG. 13A), PD-L1 cell density (FIG. 13B), and PD-L1 TPS (FIG. 13C), and PD-L1 CPS (FIG. 13D) in tumor regions of "responder" and "non-responder" patient (subject) biopsies.

Patients participating in part II of the study, had failed radiation therapy and one or more of cancer-related surgery, chemotherapy, immunotherapy, or other therapy prior to enrollment in the study. Tumors of participating patients, located in the neck (12), tongue (8), oropharynx (4), oral cavity (4), hypopharynx (2), skin (2), sinus (1) and/or nasal cavity (1), were measured before treatment and upon conclusion of treatment. The change in tumor size (largest unidimensional tumor diameter on CT scan) in response to treatment is depicted in FIG. 11, with the best percent change from baseline provided for patients containing more than 1 tumor. Patients having tumors that decreased in size by 30% or more were considered to be "responders" to treatment.

Patients (subjects) that did not have prior chemotherapy treatment exhibited a higher trend in responsiveness to anti-EGFR-IR700 PIT treatment.

For purposes of the immunohistochemistry assessment, patient samples were collected and assessed pre- and post-treatment as follows: pre-treatment tumor biopsies were collected within 12 months of treatment. Post-treatment biopsies were collected after cycle 1 or after subsequent treatment cycles. EGFR and PD-L1 expression were determined based on tumor biopsies and measured using Dako EGFR pharmDx assay (clone 2-18C9) and Dako PD-L1 pharmDx kit (clone 22C3 and 28-8), respectively. Cytokine levels in the patient's blood and immunophenotypes of the patient's peripheral blood mononuclear cells (PBMCs) were also assessed, as described in Examples 6 and 7 below.

Figures 7A, 7B:
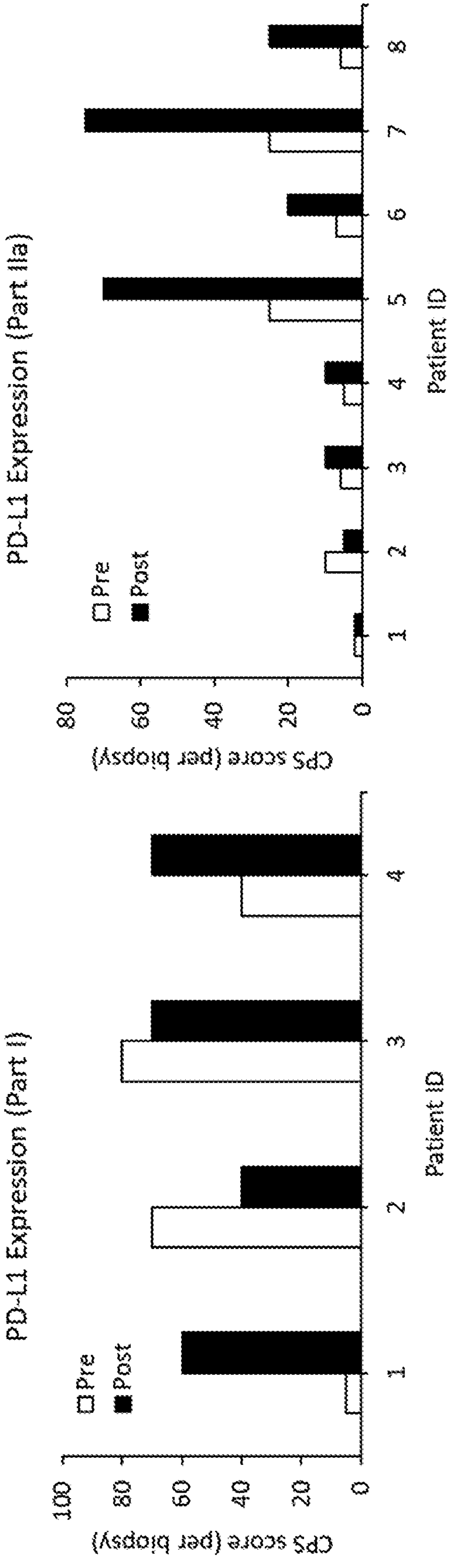
FIGS. 7A-7B show the combined positive score (CPS) of PD-L1 expression, as measured by immunohistochemistry in pre-treatment and post-treatment tumor biopsies collected from patients participating in part I (FIG. 7A) and part II (FIG. 7B) of the clinical study as described in Example 5.

As shown in FIGS. 7A-7B, an increase in PD-L1 expression post treatment was observed. This observation was consistent with induction of intra-tumoral interferon-gamma (IFNγ), and evidence of acute inflammation following PIT treatment. Of the patients with pre- and post-treatment biopsies in part I (FIG. 7A; n=4) and part IIa (FIG. 7B; n=8) of the study, PD-L1 expression increased in tumor and immune cells in 8 out of 12 cases. The results showed that treatment with the conjugate followed by light illumination was associated with induction of PD-L1 expression in tumor and immune cells, consistent with immune activation following acute treatment.

Example 6

Assessment of the Relationship Between Pre-Treatment Systemic Cytokine and Chemokine Levels and Response to Treatment Plasma cytokine levels in the patient blood were assessed in samples from the patients in the clinical study described in Example 5 above, and the relationship between the plasma cytokine levels and response to the anti-EGFR antibody-IR700 treatment and PIT were analyzed.

For plasma cytokine and chemokine analysis, patient blood was collected from a total of 13 patients at 4 different time points: one day pre-treatment, and at +7, +14, and +28 days post treatment. Plasma levels of 34 different cytokines and chemokines were analyzed using the ProcartaPlex Human Cytokine & Chemokine Panel 1A 34plex multiplex immunoassay kit (Thermo Fisher, Carlsbad, USA). Each sample was tested in technical triplicates. Levels above the lower limit of detection were found for 18 out of 34 cytokines. Using the average linkage clustering method and the Euclidian distance measurement method, heatmaps (FIG. 8) were generated for the cytokines and chemokines across patients exhibiting various overall response score: complete response to treatment (CR), partial response to treatment (PR), stable disease (SD) or progressive disease (PD).

Figure 8:
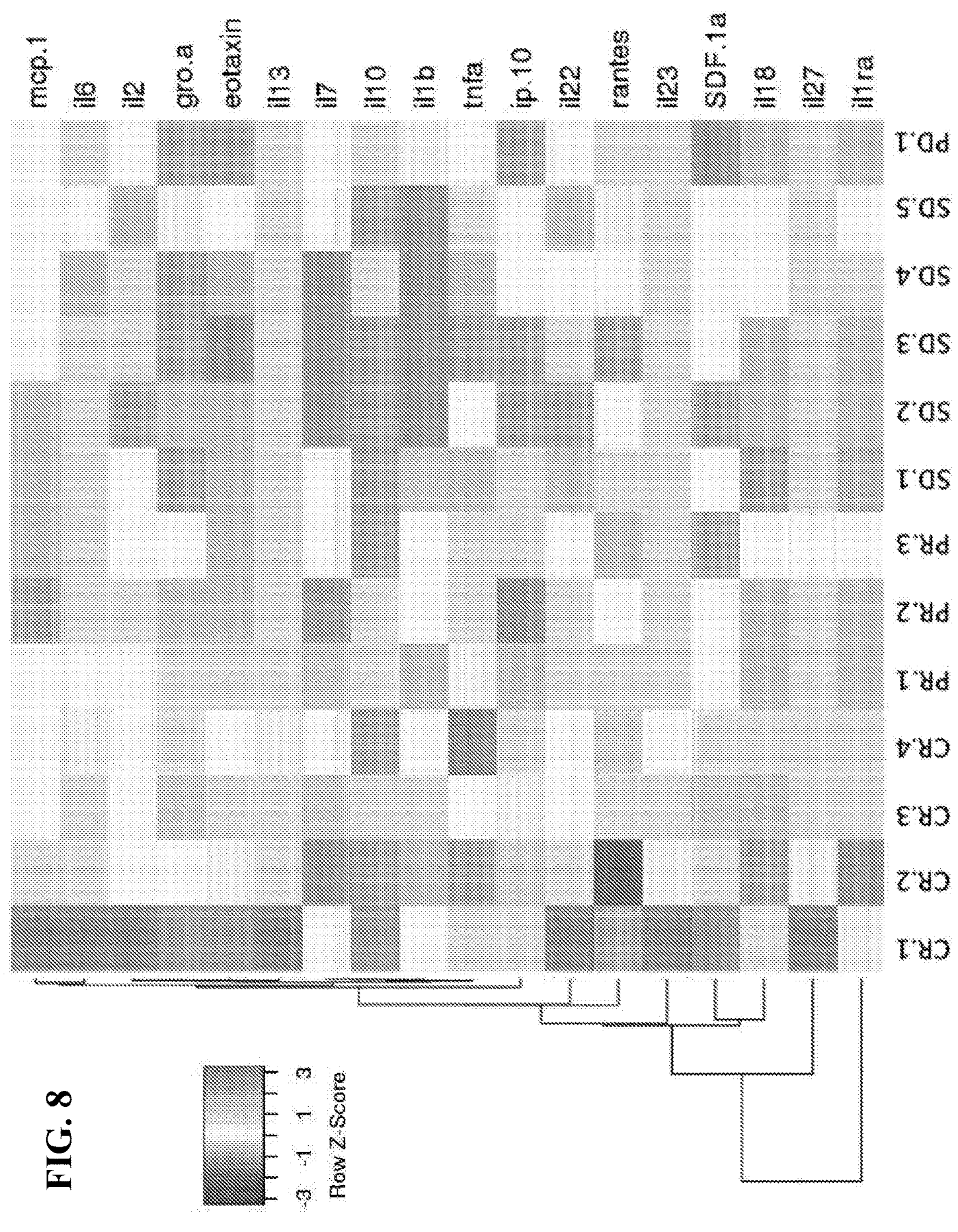
FIG. 8 shows a heatmap of pre-treatment cytokine and chemokine levels plotted by best target tumor response. Using the average linkage clustering method and the Euclidian distance measurement method, a heat map was generated for cytokines and chemokines across patient best target tumor response of complete response to treatment (CR), partial response to treatment (PR), stable disease (SD) or progressive disease (PD).

The heatmap showed a pattern of cytokine and chemokine expression that differed between the group of responders (patients exhibiting CR and PR) and non-responders (patients exhibiting PD and SD), using the cytokine expression for MCP-1, IL-6, IL-2, GRO alpha, Eotaxin, IL-13, IL-7, IL-10, IL-1β, TNF-α, IP-10, IL-22, RANTES, IL-23, SDF-1α, IL-8, IL-27 and IL-1Rα. In 13 samples tested, elevated pre-treatment plasma cytokine and chemokine levels were observed in 4 of the 7 responders (3 of 4 CR; 1 of 3 PR) and only in 1 of the 6 non-responders (1 of 5 SD; 0 of 1 PD) (FIG. 8).

Figure 9A:
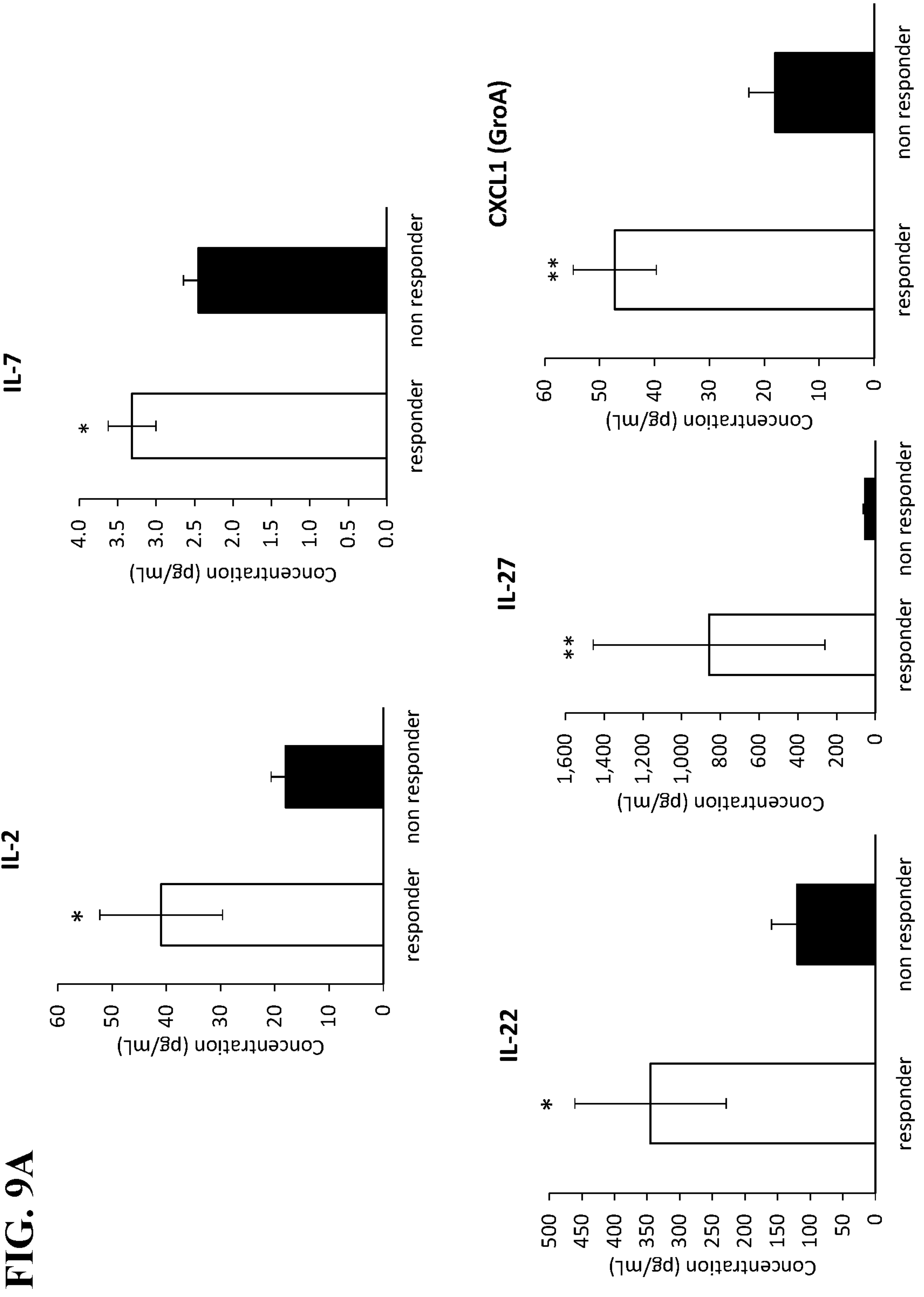
FIGS. 9A-9B show the levels of individual plasma cytokines and chemokines, IL-2, IL-7, IL-22, IL-27 and CXCL1 (GroA) (FIG. 9A), IL-113, IL-6, IL-23 and CXCL10 (IP-10) (FIG. 9B) obtained from pre-treatment blood samples, in responders (patients exhibiting a CR or a PR following treatment) compared to levels in non-responders (patients exhibiting a SD or PD following treatment). $*p \leq 0.05$; $p \leq 0.01$ FIG. 10** summarizes the expression of immunophenotype markers (cell surface markers and cytokines) related the innate immunity and adaptive immunity (DCs=dendritic cells; NK=natural killer cells; Lymph=lymphocyte activation (NKT, Pan-CD3); CD4=CD4 subsets; CD8=CD8 subsets) in post-treatment PBMC samples obtained from patients in the clinical study that exhibited various responses to the treatment (CR=complete response; PR=partial response; SD=stable disease; PD=progressive disease), based on flow cytometric analysis. Shown is a heat map and an arbitrary quantification of the degree of activation of each subset.
Figure 9B:
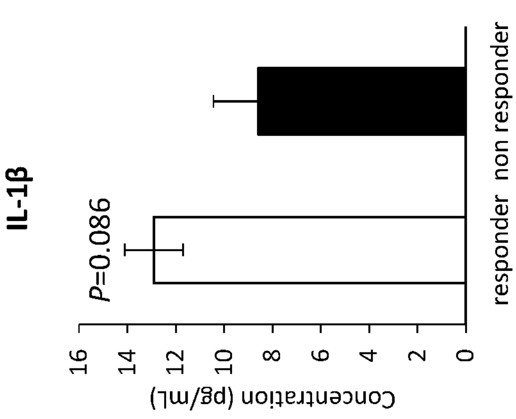
Figure 9B:
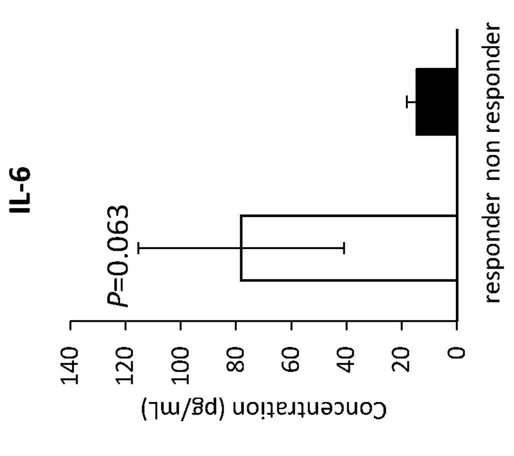
Figure 9B:
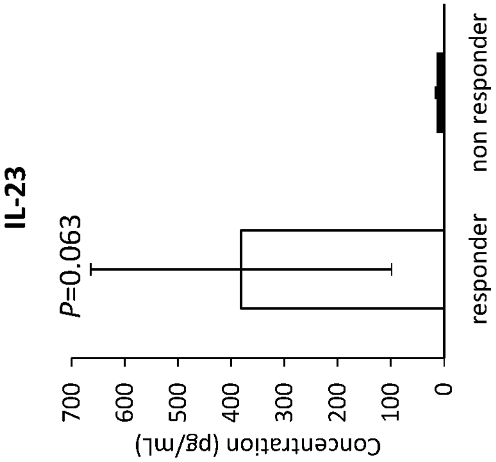
Figure 9B:
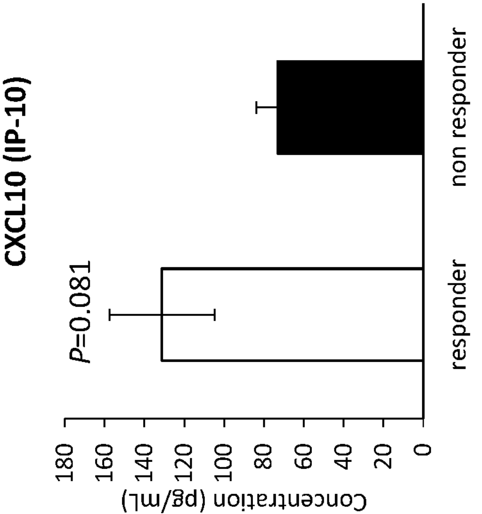

For the analysis shown in FIGS. 9A-9B, patients were grouped as "responders" if they exhibited CR or PR following treatment or "non-responders" if they exhibited SD or PD following treatment. The samples from these groups were assessed for a subset of cytokines and chemokines, comparing the pre-treatment levels in each group. Of the 18 detectable cytokines and chemokines, five (IL-2, IL-7, IL-22, IL-27, and CXCL1 [GroA]) were statistically increased in pre-treatment samples in responders compared to non-responders (FIG. 9A). Additionally, four (IL-1β, IL-6, IL-23, and CXCL10 [IP10]) showed a trend towards increased concentration in responders compared to non-responders (FIG. 9B). The results indicate a potential biomarker signature for predicting the efficacy of PIT treatment identified from a subset of pre-treatment plasma cytokines and chemokines.

Example 7

Systemic Immunophenotyping of Peripheral Blood Mononuclear Cells (PBMCs)

Expression of various cell markers was assessed to determine the immunophenotypes of peripheral blood mononuclear cells (PBMCs) obtained from the patients in the clinical study described in Example 5 above.

Patient blood was collected at multiple time points for cycle 1, prior to infusion (one day pre-light treatment, +7, +14, and +28 days post-conjugate infusion), and during subsequent cycles of treatment when available. For immunophenotyping, PBMCs were collected from 18 patients, immunostained for various panels of immune cell markers using standard procedures and analyzed by flow cytometry. For monocyte cytokine secretion, PBMCs were seeded and stimulated with 0 or 1 ng/mL of lipopolysaccharide (LPS) in the presence of 1 ng/mL of brefeldin A. Intracellular cytokine staining was performed 24 hours after stimulation using standard fixation and permeabilization protocols. Immune activation was assessed by comparing post-treatment with pre-treatment values.

The markers for staining for the flow cytometry panel included the following: CCR4, CCR6, CD123, CD127, CD14, CD141, CD16, CD163, CD1C, CD25, CD3, CD33, CD4, CD44, CD45RA, CD45RO, CD56, CD62L, CD69, CD8, CD86, CXCR3, HLA-DR, IL-10, IL-12p40, IL-6 and TNF.

Figure 10:
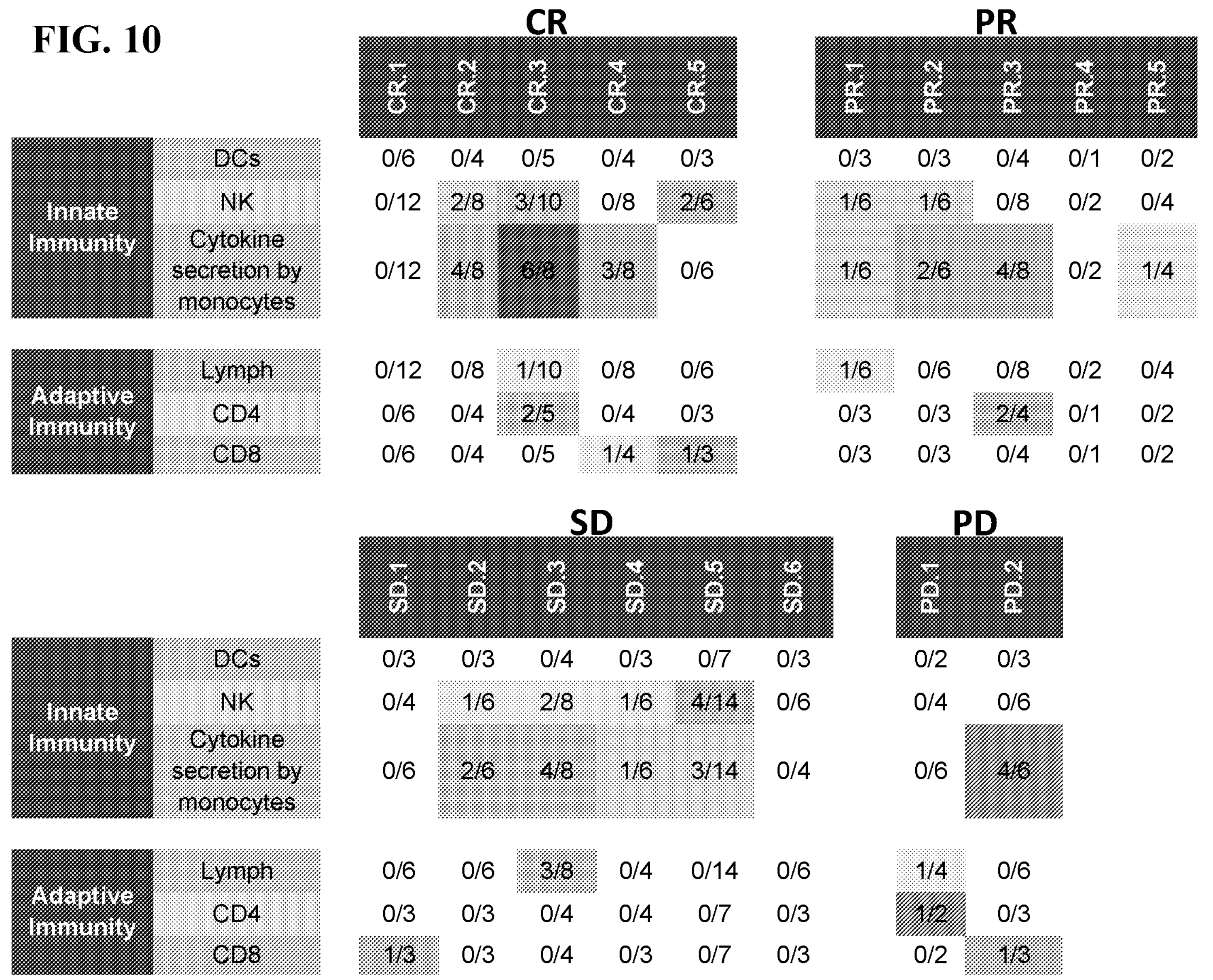

As shown in FIG. 10, results from the immunophenotyping studies from post-treatment samples demonstrated immune activation in the tumor microenvironment. The results showed that innate immune activation signals were present after treatment with the conjugate followed by illumination at 690 nm, regardless of best target tumor response. Nine of 18 patients showed upregulation of NK cells levels and/or activity. Twelve of 18 patients showed enhancement of cytokine secretion by monocytes. Adaptive immune activation signals were also observed in some patients. In general, 15 of 18 patients exhibited signs related to immune activation after treatment with the conjugate followed by light illumination, regardless of best target tumor response. The results were consistent with activation of innate and adaptive immunity after treatment with the conjugate followed by illumination.

Example 8

Biomarker Expression in Tumors and Responsiveness to Treatment

Tumor biopsies, described in Example 5, were analyzed for the presence of biomarkers, including CD3, CD4, CD8, CD11b, CD11c, CD14, CD15, CD25, CD45RO, CD56, CD68, CD69, CD163, CTLA4, FOXP3, Granzyme B, HLA-DR, Ki67, PanCK, PD-L1, and PD1, using the MultiOmyx™ multiplexing platform. Biomarker expression was evaluated in the central tumor area, in the stroma, and in the whole tumor tissue (central tumor area+stroma) using multiple regions of interest (ROI) in biopsies from patients classified as "responder" (CR and PR) and "non-responder" (SD and PD). For each biomarker, the average of all ROIs was used to represent the expression of that biomarker in a patient. Biopsies were collected pre- and post-anti-EGFR-IR700 PIT treatment. Data processing and analyses were completed using MS-EXCEL and MATLAB (MathWorks, Inc.).

A. PD-L1 in Whole Tissue and Tumor Region

Programmed death-ligand 1 (PD-L1)-positive cell density was determined in whole tumor tissue and central tumor area of "responder" and "non-responder" patients prior to anti-EGFR-IR700 PIT treatment. The results are provided in Tables 1 and 2, and depicted in FIGS. 12A-12D and FIGS. 13A-13D. In the tumor area and in the whole tissue, the Combined Positive Score (CPS) was calculated as 100*(Number of PD-L1 positive cells/Total number of tumor cells), and the Tumor Proportion Score (TPS) was calculated as 100*(Number of PD-L1 positive tumor cells/Total number of tumor cells). The Student's t-test was used to calculate the P value of pre-treatment PD-L1 expression in the "Responder" vs. "Non-responder" groups.

TABLE 1

| Whole tissue PD-L1 expression pre-treatment | | | | |
|---|---|---|---|---|
| Whole tumor tissue | PD-L1$^+$ tumor cells (PD-L1$^+$ PanCK$^+$)/mm$^2$ P = 0.015 | Total PD-L1$^+$ cells/mm$^2$ P = 0.02 | TPS P = 0.009 | CPS P = 0.015 |
| Responders (n = 13) | 560 | 1223 | 15.76 | 32.26 |
| Non-responders (n = 8) | 1653 | 2806 | 49.04 | 72.49 |

TABLE 2

| Tumor region PD-L1 expression pre-treatment | | | | |
|---|---|---|---|---|
| Central Tumor region | PD-L1$^+$ tumor cells (PD-L1$^+$ PanCK$^+$)/mm$^2$ P = 0.037 | Total PD-L1$^+$ cells/mm$^2$ P = 0.032 | TPS P = 0.034 | CPS P = 0.036 |
| Responders (n = 10) | 1204 | 1502 | 19.6 | 24.49 |
| Non-responders (n = 8) | 2747 | 3280 | 49.04 | 57.82 |

PD-L1+ tumor cell density, and total PD-L1+ cell density in the whole tumor biopsy section as well as in the central tumor area were all significantly reduced pre-treatment in patients ending up responding to anti-EGFR-IR700 PIT treatment compared to patients who did not respond to the treatment. Thus, these results indicate that low PD-L1 expression is a useful marker for predicting responsiveness to anti-EGFR-IR700 PIT treatment.

B. T-Helper Cells in Non-Tumor Region

Figure 14:
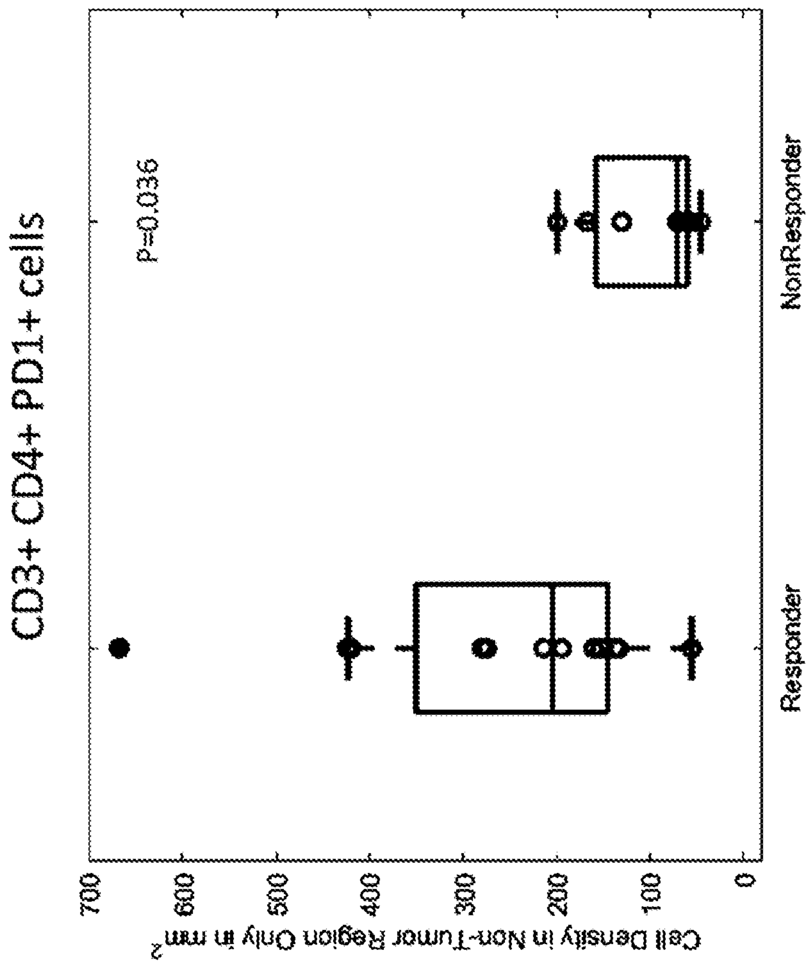
FIG. 14 illustrates the density of CD3+CD4+PD1+ cells in the non-tumor region of "responder" and "non-responder" patients (subjects) prior to anti-EGFR-IR700 PIT treatment.

The stromal region of pre-anti-EGFR-IR700 PIT treatment biopsies of 7 "responder" and 12 "non-responder" patients was analyzed for the presence of cells expressing CD3, CD4, and PD1. CD3 and CD4 dual expression is characteristic of follicular T helper (Tfh) cells. Stromal regions of "responder" patient biopsies contained an average of 260 CD3+CD4+PD1+ cells/mm$^2$ while "non-responder" patient biopsies contained an average of 106 CD3+CD4+PD1+ cells/mm$^2$ (P=0.036) (FIG. 14). These results indicate that the presence of PD1+ expressing CD3+CD4+ T-helper cells in non-tumor tissue is predictive of responsiveness of a subject to IR700 PIT treatment.

C. PD-L1:PD1 in Whole Tissue

Figures 15, 16:
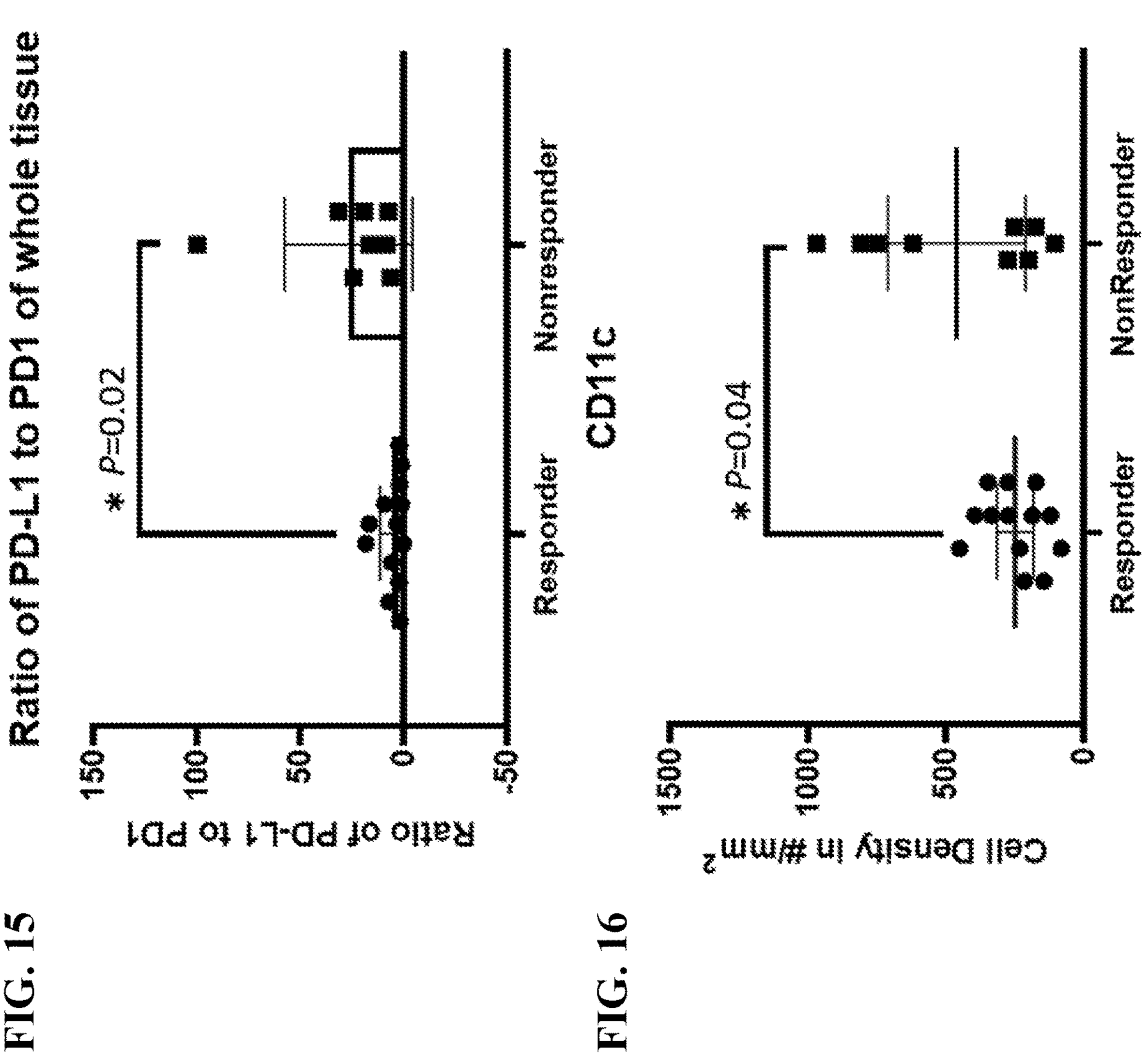
FIG. 15 depicts the ratio of PD-L1 to PD1 in whole tissue biopsies collected from "responder" and "non-responder" patients prior to anti-EGFR-IR700 PIT treatment.
FIG. 16 illustrates the CD11c-expressing cell density per area in the tumor region of "responder" and "non-responder" patients (subjects) prior to anti-EGFR-IR700 PIT treatment.

The ratio of PD-L1 to PD1 was measured in pretreated whole tissue biopsies from 13 "responder" and 8 "non-responder" patients (FIG. 15). Patients responsive to IR700 PIT treatment had a lower ratio of PD-L1 to PD1 than those who were non-responsive (5.39±5.94 vs. 26.54±30.89; P=0.025). This result indicates a low PD-L1 to PD1 ratio as predictive of subjects responsive to IR700 PIT treatment.

D. CD11c in the Tumor Region

The density of cells expressing CD11c, such as dendritic cells, was determined in the central tumor region of biopsies collected from 10 "responder" and 8 "non-responder" patients prior to anti-EGFR-IR700 PIT treatment (FIG. 16). Patients responding to anti-EGFR-IR700 PIT treatment contained reduced CD11c+ cell density than those who did not respond to treatment. Hence, low CD11c+ cell density correlates with response to anti-EGFR-IR700 PIT treatment.

E. FoxP3 in Whole Tissue

Figure 17:
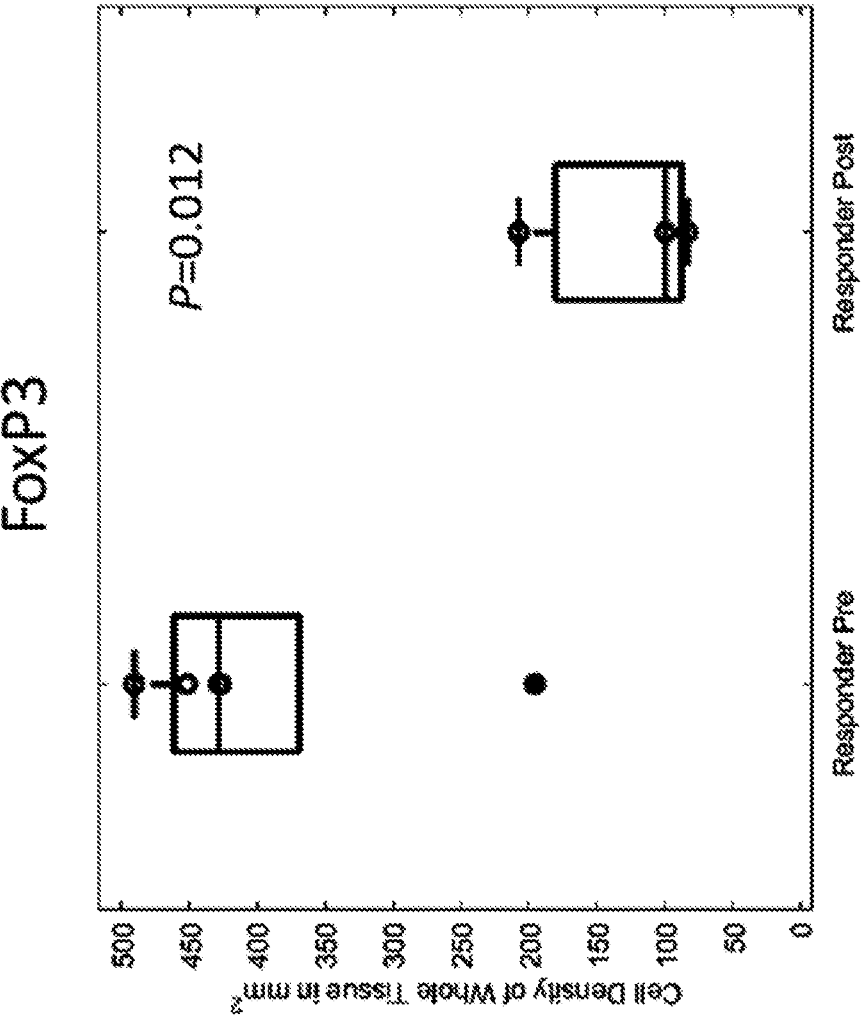
FIG. 17 illustrates the FoxP3-expressing cell density in whole tissue of "responder" patients (subjects) prior to and after anti-EGFR-IR700 PIT.

Biopsies taken from complete responders before (n=5) and after (n=3) anti-EGFR-IR700 PIT treatment were analyzed for cells expressing FoxP3 (e.g., regulatory T cells (Treg)) in whole tissue, including the central tumor region and the surrounding stroma (FIG. 17). Patients responsive to anti-EGFR IR700 PIT treatment exhibited a reduction in FoxP3-expressing cells following treatment. These results indicate FoxP3-expressing cells as markers to monitor anti-EGFR-IR700 PIT treatment, such as for the progress and/or effectiveness of the treatment.

F. Other Protein Markers in the Tumor Region

Figures 18, 19, 20:
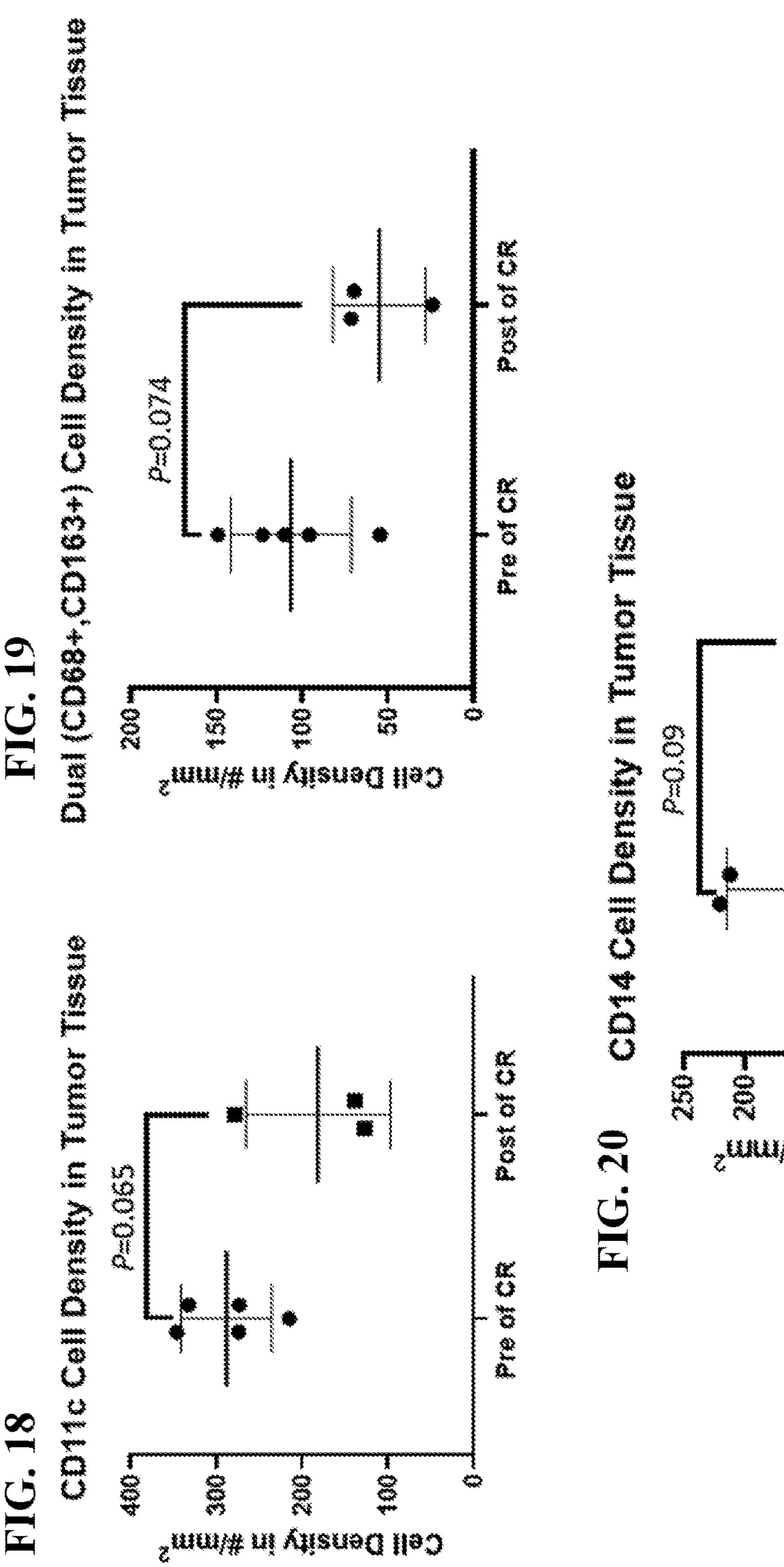
FIG. 18 shows the CD11c-expressing cell density in the tumor region of CR patients prior to (n=5) and after (n=3) anti-EGFR-IR700 PIT.
FIG. 19 shows the CD68 and CD163-expressing cell density in the tumor region of CR patients prior to (n=5) and after (n=3) anti-EGFR-IR700 PIT.
FIG. 20 shows the CD14-expressing cell density in the tumor region of CR patients prior to (n=5) and after (n=3) anti-EGFR-IR700 PIT.

Biopsies taken from complete responders before (n=5) and after (n=3) anti-EGFR-IR700 PIT treatment were analyzed for cells expressing other protein markers in the central tumor regions of biopsies, to monitor IR700 PIT treatment. Exemplary biomarkers or biomarker combinations that decreased in complete responders following anti-EGFR-IR700 PIT treatment are listed in Table 3 below and depicted in FIGS. 18-20.

TABLE 3

| Tumor region expression pre-treatment | | | |
|---|---|---|---|
| Marker(s) | Pre of CR | Post of CR | p-value |
| CD11c/mm$^2$ | 288 | 181 | 0.065 |
| (CD163, CD68)/mm$^2$ | 106 | 55 | 0.074 |
| CD14/mm$^2$ | 160 | 68 | 0.09 |

Example 9 mRNA Expression and Responsiveness to Treatment

RNA extractions from formalin-fixed paraffin embedded (FFPE) sectioned biopsies, collected from "responder" (n=10) and "non-responder" (n=6) patients from the anti-EGFR-IR700 PIT phase IIa clinical studies described above, were analyzed by NanoString nCounter® (NeoGenomics) using PanCancer 10360 gene signature panel. Transcript levels that were increased and decreased in "responder" patients compared to "non-responder" patients are provided in Table 4 and Table 5, respectively.

TABLE 4

| mRNA | Responder (relative expression) | Non-Responder (relative expression) | Responder: Non-Responder Ratio | P |
|---|---|---|---|---|
| ANGPT1 | 0.06 | 0.03 | 1.95 | 0.038 |
| BMP2 | 0.60 | 0.28 | 2.11 | 0.076 |
| BRCA2 | 0.22 | 0.16 | 1.35 | 0.071 |
| CD58 | 0.21 | 0.17 | 1.24 | 0.067 |
| CPA3 | 0.83 | 0.22 | 3.75 | 0.026 |
| CXCL14 | 19.33 | 3.22 | 6.00 | 0.026 |
| HDC | 0.14 | 0.08 | 1.64 | 0.096 |
| IL18 | 1.16 | 0.62 | 1.87 | 0.020 |
| IL1RN | 0.67 | 0.35 | 1.90 | 0.089 |
| KIT | 0.31 | 0.12 | 2.51 | 0.044 |
| KRAS | 0.57 | 0.42 | 1.37 | 0.084 |
| MAP3K5 | 0.54 | 0.33 | 1.63 | 0.020 |
| MS4A2 | 0.10 | 0.05 | 1.97 | 0.063 |
| NECTIN1 | 7.86 | 4.31 | 1.82 | 0.069 |
| OAZ1 | 6.10 | 4.44 | 1.37 | 0.032 |
| RASAL1 | 0.08 | 0.04 | 2.12 | 0.094 |
| RB1 | 1.23 | 0.85 | 1.45 | 0.038 |
| RPL23 | 44.16 | 33.72 | 1.31 | 0.061 |
| S100A8 | 178.08 | 83.84 | 2.12 | 0.093 |
| S100A9 | 165.37 | 78.74 | 2.10 | 0.071 |
| SELP | 0.15 | 0.06 | 2.44 | 0.064 |
| SGK1 | 3.84 | 2.30 | 1.67 | 0.079 |
| STAT3 | 2.65 | 1.83 | 1.45 | 0.026 |
| SYK | 0.69 | 0.43 | 1.59 | 0.036 |
| TICAM1 | 0.34 | 0.21 | 1.59 | 0.030 |
| TPSAB1/B2 | 3.68 | 1.01 | 3.64 | 0.048 |

TABLE 5

| mRNA | Responder (relative expression) | Non-Responder (relative expression) | Responder: Non-Responder Ratio | P |
|---|---|---|---|---|
| APOE | 0.94 | 2.41 | 0.39 | 0.029 |
| BATF3 | 0.10 | 0.20 | 0.48 | 0.006 |
| BBC3 | 0.31 | 0.46 | 0.68 | 0.076 |
| BCL6B | 0.10 | 0.16 | 0.62 | 0.028 |
| CASP9 | 0.18 | 0.28 | 0.64 | 0.018 |
| CCNB1 | 1.88 | 2.62 | 0.72 | 0.072 |
| CCND1 | 1.74 | 3.30 | 0.53 | 0.029 |
| CD40 | 0.38 | 0.79 | 0.47 | 0.067 |
| CDC25C | 0.05 | 0.10 | 0.55 | 0.072 |
| CNTFR | 0.03 | 0.15 | 0.17 | 0.064 |
| COL11A2 | 0.02 | 0.03 | 0.57 | 0.047 |
| CSF1 | 0.28 | 0.43 | 0.65 | 0.057 |
| CSF2 | 0.13 | 0.26 | 0.48 | 0.035 |
| CSF3 | 0.01 | 0.05 | 0.28 | 0.015 |
| CTNNB1 | 6.58 | 9.26 | 0.71 | 0.010 |
| DKK1 | 0.18 | 0.41 | 0.44 | 0.063 |
| DLL4 | 0.07 | 0.10 | 0.68 | 0.015 |
| EGF | 0.02 | 0.07 | 0.35 | 0.010 |
| EIF2B4 | 0.22 | 0.30 | 0.74 | 0.030 |
| ERCC3 | 0.86 | 1.09 | 0.78 | 0.063 |
| ESR1 | 0.02 | 0.05 | 0.34 | 0.008 |
| FADD | 0.92 | 2.08 | 0.44 | 0.058 |

TABLE 5-continued

| mRNA | Responder (relative expression) | Non-Responder (relative expression) | Responder: Non-Responder Ratio | P |
|---|---|---|---|---|
| FCGRT | 1.18 | 1.62 | 0.73 | 0.086 |
| FGF18 | 0.03 | 0.08 | 0.41 | 0.098 |
| FUT4 | 0.13 | 0.20 | 0.65 | 0.062 |
| FYN | 0.50 | 0.91 | 0.55 | 0.055 |
| GLS | 0.45 | 0.84 | 0.53 | 0.003 |
| GPC4 | 0.14 | 0.58 | 0.25 | 0.078 |
| GZMK | 0.13 | 0.33 | 0.38 | 0.084 |
| MACS | 0.49 | 0.71 | 0.68 | 0.025 |
| HSD11B1 | 0.05 | 0.20 | 0.27 | 0.028 |
| ICAM5 | 0.04 | 0.08 | 0.49 | 0.077 |
| IF135 | 1.13 | 2.07 | 0.55 | 0.063 |
| IL11 | 0.30 | 1.70 | 0.18 | 0.076 |
| IL11RA | 0.08 | 0.13 | 0.65 | 0.031 |
| IL2 | 0.01 | 0.02 | 0.62 | 0.096 |
| IL2RA | 0.11 | 0.19 | 0.60 | 0.089 |
| IL32 | 0.90 | 2.19 | 0.41 | 0.050 |
| ITGAV | 3.25 | 4.33 | 0.75 | 0.091 |
| KIR2DL3 | 0.01 | 0.02 | 0.52 | 0.094 |
| LIF | 0.10 | 0.31 | 0.32 | 0.060 |
| LOXL2 | 0.16 | 0.32 | 0.51 | 0.091 |
| MAP3K12 | 0.05 | 0.07 | 0.73 | 0.044 |
| MFGE8 | 1.52 | 2.42 | 0.63 | 0.085 |
| NCAM1 | 0.10 | 0.46 | 0.23 | 0.066 |
| NFATC2 | 0.18 | 0.40 | 0.44 | 0.060 |
| NFIL3 | 0.73 | 1.05 | 0.70 | 0.091 |
| NLRP3 | 0.02 | 0.07 | 0.37 | 0.031 |
| NOTCH2 | 1.73 | 2.26 | 0.76 | 0.033 |
| P4HA1 | 0.73 | 1.31 | 0.56 | 0.026 |
| PF4 | 0.01 | 0.02 | 0.49 | 0.037 |
| PGPEP 1 | 0.07 | 0.12 | 0.54 | 0.001 |
| PIK3R2 | 0.94 | 1.19 | 0.79 | 0.066 |
| PLOD2 | 0.64 | 1.78 | 0.36 | 0.029 |
| POLD1 | 0.20 | 0.25 | 0.81 | 0.079 |
| POS_D(2) | 1.20 | 2.20 | 0.55 | 0.092 |
| POS_F(0.125) | 1.18 | 1.86 | 0.63 | 0.085 |
| PRKACB | 0.31 | 0.41 | 0.75 | 0.081 |
| PSMB5 | 3.33 | 4.10 | 0.81 | 0.062 |
| RAD51C | 0.18 | 0.24 | 0.75 | 0.077 |
| RIPK2 | 0.41 | 0.65 | 0.63 | 0.002 |
| ROR2 | 0.22 | 0.34 | 0.64 | 0.057 |
| RPTOR | 0.36 | 0.47 | 0.75 | 0.019 |
| RRM2 | 0.15 | 0.22 | 0.70 | 0.098 |
| SERPINA1 | 0.32 | 1.20 | 0.26 | 0.090 |
| SF3A1 | 1.15 | 1.60 | 0.72 | 0.008 |
| SNAI1 | 0.09 | 0.19 | 0.49 | 0.007 |
| SPP1 | 2.38 | 5.78 | 0.41 | 0.020 |
| SRP54 | 0.79 | 1.07 | 0.74 | 0.042 |
| STC1 | 0.08 | 0.21 | 0.39 | 0.016 |
| TBX21 | 0.03 | 0.05 | 0.62 | 0.060 |
| TIE1 | 0.19 | 0.28 | 0.69 | 0.055 |
| TMEM140 | 0.20 | 0.48 | 0.41 | 0.049 |
| TNFRSF8 | 0.02 | 0.04 | 0.62 | 0.079 |
| TNFSF12 | 0.34 | 0.50 | 0.67 | 0.012 |
| TNFSF13 | 0.19 | 0.31 | 0.62 | 0.098 |
| TWIST1 | 0.24 | 0.77 | 0.31 | 0.088 |
| VEGFA | 1.12 | 1.75 | 0.64 | 0.015 |
| WNT11 | 0.05 | 0.11 | 0.43 | 0.052 |
| WNT5B | 0.06 | 0.11 | 0.50 | 0.076 |

The present invention is not intended to be limited in scope to the particular disclosed embodiments, which are provided, for example, to illustrate various aspects of the invention. Various modifications to the compositions and methods described will become apparent from the description and teachings herein. Such variations may be practiced without departing from the true scope and spirit of the disclosure and are intended to fall within the scope of the present disclosure.

The invention claimed is:

1. A method of treating a tumor that is a head or neck cancer in a subject, the method comprising administering to the subject a photoimmunotherapy (PIT) treatment, thereby treating the tumor, wherein the PIT treatment comprises a conjugate comprising a silicon phthalocyanine dye and an EGFR binding molecule; and wherein the subject has been selected for treatment by:

a) measuring in a sample from the subject a first level of an immune checkpoint biomarker comprising a PD-L1 expression;

b) comparing the first level of PD-L1 from the subject to a first threshold level of PD-L1 expression, wherein the first threshold level is a Combined Positive Score (CPS) of PD-L1 expression equal to 30; and c) selecting the subject for treatment if the first level from the subject is lower than the first threshold level.

2. The method of claim 1, wherein the sample is a tumor sample, a blood sample, or a serum sample.

3. The method of claim 1, wherein the first threshold level is measured as a Combined Positive Score (CPS) equal to the number of cells staining positive for the immune checkpoint biomarker, divided by the total number of tumor cells, multiplied by 100.

4. The method of claim 1, wherein the PIT treatment comprises irradiating an area proximal to the tumor at a wavelength of at or about 660 nm to at or about 740 nm.

5. The method of claim 1, wherein the EGFR binding molecule is cetuximab or a fragment thereof.

6. The method of claim 1, wherein the method further comprises:

measuring a second level of the immune checkpoint biomarker in a second sample from the subject after the PIT treatment;

determining whether the second level of the immune checkpoint biomarker is increased in the subject relative to the first level measured prior to the PIT treatment; and if the second level is increased relative to the first level, administering an immune checkpoint inhibitor to the subject.

7. The method of claim 1, wherein the PIT treatment comprises exposing the conjugate to light that has a wavelength within a range of at or about 660 nm to at or about 740 nm.

8. The method of claim 1, wherein the PIT treatment comprises exposing the conjugate to light that has a wavelength of at or about 690 nm.

9. The method of claim 1, wherein the silicon phthalocyanine dye comprises the formula:

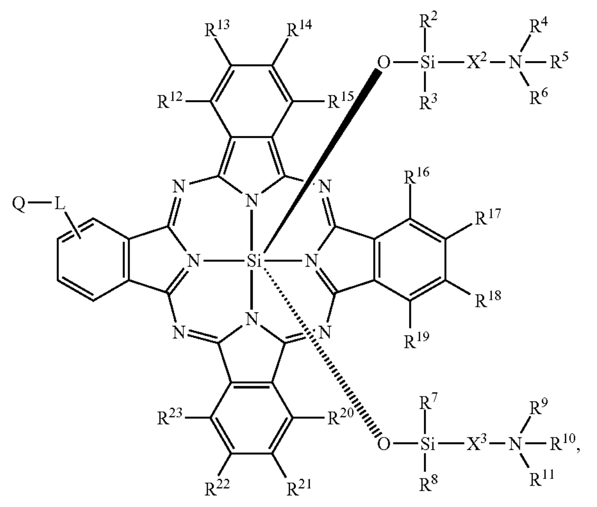

wherein:

L is a linker;

Q is a reactive group for attachment of the dye to the EGFR binding molecule;

$R^2$, $R^3$, $R^7$, and $R^8$ are each independently selected from among substituted alkyl and substituted aryl;

$R^4$, $R^5$, $R^6$, $R^9$, $R^{10}$, and $R^{11}$ are each independently selected from among hydrogen, substituted alkyl, substituted alkanoyl, substituted alkoxycarbonyl, substituted alkylcarbamoyl, and a chelating ligand, wherein at least one of $R^4$, $R^5$, $R^6$, $R^9$, $R^{10}$, and $R^{11}$ comprises a water soluble group;

$R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ are each independently selected from among hydrogen, halogen, substituted alkylthio, substituted alkylamino and substituted alkoxy; and $X^2$ and $X^3$ are each independently $C_1$-$C_{10}$ alkylene.

10. The method of claim 7, wherein the silicon phthalocyanine dye is IR700.

11. The method of claim 7, wherein the EGFR binding molecule is cetuximab or a fragment thereof.

12. The method of claim 7, wherein the silicon phthalocyanine dye comprises the formula:

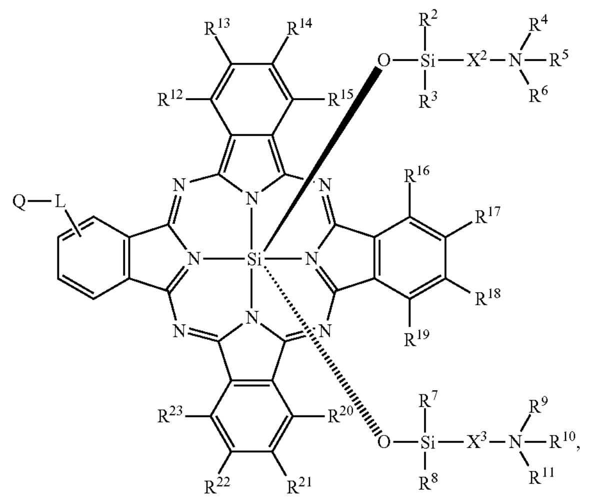

wherein:

L is a linker;

Q is a reactive group for attachment of the dye to the EGFR binding molecule;

$R^2$, $R^3$, $R^7$, and $R^8$ are each independently selected from among substituted alkyl and substituted aryl;

$R^4$, $R^5$, $R^6$, $R^9$, $R^{10}$, and $R^{11}$ are each independently selected from among hydrogen, substituted alkyl, substituted alkanoyl, substituted alkoxycarbonyl, substituted alkylcarbamoyl, and a chelating ligand, wherein at least one of $R^4$, $R^5$, $R^6$, $R^9$, $R^{10}$, and $R^{11}$ comprises a water soluble group;

$R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ are each independently selected from among hydrogen, halogen, substituted alkylthio, substituted alkylamino and substituted alkoxy; and $X^2$ and $X^3$ are each independently $C_1$-$C_{10}$ alkylene.

13. The method of claim 8, wherein the silicon phthalocyanine dye is IR700.

14. The method of claim 8, wherein the EGFR binding molecule is cetuximab or a fragment thereof.

15. The method of claim 10, wherein the EGFR binding molecule is cetuximab or a fragment thereof.

16. The method of claim 12, wherein the EGFR binding molecule is cetuximab or a fragment thereof.

17. The method of claim 1, wherein the silicon phthalocyanine dye is IR700.

* * * * *